US008048410B2

(12) United States Patent
Sehgal et al.

(10) Patent No.: US 8,048,410 B2
(45) Date of Patent: Nov. 1, 2011

(54) IN VIVO AND EX VIVO GENE TRANSFER INTO RENAL TISSUE USING GUTLESS ADENOVIRUS VECTORS

(75) Inventors: Lakshman R. Sehgal, Monarch Beach, CA (US); Jonathan Wong, Palo Alto, CA (US)

(73) Assignee: Biovec, LLC, Chicago, IL (US)

( * ) Notice: Subject to any disclaimer, the term of this patent is extended or adjusted under 35 U.S.C. 154(b) by 0 days.

(21) Appl. No.: 12/778,360

(22) Filed: May 12, 2010

(65) Prior Publication Data

US 2010/0249221 A1    Sep. 30, 2010

Related U.S. Application Data

(63) Continuation of application No. 12/320,434, filed on Jan. 26, 2009, which is a continuation-in-part of application No. 11/650,478, filed on Jan. 8, 2007, now Pat. No. 7,501,114, which is a continuation-in-part of application No. 10/725,013, filed on Dec. 2, 2003, now Pat. No. 7,179,459.

(60) Provisional application No. 60/430,099, filed on Dec. 2, 2002.

(51) Int. Cl.
*A61K 48/00* (2006.01)
*C07H 21/04* (2006.01)

(52) U.S. Cl. ........................ 424/93.2; 536/23.2; 536/23.5

(58) Field of Classification Search ........................ None
See application file for complete search history.

(56) References Cited

U.S. PATENT DOCUMENTS

| | | | |
|---|---|---|---|
| 4,826,811 A | 5/1989 | Sehgal et al. | |
| 4,868,116 A | 9/1989 | Morgan et al. | |
| 5,061,688 A | 10/1991 | Beissinger et al. | |
| 5,339,346 A | 8/1994 | White | |
| 5,438,041 A | 8/1995 | Zheng et al. | |
| 5,449,614 A | 9/1995 | Danos et al. | |
| 5,466,668 A | 11/1995 | Glaser et al. | |
| 5,639,625 A | 6/1997 | Carson et al. | |
| 5,661,033 A | 8/1997 | Ho et al. | |
| 5,827,824 A | 10/1998 | Light et al. | |
| 5,863,760 A | 1/1999 | Light et al. | |
| 5,869,230 A * | 2/1999 | Sukhatme | 435/1.1 |
| 5,916,874 A | 6/1999 | Fujiwara et al. | |
| 5,919,619 A | 7/1999 | Tullis | |
| 5,981,225 A | 11/1999 | Kochanek et al. | |
| 5,985,846 A | 11/1999 | Kochanek et al. | |
| 5,994,132 A | 11/1999 | Chamberlain et al. | |
| 6,083,750 A | 7/2000 | Chamberlain et al. | |
| 6,207,455 B1 | 3/2001 | Chang | |
| 6,290,949 B1 | 9/2001 | French et al. | |
| 6,328,958 B1 | 12/2001 | Amalfitano et al. | |
| 6,334,194 B1 | 12/2001 | Hihara | |
| 6,335,011 B1 | 1/2002 | Podsakoff et al. | |
| 6,342,214 B1 | 1/2002 | Tryggvason et al. | |
| 6,888,047 B1 * | 5/2005 | Wu et al. | 800/14 |
| 7,160,539 B2 * | 1/2007 | Munn et al. | 424/93.21 |
| 7,179,459 B2 | 2/2007 | Sehgal et al. | |
| 7,481,998 B2 | 1/2009 | Sehgal et al. | |
| 7,501,114 B2 | 3/2009 | Sehgal et al. | |
| 7,687,058 B2 * | 3/2010 | Sehgal et al. | 424/93.6 |
| 2002/0068713 A1 | 6/2002 | Rade et al. | |
| 2002/0193336 A1 | 12/2002 | Elkins et al. | |
| 2004/0198683 A1 | 10/2004 | Sehgal et al. | |
| 2007/0184027 A1 * | 8/2007 | Seghal et al. | 424/93.2 |

FOREIGN PATENT DOCUMENTS

| | | |
|---|---|---|
| WO | 96/06933 A1 | 3/1996 |
| WO | 99/14346 A1 | 3/1999 |
| WO | 00/46360 A1 | 8/2000 |
| WO | 01/29058 A1 | 4/2001 |

OTHER PUBLICATIONS

Parks, et al., "Effects of stuffer DNA on transgene expression from helper-dependent adenovirus vectors", J. Virol. 70 (10): 8027-8034, Oct. 1999.
GenBank Acc. No. M26434, "Human hypoxanthine phosphoribosyltransferase (HPRT) gene, complete cds", US Natl. Library of Med., Bethesda, MD, USA, Nov. 26, 2001.
Orkin, et al., "Report and Recommendations of the Panel to Assess the NIH Investment in Research on Gene Therapy", US National Institutes of Health, Bethesda, MD, USA, Dec. 7, 1995.
Verma, et al., "Gene therapy—promises, problems and prospects", Nature 389: 239-242,1997.
Rosenberg, et al., "Gene therapist, heal thyself", Science 287: 1751,2000.
Zuckerbraun, B.S., "Vascular gene therapy: a reality of the 21st century", Arch. Surg. 137: 854-861, Jul. 2002.
Esmon, C.T., "Protein C in sepsis", Ann. Med. 34: 598-605, 2002.
Waugh, et al., "Local Overexpression of Thrombomodulin for In Vivo Prevention of Arterial Thrombosis in a Rabbit Model", Circulation Research, vol. 84, No. 1, pp. 84-92, 1999.
Waugh, et al., "Thrombomodulin Overexpression to Limit Neointima Formation", Circulation, vol. 102, No. 3, pp. 332-337, 2000.
Vassalli, et al., "Gene therapy for arterial thrombosis", Cardiovascular Research, vol. 19, No. 6, pp. 459-459,1997.
Umana, et al., "Efficient FLPe recombinase enables scalable production of helper-dependent adenoviral vectors with negligible helper-virus contamination", Nature Biotechnology, vol. 19, No. 6, pp. 582-585, 2001.
Wen, et al., "Human Thrombomodulin: Complete cDNA Sequence and Chromosome Localization of the Gene", Biochemistry, vol. 26, pp. 4350-4357,1987.
Borroni, et al., "Peripheral Blood Abnormalities in Alzheimer Disease: Evidence for Early Endothelial Dysfunction", Alzheimer Disease and Associated Disorders, vol. 16, No. 3, pp. 150-155,2002.

(Continued)

*Primary Examiner* — Richard Schnizer
(74) *Attorney, Agent, or Firm* — Ping Wang; Andrews Kurth, LLP

(57) ABSTRACT

A method for treating a renal disease in a subject is disclosed. The method includes administering into a kidney of the subject with an effective amount of a gutless adenoviral vector containing a polynucleotide encoding a therapeutic agent. The gutless adenoviral vector contains the nucleotide sequence of SEQ ID NO:13 or SEQ ID NO:15 and expresses the therapeutic agent in a kidney tissue of the subject.

4 Claims, 16 Drawing Sheets
(5 of 16 Drawing Sheet(s) Filed in Color)

OTHER PUBLICATIONS

McKay, et al., "Gene Transfer Therapy in Vascular Disease", Cardiovascular Drug Reviews, vol. 19, No. 3, pp. 245-262, 2001.

Ausbel, et al., (eds) Greene Publishing Associates, "Current Protocols in Molecular Biology", Sections 9.10-9.14,1989.

Ng, et al., "Development of a FLP/fre System for Generating Helper-Dependent Adenoviral Vectors", Molecular Therapy, vol. 3, No. 5, pp. 809-815, 2001.

Bledsoe, et al., "Cytokine production in motor neurons by poliovirus replicon vector gene delivery", Nature Biotechnol., vol. 18. pp. 964-969, 2000.

Chen, et al., "Low-Dose Vaccinia Virus-Mediated Cytokine Gene Therapy of Glioma", Journal of Immunotherapy, vol. D 24, pp. 46-57, 2001.

Chen, et al., "Gene therapy for brain tumors: Regression of experimental gliomas by adenovirus-mediated gene transfer in vivo", Proc. Natl. Acad. Sci. USA, vol. 91, pp. 3054-3057, 1994.

Cui, et al., "Plasmid DNA-Entrapped Nanoparticles Engineered from Microemulsion Precursers: In Vitro and In Vivo Evaluation", Bioconjugate Chern., vol. 13, pp. 1319-1327, 2002.

Curiel, "Strategies to Adapt Adenoviral Vectors for Targeted Delivery", Annals New York Academy of Sciences, vol. 886, pp. 158-171, 1991.

Gossen, et al., "Transcriptional Activation by Tetracyclines in Mammalian Cells", Science, vol, 268, pp. 1766-1769, 1995.

Gossen, et al., "Tight control of gene expression in mammalian cells by tetracycline-responsive promoters", Proc. Natl. Acad. Sci. USA, vol. 89, pp. 5547-5551, 1992.

Fink, et al., "Gene Transfer to Neurons Using Herpes Simplex Virus-Based Vectors", Annual Rev. Neurosci., vol. 19, pp. 265-287,1996.

Flotte, et al., "Gene Expression from Adeno-associated Virus Vectors in Airway Epithelial Cells", Am. J. Respir. Cell. Mol. Biol., vol. 7, pp. 349-356,1992.

Green, et al., "A New Scalable Method for the Purification of Recombinant Adenovirus Vectors", Human Gene Therapy, vol. 13, pp. 1921-1934,2002.

Haj-Ahmand, et al., "Development of a Helper-Independent Human Adenovirus Vector and Its Use in the Transfer of the Herpes Simplex Virus Thymidine Kinase Gene", J. Virol., vol, 57., pp. 267-273, 1986.

Howell, et al., "High-Level Dystrophin Expression After Adenovirus-Mediated Dystrophin Minigene Transfer to Skeletal Muscle of Dystrophic Dogs: Prolongation of Expression with Immunosuppression", Human Gene Therapy, vol. 9, pp. 629-634, 1998.

Kay, et al., "Evidence for gene transfer and expression of factor IX in haemophilia B patients treated with an AAV vector", Nature Genetics, vol. 24, pp. 257-261, 2000.

Kessler, et al., "Gene delivery to skeletal muscle results in sustained expression and systemic delivery of a therapeutic protein", Proc. Natl. Acad. Sci. USA, vol. 96, pp. 14082-14087, 1996.

Kistner, et al., "Doxycycline-mediated quantitative and tissue-specific control of gene expression in transgenic mice", Proc. Natl. Acad. Sci. USA, vol. 93, pp. 10933-10938, 1996.

Magari, et al., "Pharmacologic Control of a Humanized Gene Therapy System Implanted into Nude Mice", J. Clin. Invest., vol. 100, pp. 173-206, 1997.

Miller, "Progress Toward Human Gene Therapy", Blood, vol. 76, pp. 271-278,1990.

Muzyczka, et al., "Use of Adeno-Associated Virus as a General Transduction Vector for Mammalian Cells", Curro Topics in Micro. and Immunology, vol. 158, pp. 97-129,1990.

Naldni, et al., "In Vivo Gene Delivery and Stable Transduction of Nondividing Cells by a Lentiviral Vector", Science, vol. 272, pp. 263-267, 1996.

No, et al., "Ecdysone-inducible gene expression in mammalian cells and transgenic mice", Proc. Natl. Acad. Sci., USA, vol. 93, pp. 3346-3351, 1996.

Pruchnic, et al., "The Use of Adeno-Associated Virus to Circumvent the Maturation-Dependent Viral Transduction of Muscle Fibers", Human Gene Therapy, vol. 11, pp. 521-536, 2000.

Ragot, et al., "Efficient adenovirus-mediated transfer of a human minidystrophin gene to skeletal muscle of mdx mice", Nature, vol. 361, pp. 647-650,1993.

Romano, et al., "Latest Developments in Gene Transfer: Achievements, Perspectives, and Controversies Over Therapeutic Applications", Stem Cells, vol. 18, pp. 19-39, 2000.

Ropert, "Liposomes as a gene delivery system", Brazilian Journal of Medical and Biological Research, vol. 32, pp. 163-169,1999.

Sakhuja, et al., "Optimization of the Generation and Propagation of Gutless Adenoviral Vectors", Human Gene Therapy, vol. 14, pp. 243-254, 2003.

Samulski, et al., "Helper-Free Stocks of Recombinant Adeno-Associated Viruses: Normal Integration Does Not Require Viral Gene Expression", Journal of Virology, vol. 63, No. 9, pp. 3822-3828,1989.

Schwarze, et al., "In Vivo Protein Transduction: Delivery of a Biologically Active Protein into the Mouse", Science, vol. 285,pp. 1569-1572, 1999.

Song, et al., "Sustained secretion of human alpha-1 antitrypsin from murine muscle transduced with adeno-associated virus vectors", Proc. Natl. Acad. Sci. USA, vol. 95, pp. 14348-14384, 1998.

Suzuki, et al., "Structure and expression of human thrombomodulin, a thrombin receptor on endothelium acting as a cofactor for protein C activation", EMBO Journal, vol. 6, pp. 1891-1897, 1987.

Wahlfors, et al., "Evaluation of recombinant alphaviruses as vectors in gene therapy", Gene Therapy, vol, 7, pp. 472-480, 2000.

Wang, et al., "A regulatory system for use in gene transfer", Proc. Natl. Acad. Sci. USA, vol. 91, pp. 8180-8184,1994.

Wang, et al., "Ligand-inducible and liver-specific target gene expression in transgenic mice", Nature Biotechnology, vol. 15, pp. 239-243, 1997.

Yamashita, et al., "Electroporation-mediated Interleukin-12 Gene Therapy Hepatocellular Carcinoma in the Mice Model", Cancer Research, vol. 61, pp. 1005-1012,2001.

Ye, et al., "Regulated Delivery of Therapeutic Proteins After In Vivo Somatic Cell Gene Transfer", Science, vol. 283, pp. 88-91, 1999.

Yi, et al., "A Cationic Lipid Emulsion/DNA Complex as a Physically Stable and Serum-Resistant Gene Delivery System", Pharmaceutical Research, vol. 17, No. 3, pp. 314-320, 2000.

Xiao, et al., "Efficient Long-Term Gene Transfer into Muscle Tissue of Immunocompetent Mice by Adeno-Associated Virus Vector", Journal of Virology, vol. 70, No. 11, pp. 8098-8108, 1996.

Xiao, et al., "Adeno-Associated Virus as a Vector for Liver-Directed Gene Therapy", Journal of Virology, vol. 72, No. 12, pp. 10222-10226, 1998.

Zhang, et al., "Long-term expression of human alpha-1 antitrypsin gene in mouse liver achieved by intravenous administration of plasmid DNA using a hydrodynamics-based procedure", Gene Therapy, vol. 7, pp. 1344-1349,2000.

Cui, et al., "Genetic Immunization Using Nanoparticles Engineered from Microemulsion Precursors", Pharmaceutical Research, vol. 19, No. 7, pp. 939-946, 2002.

Kibbe, et al., "Handbook of Pharmaceutical Excipients", 3rd Edition, Pharmaceutical Press London UK, 2000.

Lee, et al., "Crit. Rev. Ther.", Drug Carrier Systems, vol. 14, pp. 173-206, 1997.

Harui, et al., "Vaccination with helper-dependent adenovirus enhances the generation of transgene-specific CTL", Gene Therapy, vol. 11, pp. 1617-1626,2004.

Johansson, et al., "Adenoviral-Mediated Expression of Porphobilinogen Deaminase in Liver Restores the Metabolic Defect in a Mouse Model of Acute Intermittent Porphyria", Molecular Therapy, vol. 10, pp. 337-343, 2004.

Fu, et al., "Overexpression of SR-BI by Adenoviral Vector Reserves the Fibrate-Induced Hypercholesterolemia of Apolipoprotein E-Deficient Mice", Journal of Biological Chemistry, vol. 278, pp. 52559-52563, 2003.

Brevetti, et al., "Overexpression of endothelial nitric oxide synthase increases skeletal muscle blood flow and oxygenation in severe rat hund limb ischemia", The Society for Vascular Sugery, pp. 820-826, 2003.

Li, et al., J. Vase. Surg. 32: 804-813, 2000.

Tohda, et al., Arteriosclerosis, Thrombosis, and Vascular Biology, 18: 1861-1869, 1998.

Kurosawa, et al., J. Biol. Chern., 263(13): 5993-5996,1988.

Tabuchi, et al., Eur. J. Card. Thor. Surg., 26: 995-1000, 2004.

Miller, et al., FASEB J., 9: 190-199, 1995.

Crystal, Science, 270: 404-410,1995.

Read, et al., Adv. Gen., 53: 19-46, 2005.

Search Result for SEQ 10 No: 13 in U.S. Appl. No. 11/685,474.

Marth, et al., Nature Genetics, 23(4): 452-456, 1999.

Wheelan, et al., Genome Research, 11(11): 1952-1957,2001.

Kibbe, et al, "Gene Therapy for Restenosis", Circ. Res., vol. 86, pp. 829-833, 2000.

Shears, et al., "Efficient Inhibition of Intimal Hyperplasia by Adenovirus-Mediated Inducible Nitric Oxide Synthase Gene Transfer to Rats and Pigs In Vivo", J. Am. Coll. Surg., vol. 187, No. 3, pp. 295-306, 1998.

Ross, "The pathogenesis of atherosclerosis: a perspective for the 1990s", Nature, vol. 362, pp. 801-809, 1993.

Sadler, "Thrombomodulin Structure and Function", Tehomb Haemost, vol. 78, pp. 392-395,1997.

Esmon, "Thrombomodulin as a model of molecular mechanisms that modulate protease specificity and function at the vessel surface", Faseb J., vol. 9, pp. 946-955,1995.

Salomaa, et al., "Soluble thrombomodulin as a predictor of incident coronary heart disease and symptomless carotid artery atherosclerosis in the Atherosclerosis Risk in Communities (ARIC) Study: a case-cohort study", Lancet, vol. 353,pp. 1729-1734, 1999.

Palmer, et al., "Nitric oxide release accounts for the biological activity of enothelium-derived relaxing factor", Nature, vol. 88, pp. 4651-4655,1991.

Kubes, et al., "Nitric oxide: An endogenous modulator of leukocyte adhesion", Proc. Natl. Acad. Sci. USA, vol. 88, pp. 4651-4655,1991.

Steg, et al., "Reduction of Restenosis After Angioplasty in an Atheromatous Rabbit Model by Suicide Gene Therapy", Circulation vol. 96, pp. 401-411,1997.

Van Belle, et al., "Accelerated Endothelialization by Local Deliery of Recombinant Human Vascular Endothelial Growth Factor Reduces In-Stent Intimal Formation", Biochem. and Biophs. Res. Communications, vol. 235, pp. 311-316, 1997.

Salyapongse, et al., "Gene Therapy and Tissue Engineering", Tissue Engineering, vol. 26, No. 4, pp. 663-676,1999.

Kon, et al., "Bone Morphogenetic Protein-2 Stimulates Differentiation of Cultured Spinal Ligament Cells from Patients with Ossification of the Posterior Longitudinal Ligament", Calcif. Tissue Int., vol. 60, pp. 291-296,1997.

Kibbe, et al., J. Vase. Surg., 34: 156-65,2001.

He, et al., PNAS, 95: 2509-2514,1998.

Marmur, et al., "Strand Separation and Specific Recombination in Deoxyribonucleic Acids: Biological Studies", PNAS USA, vol. 46, pp. 453-461,1960.

Doty, et al., "Strand Separation and Specific Recombination in Deoxyribonucleic Acids: Physical Chemical Studies", PNAS USA, vol. 46, pp. 461-476, 1960.

Sambrook, et al., "Analysis of Genomic DNA by Southern Hybridization", Molecular Cloning: A Laboratory Manual, vol. II, pp. 9.31-9.62,1989.

Zushi, et al., "Aspartic acid 349 in the forth epidermal growth factor-like structure of human thrombomodulin plays a role in its Ca(2+)-mediated binding to protein C", The Journal of Biological Chemistry, vol. 266, No, 30, pp. 19886-19889, 1991.

Parks, et al., "A helper-dependent adenovirus vector system: Removal of helper virus by Cre-mediated excision of the viral packaging signal", PNAS, vol. 93, pp. 13565-13570, 1996.

Lieber, et al., "Recombinant Adenoviruses with Large Deletions Generated by Cre-Mediated Excision Exhibit Different Biological Properties Compared with First-Generation Vectors In Vitro and In Vivo", J. Virol., vol. 70, pp. 8944-8960, 1996.

Dittman, et al., "Human Thrombomodulin: Complete eDNA Sequence and Chromosome Localization of the Gene", Biochemistry, vol. 26, pp. 4350-4357,1987.

Beauchamp, et al., "Development of a FLP/frt System for Generating Helper-Dependent Adenoviral Vectors", Molecular Therapy, vol. 3, No. 5, pp. 809-815, 2001.

Nabel, et al., Science, vol. 249, pp. 1285-1288, 1990.

Tsiang, et al., "Functional domains of membrane-bound human thrombomodulin. EGF-like domains four to six and the serine/threonine-rich domain are required for cofactor activity", The Journal of Biological Chemistry, vol. 267, No. 9, pp. 6164-6170, 1992.

Nagashima, et al., "Alanine-scanning mutagenesis of the epidermal growth factor-like domains of human thrombomodulin identifies critical residues for its cofactor activity", The Journal of Biological Chemistry, vol. 268., No. 4,pp. 2888-2892,1993.

Gerlitz, et al., "Identification of the predominant glycosaminoglycan-attachment site in soluble recombinant human thrombomodulin: potential regulation of functionality by glycosyltransferase competition for serine474", The Biochemical Journal, vol. 295; pp. 131-140,1993.

Lin, et al., "Modulation of glycosaminoglycan additional in naturally expressed and recombinant human thrombomodulin", The Journal of Biological Chemistry, vol. 269, No. 40, pp. 25021-25030,1994.

Adler, et al., "The structure of a 19-residue fragment from the C-loop of the fourth epidermal growth factor-like domain of thrombomodulin", The Journal of Biological Chemistry, vol. 270, No. 40, pp. 23366-23372, 1995.

Weiler-Guettler, et al., "A targeted point mutation in thrombomodulin generated viable mice with a prethrombotic state", The Journal of Clinical Investigation, vol. 101, No. 9, pp. 1983-1991, 1998.

* cited by examiner i-product (2440 bps)

IN VIVO AND EX VIVO GENE TRANSFER INTO RENAL TISSUE USING GUTLESS ADENOVIRUS VECTORS

This application is a continuation of U.S. patent application Ser. No. 12/320,434, filed Jan. 26, 2009, which is a continuation-in-part of U.S. patent application Ser. No. 11/650,478, now U.S. Pat. No. 7,501,114, filed Jan. 8, 2007, which is a continuation-in-part application of U.S. patent application Ser. No. 10/725,013, now U.S. Pat. No. 7,179,459, filed Dec. 2, 2003, which claims priority from U.S. Provisional Application Ser. No. 60/430,099 filed Dec. 2, 2002. The entirety of all of the aforementioned applications is incorporated herein by reference.

FIELD

The present invention is directed to methods and compositions for the gene transfer into renal tissues and, in particular, is directed to methods and compositions for in vivo or ex vivo gene transfer to renal tissue using gutless adenovirus vector.

BACKGROUND

Kidney-targeted gene transfer has the potential to revolutionize the treatment of renal diseases. Transplanted kidneys also provide an ideal setting for ex vivo gene transfer. Several in vivo gene transfer methods have been attempted to target certain renal structures, for example, the HVJ-liposome method and renal perfusion of adenovirus for glomerular cells, intravenous injection of oligonucleotides (ODNs) for proximal tubule, intra-arterial injection of adenovirus followed by cold incubation with a vasodilator for interstitial vasculature of the outer medulla and adenoviral injection into the renal pelvis for the inner medullary collecting duct. As an ex vivo gene transfer method targeting the glomerulus, the transfusion of genetically-modified mesangial cells has been attempted. Implantation of genetically-modified tubular epithelial cells into the subcapsular region has been employed for ex vivo transfection to the interstitium.

However, although gene therapy theoretically has the distinct potential to treat renal disease at the most fundamental level, its application has been limited by the availability of an adequate system for long term gene delivery to the kidney. There still exists a need for improved gene transfer techniques, especially gene transfer vectors that are capable of mediating effective gene transfer into renal tissues with low toxicity.

SUMMARY

One aspect of the present invention relates to methods for treating a renal disease in a mammal. In one embodiment, the method comprises the step of infusing the kidney with a gutless adenoviral vector comprising a polynucleotide encoding a therapeutic agent and a regulatory element operably linked to the polynucleotide, wherein the gutless adenoviral vector comprises the nucleotide sequence of SEQ ID NO:13 or SEQ ID NO:15. In a related embodiment, the gutless adenovirus vector is infused through the vena renalis. In another related embodiment, the gutless adenovirus vector is infused through the superior mesenteric artery.

In another embodiment, the method comprises the steps of: administering a therapeutically effective amount of a gutless adenovirus vector into a segment of a renal blood vessel in vivo, wherein the gutless adenovirus vector comprises the nucleotide sequence of SEQ ID NO:13 or SEQ ID NO:15, and is capable of expressing a therapeutic agent. In a related embodiment, the gutless adenovirus vector is administered using a stent.

Another aspect of the present invention pertains to a method for improving allograft survival. The method comprises the steps of: perfusing a kidney harvested from an organ donor with a gutless adenovirus vector carrying a nucleotide sequence encoding a immune modulator and a regulatory element operably linked to the nucleotide sequence; and transplanting the perfused kidney into a subject. In a related embodiment, the immune modulator is indoleamine dioxygenase.

Another aspect of the present invention pertains to a gutless adenovirus vector comprising a polynucleotide encoding a therapeutic protein, a renal tissue specific regulatory element operably linked to the polynucleotide sequence; and a stuffer comprising the nucleotide sequence of SEQ ID NO:13 or SEQ ID NO:15.

Another aspect of the present invention pertains to a gutless adenovirus vector comprising a polynucleotide encoding an indoleamine dioxygenase, a regulatory element operably linked to the polynucleotide sequence; and a stuffer comprising the nucleotide sequence of SEQ ID NO:13 or SEQ ID NO:15.

Yet another aspect of the present invention pertains to a pharmaceutical composition for treating a renal vascular disease, comprising the gutless adenovirus vector described above and a pharmaceutically acceptable carrier.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION

Figure 1:
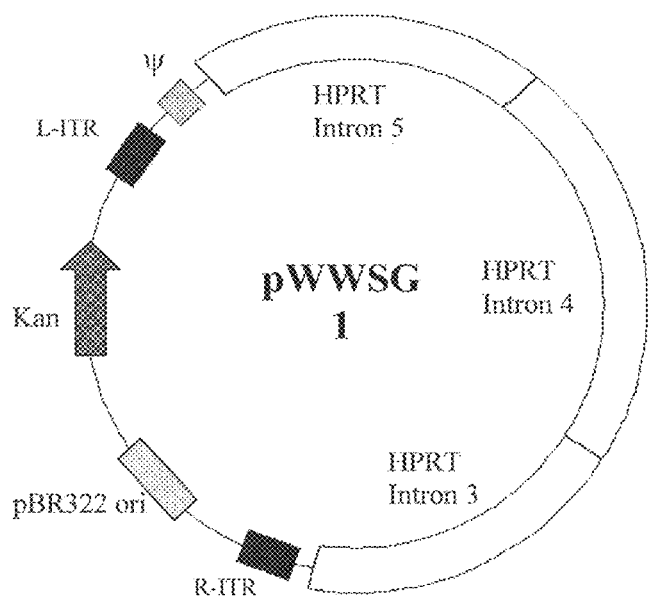
FIG. 1 is a schematic drawing of an embodiment of the backbone shuttle vector pShuttle-ITR-HPRT.

The practice of the present invention will employ, unless otherwise indicated, conventional methods of histology, virology, microbiology, immunology, and molecular biology within the skill of the art. Such techniques are explained fully in the literature. All publications, patents and patent applications cited herein, whether supra or infra, are hereby incorporated by reference in their entirety.

The primary object of the present invention is to provide methods for treating renal diseases and improving kidney allograft survival using gene transfer technologies. One aspect of the present invention relates to a method for treating a renal disease by infusing the kidney in vivo with an effective amount of gutless adenovirus vector carrying a DNA sequence encoding a therapeutic agent. The virus-mediated expression of the therapeutic agent in renal tissue ameliorates symptoms of the renal diseases. This local approach eliminates the need to inject a large quantity of virus into a patient and hence significantly reduces the viral-related toxicity.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The Gutless Adenovirus Vector

Adenoviruses (Ad) are double-stranded DNA viruses with a linear genome of about 36 kb. The adenovirus genome is complex and contains over 50 open reading frames (ORFs). These ORFs are overlapping and genes encoding one protein are often embedded within genes coding for other Ad proteins. Expression of Ad genes is divided into an early and a late phase. The early genes comprise E1a, E1b, E2a, E2b, E3 and E4, which are transcribed prior to replication of the viral genome. The late genes (e.g., L1-5) are transcribed after replication of the viral genome. The products of the late genes are predominantly components of the virion, as well as proteins involved in the assembly of virions.

The genome of an adenovirus can be manipulated such that it encodes and expresses a gene product of interest but is inactivated in terms of its ability to replicate in a normal lyric viral life cycle (Curie D T, *Ann N Y Acad Sci* 886, 158-171 [1991]). Suitable adenoidal vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium, endothelial cells, muscle cells and renal cells Additionally, introduced adenoidal DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA).

The so-called "gutless" adenovirus vectors contain a minimal amount of adenovirus DNA (i.e., the inverted terminal repeats and encapsidation signal) and are incapable of expressing any adenovirus antigens (hence the term "gutless"). The gutless adenovirus vectors provide the significant advantage of accommodating large inserts of foreign DNA while completely eliminating the problem of expressing adenoviral genes that result in an immunological response to viral proteins when a gutless rAd vector is used in gene therapy. Methods for producing gutless rAd vectors have been described, for example, in U.S. Pat. No. 5,981,225 to Kochanek et al., and U.S. Pat. Nos. 6,063,622 and 6,451,596 to Chamberlain et al; Parks et al., PNAS 93:13565 (1996) and Lieber et al., *J. Virol.* 70:8944-8960 (1996).

The "inverted terminal repeats (ITRs)" of adenovirus are short elements located at the 5' and 3' termini of the linear adenoviral genome, respectively and are required for replication of the viral DNA. The left ITR is located between 1-130 bp in the Ad genome (also referred to as 0-0.5 mu). The right ITR is located from about 3,7500 bp to the end of the genome (also referred to as 99.5-100 mu). The two ITRs are inverted repeats of each other. For clarity, the left ITR or 5' end is used to define the 5' and 3' ends of the ITRs. The 5' end of the left ITR is located at the extreme 5' end of the linear adenoviral genome; picturing the left ITR as an arrow extending from the 5' end of the genome, the tail of the 5' ITR is located at mu 0 and the head of the left ITR is located at about 0.5 mu (further the tail of the left ITR is referred to as the 5' end of the left ITR and the head of the left ITR is referred to as the 3' end of the left ITR). The tail of the right or 3' ITR is located at mu 100 and the head of the right ITR is located at about mu 99.5; the head of the right ITR is referred to as the 5' end of the right ITR and the tail of the right ITR is referred to as the 3' end of the right ITR. In the linear adenoviral genome, the ITRs face each other with the head of each ITR pointing inward toward the bulk of the genome. When arranged in a "tail to tail orientation" the tails of each ITR (which comprise the 5' end of the left ITR and the 3' end of the right ITR) are located in proximity to one another while the heads of each ITR are separated and face outward. The "encapsidation signal" or "packaging sequence" of adenovirus refers to the ψ sequence which comprises five (AI-AV) packaging signals and is required for encapsidation of the mature linear genome; the packaging signals are located from about 194 to 358 bp in the Ad genome (about 0.5-1.0 mμ).

In one embodiment, a viral backbone shuttle vector is used for the construction of gutless adenovirus vectors. The viral backbone shuttle vector contains a left and a right inverted terminal repeats of adenovirus, an encapsidation signal (ψ) of adenovirus, a pBR322 replication origin, a kanamycin resistance gene, and a stuffer sequence, which is the hypoxanthine phosphoribosyltransferase (HPRT) intron fragment with an approximately 10 kb (SEQ ID NO: 1). In one embodiment, the viral backbone shuttle vector of the present invention comprises at least 15 contiguous bases of SEQ ID NO: 1, preferably comprises at least 90 contiguous bases of SEQ ID NO: 1, more preferably comprises at least 300 contiguous bases of SEQ ID NO: 1, and most preferably comprises 3000 or more contiguous bases of SEQ ID NO: 1. In another embodiment, the viral backbone shuttle vector of the present invention comprises the nucleotide sequence of SEQ ID NO:13 or SEQ ID NO:15.

The viral backbone shuttle vector of the present invention contains multiple restriction endonuclease sites for the insertion of a foreign DNA sequence of interest. In one embodiment, the viral backbone shuttle vector contains seven unique cloning sites where the foreign DNA sequence can be inserted by molecular cloning techniques that are well known in the DNA cloning art. The foreign DNA sequence of interest typically comprises cDNA or genomic fragments that are of interest to transfer into mammalian cells. Foreign DNA sequence of interest may include any naturally occurring or synthetic DNA sequence. The foreign DNA may be identical in sequence to naturally-occurring DNA or may be mutated relative to the naturally occurring sequence. The foreign DNA need not be characterized as to sequence or function.

The size of foreign DNA that may be included in the shuttle vector will depend upon the size of the rest of the vector. If necessary, the stuffer sequence may be removed to adapt large size foreign DNA fragment. The total size of foreign DNA may vary from 1 kb to 35 kb. Preferably, the total size of foreign DNA is from 15 kb to 35 kb.

The foreign DNA may contain coding sequence for a protein, an iRNA agent, or an antisense RNA. The foreign DNA may further contain regulatory elements operably linked to the coding sequence, The term "operably linked," as used herein, refers to an arrangement of elements wherein the components so described are configured so as to perform their usual function. Thus, control elements operably linked to a coding sequence are capable of effecting the expression of the coding sequence. The control elements need not be contiguous with the coding sequence, so long as the function to direct the expression thereof. Thus, for example, intervening untranslated yet transcribed sequences can be present between a promoter sequence and the coding sequence and the promoter sequence can still be considered "operably linked" to the coding sequence. Similarly, intervening untranscribed sequences can be present between an enhancer sequence and the coding sequence and the enhancer sequence can still be considered "operably linked" to the coding sequence.

Examples of regulatory elements include, but are not limited to, transcription factor binding sites, promoters, enhancers, silencers, ribosome binding sequences, recombination sites, origins of replication, sequences which regulate RNA stability and polyadenylation signals. The promoters used may vary in their nature, origin and properties. The choice of promoter depends in fact on the desired use and on the gene of interest, in particular. Thus, the promoter may be constitutive or regulated, strong or weak, ubiquitous or tissue/cell-specific, or even specific of physiological or pathophysiological states (activity dependent on the state of cell differentiation or the step in the cell cycle). The promoter may be of eukaryotic, prokaryotic, viral, animal, plant, artificial or human origin.

Renal Specific Expression

In one embodiment, the therapeutic agent is expressed in a tissue-specific manner either using a renal-specific regulatory element or using an inducible regulatory element combined with kidney-specific induction. Examples of renal-specific regulatory element include, but are not limited to, high-capacity (type 2) $Na^+$/glucose cotransporter gene (Sglt2) promoter, Ksp-cadherin promoter, ClC-K1 chloride channel gene promoter, uromodulin promoter, Nkcc2/Slc12a1 gene promoter, and the p1 promoter of the parathyroid hormone (PTH)/PTH-related peptide receptor gene.

Examples of inducible regulatory elements include, but are not limited to, regulatory elements that responded to exogenous signals or stresses, such as heat, hormones, hypoxia, cytokines or metal ions, as well as artificial inducible systems such as the tetracycline inducible system; the FK506/rapamycin inducible system, the RU486/mifepristone inducible system, and the ecdysone inducible system. These systems are briefly described below.

Tet-onloff system. The Tet-system is based on two regulatory elements derived from the tetracycline-resistance operon of the *E. coli* Tn 10 transposon: the tet repressor protein (TetR) and the Tet operator DNA sequence (tetO) to which TetR binds. The system consists of two components, a "regulator" and a "reporter" plasmid. The "regulator" plasmid encodes a hybrid protein containing a mutated Tet repression (tetr) fused to the VP 16 activation domain of herpes simplex virus. The "reporter" plasmid contains a tet-responsive element (TRE), which controls the "reporter" gene of choice. The tetr-VP16 fusion protein can only bind to the TRE, therefore activate the transcription of the "reporter" gene, in the presence of tetracycline. The system has been incorporated into a number of viral vectors including retrovirus, adenovirus (Gossen and Bujard, *PNAS USA* 89: 5547-5551, [1992]; Gossen et al., *Science* 268: 1766-1769, [1995]; Kistner et al., *PNAS USA* 93: 10933-10938, [1996]).

Ecdysone system. The Ecdysone system is based on the molting induction system found in *Drosophila*, but modified for inducible expression in mammalian cells. The system uses an analog of the *drosophila* steroid hormone ecdysone, muristerone A, to activate expression of the gene of interest via a heterodimeric nuclear receptor. Expression levels have been reported to exceed 200-fold over basal levels with no effect on mammalian cell physiology (No et al., *PNAS USA* 93: 3346-3351, [1996]).

Progesterone-system. The progesterone receptor is normally stimulated to bind to a specific DNA sequence and to activate transcription through an interaction with its hormone ligand. Conversely, the progesterone antagonist mifepristone (RU486) is able to block hormone-induced nuclear transport and subsequent DNA binding. A mutant form of the progesterone receptor that can be stimulated to bind through an interaction with RU486 has been generated. To generate a specific, regulatable transcription factor, the RU486-binding domain of the progesterone receptor has been fused to the DNA-binding domain of the yeast transcription factor GAL4 and the transactivation domain of the HSV protein VP16. The chimeric factor is inactive in the absence of RU486. The addition of hormone, however, induces a conformational change in the chimeric protein, and this change allows binding to a GAL4-binding site and the activation of transcription from promoters containing the GAL4-binding site (Wang et al., *PNAS USA* 93: 8180-8184, [1994]; Wang et al., *Nat. Biotech* 15: 239-243, [1997]).

Rapamycin-system. Immunosuppressive agents, such as FK506 and rapamycin, act by binding to specific cellular proteins and facilitating their dimerization. For example, the binding of rapamycin to FK506-binding protein (FKBP) results in its heterodimerization with another rapamycin binding protein FRAP, which can be reversed by removal of the drug. The ability to bring two proteins together by addition of a drug potentiates the regulation of a number of biological processes, including transcription. A chimeric DNA-binding domain has been fused to the FKBP, which enables binding of the fusion protein to a specific DNA-binding sequence. A transcriptional activation domain also has been used to FRAP. When these two fusion proteins are co-expressed in the same cell, a fully functional transcription factor can be formed by heterodimerization mediated by addition of rapamycin. The dimerized chimeric transcription factor can then bind to a synthetic promoter sequence containing copies of the synthetic DNA-binding sequence. This system has been successfully integrated into adenoviral vectors. Long-term regulatable gene expression has been achieved in both mice and baboons (Magari et al., *J. Clin. Invest.* 100: 2865-2872, [1997]; Ye et al., *Science* 283:88-91, [1999]).

In one embodiment, a kidney tissue is infected with a gutless virus containing an inducible regulatory element. The infected tissue is then exposed to an inducing agent, such as tetracycline or rapamycin, or an inducing condition such as local heating or hypoxia, to induce expression of the therapeutic agent. The inducible system thus allows kidney specific expression of the therapeutic agent and minimizes the side effect of the therapeutic agent. In addition, the level and duration of the therapeutic agent expression may also be controlled by the dose of the inducing agent and the frequency of inducing agent administration. In one embodiment, the coding sequence of the therapeutic agent is controlled by the tet-on system and the expression of the therapeutic agent can be induced by an oral dose of tetracycline.

The Renal Diseases

The renal disease can be any disease or disorder that affects the function of the kidneys and for which a therapeutic gene or genes have been identified. Examples of the renal diseases include, but are not limited to, glomerulonephritis, renal vein thrombosis, diabetic nephropathy, ischemia/reperfusion injury (shock kidneys), hypertension, proteinuric kidney diseases (post glomerulonephritis), ischemic nephropathy, obstruction nephropathy, atheroembolic renal disease, chronic nephritis, congenital nephrotic syndrome, interstitial nephritis, lupus nephritis, membranoproliferative glomerulonephritis, membranous nephropathy, minimal change disease, necrotizing glomerulonephritis, nephropathy—IgA, nephrosis (nephrotic syndrome), post-streptococcal GN, reflux nephropathy, renal artery embolism, renal artery stenosis, and renal underperfusion.

The Therapeutic Agents

The therapeutic agent can be any molecule that is, when expressed in a renal tissue or in the proximity of a renal tissue, capable of ameliorating symptoms of a renal disease. The therapeutic agents include, but are not limited to, proteins, iRNA agents and antisense RNA. The term "expression," as used herein, refers to the process of transcription of mRNA from a coding sequence and/or translation of mRNA into a polypeptide.

The term "iRNA agent," as used herein, refers to small nucleic acid molecules used for RNA interference (RNAi), such as short interfering RNA (siRNA), double-stranded RNA (dsRNA), microRNA (miRNA) and short hairpin RNA (shRNA) molecules. The iRNA agents can be unmodified or chemically-modified nucleic acid molecules. The iRNA agents can be chemically synthesized or expressed from a vector or enzymatically synthesized. The use of a chemically-modified iRNA agent can improve one or more properties of an iRNA agent through increased resistance to degradation, increased specificity to target moieties, improved cellular uptake, and the like.

The term "antisense RNA," as used herein, refers to a nucleotide sequence that comprises a sequence substantially complementary to the whole or a part of an mRNA molecule and is capable of binding to the mRNA.

Protein as a Therapeutic Agent

In one embodiment, the therapeutic agent is a protein or peptide capable of ameliorates symptoms of the renal disease. For example, the therapeutic agent can be thrombomodulin for treating renal vein thrombosis (RVT) or an antibody that binds specifically to a target molecule which is involved in a renal disease (e.g., an inflammatory cytokine which has been found to be associated with the chronic kidney disease (CKD)).

The term "antibody", as used herein, is defined as an immunoglobulin that has specific binding sites to combine with an antigen. The term "antibody" is used in the broadest possible sense and may include but is not limited to an antibody, a recombinant antibody, a genetically engineered antibody, a chimeric antibody, a monospecific antibody, a bispecific antibody, a multispecific antibody, a chimeric antibody, a heteroantibody, a monoclonal antibody, a polyclonal antibody, a camelized antibody, a deimmunized antibody, a humanized antibody and an anti-idiotypic antibody. The term "antibody" may also include but is not limited to an antibody fragment such as at least a portion of an intact antibody, for instance, the antigen binding variable region. Examples of antibody fragments include Fv, Fab, Fab', F(ab'), F(ab')$_2$, Fv fragment, diabody, linear antibody, single-chain antibody molecule, multispecific antibody, and/or other antigen binding sequences of an antibody.

Examples of the therapeutic protein include, but are not limited to, thrombomodulin (TM), cytokines such as IL-1, IL-2, IL-3, IL-4, IL-5, IL-6, IL-7, IL-8, IL-9, IL-10, IL-11, IL-12, IL-13, IL-14, IL-15 and other interleukins; hematopoetic growth factors such as erythropoietin; colony stimulating factors such as G-CSF, GM-CSF, M-CSF, SCF and thrombopoietin; growth factors such as BNDF, BMP, GGRP, EGF, FGF, GDNF, GGF, HGF, IGF-1, IGF-2; KGF, myotrophin, NGF, OSM, PDGF, somatotrophin, TGF-α, TGF-β, and VEGF; antiviral cytokines such as interferons, antiviral proteins induced by interferons, TNF-α, and TNF-β; proteins involved in immune responses such as antibodies, CTLA4, hemagglutinin, MHC proteins, VLA-4, and kallikrein-kininogen-kinin system; ligands such as CD4; growth factor receptors including EGFR, PDGFR, FGFR, and NGFR, GTP-binding regulatory proteins, interleukin receptors, ion channel receptors, leukotriene receptor antagonists, lipoprotein receptors, steroid receptors, T-cell receptors, thyroid hormone receptors, TNF receptors; tissue plasminogen activator; transmembrane receptors; transmembrane transporting systems, such as calcium pump, proton pump, Na/Ca exchanger, MRP1, MRP2, P170, LRP, and cMOAT; transferrin; and tumor suppressor gene products such as APC, brca1, brca2, DCC, MCC, MTS1, NF1, NF2, nm23, p53 and Rb, and variants thereof.

A "variants" of a polypeptide is a polypeptide that differs from a native polypeptide in one or more substitutions, deletions, additions and/or insertions, such that the bioactivity of the native polypeptide is not substantially diminished or enhanced. In other words, the bioactivity of a variant may be enhanced or diminished by, less than 50%, and preferably less than 20%, relative to the native protein. Preferred variants include those in which one or more portions, such as an N-terminal leader sequence or transmembrane domain, have been removed. Other preferred variants include variants in which a small portion (e.g., 1-30 amino acids, preferably 5-15 amino acids) has been removed from the—and/or C-terminal of the mature protein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the bioactivity, secondary structure and hydropathic nature of the polypeptide.

A variant preferably exhibits at least about 70%, more preferably at least about 90% and most preferably at least about 95% sequence homology to the original polypeptide.

The term "variant' also includes a polypeptides that is modified from the original polypeptides by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a home moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross links, formation of cysteine, formation of pyroglutamate, formulation, gammacarboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

In one embodiment, the therapeutic protein is a native TM or a TM variant for the treatment of renal vein thrombosis (RVT). RVT has numerous etiologies, it occurs most commonly in patients with nephrotic syndrome (i.e., >3 g/d protein loss in the urine, hypoalbuminemia, hypercholesterolemia, edema). The syndrome is responsible for a hypercoagulable state. The excessive urinary protein loss is associated with decreased antithrombin III, a relative excess of fibrinogen, and changes in other clotting factors; all lead to a propensity to clot. Numerous studies have demonstrated a direct relationship between nephrotic syndrome and both arterial and venous thromboses. Why the renal vein is susceptible to thrombosis is unclear. The renal vein also may contain thrombus after invasion by renal cell cancer. Other less common causes include renal transplantation, Behçet syndrome, hypercoagulable states, and antiphospholipid antibody syndrome.

Thrombomodulin (TM) is an integral membrane glycoprotein expressed on the surface of endothelial cells (Sadler et al., *Thromb Haemost.*, 78:392-95 [1997]). It is a high affinity thrombin receptor that converts thrombin into a protein C activator. Activated protein C then functions as an anticoagulant by inactivating two regulatory proteins of the clotting system, namely factors Va and VI [I]a (Esmon et al., *Faseb J.*, 9:946-55 [1995]). The latter two proteins are essential for the function of two of the coagulation proteases, namely factors IXa and Xa. TM thus plays an active role in blood clot formation in vivo and can function as a direct or indirect anticoagulant.

TM and several other proteins or enzymes have been shown to reduce the process of intimal hyperplasia, whose evolution is the causes of late graft failure. For instance, Nitric oxide synthase, an enzyme expressed by endothelial cells has been shown in animal models to inhibit intimal hyperplasia, especially the inducible enzyme (iNOS) (Salmaa et al., *Lancet*, 353:1729-34 [1999]; Palmer et al., *Nature*, 327:524-26 [1987]; Kubes et al., *PNAS USA.*, 88:4651-5 [1991]).

The term "native thrombomodulin" refers to both the natural protein and soluble peptides having the same characteristic biological activity of membrane-bound or detergent solubilized (natural) thrombomodulin. These soluble peptides are also referred to as "wild-type" or "non-mutant" analog peptides. Biological activity is the ability to act as a receptor for thrombin, increase the activation of protein C, or other biological activity associated with native thrombomodulin. Oxidation resistant TM analogs are these soluble peptides that in addition to being soluble contain a specific artificially induced mutation in their amino acid sequence.

siRNA as the Therapeutic Agent

In another embodiment, short interfering RNAs (siRNA) are used as a therapeutic agent to inhibit a disease-related gene expression. For example, elevated levels of transforming growth factor-$\beta_1$ (TGF-$\beta_1$) and platelet-derived growth factor (PDGF) have been associated with the development of glomerular injury. Therefore, inhibition of the expression of TGF-$\beta_1$ and/or PDGF in kidney tissues may be used to prevent or reduce glomerular injury.

siRNAs are dsRNAs having 19-25 nucleotides. siRNAs can be produced endogenously by degradation of longer dsRNA molecules by an RNase III-related nuclease called Dicer. siRNAs can also be introduced into a cell exogenously or by transcription of an expression construct. Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing, thereby cleaving and destroying the mRNA. Cleavage of the mRNA takes place near the middle of the region bound by the siRNA strand. This sequence specific mRNA degradation results in gene silencing.

siRNAs can be expressed in vivo from adenovirus vectors. This approach can be used to stably express siRNAs in kidney tissues. In one embodiment, siRNA expression vectors are engineered to drive siRNA transcription from polymerase III (pol III) transcription units. Pol III transcription units are suitable for hairpin siRNA expression, since they deploy a short AT rich transcription termination site that leads to the addition of 2 bp overhangs (UU) to hairpin siRNAs—a feature that is helpful for siRNA function. Any 3' dinucleotide overhang, such as UU, can be used for siRNAs. In some cases, G residues in the overhang may be avoided because of the potential for the siRNA to be cleaved by RNase at single-stranded G residues.

With regard to the siRNA sequence itself, it has been found that siRNAs with 30-50% GC content can be more active than those with a higher G/C content in certain cases. Moreover, since a 4-6 nucleotide poly(T) tract may act as a termination signal for RNA pol III, stretches of >4 Ts or As in the target sequence may be avoided in certain cases when designing sequences to be expressed from an RNA pol III promoter. In addition, some regions of mRNA may be either highly structured or bound by regulatory proteins. Thus, it may be helpful to select siRNA target sites at different positions along the length of the gene sequence. Finally, the potential target sites can be compared to the appropriate genome database. Any target sequences with more than 16-17 contiguous base pairs of homology to other coding sequences may be eliminated from consideration in certain cases.

The siRNA targets can be selected by scanning an mRNA sequence for AA dinucleotides and recording the 19 nucleotides immediately downstream of the AA. Other methods can also been used to select the siRNA targets. In one example, the selection of the siRNA target sequence is purely empirically determined (see e.g., Sui et al., *Proc. Natl. Acad. Sci*. USA 99: 5515-5520, 2002), as long as the target sequence starts with GG and does not share significant sequence homology with other genes as analyzed by BLAST search. In another example, a more elaborate method is employed to select the siRNA target sequences. This procedure exploits an observation that any accessible site in endogenous mRNA can be targeted for degradation by synthetic oligodeoxyribonucleotide/RNase H method (Lee et al., *Nature Biotechnology* 20:500-505, 2002).

In one embodiment, siRNA can be designed to have two inverted repeats separated by a short spacer sequence and end with a string of Ts that serve as a transcription termination site. This design produces an RNA transcript that is predicted to fold into a short hairpin siRNA. The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary to achieve desirable results.

In another embodiment, the hairpin siRNA expression cassette is constructed to contain the sense strand of the target, followed by a short spacer, the antisense strand of the target, and 5-6 Ts as transcription terminator. The order of the sense and antisense strands within the siRNA expression constructs can be altered without affecting the gene silencing activities of the hairpin siRNA. In certain instances, the reversal of the order may cause partial reduction in gene silencing activities.

The length of nucleotide sequence being used as the stem of siRNA expression cassette can range, for instance, from 19 to 29. The loop size can range from 3 to 23 nucleotides. Other lengths and/or loop sizes can also be used.

Route of Administration

The gutless adenovirus may be introduced into the kidney by intravenous, intrarterial, or retrograde infusion. In one embodiment, the virus is infused through the vene renalis. In another embodiment, the virus is infused through the superior mesenteric artery. In yet another embodiment, the virus is infused through a retrograde catheter into the pyelic cavity. Since only a relatively small amount of virus is needed for the kidney infusion, the virus-related toxicity is reduced. In yet another embodiment, the kidney is perfused with the virus, i.e., the virus enters the kidney through the vene renalis or the superior mesenteric artery, and is collected through the superior mesenteric artery or vene renalis. Since the leftover virus does not enter the blood circulation, a large amount of virus may be used for the perfusion. In addition, a close-circuit perfusion allows constant exposure to virus over an extended period of time (e.g., 10-60 minutes) and hence significantly increases the number of infected cells.

In another embodiment, the virus is administered into a segment of a renal blood vessel in vivo. In a related embodiment, the gutless adenovirus vector is administered using a stent. The viral vector is embedded in the stent and is released only at a treatment site. Since the viral infection is restricted at the treatment site and the surrounding area, only a small amount of the virus is needed and the virus-related toxicity is reduced.

Another aspect of the present invention relates to a method for improving allograft survival. The method comprises the steps of perfusing a kidney harvested from an organ donor with a gutless adenovirus vector carrying a nucleotide sequence encoding an immune modulator and a regulatory element operably linked to the nucleotide sequence; and transplanting the perfused kidney into a subject. The term "immune modulator," as used herein, refers to a polypeptide or a polynucleotide capable of modulating an immune response and improving allograft survival.

In one embodiment, the immune modulator is indoleamine dioxygenase (IDO). IDO is an enzyme that is expressed in the placenta and plays an important role in foeto-maternal tolerance. IDO metabolizes the amino acid tryptophan. The function of T cells, the most important cell-type involved in organ transplant rejection, is dependent on tryptophan. In addition, the metabolites of tryptophan (kynurenines) are toxic to T-cells. It has been shown that over-expression of IDO in renal tissues protects against renal transplant damage.

Typically, kidneys must be preserved prior to transplantation to obtain proper pathology assessment of the suitability of the organ for transplantation. Lack of proper preservation leads to degradation of organ function due to thrombosis (blood clotting), ischemia (lack of oxygen), or ischemia followed by reperfusion (the restoration of blood flow upon transplantation). These events bring about inflammation, cell death, and eventually failure of the organ. Kidney preservation is a process in which the renal artery is connected to a kidney perfusion machine in order to simulate the normal process by which nutrients are supplied to the kidney. A solution is continuously perfused through a closed circuit which includes the kidney, which is typically maintained at a low temperature (e.g., 5° C.) to reduce the cell metabolic rate and oxygen consumption. During the perfusion process, the perfusion pressure, flow, and vascular resistance, as well as the organ's chemistries, including base excess, oxygen saturation, calcium, potassium, hematocrit, $pO_2$, pH, and bicarbonate, are monitored closely to prevent tissue damage. The adenovirus vectors can be added to the perfusion solution and infect the kidney tissue during the perfusion period. Kidney perfusion solutions are commercially available. In one embodiment, the kidney perfusion solution is Lactated Ringer's solution.

In one embodiment, the regulatory element is a constitutive promoter, such as CMV or RSV promoter. In another embodiment, the gutless adenovirus contains the nucleotide sequence of SEQ ID NO:25 or SEQ ID NO:26.

In another embodiment, the gutless adenovirus is suspended in the perfusion solution to a final concentration of $10^9$-$10^{12}$ particles/ml and perfused for a period of 10-120 minutes.

Another aspect of the present invention pertains to a gutless adenovirus vector comprising a polynucleotide encoding a therapeutic agent, a renal-specific regulatory element or inducible regulatory element operably linked to the polynucleotide sequence; and a stuffer comprising the nucleotide sequence of SEQ ID NO:13 or SEQ ID NO:15.

In one embodiment, the renal-specific regulatory element is selected from the group consisting of high-capacity (type 2) Na+/glucose cotransporter gene (Sglt2) promoter, Ksp-cadherin promoter, ClC-K1 chloride channel gene promoter, uromodulin promoter, Nkcc2/Slc12a1 gene promoter, and the p1 promoter of the parathyroid hormone (PTH)/PTH-related peptide receptor gene.

In another embodiment, the inducible regulatory element is selected from the group consisting of heat inducible regulatory elements, hormone inducible regulatory elements, hypoxia inducible regulatory elements, cytokine inducible regulatory elements, metal ion inducible regulatory elements, and artificial inducible regulatory elements.

Yet another aspect of the present invention pertains to a pharmaceutical composition for treating a renal vascular disease, comprising the gutless adenovirus vector described above and a pharmaceutically acceptable carrier. As used herein, a "pharmaceutically acceptable carrier" is intended to include any and all solvents, solubilizers, stabilizers, absorbents, bases, buffering agents, controlled release vehicles, diluents, emulsifying agents, humectants, dispersion media, antibacterial or antifungal agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

The pharmaceutical composition is formulated to be compatible with its intended route of administration. Solutions or suspensions used for parenteral application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In all cases, the injectable composition should be sterile and should be fluid to the extent that easy syringability exists. It must be stable under the conditions of manufacture and storage and must be preserved against the contaminating action of microorganisms such as bacteria and fungi. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like.

It is especially advantageous to formulate parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The present invention is further illustrated by the following examples which should not be construed as limiting. The contents of all references, patents and published patent applications cited throughout this application, as well as the Figures and Tables are incorporated herein by reference.

EXAMPLE 1

Construction of Gutless Viral Backbone Shuttle Vector pShuttle-ITR-HPRT 1.1 Creation of pShuttle-ITR An embodiment of a gutless viral backbone shuttle vector pShuttle-ITR-HPRT is shown in FIG. 1. Sequence portion containing R-ITR, PBR322 ori, Kan, L-ITR, and encapsidation signal was obtained from the pAdEasy® system from STRATEGENE®. At bp 3667 of the original pShuttle sequence, there is a BamHI site just beyond the R-ITR. PCR primers were designed to include the BamHI site and then were to create an EcoRI site at the end of the R-ITR. The R-ITR was PCR replicated and then digested with BamHI and EcoRI to create sticky ends. The viral backbone was then cut with both BamHI and EcoRI. The BamHI cut the backbone at bp 3667 and there was also an EcoRI site inside the MCS at bp 377. The backbone portion of the plasmid was then gel purified and the PCR replicated R-ITR was recloned into position. This essentially puts the L-ITR, encapsidation signal, MCS, and R-ITR all in close proximity to each other.

1.2 Creation of pShuttle-ITR-HPRT

Insertion of the HPRT introns was a two step cloning process. First, the viral backbone pShuttle-ITR was digested with EcoRI and XbaI, both enzyme sites are in the MCS. The HPRT source was also digested with EcoRI and XbaI yielding a 7477 bp fragment that was cloned into the EcoRI/XbaI digested viral backbone. Then the HPRT source was digested with only XbaI yielding a 2715 bp fragment. One of the XbaI sites in this cut is the same XbaI site that was cut from the EcoRI/XbaI double digest in step 1. The viral backbone was cut with only XbaI and the 2715 bp fragment was inserted.

Overall, from the HPRT source, the HPRT stuffer sequence is inserted into the viral backbone in reverse orientation, hence intron 5, then 4, then 3. The 2715 bp fragment was inserted and checked to follow the original source sequence. The new plasmid is designated as pShuttle-ITR-HPRT (SEQ ID NO:1).

EXAMPLE 2

Construction and Preparation of Gutless Viral Shuttle Vector Carrying Human Thrombomodulin or lacZ Gene 2(a) Construction and Preparation of Gutless Viral Shuttle Vector Carrying Human Thrombomodulin Gene 2(a)-1 Creation of pCMV-hTM The insertion of hTM into the gutless adenovirus backbone first required the creation of a CMV-hTM expression cassette. The intermediate vector used was pcDNA3.1/Zeo(+) (Invitrogen). A CMV promoter is available commercially and a CMV promoter was cloned into the multiple cloning sites (MCS) at the XbaI/EcoRV restriction enzyme site locations. The CMV from ps5 was removed using XbaI/EcoRV.

pcDNA3.1/Zeo(+) was cleaved inside the MCS using both XbaI and EcoRV as well. The CMV promoter was then ligated. Due to the location of the enzyme sites in the MCS, the CMV promoter (SEQ ID NO:4) was inserted in a backwards orientation relative to the pcDNA3.1/Zeo(+) plasmid. The amino acid sequence of human thrombomodulin (SEQ ID NO: 2) and the DNA sequence encoding human thrombomodulin (SEQ ID NO: 3) have been reported (Suzuki et al. *EMBO J.* 6:1891-1897, [1987]). The human TM cDNA (SEQ ID NO:5) was obtained from Dr. Sadler (Dittman et al., *Biochemistry*, 26(14):4350-4357 [1987]) which the sequence was also submitted to ATCC and to GenBank. The human TM gene was removed from the plasmid using EcoRI and inserted into pcDNA3.1/Zeo(+), also in the reverse orientation to pcDNA3.1/Zeo(+) downstream of the inserted CMV promoter.

2(a)-2 Creation of pShuttle-ITR-HPRT-CMV-TM

The expression cassette in pCMV-hTM was removed by digesting with PmeI. The gutless adenovirus backbone pshuttle-ITR-HPRT was linearized using SmaI which cuts the plasmid at bp 381. The CMV-hTM cassette was ligated to the gutless virus in the forwards orientation. Sequence of the expression cassette (from PmeI site to PmeI site) is shown in SEQ ID NO:6. The new plasmid is designated as pShuttle-ITR-HPRT-CMV-TM.

2(a)-3 Creation of pTMadap

The following linker containing a BstEII and SfiI site was inserted into the BstEII and Bsu36I sites of pShuttle-ITR-HPRT-CMV-TM, resulting in the vector pTMadap (SEQ ID NO:7).

```
                                             (SEQ ID NO: 8)
5'-gtaacactgg cccaggaggc ctttctggtg acccc-3'

(SEQ ID NO: 9)
3'-tgacc gggtcctccg gaaagaccac tggggatt-5'
```

Creation of pTMadap-stuffer1

Based on the published sequence HSU71148 of the human X chromosome region q28 the following PCR primers were synthesized:

```
Forward:
5' TAGTTCCTTCTGCCTGGAATAC 3'       (SEQ ID NO: 10)

Reverse:
5' CAAGTCACAAGGATGGACTACA 3'       (SEQ ID NO: 11)
```

Amplification of a human DNA sample resulted in the amplification of a 18524 bp DNA fragment (stiffer 1, SEQ ID NO: 12). Stuffer 1 was cut with the restriction enzymes BstEII and SfiI and the resulting fragment of approximately 18371 bp was inserted into the BsteII and SfiI sites of pTMadap, resulting in pTMadap-stuffer1.

2(a)-4 Creation of pTMadap-stuffer1-short

To reduce the size of the stuffer1 fragment in pTMadap-stuffer1, pTMadap-stuffer1 was digested with SanDI and BstEII and the resulting DNA ends were modified by a fill-in reaction with Klenow. Re-ligation resulted in the 25207 bp vector pTMadap-stuffer1-short. The sequence of stuffer1-short fragment is shown in SEQ ID NO:13.

2(a)-5 Creation of pTMadap-stuffer1-short-stuffer2

The plasmid p2-2 (SEQ ID NO: 14, obtained from GenBank) was cut with NotI and the resulting fragment of approximately 5954 bp (stuffer 2, SEQ ID NO: 15) was inserted into the NotI site of pTMadap-stuffer1 short, resulting in pTMadap-stuffer1-short-stuffer2.

2(a)-6 Removal of PacI Site from pTMadap-stuffer1short-Stuffer2

Figure 2:
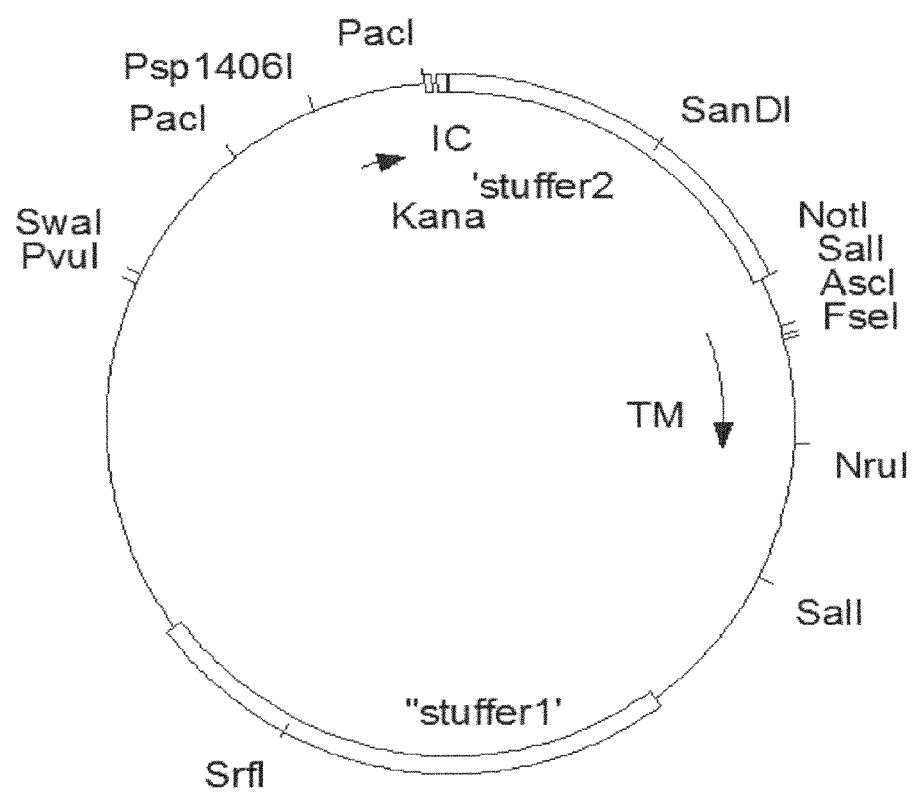
FIG. 2 is a schematic drawing of an embodiment of the full length backbone vector pTM-final.

Plasmid pTMadap-stuffer1-short-stuffer2 was cut with AclI and BsiW1. The resulting 28790 bp fragment was isolated from gel. pShuttle-ITR-HPRT (SEQ ID NO:1) was cut with AclI and Acc65I. The resulting 1966 bp fragment was ligated into the isolated 28790 bp fragment, resulting in the full length backbone vector pTM-final (FIG. 2 and SEQ ID NO: 16).

2(b) Construction and Preparation of Gutless Viral Shuttle Vector Carrying LacZ Gene The insertion of LacZ also required creation of an intermediate vector to create the expression cassette. pcDNA3.1/Zeo (+) was again used. First, a portion of the vector from the end of the MCS, restriction enzyme site, ApaI, to the beginning of the SV40 poly A, restriction site NaeI, was removed and the vector relegated to itself. Then the LacZ gene was inserted into the vector MCS using NotI/XbaI. The expression cassette, containing CMV promoter, LacZ gene, and SV40 poly A, was removed using NruI/SalI retraction enzymes and blunt-end cloned into the gutless adenovirus at the SmaI restriction enzyme site.

EXAMPLE 3

Preparation of Gutless Adenovirus Carrying Human Thrombomodulin Gene (Gutless Ad.hTM)

The gutless Ad.hTM was prepared according to the following protocol:

1. Linearize pTM-final by digestion with PacI. The completeness of the digestion is confirmed by electrophoresis using a small aliquot of the digestion product. It's not necessary to gel purify the digested pTM-final for transfection described in step 2).

2. Transfect 293FLP cells grown in a 60 mm dish at about 80% confluence with about 5 μg of PacI-digested pTM-final using lipofectamine. 293FLP cells are 293 cells engineered to express the flp gene product, which recognizes the FRS flanking the encapsidation signal and cleaves out the encapsidation signal thereby not allowing helper-viral DNA to be packaged. (Beauchamp et al., *Molecular Therapy*, 3(5):809-815 [2001]; Umana et al., *Nature Biotechnology*, 19:582-585 [2001]).

3. Twenty-four hours after the transfection, infect the cells with helpervirus H10 in 2% DMEM-F12 at a multiplicity of infection (MOI) of 10.

4. Remove the cells from the plate (preferably with a cell scraper) after the appearance of cytopathic effect (CPE), place the cells in a sterile 15 ml tube, and lyse the cells by three freeze-and-thaw cycles. Precipitate the cell debris by spinning the lysate for 5 minutes at 4000 rpm and harvest the supernatant. The supernatant is designated as P0 (passage number 0) supernatant.

5. Infect 293FLP cells in two T75 flask at 80% confluency with 4 ml of P0 supernatant and with the helpervirus at MOI of 1.

6. Continue passaging virus in the manner described in steps 4 and 5 until passage 6 and confirm that helpervirus is added at an MOI of 1 at each passage.

7. Add the P6 supernatant to 8 T500 flasks containing 293FLP cells at 80% confluency and infect the cells with the helpervirus at a MOI of 1.

8. Following CPE, harvest the cells into 500 ml sterile tubes. Centrifuge the cell suspension at 4500 rpm, 4° C. for 10 minutes.

9. Resuspend the cell pellet in 2% DMEM-F12 (the pellet can be stored at −80° C. at this stage).

10. Freeze-thaw the resuspended cell pellet three times. Spin down the cell debris by centrifugation at 4000 rpm, 4° C. for 10 minutes.

11. Transfer the supernatant, which contains the released virus, to a fresh sterile culture tube and subject the supernatant to a second round of centrifugation to further remove cell debris.

12. Transfer the supernatant to a fresh sterile tube. The virus is ready for CsCl-purification.

13. To purify the virus, ultra-clear SW41 (Beckman) tubes were prepared by soaking in Ultra Pure Water, then 70% ETOH. Cotton swabs (one swab for each tube) were used to completely dry out the tube, and two tubes were used per sample.

14. Preparation of the first gradient: 2.5 mL CsCl—Density 1.25, and 2.5 mL CsCl—Density 1.40. Place the 1.25 density CsCl into the Beckman tubes first. Underlay slowly the high density, 1.40 CsCl using a sterile pasteur pipette, and overlay an equal amount (in mL) of CVL, about 4.25 ml/tube. Samples were centrifuged in a SW41 rotor with speed: 35,000 rpm at 20° C. for 1 hour and with acceleration: 1 and deceleration: 4. The lower opalescent band was collected using 1 or 3 mL syringe with green cap needles.

Preparation of second gradient: CsCl was prepared to density 1.33 g/mL. Two fresh ultra-clear tubes were placed 8 mL of CsCl and overlay the band just recovered after the first spin. (To equilibrate the tubes, measure before the volume of the recovered band and divide equally in the 2 tubes). Samples were centrifuged at the conditions above for 18 hours. The opalescent band was recovered and collected in a sterile eppendorf tube. (From this moment, keep the tube always on ice). Samples were dialyze with dialysis buffer: (1) 10× Dialysis Buffer: 100 mM Tris-pH 7.4, 10 mM $MgCl_2$; (2) 1× Dialysis Buffer (2 Liters): 400 mL Glycerol, 200 mL 10× Dialysis Buffer 140 mL, and Ultra Pure Water. The dialyzed samples were immediately stored at −70° C.

(c) Determination of Virus Titer

BioRad protein estimation kit was used with 1:5 diluting, and placing 1 ml in each disposable cuvette. Standards were set up at 0, 1, 2, 5 10, and 15 µg/ml. (BSA is fine). Sample cuvettes were prepared using 1-10 µl of sample, depending on estimate of titer. (Sample OD must be within the linear range of the standard line.) OD was taken at 595λ and formula of the line was calculated from standards. The protein concentration of the samples was calculated using this formula. The following formula was used to convert protein concentration to titer: $[12.956+224.15 (\mu g/ml)] \times 10^8$.

EXAMPLE 4

Figure 3:
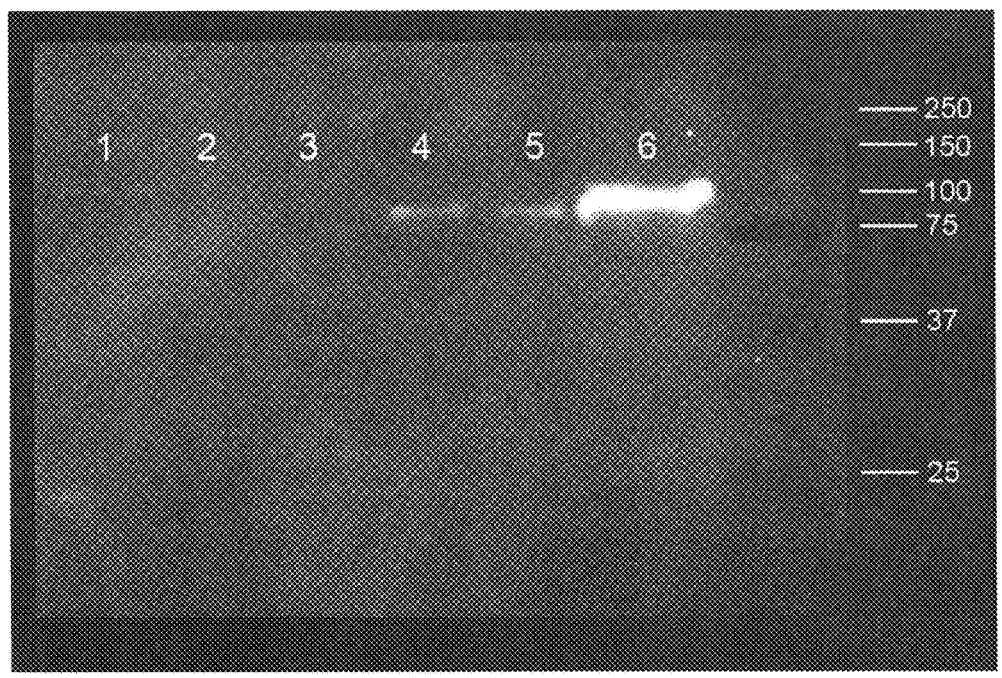
FIG. 3 is a picture of a Western blot showing hTM expression in HEK 293 cells transfected with pTM-final (the full size backbone of gutless Ad.hTM). Lanes 1-3: lysate from control cells; Lanes 4-6, lysate from pTM-final transfected cells.

Expression of Human Thrombomodulin (hTM) In Vitro (A) Expression of hTM in HEK 293 Cells Transfected with pTM-Final HEK 293 cells were cultured in a 6 well cluster and transfected with 1 µg of pTM-final. After 24 hours, the cells were washed with PBS and lysed in 125 µl RIPA buffer with protease inhibitors Protein samples (16 µl) were separated on 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) was used to detect the proteins. As shown in FIG. 3, hTM expression was detectable in cells transfected with pTM-final.

The RIPA buffer was prepared according the following recipe: mixing 100 µl Igepal ca-630, 50 mg sodium deoxycholate, 500 µl 20% SDS, 10 mM β-mercapto ethanol, and 1 ml 10×PBS, and add water to a final volume of 10 ml at room temperature. A cocktail of protease inhibitors containing 11.5 µl PMSF (from 34.8 mg/ml in isopropanol, 64 µl Benzamidine (from 15.6 mg/ml stock), 100 µl sodium orthovanadate (100 mM), 5 µl pepstadine (from 1 mg/ml stock), 1 µl leupeptine (from 5 mg/ml stock), and 1 µl aprotin (from 5 mg/ml stock) was added to the RIPA buffer immediately before use.

(B) Expression of hTM in P2 Lysate of 293FLP Cells

Figure 4:
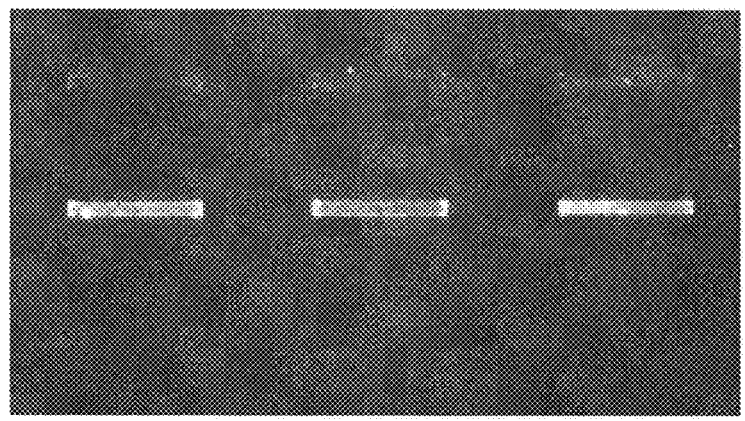
FIG. 4 is a picture of a Western slot blot showing hTM expression in 293FLP cells (passage number 2 (P2) during viral amplification). Row 1, lane 1-3: TM detection using 5 ul cell lysate of P2. Row 2, lane 1-3: TM detection using 30 ul cell lysate of P2. Row 3, lane 1-3: negative control cells.

The P2 lysate was generated as described in Example 3. After CPE was observed, 293FLP cells were detached from the bottom of the culture flask by repeated tapping of the flask. 1 ml of the total of 10 ml of cell suspension was used for the detection of TM expression. The cells in the 1 ml cell suspension were collected by centrifugation for 10 min at 300×g and lysed in 250 µl RIPA buffer. 7 ul of 5× loading buffer was added to 35 µl of the lysed cells and the resulting solution was immersed in boiling water for 3 minutes. 5 and 30 ul of boiled cell lysate were diluted with 250 ul TBS (137 mM sodium chloride, 10 mM Tris, pH is 7.4 at +25° C.) and transferred to a nitrocellulose membrane using a slotblot device (Bio-Dot SF, Biorad). Primary antibody (goat anti-hTM (c-17) 1:2000 dilution, Santa Cruz) and secondary antibody (polyclonal rabbit anti-goat immunoglobulins/HRP, 1:4000 dilution, DakoCytomation)) were used to detect the proteins. As shown in FIG. 4, hTM was detectable in the P2 lysate.

The 5× loading buffer was prepared by mixing 20.0 ml 30% SDS, 11.5 ml 2M sucrose, 6.5 ml 2M Tris-HCL pH 6.8, 2.0 ml beta-mercaptoethanol and bromophenolblue. The RIPA buffer was prepared as described in Example 4(A). A cocktail of protease inhibitors containing 11, 5 µl PMSF (from 34, 8 mg/ml in isopropanol, 64 µl Benzamidine (from 15, 6 mg/ml stock), 100 µl sodium orthovanadate (100 mM), 5 µl pepstadine (from 1 mg/ml stock), 1 µl leupeptine (from 5 mg/ml stock), and 1 µl aprotin (from 5 mg/ml stock) was added to the RIPA buffer immediately before use.

(C) Expression of TM in Virus Infected Vena Cava

Vena cava was excised from rats and cut into six segments of approximately 3 mm long. The segments were incubated for 30 minutes in medium containing gutless luc or TM virus. After incubation, the segments were washed three times and transferred to a 24-well plate containing DMEM. The segments were incubated overnight in an atmosphere of 95% $O_2$ and 5% $CO_2$ with gentle shaking. After 24 hours of incubation the segments were frozen. The frozen sections were thawed in lysis buffer and loaded onto a 7.5% SDS acrylamide gel. After blotting, the blot was probed with an antibody against human TM.

Figure 5:
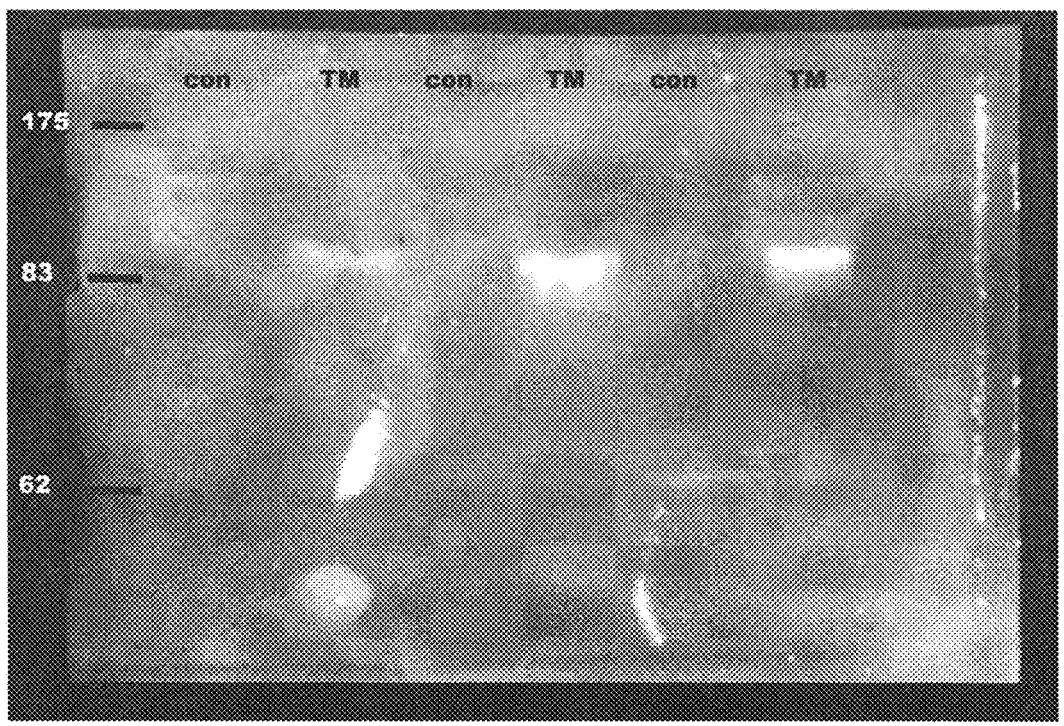
FIG. 5 is a picture of a Western blot showing hTM expression in rat vena cava infected with gutless TM virus.

The Western blot clearly shows that within 24 hours TM expression can be detected (FIG. 5).

As a control, the same HUVEC cells will be infected the gutless adenovirus expressing LacZ. These cells will subsequently be stained with X-gal to look for blue cells. This will demonstrate the viability of the gutless adenovirus backbone itself.

(D) TM Expression in HEK 293 Cells Infected with TM Gutless Virus Passage 1-6

The TM-vector backbone was released by digestion with PacI. 293CRE cells were cultured in a 60 mm dish at 80% confluency. Cells were transfected with 5 µg of PacI digested TM-vector backbone. After 24 hours, 2% DMEM-F12 containing helper virus with a MOI of 10 was added. Following CPE, cells were removed from the dish and medium and cells were collected a in a sterile 15 ml tube. Cells went through three freeze/thaw cycles and the resulting suspension was centrifuged for 5 minutes at 4000 rpm. The cleared lysate was collected and name P=0.

4 ml of P=0 supernatant was added to 2 T75 dish containing 293CRE cells at 80% confluence. Cells were subsequently infected with helpervirus at MOI of 1. Following CPE, cells were removed from the dish and medium and cells were collected a in a sterile 15 ml tube. Cells went through three freeze/thaw cycles and the resulting suspension was centrifuged for 5 minutes at 4000 rpm. The cleared lysate was collected and name P=1. This procedure was repeated until P=6.

Figure 6:
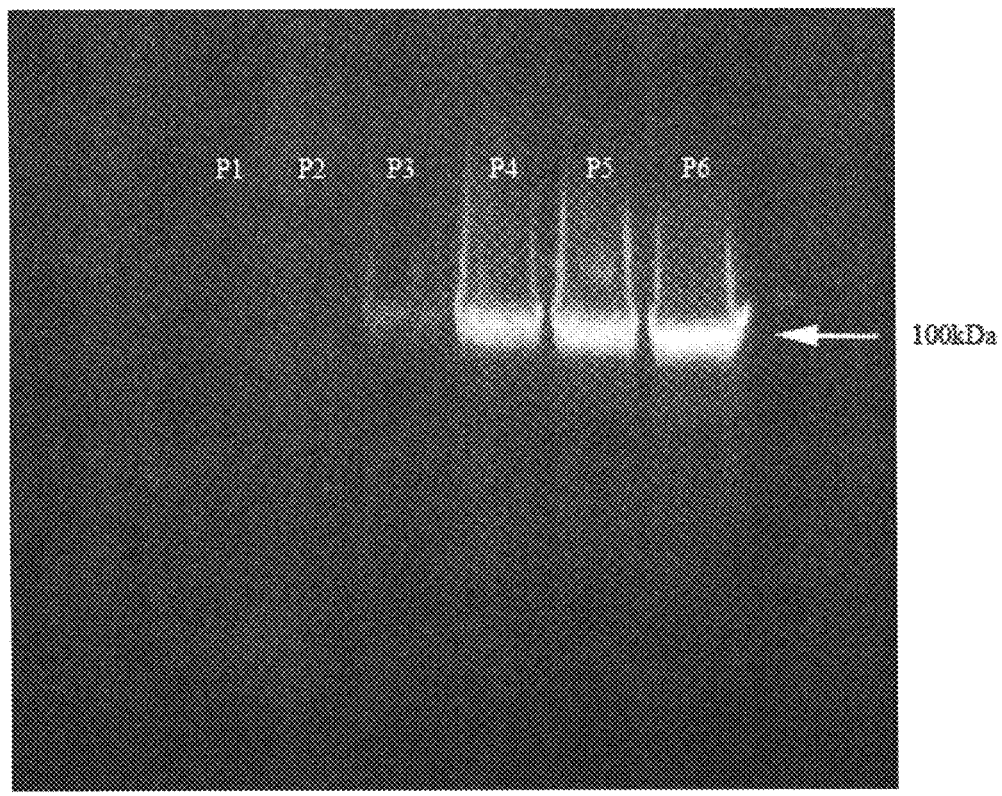
FIG. 6 is a picture of a Western bolt showing TM expression in CRE cells at passage number 1-6 (P1-P6).
Figure 7:
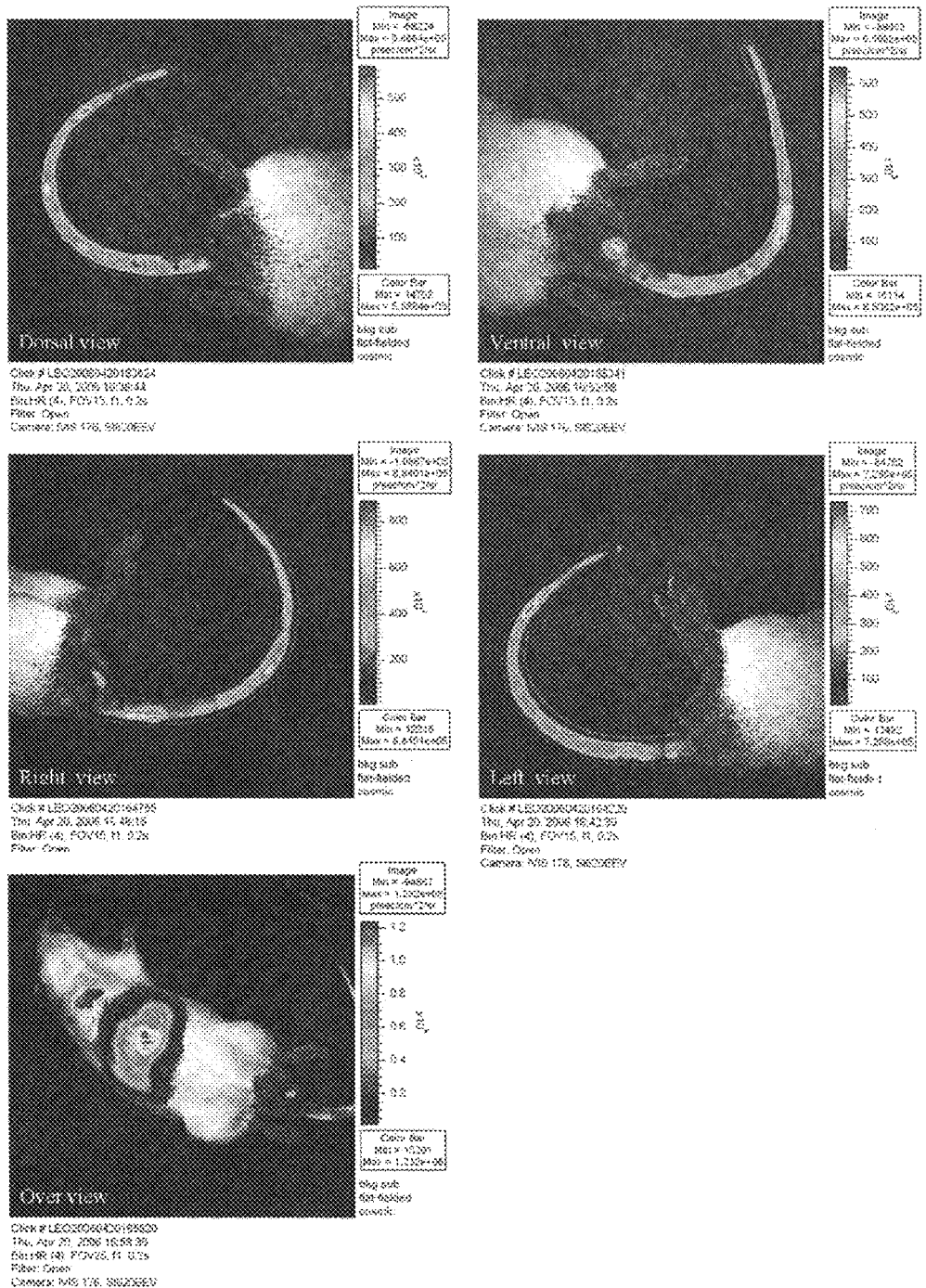
FIG. 7 is a composite of images showing gutless adenovirus-mediated luciferase expression in rat tail vein.
Figure 8:
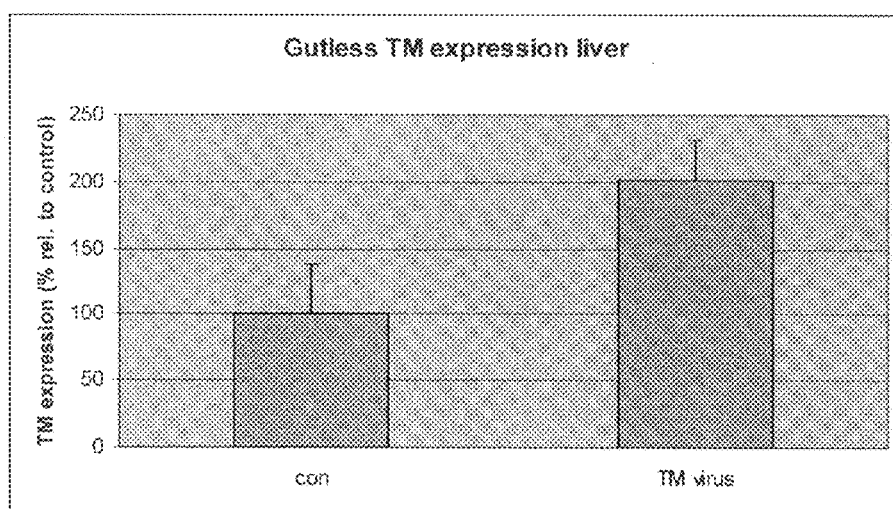
FIG. 8 is a diagram showing TM expression in livers of non-infected rats (con) and TM gutless virus infected rats (TM virus).

HEK 293 cells were cultured in a 6 well cluster and transfected with 200 µl of TM gutless virus of passage 1-6. After 24 hours, the cells were washed with PBS and lysed in 125 µl RIPA buffer. Protein samples (16 µl) were separated on a 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) were used to detect the proteins. As shown in FIG. 6, TM expression is higher in cells infected with virus of higher passage numbers, indicating successful amplification of TM gutless virus in 293CRE cells.

The RIPA buffer (10 ml) was prepared as follows: 100 µl Igepal ca-630, 50 mg sodium deoxycholate, 500 µl % SDS, 10 mM β-mercapto ethanol, 1 ml 10×PBS, add water to make up 10 ml. Immediately before use, the following protease inhibitors were added to the RIPA buffer: 115 µl PMSF (from 34,8 mg/ml in isopropanol), 64 µl Benzamidine (from 15,6 mg/ml stock), 100 µl sodium orthovanadate (100 mM), 5 µl pepstatin (from 1 mg/ml stock), 1 µl leupeptin (from 5 mg/ml stock), 1 µl aprotin (from 5 mg/ml stock).

EXAMPLE 5

Composition of the Complete Viral Delivery System (CVDS)

The Complete Viral Delivery System composes of 1:1 mixture of Ham's F12 medium and DMEM, an effective amount of a gutless virus vector carrying a polynucleotide encoding a thrombomodulin protein or a variant of a thrombomodulin protein, and an a cellular oxygen carrier. Preferred oxygen carrier includes: unmodified or chemically modified hemoglobin in the range of 3 g/dl to 10 g/dl and perfluorochemical emulsions. The CVDS may optionally contain 1 mM L-glutamine (Sigma), 1.5 g/L sodium bicarbonate (Sigma), 1× antibiotic-antimycotic (GIBCO® 15240). The CVDM maintains tissue viability during the viral treatment of blood vessel.

EXAMPLE 6

Ex Vivo Treatment of Cardiovascular Disease

A vein segment is harvested from the leg and is stored in Ham's F12 medium. Gutless adenovirus suspended in CVDM is then injected into the isolated vein segment and incubated for 10 to 40 minutes depending on the desired level of transfection. The infection may be performed under pressure to enhance efficiency.

After the incubation, the vein segment is washed several times to eliminate all viral particles that have not entered the endothelial cells of the vein segment, and is then grafted into the desired treatment site. The thorough rinse avoids the spread of the viral vector to other organs of the body following in situ grafting, and any systemic immune response to the viral vector.

EXAMPLE 7

In Vivo Treatment for Peripheral Vascular Disease

In this application, the vein in the leg is treated following evacuation of the clot. A catheter is inserted in the leg vein and both the proximal and distal balloons are inflated to isolate the vein segment to be transfected. The segment is evacuated of all blood, rinsed with physiologic saline. The segment is then filled with the CVDS described above, under pressure. The isolated vein segment is exposed to the CVDS for a period of 10 to 45 minutes, depending upon the desired transfection efficiency.

EXAMPLE 8

In Vivo Expression of TM by Intravenous Infusion of Viral Vectors Material and Methods Infection with gutless TM virus: 3 male Wistar rats weighing approximately 300 grams were intravenously injected in the tail vein with a low dose of gutless TM virus (approximately $2\times10^{10}$ viral particles) in a total volume of 500 ul of sucrose buffer. After three weeks, the animals were sacrificed and liver tissue and blood plasma was collected and immediately frozen in liquid nitrogen.

TM expression in the liver was determined by western blotting. Approximately 500 mg of liver tissue was homogenized in 2 ml of RIPA buffer. Liver protein samples (20 µg) were separated on a 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) were used to detect the proteins.

Detection of rat Anti-TM antibodies in the plasma of TM infected rats: HEK 293 cells were cultured in a 6 well cluster. 3 wells were infected with 100 µl of TM gutless virus (approximately $4\times10^9$ virus particles) and 3 wells received no virus. After 24 hours, non-infected and TM infected cells were washed with PBS and lysed in 125 µl RIPA buffer. Protein samples (16 µl) were separated on a 7.5% polyacrylamide/SDS gel and transferred to nitrocellulose membrane. Blots containing protein from both TM expressing cells and non-infected cells were incubated with primary antibody TM (c-17) (1:2000, Santa Cruz) or plasma from TM infected rats (1:20, 1:100 and 1:1000 dilution). Detection of primary antibodies was performed using Polyclonal Rabbit Anti-Goat Immunoglobulins/HRP (1:4000, DakoCytomation) and Polyclonal Rabbit Anti-Rat Immunoglobulins/HRP (1:4000, DakoCytomation), respectively. RIPA buffer was prepared as described in Example 4.

Figure 9:
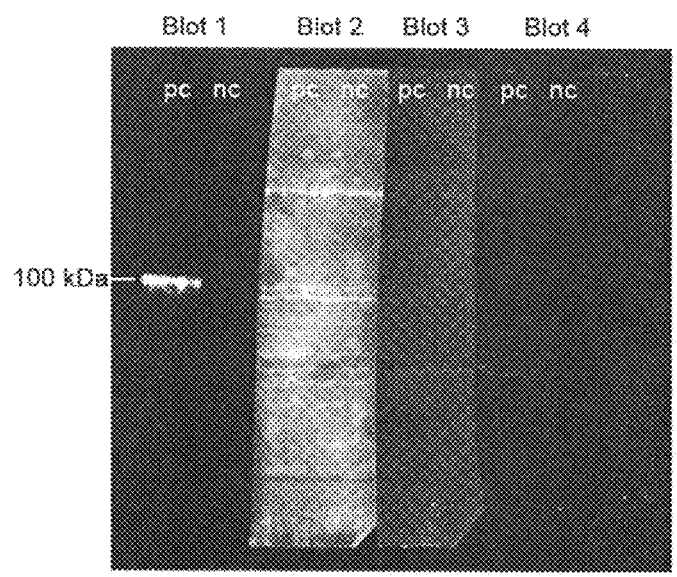
FIG. 9 is a picture of Western blots using a anti-TM antibody (blot 1) and plasma from animals infected with TM virus (blots 2-4).

TM expression in the liver: No adverse effects of the injection of gutless TM virus could be detected. Animals displayed normal growth characteristics and did not suffer from excessive bleeding. Three weeks after injection, animals were sacrificed and no internal bleeding could be detected. Liver TM expression was evaluated using western-blot. TM expression was elevated two-fold above background levels, indicating modest over-expression of TM gutless virus in the liver three weeks after infection (FIG. 8).

To detect TM antibodies in the plasma of rats infected with the gutless TM virus, four western blots were made. Each blot contains a protein sample from human cells expressing TM (positive control) and a sample from the same cells that do not produce TM (negative control). Blot 1 was probed with a commercial antibody against TM (FIG. 9, blot 1), indicating the presence of human TM only in the positive control lane. Blots 2, 3 and 4 were probed with plasma from animals infected with TM virus in the dilution 1:20, 1:100 and 1:1000, respectively. Although some immunoreactivity is observed, the plasma of rats did not lead to the specific detection of TM in the positive control lane. Therefore, the plasma of these rats do not contain detectable levels of rat IgG antibodies against human TM.

Conclusion: Intravenous administration of low dose gutless TM virus into rat tail vein resulted in modest expression of TM in the liver of the recipient rats three weeks after injection. The viral injection did not result in the production of IgG antibodies against TM.

EXAMPLE 9

Adenovirus-Mediated In Vivo Gene Transfer to Vena Cava

Inbred male Brown Norway rats (BN/rijHsd, Harlan, Netherlands) with an age of 11 weeks were used. Animals were housed in a light and temperature controlled environment and fed standard rodent chow and water ad libitum. Rats were anaesthetized with isoflurane (3% in $O_2$). The vene cava with the branches was exposed by a mid-line incision. The vene cava was clamped just below the vene renalis of the left kidney. All accessible sidebranches of the vena cava in the region between the vena renalis and the bifurcation were also clamped. The virus particles were administered through an insulin syringe (29-gauge needle) with a volume of 290 ul containing $2\times10^{11}$ virus particles. After injection of the viral solution, the syringe with needle was not removed from the vena cava but remained in place during the following incubation period of 20 minutes. Subsequently, the clamps on the sidebranches of the vene cava were removed. The transfected segment of vena cava was washed by making a puncture with a needle 25-gauge needle just below the clamp near the vena renalis. The expelled blood containing excess virus was absorbed with a cotton bud. After bleeding a volume of approximately 0.5 ml, the bleeding was stopped by applying a pressure on the puncture site with a cottonswab. Subsequently, the clamp near the vene renalis was released and the abdomen was sutured. For post-operative pain relief, the rats received buprenorphin (Temgesic®) 10 µg/kg subcutaneously. The rats were allowed to recover with access to water and food ad libitum.

Two days after the transfection procedure, rats were anaesthetized with isoflurane (3% in $O_2$). The vene cava was exposed by a mid-line incision and clamped just below the vena renalis of the left kidney. The abdomen was temporarily closed during the incubation time of 2 hours. Subsequently, the abdomen was reopened and blood was collected from the aorta. The vena cava was harvested from the bifurcation till above the clamp. The vene cava was opened longitudinally and the thrombus was removed and placed in saline for size evaluation. The results of the experiment were summarized in Table I.

TABLE I

Vena cava thrombus in the experimental animals

| Group | Thrombus size in individual animals |
|---|---|
| sucrose | 1623.98 |
|  | 1507.23 |
|  | 239.84 |
|  | 398.25 |
|  | 107.97 |
|  | 32.24 |
|  | 85.40 |
| gfp virus | 97.00 |
|  | 107.13 |
|  | 158.93 |
|  | 0.00 |
|  | 89.04 |
|  | 87.63 |
|  | 1281.56 |
|  | 137.13 |
| TM virus | 0.00 |
|  | 280.04 |
|  | 0.00 |
|  | 0.00 |
|  | 140.21 |
|  | 60.65 |
|  | 0.00 |
|  | 108.69 |

EXAMPLE 10

Adenovirus-Mediated Gene Transfer to Kidney Via Intravenous Infusion

This example describes the procedure for slowly infusing a recombinant adenovirus into the renal circulation. Male Sprague-Dawley rats (100-150 g) were injected intramuscularly with 20,000 units of penicillin, anesthetized with ketamine (70 mg/kg, ip) and xylazine (7 mg/kg, ip) and underwent surgical exposure of the right kidney, the aorta and the right renal blood vessels. The right renal blood flow was interrupted by clamping the aorta above and below the right renal artery and the superior mesenteric artery (SMA). This setting selectively excluded the right kidney without interrupting the blood circulation through the left kidney and allowed infusion of virus into the right kidney through the SMA. A 27-gauge winged infusion needle was inserted into the SMA and fixed in place with a microaneurism clamp. 1.5 ml of recombinant adenovirus in phosphate buffered saline (PBS) containing 5 units of heparin/ml were slowly infused into the right kidney with a Razel A-99 syringe pump at a flow rate of 0.1 ml/min. The right kidney was packed with ice during the infusion to minimize ischemic damage. Renal circulation was reestablished at the end of infusion. The abdominal cavity was closed with sutures. The animal was placed on a warm pad to recover from the anesthesia and was returned to its cage after recovery.

EXAMPLE 11

Adenovirus-Mediated Gene Transfer to Kidney Via Balloon Catheter

In this application, a catheter is inserted in a vein near or in the kidney. Both the proximal and distal balloons are inflated to isolate the vein segment to be transfected. The segment is evacuated of all blood, rinsed with physiologic saline. The segment is then filled with the CVDS described above, under pressure. The isolated vein segment is exposed to the CVDS for a period of 10 to 45 minutes, depending upon the desired transfection efficiency.

EXAMPLE 12
In Vivo Treatment with Virus Containing Stent

In this application, a virus-coated stent is placed at a treatment site in or near the kidney. Alternatively, the virus may be embedded in the stent and is releases gradually through a time-releasing mechanism well-known to one skilled in the art.

EXAMPLE 13
Construction of Gutless Adenovirus Vectors Carrying the IDO Gene Rat and human IDO cDNA were amplified by RT-PCR using the following set of primers:
Forward primer (containing a FseI restriction site):

(SEQ ID NO: 17)
5'-TATTTATTGGCCGGCCGCGTTAAGATACATTGATGAG-3'

Reverse primer (containing a SbfI restriction site):

(SEQ ID NO: 18)
5'-TATTTATTCCTGCAGGTCGTAGGTCAAGGTAGTAGA-3'.

The amplified rat IDO cDNA (SEQ ID NO:19) and human IDO cDNA (SEQ ID NO:20) were cloned into expression plasmids pAdTrackCMV-rIDO and pAdTrackCMV-hIDO, respectively.

Expression cassettes comprising a CMV promoter, IDO cDNA and poly-adenylation signal were constructed using PCR. PCR primers were equipped with additional restriction enzyme sites to facilitate cloning into the gutless backbone vector.

Forward primer (containing a FseI restriction site):

(SEQ ID NO: 17)
tatttattggccggcCGCGTTAAGATACATTGATGAG

Reverse primer (containing a SbfI restriction site):

(SEQ ID NO: 18)
tatttattcctgcaggTCGTAGGTCAAGGTAGTAGA

Figure 10:
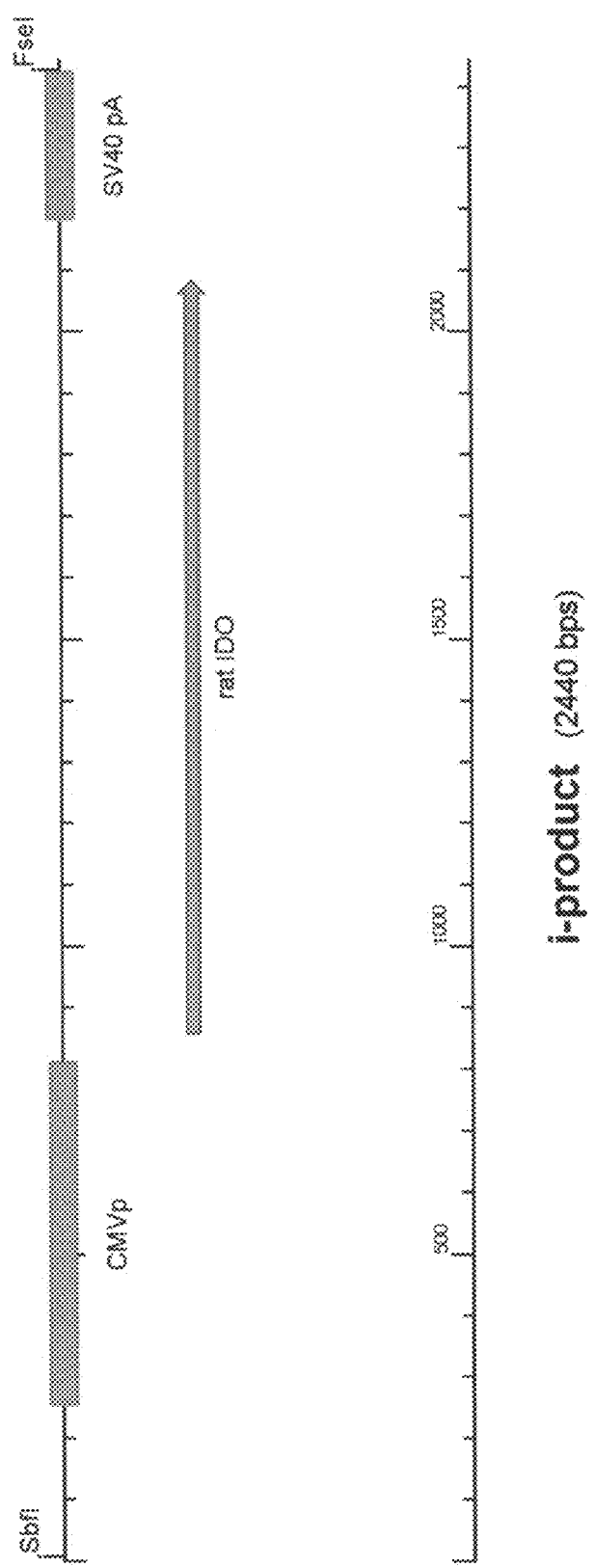
FIG. 10 is a schematic drawing of an embodiment of the rat IDO expression cassette.
Figure 11:
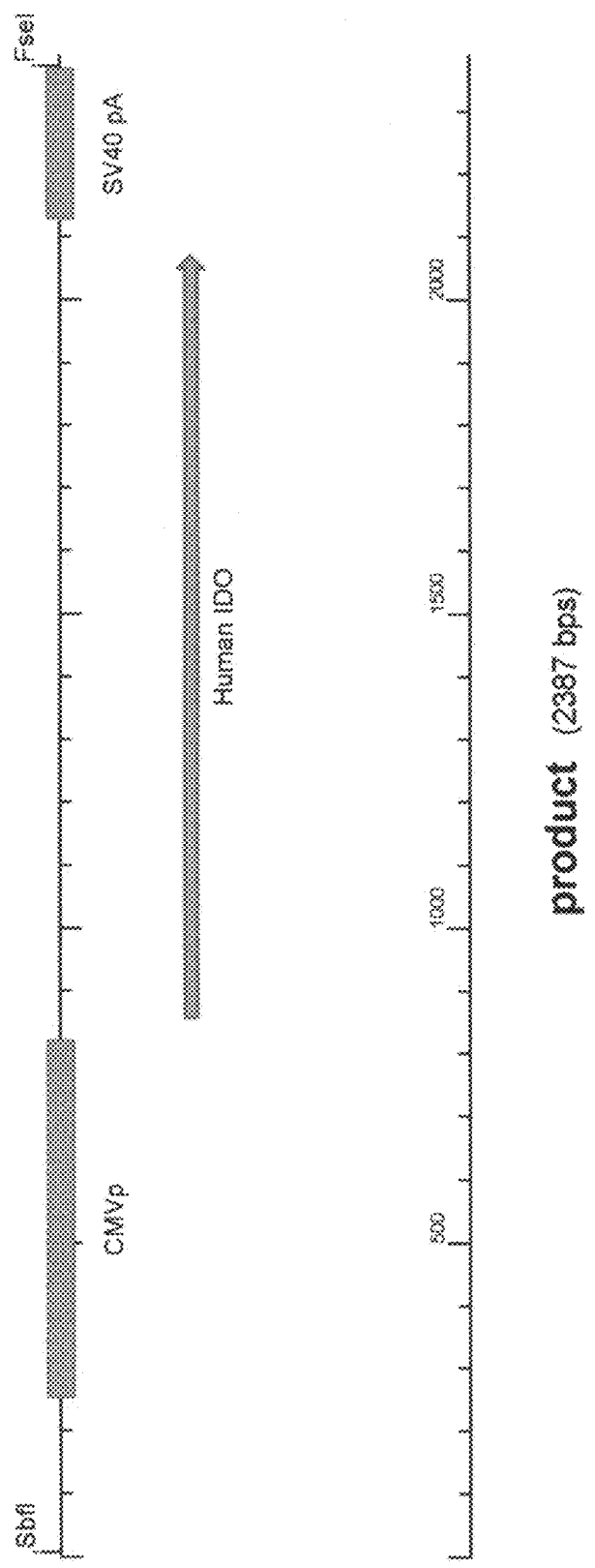
FIG. 11 is a schematic drawing of an embodiment of the human IDO expression cassette.

The resulting PCR fragments were cloned into pGEM-T-EASY for sequencing and cloning. Sequencing confirmed the presence of rat IDO expression cassette (FIG. 10, SEQ ID NO:21) and human IDO expression cassette (FIG. 11, SEQ ID NO:22).

Figure 12:
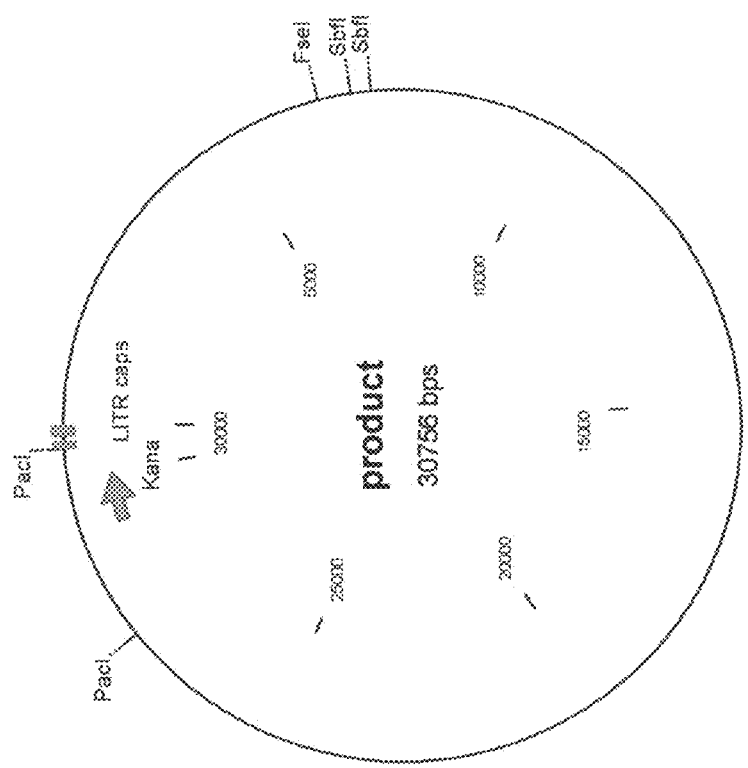
FIG. 12 is a schematic drawing of a gutless backbone vector.
Figure 13:
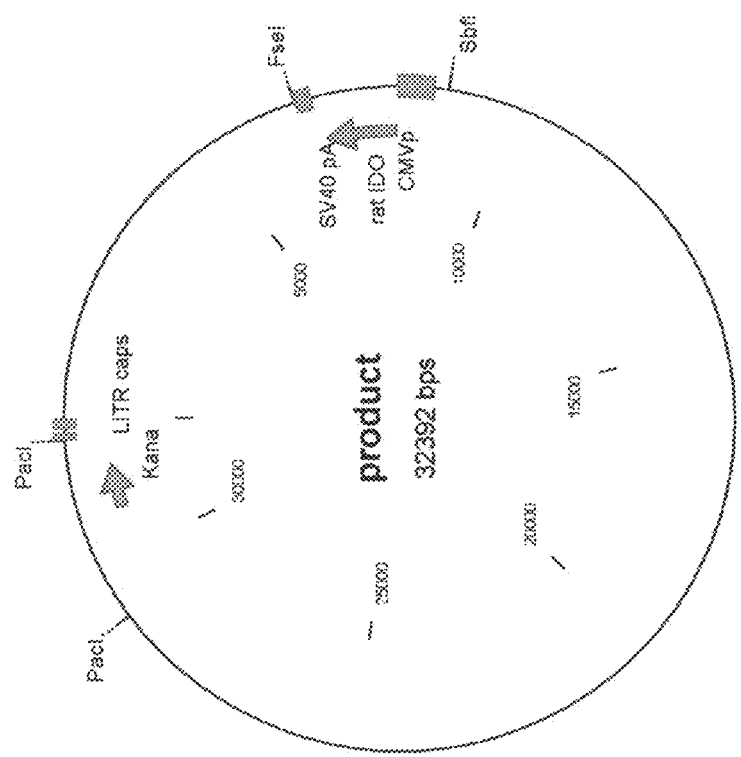
FIG. 13 is a schematic drawing of an embodiment of the rat gutless IDO backbone vector.
Figure 14:
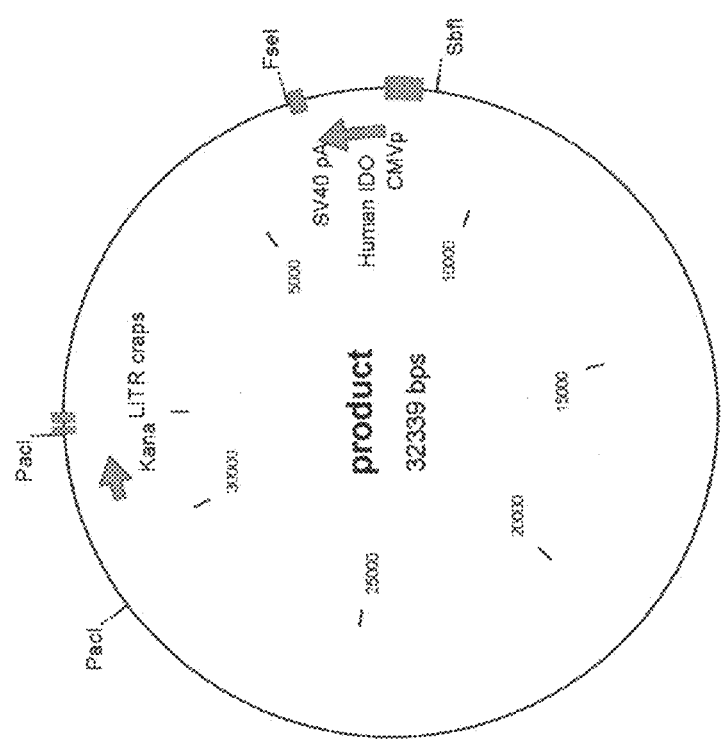
FIG. 14 is a schematic drawing of an embodiment of the human gutless IDO backbone vector.

The gutless backbone (SEQ ID NO:23, FIG. 12) was cut with SbfI and FseI to release the TM expression cassette. The backbone was subsequently dephosphorylated to prevent vector self-ligation. Rat and human IDO expression cassettes were released from pGEM-T-Easy by digestion with FseI and SbfI and ligated into the FseI and SbfI sites of the gutless backbone. The resulting constructs prIDO-final (FIG. 13, SEQ ID NO:24) and phIDO-final (FIG. 14, SEQ ID NO:25) were cloned in E-coli DH5α. DNA midipreps were generated for the production of high quality plasmid DNA. Gutless adenovirus containing rat IDO or human IDO was produced using the procedure described in Example 3.

EXAMPLE 14
Perfusion of Kidney Transplant with Gutless Adenovirus Vectors Carrying the IDO Gene The experiment was carried out in Fisher-Lewis kidney transplantation model. Gutless adenoviruses carrying the IDO gene (Ad.TIDO) or luciferase gene (Ad.TL) were surface-modified with cyclic arginine-glycine-aspartic acid (RGD) peptides through a bifunctional polyethyleneglycol) linker for integrin alpha(v) beta(3) specific delivery. The resulting RGD modified viruses were designated RGD-Ad.TIDO and Ad.TL. The transplanted kidneys were incubated with either RGD-AdTIDO (n=6) or RGD-AdTL (n=5) at 4° C. for 20 min with saline. The transplanted animals were sacrificed at day 7. The transplanted kidneys were isolated and subjected to Western blot and immunohistological examination.

Figure 15:
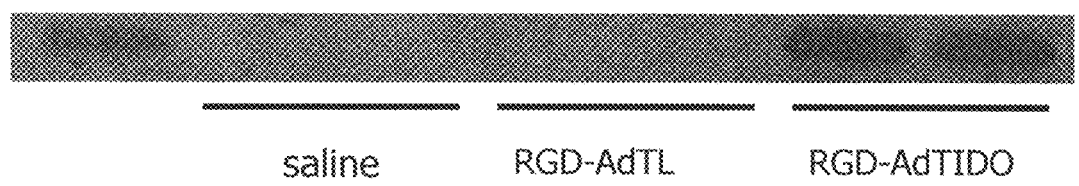
FIG. 15 is a picture of a Western blot showing gutless adenovirus mediated IDO expression in transplanted kidney (lane 1=hIDO control, other lanes as indicated)
Figure 16A:
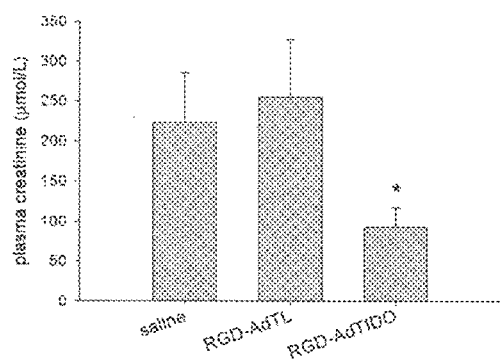
FIG. 16 is a composite of graphs showing reduction of plasma creatinin levels (panel A), ED-1 staining (panel B), CD8 staining (panel C) and smooth muscle actin score (panel D) in kidney tissue infected by gutless adenovirus carrying the IDO gene.
Figure 16B:
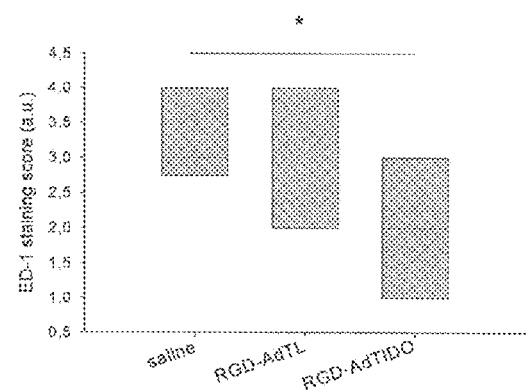
Figure 16C:
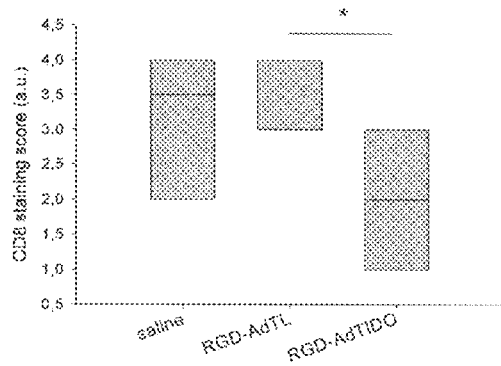
Figure 16D:
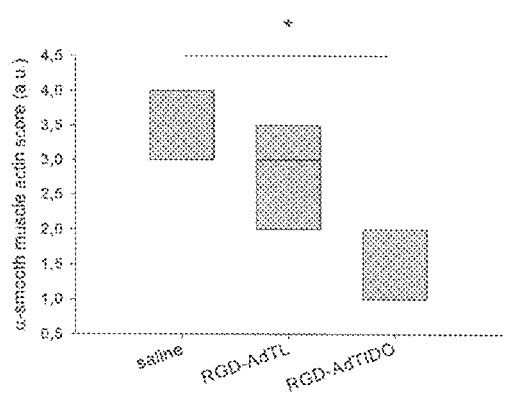

As shown in FIG. 15, IDO expression was detected in the kidneys infected with RGD-AdTIDO but not in kidneys infected with RGD-AdTL. FIGS. 16A-16D shows that, comparing to kidneys perfused with saline or control virus (RGD-AdTL), kidneys infected with RGD-AdTIDO showed reduced plasma creatinin levels (FIG. 16A). Kidneys infected with RGD-AdTIDO also showed reduced tissue damage, as evidenced by the reduced ED-1 staining (FIG. 16B), reduced macrophage influx (FIG. 16C, CD-8 staining for T-lymphocytes), and reduced fibrotic response (FIG. 16D, staining for smooth muscle actin).

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

LIST OF THE SEQUENCES

SEQ ID NO:1 (pShuttle-ITR/HPRT)
SEQ ID NO:2 (human TM amino acid sequence)
SEQ ID NO:3 (human TM nucleotide sequence)
SEQ ID NO:4 (CMV promoter)
SEQ ID NO:5 (hTM cDNA)
SEQ ID NO:6 (CMV-hTM expression cassette)
SEQ ID NO:7 (pTMadap)
SEQ ID NO:8 (BstII linker)
SEQ ID NO:9 (SfiI linker)
SEQ ID NO:10 (Forward PCR primer)
SEQ ID NO:11 (Reverse PCR primer)
SEQ ID NO:12 (Stuffer 1)
SEQ ID NO: 13 (Stuffer 1-Short)
SEQ ID NO:14 (p2-2)
SEQ ID NO:15 (Stuffer 2)
SEQ ID NO:16 (pTM-final)
SEQ ID NO: 17: IDO RT-PCR forward primer (containing a FseI restriction site)
SEQ ID NO: 18: IDO RT-PCR reverse primer (containing a SbfI restriction site)
SEQ ID NO:19: rat IDO cDNA
SEQ ID NO:20: human IDO cDNA
SEQ ID NO:21: rat IDO expression cassette
SEQ ID NO:22: human IDO expression cassette
SEQ ID NO:23: gutless backbone vector
SEQ ID NO:24: prIDO-final
SEQ ID NO:25: phIDO-final

What is claimed is:

1. A gutless adenovirus vector comprising the nucleotide sequence of SEQ ID NO:22.

2. A gutless adenovirus vector comprising the nucleotide sequence of SEQ ID NO:21.

3. A pharmaceutical composition for treating a renal disease, comprising:
   the gutless adenovirus vector of claim 1; and
   a pharmaceutically acceptable carrier.

4. A pharmaceutical composition for treating a renal disease, comprising:
   the gutless adenovirus vector of claim 2; and
   a pharmaceutically acceptable carrier.

* * * * *

SEQUENCE LISTING

<160> NUMBER OF SEQ ID NOS: 25

<210> SEQ ID NO 1
<211> LENGTH: 13602
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 1

```
catcatcaat aatataccct attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg      180
gtgtgcgccg gtgtacacag gaagtgacaa ttttcgcgcg gttttaggcg gatgttgtag     240
taaatttggg cgtaaccgag taagatttgg ccatttcgc gggaaaactg aataagagga      300
agtgaaatct gaataatttt gtgttactca tagcgcgtaa tactggtacc gcggccgcct     360
cgagtctaga actagtggat cccccgggct gcaggaattc tgatggctct caaaattcct     420
gcctccttta gggataaaag actttaagac tttttaacaa aaagaaaaa gaaaaaaaa      480
attcctgcct cctggtgtac acacacgaaa gggttccctc cccttgaatg tgaccaggat     540
ctgtgaaaat aacgggatag ccgctcctgt gattaggtta tgtggtagac tagagcaaga     600
ttctcctgct ggttttgaag aagtcagctg ccatgttgtg agactgtcat gggctagggc     660
atgagccttt aaatatctgg gagcaacccc tggccagcag ccagtgagaa aacgggccct     720
cagtcctaca atcacaagga actaaattct gccaacaacc tgaaggaact ttgaagagga     780
tcatgagtcc cttgattcag cttgatgagc ccctgagcag aggatacagc taacttgtac     840
tagggaagta taaaaacat gcatgggaat gatatatatc aacttaagg ataattgtca      900
tacttctggg aatgaaggga agaaatggg gctttagttg tattatgatc tttaatttct      960
caaaaaat aagatcagaa gcaaatatgg caaaatgtta atacttttgt gggtacgtag     1020
gtattcagca tacccttttt tctgagttca aaatatttta taattaaaat gaaatgcagg    1080
ccaggcacag tggctcatgc ctataatacc agcactttgc gaggccgagg tgggaggatg    1140
gcttgaggcc agaccagcct ggccaacatg gcaaaccccc atctctactt aaaaaaaaaa    1200
aaactatata tatatatatg tgtgtgtgtg tgtatatata tatatgtata tatatttata    1260
tatgtgtgta tatatatata tgtatatata tttatatatg tgtgtgtata tatatata     1320
cacacacaca catatataca tacatacata cacacacaca cacacacaat tagccaggca    1380
tggtggcgca cacctgtagt cccagctact tgggaggctg agacatgaga attgcttgaa    1440
cctgggaggc agagtagtta gtgagctgag atcataccac tgcactccag cctggtgaca    1500
gagtgagact ctgtcttaaa aaaataaaa attaaaatta aatgcaaaag gtccaagtga    1560
attgaagagg aaaggggtat caaggaaggt tttgtggagg tgacgtttga gctgggtctt    1620
aaatgactta aacatgggat aagaaggag ggaataagga catttcaggt acgagaaata     1680
aggagcaaac agtggaaaca acctaacgtc tgtcaaccag tgaatggata acaaaaatgt    1740
aattcagatg gtatccaact tacgatggtt caacatgaga ttttttctgac tttaggatag    1800
atttatcaaa gtagtaaatc cattttcaac ttatgatatt ttcaacttca gatgggttta    1860
tcaggacaca gttgaggaac acctgtctat ccatacaatt tggcaataaa aaggaaatga    1920
gtgcagatat actccacaac atgaatgaac cttgaaaaca ttaagtgaga gaagccagat    1980
```

```
acaaaaggcc acatattgta tgattctatt tatacaaaat gtccagaata ggcaaatctt    2040
atagacagca agtaggtaga tgatcagttt gctaggtgct gggggaaggg gaaatgggga    2100
gtgatggcta aggggattgg gtttctttgt ggggcaatga aaatgtttta aaattgagcg    2160
tgataatgat tgcacaatgc tgcatatata tataatctat agattatata tatataaaga    2220
gaggctgtta gacagtgata agtgatatat atatatatat acatagagag agagagagag    2280
agagagagag gctgttagtg ataagtgatc aggaaaataa aagtattgag gaggaatacg    2340
aagttgacgg tgtgaaaaca tgagatttta tataggatgg ccagggaagg ccttaatgag    2400
aaagtgactt atgagtaaaa acaagggatc ctaaacctta gcatgcatca gaatcactcg    2460
gaaacttgtt aaagcatagc ttgctgggcc tcatcacaga tattttgatt cggtaggttc    2520
ttgtctgata ttaatacttt tggtctaggg aaccacattt tgagaaccac tgagctaaag    2580
gaagtaaagg tttcccttag tttactagct ggtaaccta ggaaactgct tagcctctcg    2640
gtgctaagat acaaaatact ttagcacata ataacacatg gaaatagtc tataaattat    2700 aaatattatt ttttatgtac caaatattac ataagacaaa atctaagcaa gatatatata    2760
tatatacata aaatataaga tatatatgta tatattatat atagataaat agagagagag    2820
agttatgttt agaagaaaaa tacttcaaac taaaaaaaga gaggtaggaa gtataccatt    2880
ccattattgg taaaaacaaa ttactaagta gtctttacaa aaaaccaatc tcactccttt    2940
agaacacaag cccaccatta aaactgatgc agaggaattt ctctccctgg cttacccttta   3000 ggatggtgca tactaagtta gaaaagtcat aaatgttata ttaaaagtaa atgtgaactt    3060
acttccacaa tcaagacatt ctagaagaaa aagagaaatg aaaatcagta caatgaataa    3120
aacggtattt ccaattataa gtcaaatcac atcataacaa ccctaaggaa ttatccaaac    3180
tcttgttttt agatgcttta ttatatcaaa ctctcccttta aacaagtggc ccatctgctg    3240
ggatttggaa gcctgtaata ctgaaatttt catcataatg gaaattttaa aaacagaatt    3300
tgacccacct gttttaaaa cactttcatt acttaacaag aggtctaatc ttgggcaagt    3360
cttgaaattt ctctggcctt agtttcccat gtgttaaatg aaacttgaag cagttggtct    3420
cttatagtct cctgactcta acattctaag aattatattt gtacaataac tcaaaaatca    3480
cataatttaa tttaccatat ggactccaaa atatatttc tcattaggct aaacttgatc    3540
tgcattttct ggatgtgtcc atattcttgg actacactaa aacatgatac caatgcttcc    3600
tctcaccata aaccctcact tcgctttcta catttaagaa ttttatagct ggaagagtcc    3660
ttaacagaaa ataccatcta ataattaccc ctcaaaatcg agaaagtcct atctgttctt    3720
atgctagtta taagaatgag gcagcatttc acataatggt tataaacact gccacaagaa    3780
gattcatgat gtgttgttta tctgtagctc tcatcatact ctgtcatata actatagcat    3840
taagatttta atgttctata tattcttcta agacagtgtt taccagagta aggcacaaaa    3900
gatccactgg tttgcaagaa agattagaac ttttaaattt tttacctcac cttgtttaat    3960
ctatattttt gtatgtattt tgtaacatat atattattat taccataaat catatataat    4020
ttaaaatgca tatattaggg gtaaatgctc aggaaacttt ttataaattg ggcatgcaaa    4080
tacaagtttg aagactcact gttctaggta ttaaaagtaa agttataacc aagtaaagct    4140 tccaccttt catgtctcaa agcagtttat tgttggaggt aagatctctt agaagcctaa    4200
acaggtccaa gtacagaatg aagtaaggct agcccataac ttgtggcaag caattcatac    4260
tatttctctc atgctgagct ctcctcagtg aagcagctac tatagacaac tgcagcctat    4320
tggtagccta ttttacaggc aggaaaaaaa ttacttttta ttcaaagtgg aactcaggac    4380
```

```
atgggagaa aatgaataca aaaataggg tcaatccaaa ggcacacagc aaatgagtaa      4440
cacagttatg ttttttcccc atttgtatga ggtcccagta aattctaagt aaactgcaaa   4500
tttaataata cactaaaaaa gccatgcaat tgttcaaatg aatcccagca tggtacaagg   4560
agtacagaca ctagagtcta aaaacaaaa gaatgccatt attgagtttt tgaattatat    4620
caagtagtta catctctact taataaatga gaaaacgag gataagaggc catttgataa    4680
aatgaaaata gccaagaagt ggtattagag acttgaatac aggtattcgg gtccaaagtt   4740
catctgctca aatactaact ggggaaaaga gggaaaaata tttatataca tatatatctg   4800
cacacaaaaa tacccccaaa agacaaaatg aggccaggca gggtggctca cacccgtaat   4860
cccggtactt tgggaggctg aggcaggtgg atacctgaga tcaggagttg gagatcagcc   4920
tggtcaacat ggtgaaaccc tgtctctact aaagataaaa aaattagcca ggcatggtgg   4980
cgtgcgcctg taatcccagc tacttgggag tctgaggcag gagaatcact tgaactggga   5040
aggggaggtt gcagtgagcc aagatcgtac tactgcactc cagcctgggc agcagagtga   5100
gactccatca aaaaataaa taaataaata aatacaatg aaacagaaag ttcaaataat     5160
cccataatct taccaccaag aaataacttt cactcgttat acttattgat ttttccataa   5220
taaatgtact ttactgtgac tatcatgaaa agaaagttat tttagaaaca gagaactgtt   5280
tcagatcaaa tctatgtagt agaacagagc cattaggtgg gaaagacgag atcaaactaa   5340
atctcagaag gcctaaaagg ctaggtccat tccagcacta aaaactgacc agacaagtaa   5400
tggcttcaac agcttctaaa tatggacaaa gcatgctgaa agggaaggac aggtctaaca   5460
gtggtatatg aaatgaacag gagggcaaa gctcatttct cctctgaagt tttccaaaga    5520
tgctgaggag gacattagtt tgacatgacc ctgatatggg acaagataat ttcacagaag   5580
ttttacatgt taaagttttc ttatagatac tcattcaagt aagcaatgaa cactaaaatc   5640
taaagaaaga aaagagcttt agagtcaggt ctgtattcaa attcaagctc taccacttac   5700
tggttctgtg actttgggca agtctttaa ccttattaag tcttaatttc ctgatttgta    5760
aaatggggat atcgtctccc tcacaggatt gttgtgaaac tttatgaga ttaatgcctt    5820 tatatttggc atagtgtaag taaacaataa ctggcagctt caaaaaaaaa aagcagtagc   5880
attccatcat ttattattgg ttactctcaa aaagttttc aatgtactag aagataaata    5940
ttcaaatacc ttaatatctc cattatttc aggtaaacag catgctcctg aacaaccaat    6000
gggtcaacaa ataaattaaa agggaaatct aaaaacatct tgatattaaa ctacatggaa   6060
gcacaatata ccaaaaccaa tggttcacac taggagaatt ttaaggtaca agaaaactct   6120
ttgagatttc ttaaaataat agtatgtctg aatttattga gtgatttacc agaaactgtt   6180
gtaagagctc tacttgcatt atagcactta atcctcttaa ctctatggct gctattatca   6240
acctcaccct aatcacatat gggacacaga gaggttaagt aacttgccca aggtcagagt   6300
taggaagtac taagccatgc tttgaatcag ttgtcaggct ccggaactca cactttcagc   6360
cactacataa tactgctttg ctatctttta ggaaactatg tgagtctacc tcacatagac   6420
tcacataggt ttgttttttt tttttttta aaggctatct tttcccccat caatgttttt    6480
tgaaggatcc caaattagag tcccacagag gcagacagca gtacttgaca atatggacat   6540
ttaaggttaa tgttggattc tactgtcttt ttactacatg acctagggaa cgataattaa   6600
cctagactgc ttccaagggt taaataaccc atttagttat actatgtaaa ttatctctta   6660
gtgattgatt gaaagcacac tgttactaat tgactcggta tgaagtgctt ttttttcttc   6720
cctttcaaga tacatacctt tccagttaaa gttgagagat catctccacc aattactttt   6780
```

-continued

```
atgtccctg ttgactggtc attctagtta aaaaaaaaaa aaactatata tatatatatc    6840
tacacacaca tatgtatatg tatatcctta tgtacacaca caaacttcaa attaaatgag    6900
aactagaaga tttgagaagt tagctagcta atatccatag cattatgata ttctaaatga    6960
tatgaattat aagaattagg tttcctgaaa tgaatgacta gaaaactttc aagtagagat    7020
tagtaaaaat taaaaagtcc taatcggcca ttactgattt tgatgtttta agagtcctaa    7080
aaaatgggtt acatccattt ttaagtgggt agtattataa cagccaccca tcttcaatca    7140
cagtgatttc tgaattgtga gggaagttat tagcatgaca ggtgtctggt tctggccctg    7200
tacgattccc atgagtcaag caaattgtaa gggctggtct atatcacacc caaccccaag    7260
gatatgtccc tcaaaagtct agcccaggcc ccgtcatctt cagcatcatc tgggaaacca    7320
ggtctgatta gtagtccttt aaggaatacc tcttaggctc ccattttact gctatcacag    7380
aatccaataa aacccttaca ggagattcaa tgggaaatgc tcaacaccca ctgtagttgg    7440
tggtgacaat gaccataatt tggctgtgct ggattcagga cagaaaattt gggtgaaaga    7500
gcaggtgaac aaaagagctt cgacttgccc tagcagagag caagccatac cataccacaa    7560
agccacagca attacaacgg tgcagtacca gcacagtaaa tgaacaaagt agagcccaga    7620
aacagaccca gaactatatg aggatttagt atacaataaa gatggtattt cgagtcagta    7680
gggaaaagat gaattattca ataaatgatg tttggccaac tagtaaccca tttgggaaaa    7740
aataaaagta tggtccctac ctcacagcat acacaaaaat aaattccaga cggattaaaa    7800
tctaaatgta aaaaataaag ccataagtgg actggaagaa aatagagaat ttttttttaac    7860
atccgtagaa agggtaaaaa cccaggcatg acatgaacca aaactgaaga ggttctgtaa    7920
caaatacccc cttttatata ttgggctcca acaataagaa cccataggaa atggagaat    7980
gaacacaaat agacaattta tagaagagaa ggttataagg tgtaaaatta tatctatctg    8040
agaaacaaac actaaaacaa tgtgattcta ctgttctccc acccatactg gcaaaactta    8100
agcctgataa tatgctgagg ggaaataagc actcttgttg gtgagagtat taattggcat    8160
agcttctttt gaaatgaca tagcaatacc tgttaaaatt gcaaacatgc atgtcactta    8220
atccagtaat cccacttctg ggaatcaatg ctacaaaaac actgacaagt atacaaagat    8280
acattcaaga gtgttcactg gccgggtgc ggtggcttca tgcctgtaat cccaggagg    8340
cagaggcaag acgatcgctt gaccccagga gttcaaggcc agcccgagaa acacagcaag    8400
accctgtctc tctttttttt atttaaaaaa taaatgttca ctgtatcagt tgttcacaaa    8460
aacaaaccaa catgtccatt aacagggaac catttaaatt aatcaagttc atctacacaa    8520
tgtaatacca tgcaactatt aaaaagcacc tgataatcca aagcacactg agacagaata    8580
atgctattaa aaacaccaag tagtggaaca ctgtgttgcc tatgacacca ttttattca    8640
acatttaaac aaatttgtaa cagcaattac atgagtagtg acaatggcgt ttatgagact    8700
tttcactttt atgtgcttct attttttgtta tgcttctata tatacatcca tttattatgg    8760
agtgttactt tcaaaaatca caaatgggc agtattattt ggtgttgcaa ggtgagcata    8820
tgacttctga tatcaacctt tgcatattac ttctcaattt agggaaatta cagacatccc    8880
ttattctaac taacttaaaa cccagcattt caaacataca gaattgatgg ggaaaaaaaa    8940
gaaagaagaa agaaagaaaa ggcaacaagc ttcagatgac agtgactcac atcaaattat    9000
ttataaaatc tgttaaatag tgccatcttc tggagatacc tggtattaca gtccaactcc    9060
agttgatgtc tttacagaga caagaggaat aaaggaaaaa atattcaaga actgaaaagt    9120
atggagtcat ggaaaaattg ctgtgatcca aaggctacgg tgataggaca agaaacaaga    9180
```

```
gaactccaag cagtaagaca ctgctgttct attagcatcc aaacctccat actcctgttt    9240
gccccaaggc ttttttaaaa aatagagaca ggatctcact attttgctca ggctggtctt    9300
gaactcctgg actcaagcta tcctcctgcc tcggcctcct aaagtgccga gattacaggc    9360
ttgagtcacc atacctggct atttatttt  tcttaactct cttgcctggc ctatagccac    9420
catgaagct  aataaagaat attaatttaa gagtaatggt atagttcact acattggaat    9480
acaggtataa gtgcctacat tgtacatgaa tggcatacat ggatcaatta ccccacctgg    9540
gtggccaaag gaactgcgcg aacctccctc cttggctgtc tggaacaagc ttcccactag    9600
atcctttac  tgagtgcctc cctcatcttt aattatggtt aagtctagga taacaggact    9660
ggcaaaggtg aggggaaagc ttcctccaga gttgctctac cctctcctct accgtcctat    9720
ctcctcactc ctctcagcca aggagtccaa tctgtcctga actcagagcg tcactgtcaa    9780
ctacataaaa ttgccagaga agctctttgg gactacaaac atacccctt  aatgtcttta    9840
tttctatttt gtctacctct tcagtctagg tgaaaaaata ggaaggataa tagggaagaa    9900
ctttgtttat gcctacttat ccgcccctag gaattttgaa aacctctagg tagcaataag    9960
aactgcagca tggtatagaa aaagaggagg aaagctgtat agaaatgcat aataaatggg   10020
caggaaaaga actgcttgga acaaacaggg aggttgaact ataaggagag aaagcagaga   10080
ggctaatcaa caaggctggg ttcccaagag ggcatgatga gactattact aaggtaggaa   10140
ttactaaggg ctccatgtcc ccttagtggc ttagtactat gtagcttgct ttctgcagtg   10200
aacttcagac ccttctttta ggatcctaga atggactttt tttttttatc ggaaaacagt   10260
cattctctca acattcaagc aggccccaag tctaccacac tcaatcacat tttctcttca   10320
tatcataatc tctcaaccat tctctgtcct tttaactgtt tttctatacc ctgatcaaat   10380
gccaacaaaa gtgagaatgt tagaatcatg tatttttaga ggtagactgt atctcagata   10440
aaaaaaaagg gcagatattc cattttccaa aatatgtatg cagaaaaaat aagtatgaaa   10500
ggacatatgc tcaggtaaca agttaatttg tttacttgta ttttatgaat tccctaaaac   10560
ctacgtcacc cgccccgttc ccacgccccg cgccacgtca caactccac  cccctcatta   10620
tcatattggc ttcaatccaa aataaggtat attattgatg atgttaatta acatgcatgg   10680
atccatatgc ggtgtgaaat accgcacaga tgcgtaagga gaaataccg  catcaggcgc   10740
tcttccgctt cctcgctcac tgactcgctg cgctcggtcg ttcggctgcg gcgagcggta   10800
tcagctcact caaaggcggt aatacggtta tccacagaat caggggataa cgcaggaaag   10860
aacatgtgag caaaaggcca gcaaaaggcc aggaaccgta aaaaggccgc gttgctggcg   10920
ttttccata  ggctccgccc ccctgacgag catcacaaaa atcgacgctc aagtcagagg   10980
tggcgaaacc cgacaggact ataaagatac caggcgtttc cccctggaag ctccctcgtg   11040
cgctctcctg ttccgaccct gccgcttacc ggatacctgt ccgcctttct cccttcggga   11100
agcgtggcgc tttctcatag ctcacgctgt aggtatctca gttcggtgta ggtcgttcgc   11160
tccaagctgg gctgtgtgca cgaaccccc  gttcagcccg accgctgcgc cttatccggt   11220
aactatcgtc ttgagtccaa cccggtaaga cacgacttat cgccactggc agcagccact   11280
ggtaacagga ttagcagagc gaggtatgta ggcggtgcta cagagttctt gaagtggtgg   11340
cctaactacg gctacactag aaggacagta tttggtatct gcgctctgct gaagccagtt   11400
accttcggaa aaagagttgg tagctcttga tccggcaaac aaaccaccgc tggtagcggt   11460
ggttttttg  tttgcaagca gcagattacg cgcagaaaaa aaggatctca agaagatcct   11520
ttgatctttt ctacggggtc tgacgctcag tggaacgaaa actcacgtta agggattttg   11580
```

```
gtcatgagat tatcaaaaag gatcttcacc tagatccttt taaattaaaa atgaagtttt    11640
aaatcaatct aaagtatata tgagtaaact tggtctgaca gttaccaatg cttaatcagt    11700
gaggcaccta tctcagcgat ctgtctattt cgttcatcca tagttgcctg actcccgtc    11760 gtgtagataa ctacgatacg ggagggctta ccatctggcc ccagtgctgc aatgataccg    11820
cgagacccac gctcaccggc tccagattta tcagcaataa accagccagc cggaagggcc    11880
gagcgcagaa gtggtcctgc aactttatcc gcctccatcc agtctattaa ttgttgccgg    11940
gaagctagag taagtagttc gccagttaat agtttgcgca acgttgttgc cattgctgca    12000
gccatgagat tatcaaaaag gatcttcacc tagatccttt tcacgtagaa agccagtccg    12060
cagaaacggt gctgaccccg gatgaatgtc agctactggg ctatctggac aagggaaaac    12120
gcaagcgcaa agagaaagca ggtagcttgc agtgggctta catggcgata gctagactgg    12180
gcggttttat ggacagcaag cgaaccggaa ttgccagctg gggcgccctc tggtaaggtt    12240
gggaagccct gcaaagtaaa ctggatggct ttcttgccgc caaggatctg atggcgcagg    12300
ggatcaagct ctgatcaaga gacaggatga ggatcgtttc gcatgattga acaagatgga    12360
ttgcacgcag gttctccggc cgcttgggtg gagaggctat tcggctatga ctgggcacaa    12420
cagacaatcg gctgctctga tgccgccgtg ttccggctgt cagcgcaggg gcgcccggtt    12480
ctttttgtca agaccgacct gtccggtgcc ctgaatgaac tgcaagacga ggcagcgcgg    12540
ctatcgtggc tggccacgac gggcgttcct tgcgcagctg tgctcgacgt tgtcactgaa    12600
gcgggaaggg actggctgct attgggcgaa gtgccggggc aggatctcct gtcatctcac    12660
cttgctcctg ccgagaaagt atccatcatg gctgatgcaa tgcggcggct gcatacgctt    12720
gatccggcta cctgcccatt cgaccaccaa gcgaaacatc gcatcgagcg agcacgtact    12780
cggatggaag ccggtcttgt cgatcaggat gatctggacg aagagcatca ggggctcgcg    12840
ccagccgaac tgttcgccag gctcaaggcg agcatgcccg acggcgagga tctcgtcgtg    12900
acccatggcg atgcctgctt gccgaatatc atggtggaaa atggccgctt ttctggattc    12960
atcgactgtg gccggctggg tgtggcggac cgctatcagg acatagcgtt ggctacccgt    13020
gatattgctg aagagcttgg cggcgaatgg gctgaccgct tcctcgtgct ttacggtatc    13080
gccgctcccg attcgcagcg catcgccttc tatcgccttc ttgacgagtt cttctgaatt    13140
ttgttaaaat ttttgttaaa tcagctcatt ttttaaccaa taggccgaaa tcggcaaaat    13200
cccttataaa tcaaaagaat agaccgagat agggttgagt gttgttccag tttggaacaa    13260
gagtccacta ttaaagaacg tggactccaa cgtcaaaggg cgaaaaaccg tctatcaggg    13320
cgatggccca ctacgtgaac catcacccta atcaagtttt ttggggtcga ggtgccgtaa    13380
agcactaaat cggaacccta aagggagccc ccgatttaga gcttgacggg gaaagccggc    13440
gaacgtggcg agaaaggaag ggaagaaagc gaaaggagcg ggcgctaggg cgctggcaag    13500
tgtagcggtc acgctgcgcg taaccaccac acccgccgcg cttaatgcgc cgctacaggg    13560
cgcgtccatt cgccattcag gatcgaatta attcttaatt aa                      13602
```

<210> SEQ ID NO 2  
<211> LENGTH: 575  
<212> TYPE: PRT  
<213> ORGANISM: Homo sapiens

<400> SEQUENCE: 2

```
Met Leu Gly Val Leu Val Leu Gly Ala Leu Ala Leu Ala Gly Leu Gly
1               5                   10                  15
```

```
Phe Pro Ala Pro Ala Glu Pro Gln Pro Gly Gly Ser Gln Cys Val Glu
             20                  25                  30

His Asp Cys Phe Ala Leu Tyr Pro Gly Pro Ala Thr Phe Leu Asn Ala
         35                  40                  45

Ser Gln Ile Cys Asp Gly Leu Arg Gly His Leu Met Thr Val Arg Ser
 50                  55                  60

Ser Val Ala Ala Asp Val Ile Ser Leu Leu Asn Gly Asp Gly Gly
 65                  70                  75                  80

Val Gly Arg Arg Arg Leu Trp Ile Gly Leu Gln Leu Pro Pro Gly Cys
                 85                  90                  95

Gly Asp Pro Lys Arg Leu Gly Pro Leu Arg Gly Phe Gln Trp Val Thr
             100                 105                 110

Gly Asp Asn Asn Thr Ser Tyr Ser Arg Trp Ala Arg Leu Asp Leu Asn
             115                 120                 125

Gly Ala Pro Leu Cys Gly Pro Leu Cys Val Ala Val Ser Ala Ala Glu
         130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                 165                 170                 175

Pro Leu Ala Val Glu Pro Gly Ala Ala Ala Ala Val Ser Ile Thr
             180                 185                 190

Tyr Gly Thr Pro Phe Ala Ala Arg Gly Ala Asp Phe Gln Ala Leu Pro
         195                 200                 205

Val Gly Ser Ser Ala Ala Val Ala Pro Leu Gly Leu Gln Leu Met Cys
210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
                 245                 250                 255

Asn Ala Ile Pro Gly Ala Pro Arg Cys Gln Cys Pro Ala Gly Ala Ala
             260                 265                 270

Leu Gln Ala Asp Gly Arg Ser Cys Thr Ala Ser Ala Thr Gln Ser Cys
         275                 280                 285

Asn Asp Leu Cys Glu His Phe Cys Val Pro Asn Pro Asp Gln Pro Gly
290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                 325                 330                 335

Pro Gln Arg Cys Val Asn Thr Gln Gly Gly Phe Glu Cys His Cys Tyr
             340                 345                 350

Pro Asn Tyr Asp Leu Val Asp Gly Glu Cys Val Glu Pro Val Asp Pro
         355                 360                 365

Cys Phe Arg Ala Asn Cys Glu Tyr Gln Cys Gln Pro Leu Asn Gln Thr
370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
                 405                 410                 415

Cys Asp Pro Asn Thr Gln Ala Ser Cys Glu Cys Pro Glu Gly Tyr Ile
             420                 425                 430

Leu Asp Asp Gly Phe Ile Cys Thr Asp Ile Asp Glu Cys Glu Asn Gly
         435                 440                 445
```

```
Gly Phe Cys Ser Gly Val Cys His Asn Leu Pro Gly Thr Phe Glu Cys
        450                 455                 460
Ile Cys Gly Pro Asp Ser Ala Leu Ala Arg His Ile Gly Thr Asp Cys
465                 470                 475                 480
Asp Ser Gly Lys Val Asp Gly Gly Asp Ser Gly Ser Gly Glu Pro Pro
                485                 490                 495
Pro Ser Pro Thr Pro Gly Ser Thr Leu Thr Pro Pro Ala Val Gly Leu
                500                 505                 510
Val His Ser Gly Leu Leu Ile Gly Ile Ser Ile Ala Ser Leu Cys Leu
            515                 520                 525
Val Val Ala Leu Leu Ala Leu Leu Cys His Leu Arg Lys Lys Gln Gly
        530                 535                 540
Ala Ala Arg Ala Lys Met Glu Tyr Lys Cys Ala Ala Pro Ser Lys Glu
545                 550                 555                 560
Val Val Leu Gln His Val Arg Thr Glu Arg Thr Pro Gln Arg Leu
                565                 570                 575

<210> SEQ ID NO 3
<211> LENGTH: 1725
<212> TYPE: DNA
<213> ORGANISM: Homo sapiens

<400> SEQUENCE: 3
atgcttgggg tcctggtcct tggcgcgctg ccctggccg gcctggggtt ccccgcaccc      60
gcagagccgc agccgggtgg cagccagtgc gtcgagcacg actgcttcgc gctctacccg     120
ggccccgcga ccttcctcaa tgccagtcag atctgcgacg actgcggggg ccacctaatg     180
acagtgcgct cctcggtggc tgccgatgtc atttccttgc tactgaacgg cgacggcggc     240
gttggccgcc ggcgcctctg gatcggcctg cagctgccac ccggctgcgg cgaccccaag     300
cgcctcgggc cctgcgcggg cttccagtgg gttacgggag acaacaacac cagctatagc     360
aggtgggcac ggctcgacct caatggggct cccctctgcg gcccgttgtg cgtcgctgtc     420
tccgctgctg aggccactgt gcccagcgag ccgatctggg aggagcagca gtgcgaagtg     480
aaggccgatg gcttcctctg cgagttccac ttcccagcca cctgcaggcc actggctgtg     540
gagcccggcg ccgcggctgc cgccgtctcg atcacctacg caccccgtt cgcggcccgc     600 ggagcggact tccaggcgct gccggtgggc agctccgccg cggtggctcc cctcggctta     660
cagctaatgt gcaccgcgcc gcccggagcg gtccaggggc actgggccag ggaggcgccg     720
ggcgcttggg actgcagcgt ggagaacggc ggctgcgagc acgcgtgcaa tgcgatccct     780
ggggctcccc gctgccagtg cccagccggc gccgccctgc aggcagacgg cgctcctgc      840 accgcatccg cgacgcagtc ctgcaacgac ctctgcgagc acttctgcgt tcccaacccc     900
gaccagccgg gctcctactc gtgcatgtgc gagaccggct accggctggc ggccgaccaa     960
caccggtgcg aggacgtgga tgactgcata ctggagccca gtccgtgtcc gcagcgctgt    1020
gtcaacacac agggtggctt cgagtgccac tgctacccta actacgacct ggtggacggc    1080
gagtgtgtgg agcccgtgga cccgtgcttc agagccaact cgagtacca gtgccagccc    1140 ctgaaccaaa ctagctacct ctgcgtctgc gccgagggct tcgcgcccat tcccacgag     1200 ccgcacaggt gccagatgtt ttgcaaccag actgcctgtc cagccgactg cgaccccaac    1260
acccaggcta gctgtgagtg ccctgaaggc tacatcctgg acgacggttt catctgcacg    1320
gacatcgacg agtgcgaaaa cggcggcttc tgctccgggg tgtgccacaa cctcccggt     1380 accttcgagt gcatctgcgg gccgactcg gcccttgccc gccacattgg caccgactgt    1440
```

```
gactccggca aggtggacgg tggcgacagc ggctctggcg agcccccgcc cagcccgacg    1500
cccggctcca ccttgactcc tccggccgtg gggctcgtgc attcgggctt gctcataggc    1560
atctccatcg cgagcctgtg cctggtggtg gcgcttttgg cgctcctctg ccacctgcgc    1620
aagaagcagg gcgccgccag ggccaagatg gagtacaagt gcgcggcccc ttccaaggag    1680
gtagtgctgc agcacgtgcg gaccgagcgg acgccgcaga gactc                   1725
```

<210> SEQ ID NO 4
<211> LENGTH: 649
<212> TYPE: DNA
<213> ORGANISM: Homo sapiens
<220> FEATURE:
<221> NAME/KEY: misc_feature
<222> LOCATION: (1)..(649)
<223> OTHER INFORMATION: n= a, c, g, t, unknown or other

<400> SEQUENCE: 4

```
tctagacgcg ttgacattga ttattgacta gttattaata gtaatcaatt acggggtcat     60
tagttcatag cccatgatat catatggagt tccgcgttac ataacttacg gtaaatggcc    120
cgcctggctg accgcccaac gacccccgcc cattgacgtc aataatgacg tatgttccca    180
tagtaacgcc aatagggact ttccattgac gtcaatgggt ggagtattta cggtaaactg    240
cccacttggc agtacatcaa gtgtatcata tgccaagtac gccccctat tgacgtcaat     300 gacggtaaat ggcccgcctg gcattatgcc cagtncatga ccttatggga ctttcctact    360
tggcagacat ctacgtatta gtcatcgcta ttaccatggt gatgcggttt tggcagtaca    420
tcaatgggcg tggatagcgg tttgactcac ggggattttc caagtctcca ccccattgac    480
gtcaatggga gtttgttttg gcaccaaaat caacgggact ttccaaaatg tcgtaacaac    540
tccgccccat tgacgcaaat gggcggtagg cgtgtacggt gggaggtcta taagcagga    600 gctctctggc taactagaga acccctgctt actggcttat cgagatatc                649
```

<210> SEQ ID NO 5
<211> LENGTH: 3693
<212> TYPE: DNA
<213> ORGANISM: Homo sapiens

<400> SEQUENCE: 5

```
ggcagcgcgc agcggcaaga agtgtctggg ctgggacgga caggagaggc tgtcgccatc     60
ggcgtcctgt gcccctctgc tccggcacgg ccctgtcgca gtgcccgcgc tttcccggc    120 gcctgcacgc ggcgcgcctg ggtaacatgc ttggggtcct ggtccttggc gcgctggccc    180
tggccggcct ggggttcccc gcacccgcag agccgcagcc gggtggcagc cagtgcgtcg    240
agcacgactg cttcgcgctc tacccgggcc ccgcgacctt cctcaatgcc agtcagatct    300
gcgacggact gcggggccac ctaatgacag tgcgctcctc ggtggctgcc gatgtcattt    360
ccttgctact gaacggcgac ggcggcgttg gccgccggcg cctctggatc ggcctgcagc    420
tgccacccgg ctgcgcgac cccaagcgcc tcgggcccct gcgcggcttc cagtgggtta    480
cgggagacaa caacaccagc tatagcaggt gggcacggct cgacctcaat ggggctcccc    540
tctgcggccc gttgtgcgtc gctgtctccg ctgctgaggc cactgtgccc agcgagccga    600
tctgggagga gcagcagtgc gaagtgaagg ccgatggctt cctctgcgag ttccacttcc    660
cagccacctg caggccactg gctgtggagc ccggcgccgc ggctgccgcc gtctcgatca    720 cctacgcac cccgttcgcg gcccgcgag cggacttcca ggcgctgccg gtgggcagct    780
ccgccgcggt ggctccccctc ggcttacagc taatgtgcac cgcgccgccc ggagcggtcc    840
```

```
agggggcactg ggccagggag gcgccgggcg cttgggactg cagcgtggag aacggcggct    900
gcgagcacgc gtgcaatgcg atccctgggg ctccccgctg ccagtgccca gccggcgccg    960
ccctgcaggc agacgggcgc tcctgcaccg catccgcgac gcagtcctgc aacgacctct   1020
gcgagcactt ctgcgttccc aaccccgacc agccgggctc ctactcgtgc atgtgcgaga   1080
ccggctaccg gctggcggcc gaccaacacc ggtgcgagga cgtggatgac tgcatactgg   1140
agcccagtcc gtgtccgcag cgctgtgtca acacacaggg tggcttcgag tgccactgct   1200
accctaacta cgacctggtg gacggcgagt gtgtggagcc cgtggacccg tgcttcagag   1260
ccaactgcga gtaccagtgc cagcccctga accaaactag ctacctctgc gtctgcgccg   1320
agggcttcgc gcccattccc cacgagccgc acaggtgcca gatgttttgc aaccagactg   1380
cctgtccagc cgactgcgac cccaacaccc aggctagctg tgagtgccct gaaggctaca   1440
tcctggacga cggtttcatc tgcacggaca tcgacgagtg cgaaaacggc ggcttctgct   1500
ccggggtgtg ccacaacctc cccggtacct tcgagtgcat ctgcgggccc gactcggccc   1560
ttgcccgcca cattggcacc gactgtgact ccggcaaggt ggacggtggc gacagcggct   1620
ctggcgagcc ccgcccagc cgacgcccg gctccacctt gactcctccg gccgtggggc   1680
tcgtgcattc gggcttgctc ataggcatct ccatcgcgag cctgtgcctg gtggtggcgc   1740 tttgtggcgct cctctgccac ctgcgcaaga agcagggcgc cgccagggcc aagatggagt   1800
acaagtgcgc ggccccttcc aaggaggtag tgctgcagca cgtgcggacc gagcggacgc   1860
cgcagagact ctgagcggcc tccgtccagg agcctggctc cgtccaggag cctgtgcctc   1920 ctcacccca gctttgctac caaagcacct tagctggcat tacagctgga aagaccctc   1980 cccgcacccc ccaagctgtt ttcttctatt ccatggctaa ctggcgaggg ggtgattaga   2040
gggaggagaa tgagcctcgg cctcttccgt gacgtcactg gaccactggg caatgatggc   2100
aattttgtaa cgaagacaca gactgcgatt tgtcccaggt cctcactacc gggcgcagga   2160
gggtgagcgt tattggtcgg cagccttctg ggcagacctt gacctcgtgg gctagggatg   2220
actaaaatat ttatttttt taagtattta ggttttttgt tgtttccttt gttcttacct   2280
gtatgtctcc agtatccact ttgcacagct ctccggtctc tctctctcta caaactccca   2340
cttgtcatgt gacaggtaaa ctatcttggt gaattttttt ttcctagccc tctcacattt   2400
atgaagcaag ccccacttat tccccattct tcctagtttt ctcctcccag gaactgggcc   2460
aactcacctg agtcacccta cctgtgcctg accctacttc ttttgctctt agctgtctgc   2520
tcagacagaa cccctacatg aaacagaaac aaaaacacta aaataaaaa tggccatttg   2580 ctttttcacc agatttgcta atttatcctg aaatttcaga ttcccagagc aaaataattt   2640
taaacaaagg ttgagatgta aaaggtatta aattgatgtt gctggactgt catagaaatt   2700
acacccaaag aggtatttat ctttacttt aaacagtgag cctgaatttt gttgctgttt   2760
tgatttgtac tgaaaaatgg taattgttgc taatcttctt atgcaatttc ctttttgtt   2820 attattactt attttttgaca gtgttgaaaa tgttcagaag gttgctctag attgagagaa   2880
gagacaaaca cctcccagga gacagttcaa gaaagcttca aactgcatga ttcatgccaa   2940
ttagcaattg actgtcactg ttccttgtca ctggtagacc aaaataaaac cagctctact   3000
ggtcttgtgg aattgggagc ttgggaatgg atcctggagg atgcccaatt agggcctagc   3060
cttaatcagg tcctcagaga atttctacca tttcagagag gccttttgga atgtggcccc   3120
tgaacaagaa ttggaagctg ccctgcccat gggagctggt tagaaatgca gaatcctagg   3180 ctccaccccca tccagttcat gagaatctat atttaacaag atctgcaggg ggtgtgtctg   3240
```

```
ctcagtaatt tgaggacaac cattccagac tgcttccaat tttctggaat acatgaaata    3300
tagatcagtt ataagtagca ggccaagtca ggcccttatt ttcaagaaac tgaggaattt    3360
tctttgtgta gctttgctct ttggtagaaa aggctaggta cacagctcta gacactgcca    3420
cacagggtct gcaaggtctt tggttcagct aagctaggaa tgaaatcctg cttcagtgta    3480
tggaaataaa tgtatcatag aaatgtaact tttgtaagac aaaggttttc ctcttctatt    3540
ttgtaaactc aaaatatttg tacatagtta tttatttatt ggagataatc tagaacacag    3600
gcaaaatcct tgcttatgac atcacttgta caaaataaac aataacaat gtgaaaaaaa     3660 aaaaaaaaaa aaaaaaaaa aaaaaaaaa aaa                                    3693

<210> SEQ ID NO 6
<211> LENGTH: 4457
<212> TYPE: DNA
<213> ORGANISM: Homo sapiens
<220> FEATURE:
<221> NAME/KEY: misc_feature
<222> LOCATION: (1)..(4457)
<223> OTHER INFORMATION: n= a, c, g, t, unknown or other

<400> SEQUENCE: 6
gtttaaacgg gccctctaga cgcgttgaca ttgattattg actagttatt aatagtaatc      60
aattacgggg tcattagttc atagcccatg atatcatatg gagttccgcg ttacataact    120
tacggtaaat ggcccgcctg gctgaccgcc caacgacccc cgcccattga cgtcaataat    180
gacgtatgtt cccatagtaa cgccaatagg gactttccat tgacgtcaat gggtggagta    240
tttacggtaa actgcccact tggcagtaca tcaagtgtat catatgccaa gtacgccccc    300
ctattgacgt caatgacggt aaatggcccg cctggcatta tgcccagtnc atgaccttat    360
gggactttcc tacttggcag acatctacgt attagtcatc gctattacca tggtgatgcg    420
gttttggcag tacatcaatg ggcgtggata gcggtttgac tcacggggat ttccaagtc     480 tccaccccat tgacgtcaat gggagtttgt tttggcacca aaatcaacgg gactttccaa    540
aatgtcgtaa caactccgcc ccattgacgc aaatgggcgg taggcgtgta cggtgggagg    600
tctatataag cagagctctc tggctaacta gagaacccct gcttactggc ttatcgagat    660
atctgcagaa ttcatctgtc gactgctacc ggcagcgcgc agcggcaaga agtgtctggg    720
ctgggacgga caggagaggc tgtcgccatc ggcgtcctgt gccctctgc tccggcacgg     780 ccctgtcgca gtgccgcgc tttccccggc gcctgcacgc ggcgcgcctg ggtaacatgc      840
ttggggtcct ggtccttggc gcgctggccc tggccggcct ggggttcccc gcacccgcag    900
agccgcagcc gggtggcagc cagtgcgtcg agcacgactg cttcgcgctc tacccgggcc    960
ccgcgacctt cctcaatgcc agtcagatct gcgacggact gcggggccac ctaatgacag   1020
tgcgctcctc ggtggctgcc gatgtcattt ccttgctact gaacggcgac ggcggcgttg   1080
gccgccggcg cctctggatc ggcctgcagc tgccacccgg ctgcggcgac cccaagcgcc   1140 tcgggccct gcgcggcttc cagtgggtta cgggagacaa caaccagc tatagcaggt     1200 gggcacggct cgacctcaat ggggctcccc tctgcgccc gttgtgcgtc gctgtctccg    1260
ctgctgaggc cactgtgccc agcgagccga tctgggagga gcagcagtgc gaagtgaagg   1320
ccgatggctt cctctgcgag ttccacttcc agccccctg caggccactg gctgtggagc    1380
ccggcgccgc ggctgccgcc gtctcgatca cctacggcac cccgttcgcg gcccgcggag   1440
cggacttcca ggcgctgccg gtgggcagct ccgccgcggt ggctcccctc ggcttacagc   1500
taatgtgcac cgcgccgccc ggagcggtcc aggggcactg ggccagggag gcgccgggcg   1560
```

```
cttgggactg cagcgtggag aacggcggct gcgagcacgc gtgcaatgcg atccctgggg    1620
ctccccgctg ccagtgccca gccggcgccg ccctgcaggc agacgggcgc tcctgcaccg    1680
catccgcgac gcagtcctgc aacgacctct gcgagcactt ctgcgttccc aaccccgacc    1740
agccgggctc ctactcgtgc atgtgcgaga ccggctaccg gctggcggcc gaccaacacc    1800
ggtgcgagga cgtggatgac tgcatactgg agcccagtcc gtgtccgcag cgctgtgtca    1860
acacacaggg tggcttcgag tgccactgct accctaacta cgacctggtg gacggcgagt    1920
gtgtggagcc cgtggacccg tgcttcagag ccaactgcga gtaccagtgc agcccctga    1980 accaaactag ctacctctgc gtctgcgccg agggcttcgc gcccattccc cacgagccgc    2040
acaggtgcca gatgttttgc aaccagactg cctgtccagc cgactgcgac cccaacaccc    2100
aggctagctg tgagtgccct gaaggctaca tcctggacga cggtttcatc tgcacggaca    2160
tcgacgagtg cgaaaacggc ggcttctgct ccggggtgtg ccacaacctc cccggtacct    2220
tcgagtgcat ctgcgggccc gactcggccc ttgcccgcca cattggcacc gactgtgact    2280
ccggcaaggt ggacggtggc gacagcggct ctggcgagcc cccgcccagc ccgacgcccg    2340
gctccacctt gactcctccg gccgtggggc tcgtgcattc gggcttgctc ataggcatct    2400
ccatcgcgag cctgtgcctg gtggtggcgc ttttggcgct cctctgccac ctgcgcaaga    2460
agcagggcgc cgccagggcc aagatggagt acaagtgcgc ggccccttcc aaggaggtag    2520
tgctgcagca cgtgcggacc gagcggacgc cgcagagact ctgagcggcc tccgtccagg    2580
agcctggctc cgtccaggag cctgtgcctc ctcaccccca gctttgctac caaagcacct    2640
tagctggcat tacagctgga gaagaccctc cccgcacccc ccaagctgtt ttcttctatt    2700
ccatggctaa ctggcgaggg ggtgattaga gggaggagaa tgagcctcgg cctcttccgt    2760
gacgtcactg gaccactggg caatgatggc aattttgtaa cgaagacaca gactgcgatt    2820
tgtcccaggt cctcactacc gggcgcagga gggtgagcgt tattggtcgg cagccttctg    2880
ggcagacctt gacctcgtgg gctagggatg actaaaatat ttatttttt taagtattta    2940 ggttttgtt tgtttccttt gttcttacct gtatgtctcc agtatccact ttgcacagct    3000
ctccggtctc tctctctcta caaactccca cttgtcatgt gacaggtaaa ctatcttggt    3060
gaattttttt ttcctagccc tctcacattt atgaagcaag ccccacttat tccccattct    3120
tcctagtttt ctcctcccag gaactgggcc aactcacctg agtcacccta cctgtgcctg    3180
accctacttc ttttgctctt agctgtctgc tcagacagaa cccctacatg aaacagaaac    3240
aaaaacacta aaaataaaaa tggccatttg ctttttcacc agatttgcta atttatcctg    3300
aaatttcaga ttcccagagc aaaataattt taaacaaagg ttgagatgta aaaggtatta    3360
aattgatgtt gctggactgt catagaaatt acacccaaag aggtatttat ctttacttt    3420 aaacagtgag cctgaatttt gttgctgttt tgatttgtac tgaaaaatgg taattgttgc    3480
taatcttctt atgcaatttc ctttttttgtt attattactt attttttgaca gtgttgaaaa    3540 tgttcagaag gttgctctag attgagagaa gagacaaaca cctcccagga gacagttcaa    3600
gaaagcttca aactgcatga ttcatgccaa ttagcaattg actgtcactg ttccttgtca    3660
ctggtagacc aaaataaaac cagctctact ggtcttgtgg aattgggagc ttgggaatgg    3720
atcctggagg atgcccaatt agggcctagc cttaatcagg tcctcagaga atttctacca    3780
tttcagagag gccttttgga atgtggcccc tgaacaagaa ttggaagctg ccctgcccat    3840
gggagctggt tagaaatgca gaatcctagg ctccaccccca tccagttcat gagaatctat    3900
atttaacaag atctgcaggg ggtgtgtctg ctcagtaatt tgaggacaac cattccagac    3960
```

```
tgcttccaat tttctggaat acatgaaata tagatcagtt ataagtagca ggccaagtca    4020
ggcccttatt ttcaagaaac tgaggaattt tctttgtgta gctttgctct ttggtagaaa    4080
aggctaggta cacagctcta gacactgcca cacagggtct gcaaggtctt tggttcagct    4140
aagctaggaa tgaaatcctg cttcagtgta tggaaataaa tgtatcatag aaatgtaact    4200
tttgtaagac aaaggttttc ctcttctatt ttgtaaactc aaaatatttg tacatagtta    4260
tttatttatt ggagataatc tagaacacag gcaaaatcct tgcttatgac atcacttgta    4320
caaaataaac aaataacaat gtgaaaaaaa aaaaaaaaa aaaaaaaaaa aaaaaaaaa     4380 aaaggtagca gtcgacagat gaattccacc acactggact agtggatccg agctcggtac    4440
caagcttaag tttaaac                                                   4457

<210> SEQ ID NO 7
<211> LENGTH: 17534
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: misc_feature
<222> LOCATION: (1)..(17534)
<223> OTHER INFORMATION: n= a, c, g, t, unknown or other

<400> SEQUENCE: 7
catcatcaat aatataccttt attttggatt gaagccaata tgataatgag ggggtggagt    60
ttgtgacgtg gcgcggggcg tgggaacggg gcgggtgacg tagtagtgtg gcggaagtgt   120
gatgttgcaa gtgtggcgga acacatgtaa gcgacggatg tggcaaaagt gacgttttttg   180 gtgtgcgccg gtgtacacag gaagtgacaa ttttcgcgcg gttttaggcg gatgttgtag    240
taaatttggg cgtaaccgag taagatttgg ccatttttcgc gggaaaactg aataagagga    300
agtgaaatct gaataatttt gtgttactca tagcgcgtaa tactggtacc gcggccgcct    360
cgagtctaga actagtggat cccccaaacg ggccctctag acgcgttgac attgattatt    420
gactagttat taatagtaat caattacggg gtcattagtt catagcccat gatatcatat    480
ggagttccgc gttacataac ttacggtaaa tggcccgcct ggctgaccgc ccaacgaccc    540
ccgcccattg acgtcaataa tgacgtatgt tcccatagta acgccaatag ggactttcca    600
ttgacgtcaa tgggtggagt atttacggta aactgcccac ttggcagtac atcaagtgta    660
tcatatgcca gtacgccccc ctattgacg tcaatgacgg taaatggccc gcctggcatt    720
atgcccagtn catgacctta tgggactttc ctacttggca gacatctacg tattagtcat    780
cgctattacc atggtgatgc ggttttggca gtacatcaat gggcgtggat agcggtttga    840
ctcacgggga ttttccaagt ctccacccca ttgacgtcaa tgggagtttg ttttggcacc    900
aaaatcaacg ggactttcca aaatgtcgta caactccgc cccattgacg caaatgggcg    960
gtaggcgtgt acggtgggag gtctatataa gcagagctct ctggctaact agagaacccc   1020
tgcttactgg cttatcgaga tatctgcaga attcatctgt cgactgctac cggcagcgcg   1080
cagcggcaag aagtgtctgg gctgggacgg acaggagagg ctgtcgccat cggcgtcctg   1140
tgcccctctg ctccggcacg gccctgtcgc agtgcccgcg cttccccgg cgcctgcacg   1200 cggcgcgcct gggtaacatg cttggggtcc tggtccttgg cgcgctggcc ctggccggcc   1260
tggggttccc cgcacccgca gagccgcagc cgggtggcag ccagtgcgtc gagcacgact   1320
gcttcgcgct ctacccgggc cccgcgacct tcctcaatgc cagtcagatc tgcgacggac   1380
```

-continued

| | |
|---|---|
| tgcggggcca cctaatgaca gtgcgctcct cggtggctgc cgatgtcatt tccttgctac | 1440 |
| tgaacggcga cggcggcgtt ggccgccggc gcctctggat cggcctgcag ctgccacccg | 1500 |
| gctgcggcga ccccaagcgc ctcgggcccc tgcgcggctt ccagtgggtt acgggagaca | 1560 |
| acaacaccag ctatagcagg tgggcacggc tcgacctcaa tggggctccc ctctgcggcc | 1620 |
| cgttgtgcgt cgctgtctcc gctgctgagg ccactgtgcc cagcgagccg atctgggagg | 1680 |
| agcagcagtg cgaagtgaag gccgatggct cctctgcga gttccacttc ccagccacct | 1740 |
| gcaggccact ggctgtggag cccggcgccg cggctgccgc cgtctcgatc acctacggca | 1800 |
| ccccgttcgc ggcccgcgga gcggacttcc aggcgctgcc ggtgggcagc tccgccgcgg | 1860 |
| tggctcccct cggcttacag ctaatgtgca ccgcgccgcc cggagcggtc caggggcact | 1920 |
| gggccaggga ggcgccgggc gcttgggact gcagcgtgga gaacggcggc tgcgagcacg | 1980 |
| cgtgcaatgc gatccctggg gctccccgct gccagtgccc agccggcgcc gccctgcagg | 2040 |
| cagacgggcg ctcctgcacc gcatccgcga cgcagtcctg caacgacctc tgcgagcact | 2100 |
| tctgcgttcc caaccccgac cagccgggct cctactcgtg catgtgcgag accggctacc | 2160 |
| ggctggcggc cgaccaacac cggtgcgagg acgtggatga ctgcatactg gagcccagtc | 2220 |
| cgtgtccgca gcgctgtgtc aacacacagg gtggcttcga gtgccactgc tacectaact | 2280 |
| acgacctggt ggacggcgag tgtgtggagc ccgtggaccc gtgcttcaga gccaactgcg | 2340 |
| agtaccagtg ccagcccctg aaccaaacta gctacctctg cgtctgcgcc gagggcttcg | 2400 |
| cgcccattcc ccacgagccg cacaggtgcc agatgttttg caaccagact gcctgtccag | 2460 |
| ccgactgcga ccccaacacc caggctagct gtgagtgccc tgaaggctac atcctggacg | 2520 |
| acggtttcat ctgcacggac atcgacgagt gcgaaaacgg cggcttctgc tccggggtgt | 2580 |
| gccacaacct ccccggtacc ttcgagtgca tctgcgggcc cgactcggcc cttgcccgcc | 2640 |
| acattggcac cgactgtgac tccggcaagg tggacggtgg cgacagcggc tctggcgagc | 2700 |
| ccccgcccag cccgacgccc ggctccacct tgactcctcc ggccgtgggg ctcgtgcatt | 2760 |
| cgggcttgct cataggcatc tccatcgcga gcctgtgcct ggtggtggcg cttttggcgc | 2820 |
| tcctctgcca cctgcgcaag aagcagggcg ccgccagggc caagatggag tacaagtgcg | 2880 |
| cggcccccttc caaggaggta gtgctgcagc acgtgcggac cgagcggacg ccgcagagac | 2940 |
| tctgagcggc ctccgtccag gagcctggct ccgtccagga gcctgtgcct cctcaccccc | 3000 |
| agctttgcta ccaaagcacc ttagctggca ttacagctgg agaagaccct ccccgcaccc | 3060 |
| cccaagctgt tttcttctat tccatggcta actggcgagg gggtgattag agggaggaga | 3120 |
| atgagcctcg gcctcttccg tgacgtcact ggaccactgg gcaatgatgg caattttgta | 3180 |
| acgaagacac agactgcgat ttgtcccagg tcctcactac cgggcgcagg agggtgagcg | 3240 |
| ttattggtcg gcagccttct gggcagacct tgacctcgtg ggctagggat gactaaaata | 3300 |
| tttattttt ttaagtattt aggttttgt ttgtttcctt tgttcttacc tgtatgtctc | 3360 |
| cagtatccac tttgcacagc tctccggtct ctctctctct acaaactccc acttgtcatg | 3420 |
| tgacaggtaa actatcttgg tgaatttttt tttcctagcc ctctcacatt tatgaagcaa | 3480 |
| gccccactta ttccccattc ttcctagttt tctcctccca ggaactgggc caactcacct | 3540 |
| gagtcaccct acctgtgcct gaccctactt cttttgctct tagctgtctg ctcagacaga | 3600 |
| acccctacat gaaacagaaa caaaaacact aaaaataaaa atggccattt gcttttttcac | 3660 |
| cagatttgct aatttatcct gaatttcag attcccagag caaaataatt ttaaacaaag | 3720 |
| gttgagatgt aaaaggtatt aaattgatgt tgctggactg tcatagaaat tacacccaaa | 3780 |

```
gaggtattta tctttacttt taaacagtga gcctgaattt tgttgctgtt ttgatttgta    3840
ctgaaaaatg gtaattgttg ctaatcttct tatgcaattt ccttttttgt tattattact    3900
tattttttgac agtgttgaaa atgttcagaa ggttgctcta gattgagaga agagacaaac   3960
acctcccagg agacagttca agaaagcttc aaactgcatg attcatgcca attagcaatt    4020
gactgtcact gttccttgtc actggtagac caaaataaaa ccagctctac tggtcttgtg    4080
gaattgggag cttgggaatg gatcctggag gatgcccaat tagggcctag ccttaatcag    4140
gtcctcagag aatttctacc atttcagaga ggccttttgg aatgtggccc ctgaacaaga    4200
attggaagct gccctgccca tgggagctgg ttagaaatgc agaatcctag gctccacccc    4260
atccagttca tgagaatcta tatttaacaa gatctgcagg gggtgtgtct gctcagtaat    4320
ttgaggacaa ccattccaga ctgcttccaa ttttctggaa tacatgaaat atagatcagt    4380
tataagtagc aggccaagtc aggcccttat tttcaagaaa ctgaggaatt ttctttgtgt    4440
agctttgctc tttggtagaa aaggctaggt acacagctct agacactgcc acacagggtc    4500
tgcaaggtct ttggttcagc taagctagga atgaaatcct gcttcagtgt atggaaataa    4560
atgtatcata gaaatgtaac ttttgtaaga caaaggtttt cctcttctat tttgtaaact    4620
caaaatattt gtacatagtt atttatttat tggagataat ctagaacaca ggcaaaatcc    4680
ttgcttatga catcacttgt acaaaataaa caaataacaa tgtgaaaaaa aaaaaaaaa    4740
aaaaaaaaaa aaaaaaaaaa aaaggtagc agtcgacaga tgaattccac cacactggac    4800
tagtggatcc gagctcggta ccaagcttaa gtttgggctg caggaattct gatggctctc    4860
aaaattcctg cctcctttag ggataaaaga ctttaagact ttttaacaaa aagaaaaag    4920
aaaaaaaaaa ttcctgcctc ctggtgtaca cacacagaag ggttccctcc ccttgaatgt    4980
gaccaggatc tgtgaaaata acgggatagc cgctcctgtg attaggttat gtggtagact    5040
agagcaagat tctcctgctg gttttgaaga agtcagctgc catgttgtga gactgtcatg    5100
ggctagggca tgagcctttta aatatctggg agcaacccct ggccagcagc cagtgagaaa    5160
acgggccctc agtcctacaa tcacaaggaa ctaaattctg ccaacaacct gaaggaactt    5220
tgaagaggat catgagtccc ttgattcagc ttgatgagcc cctgagcaga ggatacagct    5280
aacttgtact agggaagtat aaaaaacatg catgggaatg atatatatca actttaagga    5340
taattgtcat acttctggga atgaagggaa agaaatgggg ctttagttgt attatgatct    5400
ttaatttctc aaaaaaaata agatcagaag caaatatggc aaaatgttaa tacttttgtg    5460
ggtacgtagg tattcagcat acccttttt ctgagttcaa atatttttat aattaaaatg    5520
aaatgcaggc caggcacagt ggctcatgcc tataatacca gcactttgcg aggccgaggt    5580
gggaggatgg cttgaggcca gaccagcctg gccaacatgg caaaacccca tctctactta    5640
aaaaaaaaaa aactatatat atatatatgt gtgtgtgt gtatatatat atatgtatat     5700
atatttatat atgtgtgtat atatatatat gtatatatat ttatatatgt gtgtgtatat    5760
atatatatac acacacacac atatatacat acatacatac acacacacac acacacaatt    5820
agccaggcat ggtggcgcac acctgtagtc ccagctactt gggaggctga gacatgagaa    5880
ttgcttgaac ctgggaggca gagtagttag tgagctgaga tcataccact gcactccagc    5940
ctggtgacag agtgagactc tgtcttaaaa aaaataaaaa ttaaaattaa atgcaaaagg    6000
tccaagtgaa ttgaagagga aagggtatc aaggaaggtt ttgtggaggt gacgtttgag    6060
ctgggtctta aatgacttaa acatgggata agaagggagg gaataaggac atttcaggta    6120
cgagaaataa ggagcaaaca gtggaaacaa cctaacgtct gtcaaccagt gaatggataa    6180
```

```
caaaaatgta attcagatgg tatccaactt acgatggttc aacatgagat ttttctgact    6240
ttaggataga tttatcaaag tagtaaatcc attttcaact tatgatattt tcaacttcag    6300
atgggtttat caggacacag ttgaggaaca cctgtctatc catacaattt ggcaataaaa    6360
aggaaatgag tgcagatata ctccacaaca tgaatgaacc ttgaaaacat taagtgagag    6420
aagccagata caaaaggcca catattgtat gattctattt atacaaaatg tccagaatag    6480
gcaaatctta tagacagcaa gtaggtagat gatcagtttg ctaggtgctg ggggaagggg    6540
aaatggggag tgatggctaa ggggattggg tttcttgtg gggcaatgaa atgttttaa      6600 aattgagcgt gataatgatt gcacaatgct gcatatatat ataatctata gattatatat    6660
atataaagag aggctgttag acagtgataa gtgatatata tatatatata catagagaga    6720
gagagagaga gagagagagg ctgttagtga taagtgatca ggaaaataaa agtattgagg    6780
aggaatacga agttgacggt gtgaaaacat gagattttat ataggatggc cagggaaggc    6840
cttaatgaga aagtgactta tgagtaaaaa caagggatcc taaaccttag catgcatcag    6900
aatcactcgg aaacttgtta aagcatagct tgctgggcct catcacagat attttgattc    6960
ggtaggttct tgtctgatat taatactttt ggtctaggga accacatttt gagaaccact    7020
gagctaaagg aagtaaaggt ttcccttagt ttactagctg gtaacactgg cccaggaggc    7080
cttcctggtg acccctaagg aattatccaa actcttgttt ttagatgctt tattatatca    7140
aactctcctt taaacaagtg gcccatctgc tgggatttgg aagcctgtaa tactgaaatt    7200
ttcatcataa tggaaatttt aaaaacagaa tttgacccac ctgttttaa aacactttca     7260 ttacttaaca agaggtctaa tcttgggcaa gtcttgaaat ttctctggcc ttagtttccc    7320
atgtgttaaa tgaaacttga agcagttggt ctcttatagt ctcctgactc taacattcta    7380
agaattatat ttgtacaata actcaaaaat cacataattt aatttaccat atggactcca    7440
aaatatattt tctcattagg ctaaacttga tctgcatttt ctggatgtgt ccatattctt    7500
ggactacact aaaacatgat accaatgctt cctctcacca taaaccctca cttcgctttc    7560
tacatttaag aattttatag ctggaagagt ccttaacaga aaataccatc taataattac    7620
ccctcaaaat cgagaaagtc ctatctgttc ttatgctagt tataagaatg aggcagcatt    7680
tcacataatg gttataaaca ctgccacaag aagattcatg atgtgttgtt tatctgtagc    7740
tctcatcata ctctgtcata taactatagc attaagattt taatgttcta tatattcttc    7800
taagacagtg tttaccagag taaggcacaa aagatccact ggtttgcaag aaagattaga    7860
acttttaaat ttttttacctc accttgttta atctatattt ttgtatgtat tttgtaacat    7920
atatattatt attaccataa atcatatata atttaaaatg catatattag gggtaaatgc    7980
tcaggaaact ttttataaat tgggcatgca aatacaagtt tgaagactca ctgttctagg    8040
tattaaaagt aaagttataa ccaagtaaag cttccacctt ttcatgtctc aaagcagttt    8100
attgttggag gtaagatctc ttagaagcct aaacaggtcc aagtacagaa tgaagtaagg    8160
ctagcccata acttgtggca agcaattcat actatttctc tcatgctgag ctctcctcag    8220
tgaagcagct actatagaca actgcagcct attggtagcc tattttacag gcaggaaaaa    8280
aattactttt tattcaaagt ggaactcagg acatggggag aaaatgaata caaaaaatag    8340
ggtcaatcca aaggcacaca gcaaatgagt aacacagtta tgttttttc ccatttgtat     8400 gaggtcccag taaattctaa gtaaactgca aatttaataa tacactaaaa aagccatgca    8460
attgttcaaa tgaatcccag catggtacaa ggagtacaga cactagagtc taaaaaacaa    8520
aagaatgcca ttattgagtt tttgaattat atcaagtagt tacatctcta cttaataaat    8580
```

-continued

```
gagaaaaacg aggataagag gccatttgat aaaatgaaaa tagccaagaa gtggtattag    8640
agacttgaat acaggtattc gggtccaaag ttcatctgct caaatactaa ctggggaaaa    8700
gagggaaaaa tatttatata catatatatc tgcacacaaa aatacccca aaagacaaaa     8760 tgaggccagg caggtggct cacacccgta atcccgtac tttgggaggc tgaggcaggt      8820
ggatacctga gatcaggagt tggagatcag cctggtcaac atggtgaaac cctgtctcta    8880
ctaaagataa aaaattagc caggcatggt ggcgtgcgcc tgtaatccca gctacttggg     8940
agtctgaggc aggagaatca cttgaactgg aaggggagg ttgcagtgag ccaagatcgt     9000
actactgcac tccagcctgg gcagcagagt gagactccat cacaaaata aataaataaa     9060 taaaatacaa tgaaacagaa agttcaaata atcccataat cttaccacca agaaataact    9120
ttcactcgtt atacttattg atttttccat aataaatgta ctttactgtg actatcatga    9180
aaagaaagtt attttagaaa cagagaactg tttcagatca aatctatgta gtagaacaga    9240
gccattaggt ggggaaagacg agatcaaact aaatctcaga aggcctaaaa ggctaggtcc   9300
attccagcac taaaaactga ccagacaagt aatggcttca acagcttcta aatatggaca    9360
aagcatgctg aaagggaagg acaggtctaa cagtggtata tgaaatgaac aggagggca    9420 aagctcattt ctcctctgaa gttttccaaa gatgctgagg aggacattag tttgacatga    9480
ccctgatatg ggacaagata atttcacaga agttttacat gttaaagttt tcttatagat    9540
actcattcaa gtaagcaatg aacactaaaa tctaaagaaa gaaagagct ttagagtcag     9600 gtctgtattc aaattcaagc tctaccactt actggttctg tgactttggg caagtctttt    9660
aaccttatta agtcttaatt tcctgatttg taaaatgggg atatcgtctc cctcacagga    9720
ttgttgtgaa acttttatga gattaatgcc tttatatttg gcatagtgta agtaaacaat    9780
aactggcagc ttcaaaaaaa aaaagcagta gcattccatc atttattatt ggttactctc    9840 aaaaagttttt tcaatgtact agaagataaa tattcaaata ccttaatatc tccattattt    9900
tcaggtaaac agcatgctcc tgaacaacca atgggtcaac aaataaatta aagggaaat     9960 ctaaaaacat cttgatatta aactacatgg aagcacaata taccaaaacc aatggttcac   10020
actaggagaa ttttaaggta caagaaaact ctttgagatt tcttaaaata atagtatgtc   10080
tgaatttatt gagtgattta ccagaaactg ttgtaagagc tctacttgca ttatagcact   10140
taatcctctt aactctatgg ctgctattat caacctcacc ctaatcacat atgggacaca   10200
gagaggttaa gtaacttgcc caaggtcaga gttaggaagt actaagccat gctttgaatc   10260
agttgtcagg ctccggaact cacactttca gccactacat aatactgctt tgctatcttt   10320
taggaaacta tgtgagtcta cctcacatag actcacatag gtttgttttt tttttttttt   10380
taaaggctat cttttccccc atcaatgttt tttgaaggat cccaaattag agtcccacag   10440
aggcagacag cagtacttga caatatggac atttaaggtt aatgttggat tctactgtct   10500
ttttactaca tgacctaggg aacgataatt aacctagact gcttccaagg gttaaataac   10560
ccatttagtt atactatgta aattatctct tagtgattga ttgaaagcac actgttacta   10620
attgactcgg tatgaagtgc ttttttttct tccctttcaa gatacatacc tttccagtta   10680
aagttgagag atcatctcca ccaattactt ttatgtcccc tgttgactgg tcattctagt   10740
taaaaaaaaa aaaactata tatatatata tctacacaca catatgtata tgtatatcct   10800
tatgtacaca cacaaacttc aaattaaatg agaactagaa gatttgagaa gttagctagc   10860
taatatccat agcattatga tattctaaat gatatgaatt ataagaatta ggtttcctga   10920
aatgaatgac tagaaaactt tcaagtagag attagtaaaa attaaaaagt cctaatcggc   10980
```

```
cattactgat tgatgttttt taagagtcct aaaaaatggg ttacatccat ttttaagtgg   11040
gtagtattat aacagccacc catcttcaat cacagtgatt tctgaattgt gagggaagtt   11100
attagcatga caggtgtctg gttctggccc tgtacgattc ccatgagtca agcaaattgt   11160
aagggctggt ctatatcaca cccaaccccca aggatatgtc cctcaaaagt ctagcccagg   11220
ccccgtcatc ttcagcatca tctgggaaac caggtctgat tagtagtcct ttaaggaata   11280
cctcttaggc tcccatttta ctgctatcac agaatccaat aaaaccctta caggagattc   11340
aatgggaaat gctcaacacc cactgtagtt ggtggtgaca atgaccataa tttggctgtg   11400
ctggattcag gacagaaaat ttgggtgaaa gagcaggtga acaaaagagc ttcgacttgc   11460
cctagcagag agcaagccat accataccac aaagccacag caattacaac ggtgcagtac   11520
cagcacagta aatgaacaaa gtagagccca gaaacagacc cagaactata tgaggattta   11580
gtatacaata aagatggtat ttcgagtcag tagggaaaag atgaattatt caataaatga   11640
tgtttggcca actagtaacc catttgggaa aaaataaaag tatggtccct acctcacagc   11700
atacacaaaa ataaattcca gacggattaa aatctaaatg taaaaaataa agccataagt   11760
ggactggaag aaaatagaga attttttta acatccgtag aaagggtaaa acccaggca    11820
tgacatgaac caaaactgaa gaggttctgt aacaaatacc cccttttata tattgggctc   11880
caacaataag aacccatagg aaaatggaga atgaacacaa atagacaatt tatagaagag   11940
aaggttataa ggtgtaaaat tatatctatc tgagaaacaa acactaaaac aatgtgattc   12000
tactgttctc ccacccatac tggcaaaact taagcctgat aatatgctga ggggaaataa   12060
gcactcttgt tggtgagagt attaattggc atagcttctt ttgaaaatga catagcaata   12120
cctgttaaaa ttgcaaacat gcatgtcact taatccagta atcccacttc tgggaatcaa   12180
tgctacaaaa acactgacaa gtatacaaag atacattcaa gagtgttcac tgggccgggt   12240
gcggtggctt catgcctgta atcccaggga ggcagaggca agacgatcgc ttgaccccag   12300
gagttcaagg ccagcccgag aaacacagca agaccctgtc tctctttttt ttatttaaaa   12360
aataaatgtt cactgtatca gttgttcaca aaaacaaacc aacatgtcca ttaacaggga   12420
accatttaaa ttaatcaagt tcatctacac aatgtaatac catgcaacta ttaaaaagca   12480
cctgataatc caaagcacac tgagacagaa taatgctatt aaaaacacca agtagtggaa   12540
cactgtgttg cctatgacac cattttttatt caacatttaa acaaatttgt aacagcaatt   12600
acatgagtag tgacaatggc gtttatgaga cttttcactt ttatgtgctt ctattttgt    12660
tatgcttcta tatatacatc catttattat ggagtgttac tttcaaaaat cacaaatggg   12720
ccagtattat ttggtgttgc aaggtgagca tatgacttct gatatcaacc tttgcatatt   12780
acttctcaat ttagggaaat tacagacatc ccttattcta actaacttaa aacccagcat   12840
ttcaaacata cagaattgat ggggaaaaaa aagaaagaag aaagaaagaa aaggcaacaa   12900
gcttcagatg acagtgactc acatcaaatt atttataaaa tctgttaaat agtgccatct   12960
tctggagata cctggtatta cagtccaact ccagttgatg tctttacaga gacaagagga   13020
ataaaggaaa aaatattcaa gaactgaaaa gtatggagtc atggaaaaat tgctgtgatc   13080
caaaggctac ggtgatagga caagaaacaa gagaactcca agcagtaaga cactgctgtt   13140
ctattagcat ccaaacctcc atactcctgt ttgccccaag gcttttttaa aaaatagaga   13200
caggatctca ctattttgct caggctggtc ttgaactcct ggactcaagc tatcctcctg   13260
cctcggcctc ctaaagtgcc gagattacag gcttgagtca ccatacctgg ctattttattt  13320
tttcttaact ctcttgcctg gcctatagcc accatggaag ctaataaaga atattaattt   13380
```

```
aagagtaatg gtatagttca ctacattgga atacaggtat aagtgcctac attgtacatg    13440
aatggcatac atggatcaat tacccacct  gggtggccaa aggaactgcg cgaacctccc    13500
tccttggctg tctggaacaa gcttcccact agatccctt  actgagtgcc tccctcatct    13560
ttaattatgg ttaagtctag gataacagga ctggcaaagg tgaggggaaa gcttcctcca    13620
gagttgctct accctctcct ctaccgtcct atctcctcac tcctctcagc caaggagtcc    13680
aatctgtcct gaactcagag cgtcactgtc aactacataa aattgccaga gaagctcttt    13740
gggactacaa acacataccc ttaatgtctt tatttctatt ttgtctacct cttcagtcta    13800
ggtgaaaaaa taggaaggat aatagggaag aactttgttt atgcctactt atccgcccct    13860
aggaattttg aaacctcta  ggtagcaata agaactgcag catggtatag aaaaagagga    13920
ggaaagctgt atagaaatgc ataataaatg ggcaggaaaa gaactgcttg gaacaaacag    13980
ggaggttgaa ctataaggag agaaagcaga gaggctaatc aacaaggctg ggttcccaag    14040
agggcatgat gagactatta ctaaggtagg aattactaag ggctccatgt cccttagtg    14100 gcttagtact atgtagcttg ctttctgcag tgaacttcag acccttcttt taggatccta    14160
gaatggactt ttttttttta tcggaaaaca gtcattctct caacattcaa gcaggcccca    14220
agtctaccac actcaatcac attttctctt catatcataa tctctcaacc attctctgtc    14280
cttttaactg tttttctata ccctgatcaa atgccaacaa aagtgagaat gttagaatca    14340
tgtattttta gaggtagact gtatctcaga taaaaaaaaa gggcagatat tccattttcc    14400
aaaatatgta tgcagaaaaa ataagtatga aaggacatat gctcaggtaa caagttaatt    14460
tgtttacttg tattttatga attccctaaa acctacgtca cccgcccgt  tcccacgccc    14520 cgcgccacgt cacaaactcc accccctcat tatcatattg gcttcaatcc aaaataaggt    14580
atattattga tgatgttaat taacatgcat ggatccatat gcggtgtgaa ataccgcaca    14640
gatgcgtaag gagaaaatac cgcatcaggc gctcttccgc ttcctcgctc actgactcgc    14700
tgcgctcggt cgttcggctg cggcgagcgg tatcagctca ctcaaaggcg gtaatacggt    14760
tatccacaga atcaggggat aacgcaggaa agaacatgtg agcaaaaggc cagcaaaagg    14820
ccaggaaccg taaaaaggcc gcgttgctgg cgttttccca taggctccgc cccctgacg     14880 agcatcacaa aaatcgacgc tcaagtcaga ggtggcgaaa cccgacagga ctataaagat    14940
accaggcgtt ccccctgga  agctccctcg tgcgctctcc tgttccgacc ctgccgctta    15000
ccggatacct gtccgccttt ctcccttcgg gaagcgtggc gctttctcat agctcacgct    15060
gtaggtatct cagttcggtg taggtcgttc gctccaagct gggctgtgtg cacgaacccc    15120
ccgttcagcc cgaccgctgc gccttatccg gtaactatcg tcttgagtcc aacccggtaa    15180
gacacgactt atcgccactg gcagcagcca ctggtaacag gattagcaga gcgaggtatg    15240
taggcggtgc tacagagttc ttgaagtggt ggcctaacta cggctacact agaaggacag    15300
tatttggtat ctgcgctctg ctgaagccag ttaccttcgg aaaaagagtt ggtagctctt    15360
gatccggcaa acaaaccacc gctggtagcg gtggtttttt tgtttgcaag cagcagatta    15420
cgcgcagaaa aaaaggatct caagaagatc ctttgatctt ttctacgggg tctgacgctc    15480
agtggaacga aaactcacgt taagggattt tggtcatgag attatcaaaa aggatcttca    15540
cctagatcct tttaaattaa aaatgaagtt ttaaatcaat ctaaagtata tatgagtaaa    15600
cttggtctga cagttaccaa tgcttaatca gtgaggcacc tatctcagcg atctgtctat    15660
ttcgttcatc catagttgcc tgactccccg tcgtgtagat aactacgata cgggagggct    15720
taccatctgg ccccagtgct gcaatgatac cgcgagaccc acgctcaccg gctccagatt    15780
```

```
tatcagcaat aaaccagcca gccggaaggg ccgagcgcag aagtggtcct gcaactttat   15840
ccgcctccat ccagtctatt aattgttgcc gggaagctag agtaagtagt tcgccagtta   15900
atagtttgcg caacgttgtt gccattgctg cagccatgag attatcaaaa aggatcttca   15960
cctagatcct tttcacgtag aaagccagtc cgcagaaacg gtgctgaccc cggatgaatg   16020
tcagctactg ggctatctgg acaagggaaa acgcaagcgc aaagagaaag caggtagctt   16080
gcagtgggct tacatggcga tagctagact gggcggtttt atggacagca agcgaaccgg   16140
aattgccagc tggggcgccc tctggtaagg ttgggaagcc ctgcaaagta aactggatgg   16200 cttcttgcc gccaaggatc tgatggcgca ggggatcaag ctctgatcaa gagacaggat   16260
gaggatcgtt tcgcatgatt gaacaagatg gattgcacgc aggttctccg gccgcttggg   16320
tggagaggct attcggctat gactgggcac aacagacaat cggctgctct gatgccgccg   16380
tgttccggct gtcagcgcag gggcgcccgg ttcttttgt caagaccgac ctgtccggtg   16440
ccctgaatga actgcaagac gaggcagcgc ggctatcgtg gctggccacg acgggcgttc   16500
cttgcgcagc tgtgctcgac gttgtcactg aagcgggaag ggactggctg ctattgggcg   16560
aagtgccggg gcaggatctc ctgtcatctc accttgctcc tgccgagaaa gtatccatca   16620
tggctgatgc aatgcggcgg ctgcatacgc ttgatccggc tacctgccca ttcgaccacc   16680
aagcgaaaca tcgcatcgag cgagcacgta ctcggatgga agccggtctt gtcgatcagg   16740
atgatctgga cgaagagcat caggggctcg cgccagccga actgttcgcc aggctcaagg   16800
cgagcatgcc cgacgcgag gatctcgtcg tgacccatgg cgatgcctgc ttgccgaata   16860
tcatggtgga aaatggccgc ttttctggat tcatcgactg tggccggctg ggtgtggcgg   16920
accgctatca ggacatagcg ttggctaccc gtgatattgc tgaagagctt ggcggcgaat   16980
gggctgaccg cttcctcgtg ctttacggta tcgccgctcc cgattcgcag cgcatcgcct   17040
tctatcgcct tcttgacgag ttcttctgaa ttttgttaaa attttgtta aatcagctca   17100 tttttaacc aataggccga aatcggcaaa atcccttata aatcaaaaga atagaccgag   17160
atagggttga gtgttgttcc agtttggaac aagagtccac tattaaagaa cgtggactcc   17220
aacgtcaaag ggcgaaaaac cgtctatcag ggcgatggcc cactacgtga accatcaccc   17280
taatcaagtt ttttggggtc gaggtgccgt aaagcactaa atcggaaccc taaagggagc   17340
ccccgattta gagcttgacg gggaaagccg gcgaacgtgg cgagaaagga agggaagaaa   17400
gcgaaaggag cgggcgctag ggcgctggca agtgtagcgg tcacgctgcg cgtaaccacc   17460
acacccgccg cgcttaatgc gccgctacag ggcgcgtcca ttcgccattc aggatcgaat   17520
taattcttaa ttaa                                                    17534
```

```
<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtaacactgg cccaggaggc ctttctggtg acccc                              35

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 9
tgaccgggtc ctccggaaag accactgggg att                                         33

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tagttccttc tgcctggaat ac                                                     22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caagtcacaa ggatggacta ca                                                     22

<210> SEQ ID NO 12
<211> LENGTH: 18524
<212> TYPE: DNA
<213> ORGANISM: Homo sapiens

<400> SEQUENCE: 12
tagttccttc tgcctggaat acttcctcat ctcacttgct ttcctgcctg gcagcttcct            60
acttgccctc tggaaccagc tctagggtca ccacatctct gcttctgagt gcctcctcag           120
acacagtctg tatttcctct tccaagctct catcacaaac attgtgctgt attatatgtt           180
tctgtgtggt cttccttcta tgaggaagcc ttggaaagca ggagacttat tttagtcttc           240
tttatgtttc ttttattccc aacacattat gtctgcccca tagaccttt caataaatga            300 ttattgagtt agtgactcct tttacatgct gacaaatgtg gctcttatta ctccccattt           360
cagtatcaca tatttgtaaa agtgaatcct tcttaatcgt tttactttc tcctagtaaa            420 ttcctcatct atgcctgtct gctgctgttc tctgtgctgc tggcccttcg tttggatggc           480
atcatacagt ggagttactg ggctgtcttt gctccaatat ggctgtggaa gttaatggtc           540
attgttggag cctcagttgg aactggagtc tgggcacgaa atcctcaata tcggtaatac           600
tgctttatac aacccattgg tctctagcat gagggagcaa tatcttgact tttctcactt           660
ttgatgaagt aaggaccatt ttattttcta cctatctggg gtcttagaac tatagtataa           720
gctaacagat ctcttctgtg tttttgaaaa tttagtcttt ggtatgtatt ttcttacaaa           780
agcagtgcca tttgggggta agttgccagc cagctcacag atgcctatat aatccaaaat           840
gcacccaaaa tacagaactg gtatgccata ctagactaag cagcatgaaa ccaccctgtt           900
tttaggaaaa gacactcata ttatgtttgg tcatgaaaga tctttctcca atacagtttt           960
ggaactgggg ctcccctigt cccacccctcc agtcccaga gctttaggac tattagcagt          1020
gtaggggagg tggcttgacc aggagaccat gagtccctga dacagcagct ggggaatgag          1080
gaaagtcaaa gattggatgc cgagaaggaa agcagagcct ttgggggcag gggagagggg          1140
taccctttac cgtttccaac tcttgccctc cctgctcttg gatgcctccg ctggcccaaa          1200

```
ttcctgggag ttgctcacgc cagcatgcaa cctgcttgtt gctgggacct gcgagagtct   1260
ttcccttctc tgccacagag actgtaacta cataaaggga aaaaggggga cttaagactg   1320
ggaggctatt atgaacctcc actgggaaaa tgaggagtac aggaattccc agaaggcagc   1380
tgctcatgtg ggaaaagtgt aaagttgaaa ctaccgcacc ttttttttt ttttttttt    1440
ttttttttt ttgagacaga gtttcgctct tgttgcccag gctggagtgc aatggtgtga   1500
tctcggccca ctgcagcctc cacatcccgg gttcaagtga ttctcctgcc tcggcctcct   1560
gagtagctgg gattacaggc acctgccacc atgcccagct aattttttgt attttagta    1620
gagatagggt ttcaccatgc caggctagtt ttgaactcct gacatcaggt gatccacccg   1680
ccttggcctc ctgaagtgct gggattacag gtgtgagcca ccacgtccgg ccactacatc   1740
aactttttaa attttgtttt actaaatatg aaaatgattc agattgtgta aattacatat   1800
cacatacatg tctaagaact gtaaaacagt tacacagaga gccttggcag gtgagggaca   1860
ttcatgtata gctgtttcag agttcttaga tttttttga aagattgatg acctgtgtgg    1920
ctgtatgtgt tttattttt tatgagatat tttcagatat ctaatattaa ttgcttctca   1980
aagaatgcaa agttaaataa acatttaggt tctactaatt gatatttaga atatattcaa   2040
acttctcttt gttggtctta tttaagatgt tttgagcaag gaaaggaatt gtgtatgtgg   2100
ggttgaatgt aaggaatgta caggcgtggt cattctcatg ttaacattaa ccagtggaac   2160
atggttgggt cctacaggaa taacctctga tagcattttc tctatgatct aacttccggt   2220
gtatttgtca cccacaatac atgtatatca taaatgttca tctgtatttt gaataaacat   2280
tgtaggcctt tcagatgcat tatagagcct tttcctgatt agcggcctta ccattgctca   2340
attgtagatc tgttaaggtt attgtgcatg atacttagct aattaaactg attttgtttg   2400
agaacagttt taactcttgt tcttctttct ctttcatgtg caggtgttaa tttatcttaa   2460
tggaatagaa aggaaaatga aaatcattta tacgttttat ttgcatttaa aaatagcacc   2520
aaaaaaagaa tgttttcaaa agtaaaatat tttgctcagt tattcagatg tcaatttctt   3600
```

```
acccttttgtt aggaagagct tgatcattac caactctaca tcatgagaca acaaggcaac    3660
aaaagatgat ggaaataaca attttctttt cttcacttag aacactagct tttcacccag    3720
gacatcagcc ttctcccagc ttcacatcct gtatcaatca dacagaaaca gaactgatag    3780
gttagataca gatatatgta taaagagagt taaggaactg gctcacatta ctgtggggct    3840
ggcaagtctg aaatctccag ggcaggtgaa caggctggag acctaggagg agttgacact    3900
gcagtcctgg cacagaattt tttcctctcc aggaaaccac agttttttgct tttaaggcct    3960
tcacctgatt gcatgaggcc cacccatgct atggagggta gtctcctta ttcaaagtca     4020
gtaccttcac tgcaacagca agcttagtgt ttgattaaat aactgggtac tatagcccag    4080
ccaagttgac actcaaaact gaccatctcc ccacctcaga ccccatgatt tagcacctcc    4140
cctgctgtct ggttagctta tcctgatgtg cccctgtgtt tgtttattca ttcaataaac    4200
atttatcaag tatttactag atgccaagcc ctttttccct aagcatagag gatatgcaga    4260
tgaataaaat accaggacta gtaataatag taatgaaagt aattgcagat aacgtttatt    4320
gagcacttac tgtgtgccag gcattgtgcg aggcacatta catgtggtag ttttcttact    4380
aactaactct gtgaggtagg tccagagaag ataagtcatt tgttcatggc acatgtgaa    4440
ggggcaggac caggattccg tttgagtcag cccgactcta aagcccgggc ataactac     4500
ataactgcat agaagctgag ggcccaaagc tgaatactga tgggttgagg ggagaactag    4560
aggctgtaga tgcctggttt tgagccgtgt ggatgaagag tgaagggaga agactgcagt    4620
tggcttagga agtaaacata gcagctgtag ggtgggtcag gcatataagc ctagacccca    4680
ggtatgggcg tgaggggaag gtatgtagac agagggacgg tgatggagca aggccctgtg    4740
ggactcaggg agaatgggac ctagagcacc aggaagggtt tggccttgaa caaggggagc    4800
tattccctga ttttcatgct ggtggaaagg ccacagcatg ggtatagtgg taggtaggag    4860
tgagccgtgg agggagagta tctgatggtc cactttcacc ctccctacaa ttcccagttt    4920
atatcaggga cttgagcatc catggatttt ggtatccaca gggggtcctg gaaccaatcc    4980
cccacagata ctgagggaca actatacaag gactaggact gcattgggcc tgaattacag    5040
aaagtaagtc tttcatatat tcacactcta ggcattcctg cccttggaag aaacaacata    5100
ccaggagctg agctccctcc tcctgtgatg caagaacagt acctatgttg gtgaggggt     5160
ggtctggagt aggctcatac agagatggga aggaggagtt gagggtctgc caggaagccc    5220
tgtgttggga gggaagggat ggcattttg ggacacattg aagcctagag caggaaaca     5280
ctccatcagc tgagtggact gtggcgattc agatccgacg ggagcacaag gtggaagga    5340
aggaactgtg ggagttgaga agagagggag cctctacaga gggattgggg caaatagggg    5400
ccacgtcctc agcccacaga gcatgtgctg aagtgcccca ggcaccccag tgcactcaca    5460
gggcaccagg ggatagtgga cattttgagg aaaacagtaa tacctgacat tgttgggac    5520
accatacaaa ctactagctt gaaatagttt acaggtttat ttttaggcca cactgcattc    5580
ctttcagtga cgtcgtatct ttaagaagct gggttttcag cagttgctgt gaaaacaaaa    5640
aaggctaatg ctgtgtgaaa atccgggtga agaacaggta acgagtggga gcaccttgtc    5700
tgattccaag gcgtgggaaa tggtgagcta cctgacaggc acacgcatcc cactgggaat    5760
tagttttggt tatttaagaa taatattaac attttttcttt agatttatat gaattatttt    5820
ttctagtggc tacttagaaa tacttactaa gttagatgta attacttaaa tcagtgcaac    5880
tgttggcatt cccagccaca ttagggattt cttttggcct agaggtctat ggaggaatta    5940
ctaaattccc catgtaccta tgtactgaga acttttggga agctctgggc ctggtcccag    6000
```

```
atttcaattt tgtgggcaag aatgtacttt accagagtga ggagcagcct gcagggcgtt    6060
tgggctggag gcgggaggtt agtaagdggt tgctgaagtg gtaggcggat ggtgccgaag    6120
aaggcctcac taggcagtca tcatcaggat aggaagtggg cacgggattc aggagaaatc    6180
tggactttac agtggacagg atgtggtgac tgaacgtgac agtgtgggaa aaagaatgca    6240
gggtgattcc cgggctcatg gcttgagaaa tgagaccact gttgtgcctc caagtgacat    6300
gggaggctat agaaagtgac atgggaggct atagaaagtg acatgggagg ccatagaaag    6360
tgacatggga ggccatagaa agtgacatgg gaggccatag aaagtgacaa gggaggccat    6420
agaaagtgac atgggaggcc atagtgacat gggaggccat agaaagtgac atgggaggct    6480
atagaaagtg acatgggagg ccatagaaag tgacatggga ggccatagaa agtgacatgg    6540
gaggccatag tgacatggga ggccatagaa agtgacatgg gaggctatag aaagaggaga    6600
tacaaggttc taagtgcagg cgataatgat ctctatttgg gactggcttc atttgaggtg    6660
cctttaggag agccgagtgg cctatgcaca gctgggtctg ctatgcagca ggaaggctaa    6720
gttggagaca gatgtgagaa ctaaccatga aggaggtaat aatgcagacc aagggtctgg    6780
ttgaaatttc ttctccccca gtccaggdtg cagcgggtga gtgaaaatat gtgtgtttgt    6840
gtgtctgtct tcctagtcgg gagagaagac tgagtttgtg gctctgcgga gcatcaccat    6900
ttaaggaggg ggaaaaggag acagaaggaa ttaccagaac actccagagg gctccaagac    6960
tgtatggtgg gatctagatg gccaggagga ggggagcaaa aaggaaagag tcatccacag    7020
tatcagtagg atgccagttg aagtgttttt gctgcctccc ggttatcggt gactttgatg    7080
aaagctgtct tctggtggtc atggdggtgg aggccagatc acaaggaagc tgggaatggt    7140
agatgagata gtaggggctt gcatattcat tactgtctcg cagagagaaa cctgaggcta    7200
agaggggtct tggatcaaag gatggggtgg gtttatctgg tttcgdggct tttgtttta    7260 atgagaagga gtcatttctg tgctgctagg agggatcaat ggaataggtg gggttaaaga    7320
tacagtacgg aatctacagt tgatggcttg atgtgacaag gtcctcaagg agcctgaaag    7380
gaaggggtgg ggtccaaggg caaaaccgag gtatgagaag aaggatgcac aaggatggtt    7440
tcgagtagac agtattgttg gtagggacat gaaggaagtt tagtggtcta ttgcagctag    7500
cctgtgttcc cagtgaacct ggaaacaagg ttctcatctg tgctcaggcc tcaggccaga    7560
aagggcaagg cagcagaggg gcaaggcagc aggctgagcc ccatttcccc ttgccataat    7620
actgctgtgc ccctctggta ccgaaaatca ggagtttcca gtgcaatata atattataca    7680
agttacactg tattataatg tgtattgtct tttagtgtgt taaccaaatt actgcagtat    7740
taaatgcaaa ttatactttg tttaactgat tcttctcttc atttttagtt agaaatcctg    7800
tgttctgtca acattctcca gtttatattc attgccttaa gactgdacaa gatcatccac    7860
tggccctggc ttgtatgtaa cttttaaaat ccttaaataa acttcttttt tattataaaa    7920
gtaattcata ttcactgtac aaagcttgga aaagacggac aagcagaagt aatagcctaa    7980
tagtcaccca taatcccacc atggggagat aacatggtta gtgtttttat gtctgtgttt    8040
tatacaaaca gtttggatat aactgtgtgc accattttgt atcctgattt ttttgtttta    8100
atgttgtatc ataaacattt tatcatgtta ataaaggtc tttataaaca tgacttctaa    8160
agtttaattg atacaaaata ttcttcaagt gcatgtatca gaccatcctc ttatttctaa    8220
aatatggtat ttccattgtt gccagtgttg aatgatttta aatcatactg cagtatatat    8280
gtttatgcat taaaatttt gccttttgtt ttttggttgt tttcttagga aatagtccag    8340
aaatagtgtt actgagctag aggttgggaa ctatttgaga ttcctatata cgtatactgc    8400
```

```
actgccaact tgcttttcca aaagccatac ctggccaggc gcagtggctt acacttacag    8460
tcccagcact ttgggaggcc gaggtgagct gatcacttga gctcaggagt tcgagaccaa    8520
cctgtgcaat gtagcaagac cctgtctcaa agaaaaaaa aaaaaagcca tacccattta    8580
cactcttgct ggtggtggca tctatgtcat gcttctaaac tgtgacttca gttactgggc    8640
atttggttga aattaactgt gaataaatgg gtagatggat gcagagatag aagataagt    8700 ggcaaggtag aaattagaga acacagtata gattccacta ttaaatgcat ggaaaaaga    8760 tggagactaa aggcagaaga gttccattgc cactgggagg taaggtcatg ctagtgtttt    8820
tgttcggttt tattttctct gttgtttgat gtataatttt gcatacaata tattttatgt    8880
attaaatata gctacccttta aaaagtgaaa agtatagtaa agaattggga gcagagaaga    8940
aatgaaggga acctaagtat actccatatt taaagatggg aataatcact tctgcccaaa    9000
gtctttgata aacattcat aataaaaaat attcagtcac tcatcctaca acttcacagt    9060
gctgtatctg gagaatggtc attgggttca aaactgtttc tgttgtgacg tgaaggaaac    9120
atatctaaac aagaccaaat tttttcgtat aagatactgt cagggaaaaa aaagattagt    9180
aattttgaga gctttccaca aatgagaaga aagattttt ctgcccttca tcctctgtag    9240
atcccagttg atgaagcagt ctgagtacat gtttcccata gtgagcaaga gaaaacaagg    9300
aagcctattg agatctaaca ttccacccat gaagggaact tcagtaaaaa ggagaatctc    9360
atcacagaat ggggaacggg gaagaaaggc tgtgcataga ctctgcagag aaacctacaa    9420
tcaagaactg gtcaggagaa gtaaaattcg tatgccaact caaatcatag atctaaaaga    9480
aaatgtaaaa ctatagatct gttaggaaat aacataggac agaatctttg gggtttgcaa    9540
ttaggcagag agtacttaga aatggcactg ttaatatggt ccatacgaga gagaaatcat    9600
aaatttggac ttcctcaaaa ttaaaatgaa atgaagacag gccacagact gggagaaaat    9660
atttgcaaag cacacatcaa aacactgact gcacccaga acatacagag aactcttaaa    9720
aactcaaaac tgcaaaaaga aacacctaaa aattggcaaa agagttgaca atttgcgaag    9780
gggatataca catggcgaaa aagcacagga aaagatgctc aacgccatta caggttaggg    9840
aagacaaact acaaccagga tgagggcccg aaacacatgg cttcagaatg gtgaaactca    9900
gcaacactga cgaggccacg tgcctgggag gatgcagagg aactgggaca ctccagtgtt    9960
actggcggga aggcaggtgg tacgggcact gtagaaaatg gtttggccat ctctgatgca    10020
gttaaaagcg cacttcccgt gggacttggc tgccccactc ctgggtataa gatttacccc    10080
cagagaagtg aaagcgcgca gccttgtaga aacccacaca ccagtgtttg tagcagtctt    10140
gtttgcattt tggatagcgg ccttgtttgg ttttcacaaa ccaccctcag cggacagtca    10200
gataaactgt aggcatccat acaatggaat accactcaga tctgagaggg aacgacctgt    10260
ggatacaggg agggaacaac ttggatgaat ctcattagag acattatgtg gatggcggga    10320
agccagtctc aacaggttac ttgtctcgcg atgccatcta cataaagttc cagcagagac    10380
aaaagtacag tgagagaaca gatcagtgtt tgccggggct aatggtgggg acggtgtgat    10440
agtgaaggga cagcacggag agttttgcag ggtgacagac ctcttctgca tcctgccaac    10500
ggctgtgtga atctacttgt gtgaagactc agggaactca caccaaagga agacggtcac    10560
ttttcctact gtatgataga taattaataa aaagggagaa cggaggagtg tcgtcccagg    10620
aggcagggca ggagggcgaa gacgtgtcac aggggagcct ggccaagtgg cgcccccgga    10680
actcgtcctc tgggcttgtg tgtggatgag acaaggtcta cctggtacga cagggacata    10740
ctgggaatgc gcccttgccg tggaggcggg gacccggcag cgctacgtat ccagcatcaa    10800
```

-continued

```
cctgtatcca gcatcaaccc gccaagttca ctaacttggt aggggtgagg ttagggatcc    10860
ttaggagccc aggcagccag actttctggg gagcccattc ccatttgtgt tgccaaagta    10920
cccccagcag gttgtgggaa tgttgcctgt gaagagagtc tgttggggtg agatcttgtg    10980
tgtgtgcaca gggtgacagt tgtgtcccat ttcccgggaa gctgtgatgg cagcagaacc    11040
tagaggagcc tgagagagtg tgggagagtg ggcctctgga agagtagagg ctgcggagcc    11100
aggtgcaggg ctgtctgtca cccaaaggaa gagggactga tgactcactg agcgtgtgtg    11160
tcccctggtg gcagcaggcc ccatagtgaa cataccatac cttttctgtc ctgagcgatg    11220
ctcccagcag tcctgggaga tggaacggtc cttattcggc tcacaggaag gaccgcctta    11280
actggacaga cacagcaagg tgctaaagat gccttccatc agaggccagg ttggaagctc    11340
taaagagact tctcttgctg ttctctcacc caccccagg ttgtgtgtgt cccgctgtgg     11400
attctcatgt cctttctgtg cctggtggtc ctctactaca ttgtgtggtc cgtcttgttc    11460
ttgcgctcta tggatgtgat tgcggacagc gcaggacaca cataaccatg gccctgagct    11520
ggatgaccat cgtcgtgccc cttcttacat ttgaggtaag cgttccacgg gaagcctctt    11580
cagcccctga agcttgcgct tcccctgaca ggattctgca cccctagaaa ggcagcctct    11640
gtccctcgag ctcacagtga gcccactcca ggagagggga gagaacacag ccatctccga    11700
gagggagctt cggtgaaagg agagcatcct tcctttctct tggggcagc acgtggggct     11760 ggcagggaga agagtgcacc tttttagcca tggtgcctct gtatggctcc agtttccact    11820
ctggggaaag cagagtggga tgtcagattt gtgtattgga gtcacgtgga gaattctaga    11880
atgggagctg ttgactcctt agaacaaaca cccggaggag tttgccataa aactgctggc    11940
actgggaact tttcaagtgg ataggctatt gccgagctct gaagagggac ataaaagctc    12000
atttcgagct ttccccaggg ataggtggtt tcctgccttt ttctggcggt gctgatgttc    12060
cctcttgtgg gagctcacgc ggggtgggg tggtggggag gaactgccta atgaagtctg      12120
gcttccgcct ctgccatttt tcggtgctgg catcaaccgg gactatgtct ctttctttag    12180
attctgctgg ttcacaaact ggatggccac aacgccttct cctgcatccc gatctttgtc    12240
cccctttggc tctcgttgat cacgctgatg gcaaccacat ttggacagaa gggaggaaac    12300
cactgtatgt actcagcatt tcagaagtcc ttggtgtgtg tctggggggg gaccaggggg    12360 tgggggtgg cggatagaag tctaggaagg gatgagtccc cgagggcccc aatttagaag     12420
cttgtgtggg aaagtgaggg ctgaggaaat tctgggacct tctaagggaa gggcatgccg    12480
taactctggt gttctgctgg cctgcaccgg gacttttctc gcagtgcacg ctgccatttg    12540
aggtagaacc agacacggca ggcaacctct cagagatccc gttccctcct ctgcaaaatg    12600
gggatcaaga cagattcttc ccaggcccgg gagggtttga tggaaaatcc acatctccca    12660
cccaaacctg ggattcatcc taggtccctg ttggccgctc tgcctccccc atatccttgc    12720
tgccatcacc cgagtcttgc ctgtcttgcc ttgctaacac tctattcccc tccacctgct    12780
tgctgaggca gacacttcca aaacgatctc tgcagagggt gccttcctgg caaggctgtg    12840
ggctccatgg cacggaagcc cagagcattg cccttcggaa agccagtggg tttgggggca    12900
gggcctcact gcagcccagc agcccgggct gtgcttgctg tttgtgcctc tgcccctac     12960 cccgcacccg ggagcaggga gggcttgcac cgagctgaca ctccagtagc ctacagagag    13020
gagtagtggg actgggaaag tggctttaag gtggctccat gagttcaggc cccctcctgg    13080
ccaacccgtg catgactacc gccctcacgg attccagagg gtgacagaaa tcttgttctt    13140
gggtggcact gtcatccatg agtttatcct ggctggagaa gattagcgga agacaccgta    13200
```

```
gtctgcgcac cacagatatt ttgagactca ctggagcagt agttctcaaa tttgggcatc   13260
cagcagaatc ccaaaagggc caggaaaagg ggaccgctgg agcccaccct agcccgactc   13320
agtttctgga ggtctgggct ggggcccgag aatggcatcc ctaactaggc cccgtggacg   13380
ctgtccctgc cggtccggga accccactcc aagcaccaca gagctagcat ttgcacttct   13440
tccccatttt gggtactcaa gccctgttca ggctttgtga ctcaggagtc tggataaagt   13500
atgttatgac attgtaggag tgaaacttct tgttacggaa agaaagttaa caggaaggtc   13560
agttgagcct cgtgtgtgaa ataaaaaatt cttattttc agggtggttt ggtatccgca   13620
aagatttctg tcagtttctg cttgaaatct tcccatttct acgagaatat ggaaacattt   13680
cctatgatct ccatcacgaa gataatgaag aaaccgaaga gaccccagtt ccggagcccc   13740
ctaaaatcgc acccatgttt cgaaagaagg ccagggtggt cattacccag agccctggga   13800
agtatgtgct cccacctccc aaattaaata tcgaaatgcc agattagatg ccacttccgg   13860
ggacagagct taagtggact gggacgcact ctctccgcct tcctctgccc cctcgttcac   13920
cccgcagacc agaaccagta ctggagctgg gtctccaggt acgtccatct catgccttgt   13980
ttgcatccag cgcctatcag ccactcacca cgacgggacg cggaagtggc aggtgacggg   14040
ggtgtgtgcc agcagatgcg gatgccagga agagtgtgag aacaggggtg ggattaccgt   14100
ctgtctggga ggggctccag gtaccctct tcccgtcag acccactggg agatggctgc   14160
ttgccaggcc cccagaagga acatctgtct atacggtgct gaaatcccaa tcaaaagtat   14220
tgtttagaaa tgtatttctc cacagggctg acctcctgca gctcgctgag cactcccagg   14280
tcctcagcac tcccaggtcg tggctggggc agtcagtagg aactgtaact atgtctctga   14340
tgcaccacgt gtttagacac agcacagtcc tttttctgt tcctactgtg gaagtagttt   14400
ctctttgggc atgctgacag cagttttca tagcctcacg gatgagccct ttctacggga   14460
gtgactccat gcttgtatac agagtattta tacaaatgtt ttagcatctt catatgcgt   14520 gttaacccct agttctgtac agcatattct gttcaagtat ttttttacaa gcttgtgctg   14580
taggcacatg ccttctgctg cagaagtgga cgcccgtggc acactccccc cccccccg   14640 tggggtgcca cgccttcatg ggacattgcc acttctgccc tggaactcgt gcaggtacgt   14700
agtagctgct actgccacaa cggcaacacc aagcaagaga tggtccatgc ttttctgacg   14760
ttctcagaat agtggctagc ttcaaacctg acaagcgctg cttgaagccg gaacactaga   14820
gaatgttgct gagagcagaa acggccacgc gggtcacgac tatgcgtggg aaagtctcaa   14880
gcttccctcc tgccagcaac aagaaggctt tggagtaggc atgatgtttt cacgtgtgcg   14940 tgccgttct ccaagcactg caggttccac cgtgtgtcag aggctgcaag tttaacatcc   15000
tcctgcctga aaacaaatag gtcctttgct gaaaagaggg taaaaaaaga gctttgatct   15060
tctcagccag gagaagaggg tggtgttttc acgcgggcaa ctgctcgccg gcctacatgg   15120
ggttaattca gtctgctgc gagcacgact ccgcccttgg cactggcctc cagcaagccc   15180
tgttctcttt ggggtacagg ggaacgggat ggtttagact ttcctgctca gtgtgtaaaa   15240
aatgtagcta aagccactat ttttgctctc cttaagctgt tcaataaacc ggttcctcat   15300
tttacacgtg catgatgtgt atcttctttg ctggatgggc caggaaactg gagtggtcct   15360
ctcagccagc ctcagaggaa agaaatctct agctggcaca ggcagccagt gagtgaggct   15420
ggcggctgca ggggcacagc ctttagaatg agtccttcag tgcacaggtc ccagggtata   15480
cggggtagtg ggaggaagga ggggacgcct cgcagatgcc actgttggct gggctacacc   15540
ttgccacact tgttactgct taggaggctt tctggagtgt tccttgggtg ctacgacaat   15600
```

```
ctgcagcaga cactgtcctt tcaccgctcc tggtcctcgt ttgctcccca gtgatgtcaa   15660
cagctgagga ctgctcacgc tgcaacaaaa ggctctgcag tcgctgtcta gcttgcccta   15720
gtcgtctcta gagttctgcc tgaactgaaa ctcaagtggg gttcagctca tgacttgtgg   15780
caattgacca ggaaattcac cagttgctgt ggctggaagg attttcagtc ctgtgggttg   15840
taaccagagg ccacaggtgg attctgcctt aggctcatga gatttccgac ttgctgttga   15900
agaaaatgcc ttgtgaagtg acaacagtag ctctgaccca actgccggtg cctcgctagt   15960
tcctatacgt cccactggat cctcacagcc ccgggaagca ggtgctacta ctcttatccc   16020
cgggaggaga cagaggccga gagaggttaa gtgacgtgcc caagtcacac agctcggcag   16080
cggccgggtt gagcatcagc agtctgtttg cagacccctc actgtcaccc cctgagccag   16140
tgcgccttgg gccctgcggt caggatgtct caagcgtgga ggcatcaccg gttcgtggca   16200
gtctctggaa ggtcactgag ctctgtgccc agaatcgagt cggggagtc tgtgcagagg   16260 tggccctgtg tgtggggaca gtgtgtgaca cagacactgc tttggatgga cacctctccc   16320
gtgacctcct agcatccaat cccaaaggaa caactgttgc agagatggac cgctggacac   16380
aaacccacgt gcgtttctct ggagacactg gccaaggaaa acaaaacatg ctcgaaggcc   16440
aacagctgca tgccccaccg cgatgtgacc gcagacaccc ggggtgtaga agggtctctg   16500
cctggtgggg ggacacgtgc aggccgagga gaggcaggaa ggaggctgcc tccgactccc   16560
cactggactg catggcgacg cgtgtggtg gggcagtcag ctaagccatt tgcctaaggg   16620
gctgtcgggc atctgcgtgc tggggaccga cagtgtgggt gtgttaggag gatctgtatg   16680
gagcacattg ctgcctctgg ctaggacagg gtggaaaggg tggcgtggct acagcctgac   16740
ccatgggcac cgtcctaccc tttgttctgt gcttccgagt gtcagtcatg tgctggggtc   16800
tgtgggccca tgactcagac ggtgagctct gaccttcctg agccagggct ttgctgtagt   16860
tgtgcctggc tcaggagctc taggacaagg ggaccgctcc aggtctgcat ctacggtgtg   16920
gcagggcccc tcggcactct tgtgcactag tgtcatcttt cccattgaaa tgactgtgag   16980
gaccagaatg tgcacatgca gatgggcagc tacttgtctg ccttggccct ttattacaca   17040
acttgctggg ggtggagatg ccacccccg gcagtcagag cccctttatg atgtcatggg   17100
gctggttaca tgactgccaa ggggtgctgc tggccacact gcactagcaa gtttgccaga   17160
tggaggacaa gcgatcattg agtatggctc gctgtgaaga aagaaattcg agaggacagg   17220
atcatggctt ggaaagggtg ccttttccctc cccagttgca gtcagagacc taccttcacc   17280
cagcagatcc ttcccctgcc tgggacgacc cggggtccac tggagccct aacttgaggc   17340 tgctgacaga agaaatcgct ttccaaccttc tggccgagga agcttcgttc agaaggccgc   17400
accctgacgg tgacgtcccg ccccagggag aagataatct cctctccctc cccttttccac   17460 agaaactgtg gagactggtc agcagcaacc agttttcgtc catctggtgg gatgacagtg   17520
gggcttgtag agtgatcaat caaaaactct ttgaaaagga gattctcaaa agggacgtcg   17580
cacacaaagt gtttgccaca acttcgataa agagcttctt ccgccagcta aacttgtatg   17640
gcttccgaaa acgcgtcaa tgcactttca ggaccttcac ccgcattttc tccgcaaaaa   17700
ggctggtctc catcttgaat aaggtaatga acgacaagcc tctggagggg ttaagtcggt   17760
gggctctggg gcctggtcgg gtggaagtcc caggactgcc tcctgggaag tgggcgacct   17820
caggcagggt gtggggccat cgctgtgggc ctgtgtcccc ctctgggtgg aggtgacatg   17880
aactaagagt gaatgggggg agagggctga ggatggtgcg ggcccctctc gagtgtgtaa   17940
aatatcacag gtgccaagta gccgtatctg cgtgtcgtcc tccccggggc cagccatgtc   18000
```

```
atctggtggt tgctgtgtcc ccctgactcc acagcacatt accctgtgag gtgagcaggc    18060 cagggggagtc tggtatttgt accactgtca ccctagctgg tgtctggaga ggtgctcaag    18120
tggaagcact gaagggcgcc tggcgcagga ggtgcagatg ctcctgctgc ccttggtagg    18180
tgggcccctg gtgtgtgaaga gccagtaccc agggcctcca acccagccgg ggtgcattct    18240
gttgccagct gacactgcat gggggaggcc cagaatcttc ttccctcctg gtctgcaact    18300
tcaaagaccc tttccgccgg ccatggacac cctaatctgc cattttgagg cttttttccaa    18360 gacggaaagg cccgccacaa cttggtaaac cttgacgatg tgaacgcgag tccccagctt    18420
cctttgggga ctgggacctt ttccagaaag gcctcctggg ccagtagagt tctcttgcac    18480
aggggcgtag atggttggta gttgtagtcc atccttgtga cttg                     18524

<210> SEQ ID NO 13
<211> LENGTH: 7695
<212> TYPE: DNA
<213> ORGANISM: Homo sapiens

<400> SEQUENCE: 13
ggcccaggag gcctttctgg aaaaggtccc agtccccaaa ggaagctggg gactcgcgtt      60
cacatcgtca aggtttacca agttgtggcg ggcctttccg tcttggaaaa agcctcaaaa     120
tggcagatta gggtgtccat ggccggcgga aagggtcttt gaagttgcag accaggaggg     180
aagaagattc tgggcctccc ccatgcagtg tcagctggca acagaatgca ccccggctgg     240
gttggaggcc ctgggtactg gctcttccac accaggggcc cacctaccaa gggcagcagg     300
agcatctgca cctcctgcgc caggcgccct tcagtgcttc cacttgagca cctctccaga     360
caccagctag ggtgacagtg gtacaaatac cagactcccc tggcctgctc acctcacagg     420
gtaatgtgct gtggagtcag ggggacacag caaccaccag atgacatggc tggcccccggg   480 gaggacgaca cgcagatacg gctacttggc acctgtgata ttttacacac tcgagagggg     540
cccgcaccat cctcagccct ctccccacat tcactcttag ttcatgtcac ctccacccag     600 aggggggacac aggcccacag cgatggcccc acacctgcc tgaggtcgcc cacttcccag     660
gaggcagtcc tggacttcc acccgaccag gccccagagc ccaccgactt aaccccctcca     720 gaggcttgtc gttcattacc ttattcaaga tggagaccag ccttttttgcg gagaaaaatgc    780 gggtgaaggt cctgaaagtg cattgacgcc gttttcggaa gccatacaag tttagctggc     840
ggaagaagct ctttatcgaa gttgtggcaa acactttgtg tgcgacgtcc cttttgagaa     900 tctcctttttc aaagagtttt tgattgatca ctctacaagc cccactgtca tcccaccaga     960
tggacgaaaa ctggttgctg ctgaccagtc tccacagttt ctgtggaaag gggagggaga    1020
ggagattatc ttctccctgg ggcggacgt caccgtcagg gtgcggcctt ctgaacgaag    1080
cttcctcggc cagaggttgg aaagcgattt cttctgtcag cagcctcaag ttagggctcc    1140
cagtggaccc cgggtcgtcc caggcagggg aaggatctgc tgggtgaagg taggtctctg    1200
actgcaactg gggagggaaa ggcacccttt ccaagccatg atcctgtcct ctcgaatttc    1260
tttcttcaca gcgagccata tcaatgatc gcttgtcctc catctggcaa acttgctagt    1320
gcagtgtggc cagcagcacc ccttggcagt catgtaacca gccccatgac atcataaagg    1380
ggctctgact gccgggggt ggcatctcca cccccagcaa gttgtgtaat aaagggccaa     1440
ggcagacaag tagctgccca tctgcatgtg cacattctgg tcctcacagt catttcaatg    1500
ggaaagatga cactagtgca caagagtgcc gaggggccct gccacaccgt agatgcagac    1560
ctggagcggt cccccttgtcc tagagctcct gagccaggca caactacagc aaagccctgg    1620
```

```
ctcaggaagg tcagagctca ccgtctgagt catgggccca cagaccccag cacatgactg    1680
acactcggaa gcacagaaca aagggtagga cggtgcccat gggtcaggct gtagccacgc    1740
caccctttcc accctgtcct agccagaggc agcaatgtgc tccatacaga tcctcctaac    1800
acacccacac tgtcggtccc cagcacgcag atgcccgaca gccccttagg caaatggctt    1860
agctgactgc cccaccacac gccgtcgcca tgcagtccag tggggagtcg gaggcagcct    1920
ccttcctgcc tctcctcggc ctgcacgtgt ccccccacca ggcagagacc cttctacacc    1980
ccgggtgtct gcggtcacat cgcggtgggg catgcagctg ttggccttcg agcatgtttt    2040
gttttccttg gccagtgtct ccagagaaac gcacgtgggt ttgtgtccag cggtccatct    2100
ctgcaacagt tgttcctttg ggattggatg ctaggaggtc acgggagagg tgtccatcca    2160
aagcagtgtc tgtgtcacac actgtcccca cacacagggc cacctctgca cagactcccc    2220
cgactcgatt ctgggcacag agctcagtga ccttccagag actgccacga accggtgatg    2280
cctccacgct tgagacatcc tgaccgcagg gcccaaggcg cactggctca gggggtgaca    2340
gtgaggggtc tgcaaacaga ctgctgatgc tcaacccggc cgctgccgag ctgtgtgact    2400
tgggcacgtc acttaacctc tctcggcctc tgtctcctcc cggggataag agtagtagca    2460
cctgcttccc ggggctgtga ggatccagtg ggacgtatag gaactagcga ggcaccggca    2520
gttgggtcag agctactgtt gtcacttcac aaggcatttt cttcaacagc aagtcggaaa    2580
tctcatgagc ctaaggcaga atccacctgt ggcctctggt tacaacccac aggactgaaa    2640
atccttccag ccacagcaac tggtgaattt cctggtcaat tgccacaagt catgagctga    2700
accccacttg agtttcagtt caggcagaac tctagagacg actagggcaa gctagacagc    2760
gactgcagag ccttttgttg cagcgtgagc agtcctcagc tgttgacatc actggggagc    2820
aaacgaggac caggagcggt gaaaggacag tgtctgctgc agattgtcgt agcacccaag    2880
gaacactcca gaaagcctcc taagcagtaa caagtgtggc aaggtgtagc ccagccaaca    2940
gtggcatctg cgaggcgtcc cctccttcct cccactaccc cgtatacect gggacctgtg    3000 cactgaagga ctcattctaa aggctgtgcc cctgcagccg ccagcctcac tcactggctg    3060
cctgtgccag ctagagattt cttcctctg aggctggctg agaggaccac tccagtttcc    3120
tggcccatcc agcaaagaag atacacatca tgcacgtgta aaatgaggaa ccggtttatt    3180
gaacagctta aggagagcaa aaatagtggc tttagctaca ttttttacac actgagcagg    3240
aaagtctaaa ccatcccgtt cccctgtacc ccaaagagaa cagggcttgc tggaggccag    3300
tgccaagggc ggagtcgtgc tcgcagcaga cttgaattaa ccccatgtag gccggcgagc    3360
agttgcccgc gtgaaaacac caccctcttc tcctggctga aagatcaaa gctctttttt    3420 taccctcttt tcagcaaagg acctatttgt tttcaggcag gaggatgtta aacttgcagc    3480
ctctgacaca cggtggaacc tgcagtgctt ggagaaacgg cacgcacacg tgaaaacatc    3540
atgcctactc caaagccttc ttgttgctgg caggagggaa gcttgagact ttcccacgca    3600
tagtcgtgac ccgcgtggcc gtttctgctc tcagcaacat tctctagtgt tccggcttca    3660
agcagcgctt gtcaggtttg aagctagcca ctattctgag aacgtcagaa aagcatggac    3720
catctcttgc ttggtgttgc cgttgtggca gtagcagcta ctacgtacct gcacgagttc    3780
cagggcagaa gtggcaatgt cccatgaagg cgtggcaccc cacgggggg ggggggagt    3840 gtgccacggg cgtccacttc tgcagcagaa ggcatgtgcc tacagcacaa gcttgtaaaa    3900
aaatacttga acagaatatg ctgtacgaaa ctagggggtta acaccgcata tgaagatgct    3960
aaaacatttg tataaatact ctgtatacaa gcatggagtc actcccgtag aaagggctca    4020
```

```
tccgtgaggc tatgaaaaac tgctgtcagc atgcccaaag agaaactact tccacagtag    4080
gaacagaaaa aaggactgtg ctgtgtctaa acacgtggtg catcagagac atagttacag    4140
ttcctactga ctgccccagc cacgacctgg gagtgctgag gacctgggag tgctcagcga    4200
gctgcaggag gtcagccctg tggagaaata catttctaaa caatactttt gattgggatt    4260
tcagcaccgt atagacagat gttccttctg ggggcctggc aagcagccat ctcccagtgg    4320
gtctgacggg gaagaggggt acctggagcc cctcccagac agacggtaat cccacccctg    4380
ttctcacact cttcctggca tccgcatctg ctggcacaca ccccgtcac ctgccacttc     4440 cgcgtcccgt cgtggtgagt ggctgatagg cgctggatgc aaacaaggca tgagatggac    4500
gtacctggag acccagctcc agtactggtt ctggtctgcg gggtgaacga gggggcagag    4560
gaaggcggag agagtgcgtc ccagtccact taagctctgt ccccggaagt ggcatctaat    4620
ctggcatttc gatatttaat ttgggaggtg ggagcacata cttcccaggg ctctgggtaa    4680
tgaccaccct ggccttcttt cgaaacatgg gtgcgatttt aggggctcc ggaactgggg     4740 tctcttcggt ttcttcatta tcttcgtgat ggagatcata ggaaatgttt ccatattctc    4800
gtagaaatgg gaagatttca agcagaaact gacagaaatc tttgcggata ccaaaccacc    4860
ctgaaaaata agaattttt atttcacaca cgaggctcaa ctgaccttcc tgttaacttt     4920 cttccgtaa caagaagttt cactcctaca atgtcataac atactttatc cagactcctg     4980
agtcacaaag cctgaacagg gcttgagtac ccaaaatggg gaagaagtgc aaatgctagc    5040
tctgtggtgc ttggagtggg gttcccggac cggcagggac agcgtccacg gggcctagtt    5100
agggatgcca ttctcgggcc ccagcccaga cctccagaaa ctgagtcggg ctagggtggg    5160
ctccagcggt ccccttttcc tggccctttt gggattctgc tggatgccca aatttgagaa    5220
ctactgctcc agtgagtctc aaaatatctg tggtgcgcag actacggtgt cttccgctaa    5280
tcttctccag ccaggataaa ctcatggatg acagtgccac ccaagaacaa gatttctgtc    5340
accctctgga atccgtgagg gcggtagtca tgcacgggtt ggccaggagg gggcctgaac    5400
tcatggagcc accttaaagc cactttccca gtccactac tcctctctgt aggctactgg     5460
agtgtcagct cggtgcaagc cctccctgct cccgggtgcg gggtaggggg cagaggcaca    5520
aacagcaagc acagcccggg ctgctgggct gcagtgaggc cctgccccca aacccactgg    5580 cttttccgaag ggcaatgctc tgggcttccg tgccatggag cccacagcct tgccaggaag    5640
gcaccctctg cagagatcgt tttggaagtg tctgcctcag caagcaggtg gaggggaata    5700
gagtgttagc aaggcaagac aggcaagact cgggtgatgg cagcaaggat atggggagg    5760 cagagcggcc aacagggacc taggatgaat cccaggtttg ggtgggagat gtggattttc    5820
catcaaaccc tcccgggcct gggaagaatc tgtcttgatc cccatttttgc agaggaggga   5880 acgggatctc tgagaggttg cctgccgtgt ctggttctac ctcaaatggc agcgtgcact    5940
gcgagaaaag tccggtgca ggccagcaga acaccagagt tacggcatgc ccttccctta     6000
gaaggtccca gaatttcctc agccctcact ttcccacaca agcttctaaa ttggggccct    6060
cggggactca tcccttccta gacttctatc cgccacccc caccccctgg tcccccccca    6120
gacacacacc aaggacttct gaaatgctga gtacatacag tggtttcctc ccttctgtcc    6180
aaatgtggtt gccatcagcg tgatcaacga gagccaaagg gggacaaaga tcggatgca     6240 ggagaaggcg ttgtggccat ccagtttgtg aaccagcaga atctaaagaa agagacatag    6300
tcccggttga tgccagcacc gaaaatgggc agaggcggaa gccagacttc attaggcagt    6360
tcctccccac caccccaccc ccgcgtgagc tcccacaaga gggaacatca gcaccgccag    6420
```

| | | |
|---|---|---|
| aaaaaggcag gaaaccacct atccctgggg aaagctcgaa atgagctttt atgtccctct | 6480 | |
| tcagagctcg gcaatagcct atccacttga aaagttccca gtgccagcag ttttatggca | 6540 | |
| aactcctccg ggtgtttgtt ctaaggagtc aacagctccc attctagaat tctccacgtg | 6600 | |
| actccaatac acaaatctga catcccactc tgctttcccc agagtggaaa ctggagccat | 6660 | |
| acagaggcac catggctaaa aaggtgcact cttctccctg ccagcccac gtgctgcccc | 6720 | |
| caagagaaag gaaggatgct ctcctttcac cgaagctccc tctcggagat ggctgtgttc | 6780 | |
| tctcccctct cctggagtgg gctcactgtg agctcgaggg acagaggctg cctttctagg | 6840 | |
| ggtgcagaat cctgtcaggg gaagcgcaag cttcaggggc tgaagaggct ccccgtggaa | 6900 | |
| cgcttacctc aaatgtaaga aggggcacga cgatggtcat ccagctcagg gccatggtta | 6960 | |
| tgtgtgtcct gcgctgtccg caatcacatc catagagcgc aagaacaaga cggaccacac | 7020 | |
| aatgtagtag aggaccacca ggcacagaaa ggacatgaga atccacagcg ggacacacac | 7080 | |
| aacctggggg tgggtgagag aacagcaaga gaagtctctt tagagcttcc aacctggcct | 7140 | |
| ctgatggaag gcatctttag caccttgctg tgtctgtcca gttaaggcgg tccttcctgt | 7200 | |
| gagccgaata aggaccgttc catctcccag gactgctggg agcatcgctc aggacagaaa | 7260 | |
| aggtatggta tgttcactat ggggcctgct gccaccaggg gacacacacg ctcagtgagt | 7320 | |
| catcagtccc tcttcctttg ggtgacagac agccctgcac ctggctccgc agcctctact | 7380 | |
| cttccagagg cccactctcc cacactctct caggctcctc taggttctgc tgccatcaca | 7440 | |
| gcttcccggg aaatgggaca caactgtcac cctgtgcaca cacacaagat ctcaccccaa | 7500 | |
| cagactctct tcacaggcaa cattcccaca acctgctggg ggtactttgg caacacaaat | 7560 | |
| gggaatgggc tccccagaaa gtctggctgc ctgggctcct aaggatccct aacctcaccc | 7620 | |
| ctaccaagtt agtgaacttg gcgggttgat gctggataca ggttgatgct ggatacgtag | 7680 | |
| cgctgccggg tgacc | 7695 | |

<210> SEQ ID NO 14
<211> LENGTH: 9014
<212> TYPE: DNA
<213> ORGANISM: Artificial Sequence
<220> FEATURE:
<223> OTHER INFORMATION: Description of Artificial Sequence: Synthetic plasmid

<400> SEQUENCE: 14

| | |
|---|---|
| gggcgaattg ggcccgacgt cgcatgctcc cggccgccat ggcggccgcg ggaattcgat | 60 |
| atcactagtg aattcgcggc cggcgattgg gcccgacgtc gcatgctccc ggccgccatg | 120 |
| gcggccgcgg gaattcgatt ccttaattaa gtcgactggg acccaaactt tggagtcgtt | 180 |
| gacagatgtg acaggtgaag cctgggatga catcgccaaa aatgcaacgt ctcactcatt | 240 |
| gtcactactc ccagggctca gtcgtcactg gggaaaatct ccagaaggta gcgcgggcca | 300 |
| aggtgacagg tgtctgccaa gatctgcccg ccagactccc gggcggcgcg ctccctccct | 360 |
| gcaggccttc agcccgtcag catcccctc ctcggggccc tgctcactcc cagcctccat | 420 |
| cccccctgcca tctcctccgc cggtcgcgtg cggacacaag gatggggacc tcccagcgag | 480 |
| gagcgctctg ggcggggctc cggacgcatg cgcggccctc gtacggaagc ccggaaggag | 540 |
| gggcagggg cggtggctca ggtttctccg ggcggcggcg gcggcggcgg cggcgacggc | 600 |
| gacggcgacg gcagcgggga cggcagcagt agcgggagca gcagcgtgga cgcggctggc | 660 |
| gctggcgcca tgaacccgct gtaaggcgca ggctgtgcag cacggggtgc ggggaggag | 720 |
| gaggaggacg ccgcggtgaa gttctccgcc atgaacctga ggggcctctt ccaggacttc | 780 |

```
aacccgaggt gaggcggcgt cgttggcgcc cccgggagtc cgcgctgcgg gctcgggcgc    840
gggctggtgt tcggctccgg ggaggcacgg cgggcgagat gctgcagccc gaggacccgg    900
gcgcctgccc gagcctccct gcgggtgcaa gcggtcccca ggcaaaacag tcggcctcgg    960
cgcccgcccg cttcctcctc ccgtgcccgg tgctttcagc ccctgccgg ccacggccgg    1020
aagggcccgg ccgcgagccc cgtcctgccc caagggaacc ccattctttt ctgcttgctg   1080
tccctcattg gtgtcccaac ttcttcgtct cggttccatc ctcttctgcg ccgctgcggg   1140
ccctccattc tccgcgtcag ggccgtctca ctcgacccaa caccctacc cccaccccag    1200
ctgtttcctc cagttcctcg cagtccttgg ggttttcctt gggtttatgc ccatccctct   1260
cttgtttgct tctttgttga acggatacct gaaacactgt tgaatccttg gagtcagtgt   1320
cggggtatgg caataccctta tataatgcat ttctgggtga gcctgatcat tttccatact  1380
cattttctca tcagtcttca ctacaagttt atttgcagga agtagatatt gctgtccttc   1440
ttttccagat ggggaacacc cagtggacag tgtggagaaa acactggcta agcactcaag   1500
cgcctgtcct tgcacttgcc cgactgtttt gtaactgttc tttacccag gctgtgagct    1560
ccctgaagct gagaccatct cctgctcatc tcagtgtccc cagcgcctcc cacccaccgt   1620
atctggcaca tagtaggcac atataaaatg tttgtggaac taaactgagc ccaaagactt   1680
ggattggaga cgaggccata tgtaactggg tgattctctg cccttctttg gcccttctgt   1740
aaaatgagga gttggcctaa ctgatctctt aaatgcacta ctctccgaaa ggagtatccg   1800
tttcccttat ttgccagttg ggaagacgtg ctcagtaaat atttgtgtgc tgtaacctat   1860
gttaggtgct ttagatgctg gcggtctcag catggggtga agaagggctt gtacacttaa   1920
gatgccttac agtactgtgc agtgctgtac tgcgggggcc aactctgggg acctatgcct   1980
tggctgcttg ttgaggatga aaggaagttt taggggagta tttgtatgtt gagggtgcag   2040
tctccctagg gatggtgaca ttttaacttg tgagtcattg tgactttgta tgtgccctta   2100
ttccactttg agttcatgtt ctggttagga gtgccagtgt ctctaacacg gtgcagacat   2160
tatcattgtt ggcttcgaag gcatagagga ggtaacagaa ctaactgcag tcccttcctc   2220
tgctgcatca gggggttaag attggtctgc agggtagtag ggttggtgct gtggctggac   2280
aagccctgta tgtcttctat ttggagatgg tgataagaaa gttaagtaaa aactgaattg   2340
ttttgtgccc ttgggcaact cacttatcta ttgttttatc tgtagaatga gtataatctc   2400
tcagtggggt agggaggcca attaaggatt gattacaaag tgccttacaa atagaaagct   2460
acagtgactt gtttgcaagg tgacagagaa ttcagaagcc tcaagaaact gccttaagtg   2520
atcaaacagg ctaacggagt tgccaaagca aaatagtgct gcactgatac tacctttaac   2580
cgttttttcc tttagcccctt tccccccaa aaaaattagt atatgaaatt acagtgaaat   2640
acctggtatc taagcagatt tatagtaatt ctcaacatat tcatcaatct cttaattcta   2700
cctgcattaa aatgtatttc tacctgaaaa gtttaaaggt cttttatact gtgccatttt   2760
cctgattcat tgttgccaga ggtagtgagt tccttaattt tacagatatt tcaagaggac   2820
attggccagg tattattggt aaatcagatt tgttttttta gctggtagtg tttcacctct   2880
cctgagcact cctagttttt gacagtgtgc tttagtctcc ttccatgctg aggaaggcct   2940
tctctatagg agaaagaaaa ctgaggggtg tacacaggaa gttaccttat gctgggact    3000
caaaccttga tgctactgct ttgctccctg cctctatttt tgaaccaatt caacatctcc   3060
ctcctacccc aggaccttgt cacacactgt tctcttacc aggaatgttt ccctctcttt    3120
tcctctcctc cagacctagt gaactccatt ttatcctcac ttggcacttg ctaagggaag  3180
```

```
cattcctgac ttccctgacc agatttactg ctccctgttt ctacagttcc tgtagtattt    3240
actactcctc catcatagtg catatttgta cccttgtgtc tgtctggatg cttatttgat    3300
taatacctgc ctcccccact aaactttaag ctccatgggg tcaaggccgt gactgtgtca    3360
gtatcgtagc ctgcatactt ggaatagtac ctggctcaat aaatatttgt ggagtaaata    3420
actgaataac tctccagagc ctataagata aatctagagc tgctgctttc aatcactgct    3480
ttcctggtgg tctgtggcct ggttctcttt cttctcacac tcttcccacc ttcagagtgc    3540
agccattgct ttggagagat gggagagaac atggcactaa ggcagaatat ggctatattt    3600
actttgaaga gcatgtcttt gtcatagaaa tagtcactgt catggtttgg tgggtcccaa    3660
ggcatgggtc atggctccag atccccttc cagccttttg gatcttggta agtctgaacc     3720
cactgctgcg ttggcaaggc tctggaaact atagtgacag agaatgattc acaagtgtca    3780
acactcagat gtacagggct gccagctgac ccactctacc tatttccatc tggcactgaa    3840
ctggttgatc atgaacttct tttcataatt gcttttttagt tatgcaggtt aagacatgcc    3900
gaaacagatg taccggaccc acaaacaagt ccttccttga atgcctgagg cttcctaaca    3960
gtgaaagagc cctgttctta gagtaggcaa actgattctg aggcattgta ggtggtaggg    4020
atctggtagt aggtagcatt aggtgggctc ccggcactca ccatggagcc ttgaaatttt    4080
ctgctacttt gggggagttg ctggttcaga gaaggccctt ccaccctggt agccatgtgg    4140
cactggaagg ctgtgaaaac tctgctgggc cttcttagtc atctgttgtg agctcctgat    4200
gggagtgtgt tgtatccctc aggtgtgcta gactggaaca aaggctgaga gtgttgctc     4260 tgggggttcc aacttgtggg catggggtac tgatgagatc agtagtgttt ggagacttct    4320
gtatgctcca tcttcagaag acattctgga gtccatataa gttatcttgt ctcttgtttg    4380
aagcaggaaa aaggaatgcg attgctggta atatagttca ctaaagtcag ctacctggcc    4440
tctaacagtt atttgcaaag tatattataa cattgattcc tcaaacatct agattcctat    4500
ctcgtgccaa gtgatgtact aggtgctcta agtacaaaaa taaggaata tagtcctcct     4560 ctcaatgcgt aagcctagtg gaagaagcag aaatgaaagg gaaataagaa ttcaatagag    4620
tatgaggcat tacagtgaaa gaaaccaaat gtcttagaag tacaaatggc agagctacta    4680
attctgtctc gagcaggcag ggaagagtct atagtgaaa tgacttttga gctagatttt     4740
gaattgagct agtcttttga gccagacttt tgagctagaa ttgtagggtt gtcatcagac    4800
cagagagtag gaagggtacc ttgtgaggaa gagagagaga gatcagattg ttactgtgtc    4860
tatgtagaaa aggaagacat aagaaactcc attttgatct gtactaagaa aaattgtttc    4920
tgctttgaga tgctgttaac ctgtaacttt agtcccaacc ctgtgctcac agaaacctgt    4980
gctgtaatga atcaaggttt aatggattta gggctgtgca ggatgtacct tgttaacaat    5040
atgtttgcag gcagtatgct tggtaaaagt catcgccatt ctccattctc gattaaccag    5100
ggacacagtg cactgcggaa ggccgcaggg acatctgccc aagaaagcct gggtattgtc    5160
caaggtttcc ccccactgag acagcctgag atatggcctt gtgggaaagg aaagaccttta   5220 ccaccccca gcccgacacc cgtaaagtgt ctgtgctgag gaggagtagt gaaagagcgg    5280
ggcctctttg cagttgagat aagaggaagg cttctgtctc ctgctcatcc ctgggaatgg    5340
aatgtctctg tgtaaagctg accattccca ttcgttctat tctgagatag agaaaacca     5400 ccctgtggct ggaggcgaag tatgctggca gcaatactgc tctgttactc tttgctacac    5460
tgagttgttt gggtaaagag aaacataaat ctagcctgcg tgcacatcca ggcacagtac    5520 cttttccttga acttattcat gatacagatt cctttgctca cgtttccctg ctgaccttct    5580
```

```
ccccacctgt tgccctgcta cactcccctc gctaagatag taaaaataat gatcagtaaa   5640
tactgaggta actcagaggc tagcgctggt gcgggtcctc cgtatgctga gtgccggtcc   5700
cctgggccca ctgttctttc tctatacttt gtttctgtgt cttatttctt ttctcagtct   5760
cgtcccacct gacgagaaat acccacaggt gtggaggggc tggccccttt cagtatctca   5820
gaagggacaa agtacacaaa ggcatggggt catgatagtg cctggtatgt tcaggtagtg   5880
aagaggtcca tgtggtatga gcactgcaga tgatatgtgt cgtatgaatt aaaaatacat   5940
agttactgca aatagttttt acaggttatt gtttttaaga aagcagtatc taatgcacga   6000
gtgtactgtc agtactgtca atgaactact taccactcaa gtgactgctt acgcgtcgaa   6060
tcactagtga attcgcggcc gcctgcaggt cgaccatatg ggagagctcc caacgcgttg   6120
gatgcatagc ttgagtattc tatagtgtca cctaaatagc ttggcgtaat catggtcata   6180
gctgtttcct gtgtgaaatt gttatccgct cacaattcca cacaacatac gagccggaag   6240
cataaagtgt aaagcctggg gtgcctaatg agtgagctaa ctcacattaa ttgcgttgcg   6300
ctcactgccc gctttccagt cgggaaacct gtcgtgccag ctgcattaat gaatcggcca   6360
acgcgcgggg agaggcggtt tgcgtattgg gcgctcttcc gcttcctcgc tcactgactc   6420
gctgcgctcg tcgttcggc tgcggcgagc ggtatcagct cactcaaagg cggtaatacg   6480
gttatccaca gaatcagggg ataacgcagg aaagaacatg tgagcaaaag gccagcaaaa   6540
ggccaggaac cgtaaaaagg ccgcgttgct ggcgtttttc cataggctcc gcccccctga   6600
cgagcatcac aaaaatcgac gctcaagtca gaggtggcga aacccgacag gactataaag   6660
ataccaggcg tttccccctg gaagctccct cgtgcgctct cctgttccga ccctgccgct   6720
taccggatac ctgtccgcct ttctcccttc gggaagcgtg gcgctttctc atagctcacg   6780
ctgtaggtat ctcagttcgg tgtaggtcgt tcgctccaag ctgggctgtg tgcacgaacc   6840
ccccgttcag cccgaccgct gcgccttatc cggtaactat cgtcttgagt ccaacccggt   6900
aagacacgac ttatcgccac tggcagcagc cactggtaac aggattagca gagcgaggta   6960
tgtaggcggt gctacagagt tcttgaagtg gtggcctaac tacggctaca ctagaagaac   7020
agtatttggt atctgcgctc tgctgaagcc agttaccttc ggaaaaagag ttggtagctc   7080
ttgatccggc aaacaaacca ccgctggtag cggtggtttt tttgtttgca agcagcagat   7140
tacgcgcaga aaaaaaggat ctcaagaaga tcctttgatc ttttctacgg ggtctgacgc   7200
tcagtggaac gaaaactcac gttaagggat tttggtcatg agattatcaa aaaggatctt   7260
cacctagatc cttttaaatt aaaaatgaag ttttaaatca atctaaagta tatatgagta   7320
aacttggtct gacagttacc aatgcttaat cagtgaggca cctatctcag cgatctgtct   7380
atttcgttca tccatagttg cctgactccc cgtcgtgtag ataactacga tacgggaggg   7440
cttaccatct ggccccagtg ctgcaatgat accgcgagac ccacgctcac cggctccaga   7500
tttatcagca ataaaccagc cagccggaag ggccgagcgc agaagtggtc ctgcaacttt   7560
atccgcctcc atccagtcta ttaattgttg ccgggaagct agagtaagta gttcgccagt   7620
taatagtttg cgcaacgttg ttgccattgc tacaggcatc gtggtgtcac gctcgtcgtt   7680
tggtatggct tcattcagct ccggttccca acgatcaagg cgagttacat gatccccat   7740 gttgtgcaaa aaagcggtta gctccttcgg tcctccgatc gttgtcagaa gtaagttggc   7800
cgcagtgtta tcactcatgg ttatggcagc actgcataat tctcttactg tcatgccatc   7860
cgtaagatgc ttttctgtga ctggtgagta ctcaaccaag tcattctgag aatagtgtat   7920
gcggcgaccg agttgctctt gcccggcgtc aatacgggat aataccgcgc cacatagcag   7980
```

| | |
|---|---|
| aactttaaaa gtgctcatca ttggaaaacg ttcttcgggg cgaaaactct caaggatctt | 8040 |
| accgctgttg agatccagtt cgatgtaacc cactcgtgca cccaactgat cttcagcatc | 8100 |
| ttttactttc accagcgttt ctgggtgagc aaaaacagga aggcaaaatg ccgcaaaaaa | 8160 |
| gggaataagg gcgacacgga aatgttgaat actcatactc ttccttttc aatattattg | 8220 |
| aagcatttat cagggttatt gtctcatgag cggatacata tttgaatgta tttagaaaaa | 8280 |
| taaacaaata ggggttccgc gcacatttcc ccgaaaagtg ccacctgatg cggtgtgaaa | 8340 |
| taccgcacag atgcgtaagg agaaaatacc gcatcaggaa attgtaagcg ttaatatttt | 8400 |
| gttaaaattc gcgttaaatt tttgttaaat cagctcattt tttaaccaat aggccgaaat | 8460 |
| cggcaaaatc ccttataaat caaaagaata gaccgagata gggttgagtg ttgttccagt | 8520 |
| ttggaacaag agtccactat taaagaacgt ggactccaac gtcaaagggc gaaaaaccgt | 8580 |
| ctatcagggc gatggcccac tacgtgaacc atcaccctaa tcaagttttt tggggtcgag | 8640 |
| gtgccgtaaa gcactaaatc ggaacccctaa agggagcccc cgatttagag cttgacgggg | 8700 |
| aaagccggcg aacgtggcga aaaggaagg gaagaaagcg aaaggagcgg gcgctagggc | 8760 |
| gctggcaagt gtagcggtca cgctgcgcgt aaccaccaca cccgccgcgc ttaatgcgcc | 8820 |
| gctacagggc gcgtccattc gccattcagg ctgcgcaact gttgggaagg gcgatcggtg | 8880 |
| cgggcctctt cgctattacg ccagctgcg aaaggggat gtgctgcaag gcgattaagt | 8940 |
| tgggtaacgc cagggttttc ccagtcacga cgttgtaaaa cgacggccag tgaattgtaa | 9000 |
| tacgactcac tata | 9014 |

<210> SEQ ID NO 15
<211> LENGTH: 5954
<212> TYPE: DNA
<213> ORGANISM: Homo sapiens

<400> SEQUENCE: 15

| | |
|---|---|
| ggccgcggga attcgattcc ttaattaagt cgactgggac ccaaactttg gagtcgttga | 60 |
| cagatgtgac aggtgaagcc tgggatgaca tcgccaaaaa tgcaacgtct cactcattgt | 120 |
| cactactccc agggctcagt cgtcactggg gaaaatctcc agaaggtagc gcgggccaag | 180 |
| gtgacaggtg tctgccaaga tctgcccgcc agactcccgg gcggcgcgct ccctccctgc | 240 |
| aggccttcag cccgtcagca tccccttcct cggggccctg ctcactccca gcctccatcc | 300 |
| ccctgccatc tcctccgccg gtcgcgtgcg gacacaagga tggggacctc ccagcgagga | 360 |
| gcgctctggg cggggctccg gacgcatgcg cggccctcgt acggaagccc ggaaggaggg | 420 |
| gcaggggcg gtggctcagg tttctccggg cggcggcggc ggcggcggcg gcgacggcga | 480 |
| cggcgacggc agcggggacg gcagcagtag cgggagcagc agcgtggacg cggctggcgc | 540 |
| tggcgccatg aacccgctgt aaggcgcagg ctgtgcagca cggggtgcgg gggaggagga | 600 |
| ggaggacgcc gcggtgaagt tctccgccat gaacctgagg ggcctcttcc aggacttcaa | 660 |
| cccgaggtga ggcggcgtcg ttggcgcccc cgggagtccg cgctgcgggc tcggcgcgg | 720 |
| gctggtgttc ggctccgggg aggcacggcg ggcgagatgc tgcagcccga ggacccgggc | 780 |
| gcctgcccga gctccctgc gggtgcaagc ggtccccagg caaaacagtc ggcctcggcg | 840 |
| cccgcccgct tcctcctccc gtgccgtg cttcagccc ctgccggcc acggccgaa | 900 |
| gggccggcc gcgagccccg tcctgcccca agggaacccc attctttct gcttgctgtc | 960 |
| cctcattggt gtcccaactt cttcgtctcg gttccatcct cttctgcgcc gctgcgggcc | 1020 |
| ctccattctc cgcgtcaggg ccgtctcact cgacccaaca cccctacccc caccccagct | 1080 |

```
gtttcctcca gttcctcgca gtccttgggg ttttccttgg gtttatgccc atccctctct   1140
tgtttgcttc tttgttgaac ggatacctga aacactgttg aatccttgga gtcagtgtcg   1200
gggtatggca ataccttata taatgcattt ctgggtgagc ctgatcattt tccatactca   1260
ttttctcatc agtcttcact acaagtttat ttgcaggaag tagatattgc tgtccttctt   1320
ttccagatgg ggaacaccca gtggacagtg tggagaaaac actggctaag cactcaagcg   1380
cctgtccttg cacttgcccg actgttttgt aactgttctt taccccaggc tgtgagctcc   1440
ctgaagctga gaccatctcc tgctcatctc agtgtcccca gcgcctccca cccaccgtat   1500
ctggcacata gtaggcacat ataaaatgtt tgtggaacta aactgagccc aaagacttgg   1560
attggagacg aggccatatg taactgggtg attctctgcc cttctttggc ccttctgtaa   1620
aatgaggagt tggcctaact gatctcttaa atgcactact ctccgaaagg agtatccgtt   1680
tcccttattt gccagttggg aagacgtgct cagtaaatat ttgtgtgctg taacctatgt   1740
taggtgcttt agatgctggc ggtctcagca tggggtgaag aagggcttgt acacttaaga   1800
tgccttacag tactgtgcag tgctgtactg cggggccaa ctctggggac ctatgccttg   1860
gctgcttgtt gaggatgaaa ggaagtttta ggggagtatt tgtatgttga gggtgcagtc   1920
tccctaggga tggtgacatt ttaacttgtg agtcattgtg actttgtatg tgcccttatt   1980
ccactttgag ttcatgttct ggttaggagt gccagtgtct ctaacacggt gcagacatta   2040
tcattgttgg cttcgaaggc atagaggagg taacagaact aactgcagtc ccttcctctg   2100
ctgcatcagg gggttaagat tggtctgcag ggtagtaggg ttggtgctgt ggctggacaa   2160
gccctgtatg tcttctattt ggagatggtg ataagaaagt taagtaaaaa ctgaattgtt   2220
ttgtgccctt gggcaactca cttatctatt gttttatctg tagaatgagt ataatctctc   2280
agtggggtag ggaggccaat taaggattga ttacaaagtg ccttacaaat agaaagctac   2340
agtgacttgt ttgcaaggtg acagagaatt cagaagcctc aagaaactgc ttaagtgat   2400
caaacaggct aacggagttg ccaaagcaaa atagtgctgc actgatacta cctttaaccg   2460
tttttttcctt tagccctttt cccccaaaa aaattagtat atgaaattac agtgaaatac   2520
ctggtatcta agcagattta tagtaattct caacatattc atcaatctct taattctacc   2580
tgcattaaaa tgtatttcta cctgaaaagt ttaaaggtct tttatactgt gccattttcc   2640
tgattcattg ttgccagagg tagtgagttc cttaatttta cagatatttc aagaggacat   2700
tggccaggta ttattggtaa atcagatttg tttttttagc tggtagtgtt tcacctctcc   2760
tgagcactcc tagttttga cagtgtgctt tagtctcctt ccatgctgag gaaggccttc   2820
tctataggag aaagaaaact gagggggtgta cacaggaagt taccttatgc tggggactca   2880
aaccttgatg ctactgcttt gctccctgcc tctattttg aaccaattca acatctccct   2940
cctaccccag gaccttgtca cacactgttc tctttaccag gaatgtttcc ctctcttttc   3000
ctctcctcca gacctagtga actcctattt atcctcactt ggcacttgct aagggaagca   3060
ttcctgactt ccctgaccag atttactgct ccctgtttct acagttcctg tagtatttac   3120
tactcctcca tcatagtgca tatttgtacc cttgtgtctg tctggatgct tatttgatta   3180
atacctgcct cccccactaa actttaagct ccatggggtc aaggccgtga ctgtgtcagt   3240
atcgtagcct gcatacttgg aatagtacct ggctcaataa atatttgtgg agtaaataac   3300
tgaataactc tccagagcct ataagataaa tctagagctg ctgctttcaa tcactgcttt   3360
cctggtggtc tgtggcctgg ttctctttct tctcacactc ttcccacctt cagagtgcag   3420
ccattgccttt ggagagatgg gagagaacat ggcactaagg cagaatatgg ctatatttac   3480
```

```
tttgaagagc atgtctttgt catagaaata gtcactgtca tggtttggtg ggtcccaagg   3540
catgggtcat ggctccagat ccccttttcca gccttttgga tcttggtaag tctgaaccca   3600
ctgctgcgtt ggcaaggctc tggaaactat agtgacagag aatgattcac aagtgtcaac   3660
actcagatgt acagggctgc cagctgaccc actctaccta tttccatctg gcactgaact   3720
ggttgatcat gaacttcttt tcataattgc ttttttagtta tgcaggttaa gacatgccga   3780
aacagatgta ccggacccac aaacaagtcc ttccttgaat gcctgaggct tcctaacagt   3840
gaaagagccc tgttcttaga gtaggcaaac tgattctgag gcattgtagg tggtagggat   3900
ctggtagtag gtagcattag gtgggctccc ggcactcacc atggagcctt gaaattttct   3960
gctactttgg gggagttgct ggttcagaga aggcccttcc accctggtag ccatgtggca   4020
ctggaaggct gtgaaaactc tgctgggcct tcttagtcat ctgttgtgag ctcctgatgg   4080
gagtgtggtg tatccctcag gtgtgctaga ctggaacaaa ggctgagaag tgttgctctg   4140
ggggttccaa cttgtgggca tggggtactg atgagatcag tagtgtttgg agacttctgt   4200
atgctccatc ttcagaagac attctggagt ccatataagt tatcttgtct cttgtttgaa   4260
gcaggaaaaa ggaatgcgat tgctggtaat atagttcact aaagtcagct acctggcctc   4320
taacagttat ttgcaaagta tattataaca ttgattcctc aaacatctag attcctatct   4380
cgtgccaagt gatgtactag gtgctctaag tacaaaaata aaggaatata gtcctcctct   4440
caatgcgtaa gcctagtgga agaagcagaa atgaaaggga aataagaatt caatagagta   4500
tgaggcatta cagtgaaaga aaccaaatgt cttagaagta caaatggcag agctactaat   4560
tctgtctcga gcaggcaggg aagagtctat agtggaaatg acttttgagc tagattttga   4620
attgagctag tcttttgagc cagacttttg agctagaatt gtagggttgt catcagacca   4680
gagagtagga agggtacctt gtgaggaaga gagagagaga tcagattgtt actgtgtcta   4740
tgtagaaaag gaagacataa gaaactccat tttgatctgt actaagaaaa attgtttctg   4800
ctttgagatg ctgttaacct gtaactttag tcccaacccct gtgctcacag aaacctgtgc   4860
tgtaatgaat caaggtttaa tggatttagg gctgtgcagg atgtaccttg ttaacaatat   4920
gtttgcaggc agtatgcttg gtaaaagtca tcgccattct ccattctcga ttaaccaggg   4980
acacagtgca ctgcggaagg ccgcagggac atctgcccaa gaaagcctgg gtattgtcca   5040
aggtttcccc ccactgagac agcctgagat atggccttgt gggaaaggaa agaccttacc   5100 acccccccagc ccgacacccg taaagtgtct gtgctgagga ggagtagtga aagagcgggg   5160
cctctttgca gttgagataa gaggaaggct tctgtctcct gctcatccct gggaatggaa   5220
tgtctctgtg taaagctgac cattcccatt cgttctattc tgagatagga gaaaccacc    5280 ctgtggctgg aggcgaagta tgctggcagc aatactgctc tgttactctt tgctacactg   5340
agttgtttgg gtaaagagaa acataaatct agcctgcgtg cacatccagg cacagtacct   5400
ttccttgaac ttattcatga tacagattcc tttgctcacg tttccctgct gaccttctcc   5460
ccacctgttg ccctgctaca ctcccctcgc taagatagta aaaataatga tcagtaaata   5520
ctgaggtaac tcagaggcta gcgctggtgc gggtcctccg tatgctgagt gccggtcccc   5580
tgggcccact gttctttctc tatactttgt ttctgtgtct tatttctttt ctcagtctcg   5640
tcccacctga cgagaaatac ccacaggtgt ggaggggctg gcccctttca gtatctcaga   5700
agggacaaag tacacaaagg catgggtca tgatagtgcc tggtatgttc aggtagtgaa    5760
gaggtccatg tggtatgagc actgcagatg atatgtgtcg tatgaattaa aaatacatag   5820
ttactgcaaa tagttttttac aggttattgt ttttaagaaa gcagtatcta atgcacgagt   5880
```
gtactgtcag tactgtcaat gaactactta ccactcaagt gactgcttac gcgtcgaatc    5940
actagtgaat tcgc    5954

<210> SEQ ID NO 16
<211> LENGTH: 30756
<212> TYPE: DNA
<213> ORGANISM: Homo sapiens
<220> FEATURE:
<221> NAME/KEY: misc_feature
<222> LOCATION: (1)..(30756)
<223> OTHER INFORMATION: n= a, c, g, t, unknown or other

<400> SEQUENCE: 16
gtacggaagc ccggaaggag gggcagggggg cggtggctca ggtttctccg ggcggcggcg    60
gcggcggcgg cggcgacggc gacggcgacg gcagcggggga cggcagcagt agcgggagca    120
gcagcgtgga cgcggctggc gctggcgcca tgaacccgct gtaaggcgca ggctgtgcag    180
cacggggtgc gggggaggag gaggaggacg ccgcggtgaa gttctccgcc atgaacctga    240
ggggcctctt ccaggacttc aacccgaggt gaggcggcgt cgttggcgcc cccgggagtc    300
cgcgctgcgg gctcgggcgc gggctggtgt tcggctccgg ggaggcacgg cgggcgagat    360
gctgcagccc gaggacccgg gcgcctgccc gagcctccct gcgggtgcaa gcggtcccca    420
ggcaaaacag tcggcctcgg cgcccgcccg cttcctcctc ccgtgcccgg tgctttcagc    480
ccctgcccgg ccacggccgg aagggcccgg ccgcgagccc cgtcctgccc caagggaacc    540
ccattctttt ctgcttgctg tccctcattg gtgtcccaac ttcttcgtct cggttccatc    600
ctcttctgcg ccgctgcggg ccctccattc tccgcgtcag ggccgtctca ctcgacccaa    660 caccccctacc cccaccccag ctgttttcctc cagttcctcg cagtccttgg ggttttcctt    720
gggtttatgc ccatccctct cttgtttgct tctttgttga acggatacct gaaacactgt    780
tgaatccttg gagtcagtgt cggggtatgg caatacctta tataatgcat ttctgggtga    840
gcctgatcat tttccatact cattttctca tcagtcttca ctacaagttt atttgcagga    900
agtagatatt gctgtccttc ttttccagat ggggaacacc cagtggacag tgtggagaaa    960
acactggcta agcactcaag cgcctgtcct tgcacttgcc cgactgtttt gtaactgttc    1020
tttaccccag gctgtgagct ccctgaagct gagaccatct cctgctcatc tcagtgtccc    1080
cagcgcctcc cacccaccgt atctggcaca tagtaggcac atataaaatg tttgtggaac    1140
taaactgagc ccaaagactt ggattggaga cgaggccata tgtaactggg tgattctctg    1200
cccttctttg gcccttctgt aaaatgagga gttggcctaa ctgatctctt aaatgcacta    1260
ctctccgaaa ggagtatccg tttcccttat ttgccagttg ggaagacgtg ctcagtaaat    1320
atttgtgtgc tgtaacctat gttaggtgct ttagatgctg gcggtctcag catggggtga    1380
agaagggctt gtacacttaa gatgcctac agtactgtgc agtgctgtac tgcgggggcc    1440
aactctgggg acctatgcct tggctgcttg ttgaggatga aggaagttt tagggagta    1500 tttgtatgtt gagggtgcag tctccctagg gatggtgaca ttttaacttg tgagtcattg    1560
tgactttgta tgtgccctta ttccactttg agttcatgtt ctggttagga gtgccagtgt    1620
ctctaacacg gtgcagacat tatcattgtt ggcttcgaag gcatagagga ggtaacagaa    1680
ctaactgcag tcccttcctc tgctgcatca gggggttaag attggtctgc agggtagtag    1740
ggttggtgct gtggctggac aagccctgta tgtcttctat ttggagatgg tgataagaaa    1800
gttaagtaaa aactgaattg ttttgtgccc ttgggcaact cacttatcta ttgttttatc    1860
tgtagaatga gtataatctc tcagtggggt agggaggcca attaaggatt gattacaaag    1920

```
tgccttacaa atagaaagct acagtgactt gtttgcaagg tgacagagaa ttcagaagcc   1980
tcaagaaact gccttaagtg atcaaacagg ctaacggagt tgccaaagca aaatagtgct   2040
gcactgatac tacctttaac cgttttttcc tttagccctt ttcccccaa aaaaattagt    2100 atatgaaatt acagtgaaat acctggtatc taagcagatt tatagtaatt ctcaacatat   2160
tcatcaatct cttaattcta cctgcattaa aatgtatttc tacctgaaaa gtttaaaggt   2220
cttttatact gtgccatttt cctgattcat tgttgccaga ggtagtgagt tccttaattt   2280
tacagatatt tcaagaggac attggccagg tattattggt aaatcagatt tgttttttta   2340
gctggtagtg tttcacctct cctgagcact cctagttttt gacagtgtgc tttagtctcc   2400
ttccatgctg aggaaggcct tctctatagg agaaagaaaa ctgaggggtg tacacaggaa   2460
gttaccttat gctggggact caaaccttga tgctactgct ttgctccctg cctctatttt   2520
tgaaccaatt caacatctcc ctcctacccc aggaccttgt cacacactgt tctctttacc   2580
aggaatgttt ccctctcttt tcctctcctc cagaccagt gaactcctat ttatcctcac    2640
ttggcacttg ctaagggaag cattcctgac ttccctgacc agatttactg ctccctgttt   2700
ctacagttcc tgtagtattt actactcctc catcatagtg catatttgta cccttgtgtc   2760
tgtctggatg cttatttgat taatacctgc ctcccccact aaactttaag ctccatgggg   2820
tcaaggccgt gactgtgtca gtatcgtagc ctgcatactt gaatagtac ctggctcaat    2880 aaatatttgt ggagtaaata actgaataac tctccagagc ctataagata aatctagagc   2940
tgctgctttc aatcactgct ttcctggtgg tctgtggcct ggttctcttt cttctcacac   3000
tcttcccacc ttcagagtgc agccattgct ttggagagat gggagagaac atggcactaa   3060
ggcagaatat ggctatattt actttgaaga gcatgtcttt gtcatagaaa tagtcactgt   3120
catggtttgg tgggtcccaa ggcatgggtc atggctccag atccccttc cagccttttg    3180 gatcttggta agtctgaacc cactgctgcg ttggcaaggc tctggaaact atagtgacag   3240
agaatgattc acaagtgtca cactcagat gtacagggct gccagctgac ccactctacc    3300
tatttccatc tggcactgaa ctggttgatc atgaacttct tttcataatt gcttttagt    3360 tatgcaggtt aagacatgcc gaaacagatg taccggaccc acaaacaagt ccttccttga   3420
atgcctgagg cttcctaaca gtgaaagagc cctgttctta gagtaggcaa actgattctg   3480
aggcattgta ggtggtaggg atctggtagt aggtagcatt aggtgggctc ccggcactca   3540
ccatggagcc ttgaaatttt ctgctacttt gggggagttg ctggttcaga gaaggccctt   3600
ccaccctggt agccatgtgg cactggaagg ctgtgaaaac tctgctgggc cttcttagtc   3660
atctgttgtg agctcctgat gggagtgtgg tgtatccctc aggtgtgcta gactggaaca   3720
aaggctgaga agtgttgctc tgggggttcc aacttgtggg catggggtac tgatgagatc   3780
agtagtgttt ggagacttct gtatgctcca tcttcagaag acattctgga gtccatataa   3840
gttatcttgt ctcttgtttg aagcaggaaa aaggaatgcg attgctggta atatagttca   3900
ctaaagtcag ctacctggcc tctaacagtt atttgcaaag tatattataa cattgattcc   3960
tcaaacatct agattcctat ctcgtgccaa gtgatgtact aggtgctcta agtacaaaaa   4020
taaaggaata tagtcctcct ctcaatgcgt aagcctagtg gaagaagcag aaatgaaagg   4080
gaaataagaa ttcaatagag tatgaggcat tacagtgaaa gaaaccaaat gtcttagaag   4140
tacaaatggc agagctacta attctgtctc gagcaggcag ggaagagtct atagtggaaa   4200 tgactttga gctagatttt gaattgagct agtcttttga gccagacttt tgagctagaa    4260
ttgtagggtt gtcatcagac cagagagtag gaagggtacc ttgtgaggaa gagagagaga   4320
```

```
gatcagattg ttactgtgtc tatgtagaaa aggaagacat aagaaactcc attttgatct   4380
gtactaagaa aaattgtttc tgctttgaga tgctgttaac ctgtaacttt agtcccaacc   4440
ctgtgctcac agaaacctgt gctgtaatga atcaaggttt aatggattta gggctgtgca   4500
ggatgtacct tgttaacaat atgtttgcag gcagtatgct tggtaaaagt catcgccatt   4560
ctccattctc gattaaccag ggacacagtg cactgcggaa ggccgcaggg acatctgccc   4620
aagaaagcct gggtattgtc caaggtttcc ccccactgag acagcctgag atatggcctt   4680
gtgggaaagg aaagaccttta ccaccccca gcccgacacc cgtaaagtgt ctgtgctgag   4740
gaggagtagt gaaagagcgg ggcctctttg cagttgagat aagaggaagg cttctgtctc   4800
ctgctcatcc ctgggaatgg aatgtctctg tgtaaagctg accattccca ttcgttctat   4860
tctgagatag gagaaaacca ccctgtggct ggaggcgaag tatgctggca gcaatactgc   4920
tctgttactc tttgctacac tgagttgttt gggtaaagag aaacataaat ctagcctgcg   4980
tgcacatcca ggcacagtac cttccttga acttattcat gatacagatt cctttgctca   5040
cgtttccctg ctgaccttct ccccacctgt tgccctgcta cactcccctc gctaagatag   5100
taaaaataat gatcagtaaa tactgaggta actcagaggc tagcgctggt gcgggtcctc   5160
cgtatgctga gtgccggtcc cctgggccca ctgttctttc tctatactttt gtttctgtgt   5220 cttatttctt ttctcagtct cgtcccacct gacgagaaat acccacaggt gtggagggc   5280 tggccccttt cagtatctca gaagggacaa agtacacaaa ggcatggggt catgatagtg   5340
cctggtatgt tcaggtagtg aagaggtcca tgtggtatga gcactgcaga tgatatgtgt   5400
cgtatgaatt aaaaatacat agttactgca aatagttttt acaggttatt gttttttaaga   5460 aagcagtatc taatgcacga gtgtactgtc agtactgtca atgaactact taccactcaa   5520
gtgactgctt acgcgtcgaa tcactagtga attcgcggcc gcctcgagtc tagaactagt   5580
ggatccccca acgggccct ctagacgcgt tgacattgat tattgactag ttattaatag   5640
taatcaatta cggggtcatt agttcatagc ccatgatatc atatggagtt ccgcgttaca   5700
taacttacgg taaatggccc gcctggctga ccgcccaacg accccgccc attgacgtca   5760 ataatgacgt atgttccat agtaacgcca atagggactt ccattgacg tcaatgggtg   5820 gagtatttac ggtaaactgc ccacttggca gtacatcaag tgtatcatat gccaagtacg   5880 ccccctatt gacgtcaatg acggtaaatg gccgcctgg cattatgccc agtncatgac   5940
cttatgggac tttcctactt ggcagacatc tacgtattag tcatcgctat taccatggtg   6000
atgcggtttt ggcagtacat caatgggcgt ggatagcggt ttgactcacg gggatttcc   6060 aagtctccac cccattgacg tcaatgggag tttgttttgg caccaaaatc aacgggactt   6120
tccaaaatgt cgtaacaact ccgccccatt gacgcaaatg ggcggtaggc gtgtacggtg   6180
ggaggtctat ataagcagag ctctctggct aactagagaa ccctgctta ctggcttatc   6240 gagatatctg cagaattcat ctgtcgactg ctaccggcag cgcgcagcgg caagaagtgt   6300
ctgggctggg acggacagga gaggctgtcg ccatcggcgt cctgtgcccc tctgctccgg   6360
cacgcccctg tcgcagtgcc cgcgcttttcc ccggcgcctg cacgcggcgc gcctgggtaa   6420
catgcttggg gtcctggtcc ttggcgcgct ggcctggcc ggcctggggt tcccgcacc   6480 cgcagagccg cagccgggtg gcagccagtg cgtcgagcac gactgcttcg cgctctaccc   6540
gggccccgcg accttcctca atgccagtca gatctgcgac ggactgcggg gccacctaat   6600
gacagtgcgc tcctcggtgg ctgccgatgt catttccttg ctactgaacg gcgacggcgg   6660
cgttggccgc cggcgcctct ggatcggcct gcagctgcca cccggctgcg gcgaccccaa   6720
```

```
gcgcctcggg cccctgcgcg gcttccagtg ggttacggga gacaacaaca ccagctatag   6780
caggtgggca cggctcgacc tcaatggggc tcccctctgc ggcccgttgt gcgtcgctgt   6840
ctccgctgct gaggccactg tgcccagcga gccgatctgg gaggagcagc agtgcgaagt   6900
gaaggccgat ggcttcctct gcgagttcca cttcccagcc acctgcaggc cactggctgt   6960
ggagcccggc gccgcggctg ccgccgtctc gatcacctac ggcacccgt tcgcggcccg    7020 cggagcggac ttccaggcgc tgccggtggg cagctccgcc gcggtggctc ccctcggctt   7080
acagctaatg tgcaccgcgc cgccggagc ggtccagggg cactgggcca gggaggcgcc    7140
gggcgcttgg gactgcagcg tggagaacgg cggctgcgag cacgcgtgca atgcgatccc   7200
tggggctccc cgctgccagt gcccagccgg cgccgccctg caggcagacg ggcgctcctg   7260
caccgcatcc gcgacgcagt cctgcaacga cctctgcgag cacttctgcg ttcccaaccc   7320
cgaccagccg ggctcctact cgtgcatgtg cgagaccggc taccggctgg cggccgacca   7380
acaccggtgc gaggacgtgg atgactgcat actggagccc agtccgtgtc cgcagcgctg   7440
tgtcaacaca cagggtggct tcgagtgcca ctgctaccct aactacgacc tggtggacgg   7500
cgagtgtgtg gagcccgtgg acccgtgctt cagagccaac tgcgagtacc agtgccagcc   7560
cctgaaccaa actagctacc tctgcgtctg cgccgagggc ttcgcgccca ttccccacga   7620
gccgcacagg tgccagatgt tttgcaacca gactgcctgt ccagccgact gcgaccccaa   7680
cacccaggct agctgtgagt gccctgaagg ctacatcctg gacgacggtt tcatctgcac   7740
ggacatcgac gagtgcgaaa acggcggctt ctgctccggg gtgtgccaca acctcccgg    7800 taccttcgag tgcatctgcg ggcccgactc ggcccttgcc cgccacattg gcaccgactg   7860
tgactccggg aaggtggacg gtggcgacag cggctctggc gagccccgc ccagcccgac    7920 gcccggctcc accttgactc ctccggccgt ggggctcgtg cattcgggct gctcatagg    7980 catctccatc gcgagcctgt gcctggtggt ggcgcttttg gcgctcctct gccacctgcg   8040
caagaagcag ggcgccgcca gggccaagat ggagtacaag tgcgcggccc cttccaagga   8100
ggtagtgctg cagcacgtgc ggaccgagcg gacgccgcag agactctgag cggcctccgt   8160
ccaggagcct ggctccgtcc aggagcctgt gcctcctcac ccccagcttt gctaccaaag   8220
caccttagct ggcattacag ctggagaaga ccctcccgc acccccaag ctgttttctt     8280 ctattccatg gctaactggc gaggggtga ttagagggag gagaatgagc ctcggcctct    8340
tccgtgacgt cactggacca ctgggcaatg atggcaattt tgtaacgaag acacagactg   8400
cgatttgtcc caggtcctca ctaccgggcg caggagggtg agcgttattg gtcggcagcc   8460
ttctgggcag accttgacct cgtgggctag ggatgactaa atatttatt tttttttaagt   8520 atttaggttt ttgtttgttt cctttgttct tacctgtatg tctccagtat ccactttgca   8580
cagctctccg gtctctctct ctctacaaac tcccacttgt catgtgacag gtaaactatc   8640
ttggtgaatt ttttttttcct agccctctca catttatgaa gcaagcccca cttattcccc   8700
attcttccta gttttctcct cccaggaact gggccaactc acctgagtca ccctacctgt   8760
gcctgaccct acttcttttg ctcttagctg tctgctcaga cagaacccct acatgaaaca   8820
gaaacaaaaa cactaaaaat aaaaatggcc atttgctttt tcaccagatt tgctaattta   8880
tcctgaaatt tcagattccc agagcaaaat aattttaaac aaaggttgag atgtaaaagg   8940
tattaaattg atgttgctgg actgtcatag aaattacacc caagaggta tttatctta    9000 cttttaaaca gtgagcctga attttgttgc tgttttgatt tgtactgaaa aatggtaatt   9060
gttgctaatc ttcttatgca atttcctttt ttgttattat tacttatttt tgacagtgtt   9120
```

```
gaaaatgttc agaaggttgc tctagattga gagaagagac aaacacctcc caggagacag   9180
ttcaagaaag cttcaaactg catgattcat gccaattagc aattgactgt cactgttcct   9240
tgtcactggt agaccaaaat aaaaccagct ctactggtct tgtggaattg ggagcttggg   9300
aatggatcct ggaggatgcc caattagggc ctagccttaa tcaggtcctc agagaatttc   9360
taccatttca gagaggcctt ttggaatgtg gcccctgaac aagaattgga agctgccctg   9420
cccatgggag ctggttagaa atgcagaatc ctaggctcca ccccatccag ttcatgagaa   9480
tctatattta acaagatctg caggggggtgt gtctgctcag taatttgagg acaaccattc   9540
cagactgctt ccaattttct ggaatacatg aaatatagat cagttataag tagcaggcca   9600
agtcaggccc ttattttcaa gaaactgagg aattttcttt gtgtagcttt gctctttggt   9660
agaaaaggct aggtacacag ctctagacac tgccacacag ggtctgcaag gtctttggtt   9720
cagctaagct aggaatgaaa tcctgcttca gtgtatggaa ataaatgtat catagaaatg   9780
taacttttgt aagacaaagg ttttcctctt ctattttgta aactcaaaat atttgtacat   9840
agttatttat ttattggaga taatctagaa cacaggcaaa atccttgctt atgacatcac   9900
ttgtacaaaa taaacaaata acaatgtgaa aaaaaaaaa aaaaaaaaaa aaaaaaaaa    9960 aaaaaaagg tagcagtcga cagatgaatt ccaccacact ggactagtgg atccgagctc   10020
ggtaccaagc ttaagtttgg gctgcaggaa ttctgatggc tctcaaaatt cctgcctcct   10080
ttagggataa aagactttaa gactttttaa caaaaaagaa aagaaaaaa aaaattcctg   10140 cctcctggtg tacacacaca gaagggttcc ctccccttga atgtgaccag gatctgtgaa   10200
aataacggga tagccgctcc tgtgattagg ttatgtggta gactagagca agattctcct   10260
gctggttttg aagaagtcag ctgccatgtt gtgagactgt catgggctag gcatgagcc    10320 tttaaatatc tgggagcaac ccctggccag cagccagtga gaaaacgggc cctcagtcct   10380
acaatcacaa ggaactaaat tctgccaaca acctgaagga actttgaaga ggatcatgag   10440
tcccttgatt cagcttgatg agcccctgag cagaggatac agctaacttg tactagggaa   10500
gtataaaaaa catgcatggg aatgatatat atcaacttta aggataattg tcatacttct   10560
gggaatgaag ggaagaaat ggggctttag ttgtattatg atctttaatt tctcaaaaaa    10620
aataagatca gaagcaaata tggcaaaatg ttaatacttt tgtgggtacg taggtattca   10680
gcatacccct ttttctgagt tcaaaatatt ttataattaa aatgaaatgc aggccaggca   10740
cagtggctca tgcctataat accagcactt tgcgaggccg aggtgggagg atggcttgag   10800
gccagaccag cctggccaac atggcaaaac cccatctcta cttaaaaaaa aaaaaactat   10860
atatatatat atgtgtgtgt gtgtgtatat atatatatgt atatatattt atatatgtgt   10920
gtatatatat atatgtatat atatttatat atgtgtgtgt atatatatat atacacacac   10980
acacatatat acatacatac atacacacac acacacacac aattagccag gcatggtggc   11040
gcacacctgt agtcccagct acttgggagg ctgagacatg agaattgctt gaacctggga   11100
ggcagagtag ttagtgagct gagatcatac cactgcactc cagcctggtg acagagtgag   11160
actctgtctt aaaaaaaata aaaattaaaa ttaaatgcaa aaggtccaag tgaattgaag   11220 aggaagggg tatcaaggaa ggttttgtgg aggtgacgtt tgagctgggt cttaaatgac    11280
ttaaacatgg gataagaagg gagggaataa ggacatttca ggtacgagaa ataaggagca   11340
aacagtggaa acaacctaac gtcgtcaac cagtgaatgg ataacaaaaa tgtaattcag    11400
atggtatcca acttacgatg gttcaacatg agatttttct gacttttagga tagatttatc   11460 aaagtagtaa atccattttc aacttatgat attttcaact tcagatgggt ttatcaggac   11520
```

```
acagttgagg aacacctgtc tatccataca atttggcaat aaaaaggaaa tgagtgcaga    11580
tatactccac aacatgaatg aaccttgaaa acattaagtg agagaagcca gatacaaaag    11640
gccacatatt gtatgattct atttatacaa aatgtccaga ataggcaaat cttatagaca    11700
gcaagtaggt agatgatcag tttgctaggt gctgggggaa ggggaaatgg ggagtgatgg    11760
ctaaggggat tgggtttctt tgtgggcaa tgaaaatgtt ttaaaattga gcgtgataat    11820
gattgcacaa tgctgcatat atatataatc tatagattat atatatataa agagaggctg    11880
ttagacagtg ataagtgata tatatatata tatacataga gagagagaga gagagagaga    11940
gaggctgtta gtgataagtg atcaggaaaa taaaagtatt gaggaggaat acgaagttga    12000
cggtgtgaaa acatgagatt ttatatagga tggccaggga aggccttaat gagaaagtga    12060
cttatgagta aaacaaggg atcctaaacc ttagcatgca tcagaatcac tcggaaactt    12120
gttaaagcat agcttgctgg gcctcatcac agatattttg attcggtagg ttcttgtctg    12180
atattaatac ttttggtcta gggaaccaca ttttgagaac cactgagcta aaggaagtaa    12240
aggtttccct tagtttacta gctggtaaca ctggcccagg aggcctttct ggaaaaggtc    12300
ccagtcccca aaggaagctg gggactcgcg ttcacatcgt caaggtttac caagttgtgg    12360
cgggcctttc cgtcttggaa aaagcctcaa aatggcagat tagggtgtcc atggccggcg    12420
gaaagggtct ttgaagttgc agaccaggag ggaagaagat tctgggcctc ccccatgcag    12480
tgtcagctgg caacagaatg caccccggct gggttggagg ccctgggtac tggctcttcc    12540
acaccagggg cccacctacc aagggcagca ggagcatctg cacctcctgc gccaggcgcc    12600
cttcagtgct tccacttgag cacctctcca gacaccagct agggtgacag tggtacaaat    12660
accagactcc cctggcctgc tcacctcaca gggtaatgtg ctgtggagtc aggggacac    12720 agcaaccacc agatgacatg gctggccccg gggaggacga cacgcagata cggctacttg    12780
gcacctgtga tattttacac actcgagagg ggcccgcacc atcctcagcc ctctccccac    12840
attcactctt agttcatgtc acctccaccc agaggggac acaggcccac agcgatggcc    12900
ccacaccctg cctgaggtcg cccacttccc aggaggcagt cctgggactt ccacccgacc    12960
aggccccaga gcccaccgac ttaacccctc cagaggcttg tcgttcatta ccttattcaa    13020
gatggagacc agccttttg cggagaaaat gcgggtgaag gtcctgaaag tgcattgacg    13080
ccgttttcgg aagccataca agtttagctg gcggaagaag ctctttatcg aagttgtggc    13140
aaacactttg tgtgcgacgt ccccttttgag aatctccttt tcaaagagtt tttgattgat    13200
cactctacaa gccccactgt catcccacca gatggacgaa aactggttgc tgctgaccag    13260
tctccacagt ttctgtggaa aggggaggga gaggagatta tcttctccct ggggcgggac    13320
gtcaccgtca gggtgcggcc ttctgaacga agcttcctcg gccagaggtt ggaaagcgat    13380
ttcttctgtc agcagcctca agttagggct cccagtggac cccgggtcgt cccaggcagg    13440
ggaaggatct gctgggtgaa ggtaggtctc tgactgcaac tggggaggga aaggcaccct    13500
ttccaagcca tgatcctgtc ctctcgaatt tctttcttca cagcgagcca tactcaatga    13560
tcgcttgtcc tccatctggc aaacttgcta gtgcagtgtg ccagcagca ccccttggca    13620 gtcatgtaac cagccccatg acatcataaa gggctctga ctgccggggg gtggcatctc    13680 caccccagc aagttgtgta ataaagggcc aaggcagaca agtagctgcc catctgcatg    13740
tgcacattct ggtcctcaca gtcatttcaa tgggaaagat gacactagtg cacaagagtg    13800
ccgaggggcc ctgccacacc gtagatgcag acctggagcg gtccccttgt cctagagctc    13860
ctgagccagg cacaactaca gcaaagccct ggctcaggaa ggtcagagct caccgtctga    13920
```

```
gtcatgggcc cacagacccc agcacatgac tgacactcgg aagcacagaa caaagggtag    13980
gacggtgccc atgggtcagg ctgtagccac gccacccttt ccaccctgtc ctagccagag    14040
gcagcaatgt gctccataca gatcctccta acacacccac actgtcggtc cccagcacgc    14100
agatgcccga cagcccctta ggcaaatggc ttagctgact gccccaccac acgccgtcgc    14160
catgcagtcc agtggggagt cggaggcagc ctccttcctg cctctcctcg gcctgcacgt    14220
gtccccccac caggcagaga cccttctaca ccccgggtgt ctgcggtcac atcgcggtgg    14280
ggcatgcagc tgttggcctt cgagcatgtt ttgttttcct tggccagtgt ctccagagaa    14340
acgcacgtgg gtttgtgtcc agcggtccat ctctgcaaca gttgttcctt tgggattgga    14400
tgctaggagg tcacgggaga ggtgtccatc caaagcagtg tctgtgtcac acactgtccc    14460
cacacacagg gccacctctg cacagactcc cccgactcga ttctgggcac agagctcagt    14520
gaccttccag agactgccac gaaccggtga tgcctccacg cttgagacat cctgaccgca    14580
gggcccaagg cgcactggct cagggggtga cagtgagggg tctgcaaaca gactgctgat    14640
gctcaacccg gccgctgccg agctgtgtga cttgggcacg tcacttaacc tctctcggcc    14700
tctgtctcct cccggggata agagtagtag cacctgcttc ccggggctgt gaggatccag    14760
tgggacgtat aggaactagc gaggcaccgg cagttgggtc agagctactg ttgtcacttc    14820
acaaggcatt ttcttcaaca gcaagtcgga aatctcatga gcctaaggca gaatccacct    14880
gtggcctctg gttacaaccc acaggactga aaatccttcc agccacagca actggtgaat    14940
ttcctggtca attgccacaa gtcatgagct gaaccccact tgagtttcag ttcaggcaga    15000
actctagaga cgactagggc aagctagaca gcgactgcag agccttttgt tgcagcgtga    15060
gcagtcctca gctgttgaca tcactgggga gcaaacgagg accaggagcg gtgaaaggac    15120
agtgtctgct gcagattgtc gtagcaccca aggaacactc cagaaagcct cctaagcagt    15180
aacaagtgtg gcaaggtgta gcccagccaa cagtggcatc tgcgaggcgt cccctccttc    15240
ctcccactac cccgtatacc ctgggacctg tgcactgaag gactcattct aaaggctgtg    15300
cccctgcagc cgccagcctc actcactggc tgcctgtgcc agctagagat ttcttccctc    15360
tgaggctggc tgagaggacc actccagttt cctggcccat ccagcaaaga agatacacat    15420
catgcacgtg taaaatgagg aaccggttta ttgaacagct taaggagagc aaaaatagtg    15480
gctttagcta cattttttac acactgagca ggaaagtcta aaccatcccg ttcccctgta    15540
ccccaaagag aacagggctt gctggaggcc agtgccaagg gcggagtcgt gctcgcagca    15600
gacttgaatt aaccccatgt aggccggcga gcagttgccc gcgtgaaaac accaccctct    15660
tctcctggct gagaagatca aagctctttt tttaccctct tttcagcaaa ggacctattt    15720
gttttcaggc aggaggatgt taaacttgca gcctctgaca cacggtggaa cctgcagtgc    15780
ttggagaaac ggcacgcaca cgtgaaaaca tcatgcctac tccaaagcct tcttgttgct    15840
ggcaggaggg aagcttgaga ctttcccacg catagtcgtg acccgcgtgg ccgtttctgc    15900
tctcagcaac attctctagt gttccggctt caagcagcgc ttgtcaggtt tgaagctagc    15960
cactattctg agaacgtcag aaaagcatgg accatctctt gcttggtgtt gccgttgtgg    16020
cagtagcagc tactacgtac ctgcacgagt tccagggcag aagtggcaat gtcccatgaa    16080
ggcgtggcac cccacggggg ggggggggga gtgtgccacg ggcgtccact tctgcagcag    16140
aaggcatgtg cctacagcac aagcttgtaa aaaaatactt gaacagaata tgctgtacag    16200
aactaggggt taacaccgca tatgaagatg ctaaaacatt tgtataaata ctctgtatac    16260
aagcatggag tcactcccgt agaaagggct catccgtgag gctatgaaaa actgctgtca    16320
```

```
gcatgcccaa agagaaacta cttccacagt aggaacagaa aaaaggactg tgctgtgtct   16380
aaacacgtgg tgcatcagag acatagttac agttcctact gactgcccca gccacgacct   16440
gggagtgctg aggacctggg agtgctcagc gagctgcagg aggtcagccc tgtggagaaa   16500
tacatttcta aacaatactt ttgattggga tttcagcacc gtatagacag atgttccttc   16560
tgggggcctg gcaagcagcc atctcccagt gggtctgacg gggaagaggg gtacctggag   16620
cccctcccag acagacggta atcccacccc tgttctcaca ctcttcctgg catccgcatc   16680
tgctggcaca caccccgtc acctgccact tccgcgtccc gtcgtggtga gtggctgata    16740
ggcgctggat gcaaacaagg catgagatgg acgtacctgg agacccagct ccagtactgg   16800
ttctggtctg cggggtgaac gaggggggcag aggaaggcgg agagagtgcg tcccagtcca  16860
cttaagctct gtccccggaa gtggcatcta atctggcatt tcgatattta atttgggagg   16920
tgggagcaca tacttcccag ggctctgggt aatgaccacc ctggccttct ttcgaaacat   16980
gggtgcgatt ttagggggct ccggaactgg ggtctcttcg gtttcttcat tatcttcgtg   17040
atggagatca taggaaatgt ttccatattc tcgtagaaat gggaagattt caagcagaaa   17100
ctgacagaaa tctttgcgga taccaaacca ccctgaaaaa taagaatttt ttatttcaca   17160
cacgaggctc aactgacctt cctgttaact ttctttccgt aacaagaagt ttcactccta   17220
caatgtcata acatacttta tccagactcc tgagtcacaa agcctgaaca gggcttgagt   17280
acccaaaatg gggaagaagt gcaaatgcta gctctgtggt gcttggagtg gggttcccgg   17340
accggcaggg acagcgtcca cggggcctag ttagggatgc cattctcggg ccccagccca   17400
gacctccaga aactgagtcg ggctagggtg ggctccagcg gtcccctttt cctggccctt   17460
ttgggattct gctggatgcc caaatttgag aactactgct ccagtgagtc tcaaaatatc   17520
tgtggtgcgc agactacggt gtcttccgct aatcttctcc agccaggata aactcatgga   17580
tgacagtgcc acccaagaac aagatttctg tcaccctctg gaatccgtga gggcggtagt   17640
catgcacggg ttggccagga gggggcctga actcatggag ccaccttaaa gccactttcc   17700
cagtcccact actcctctct gtaggctact ggagtgtcag ctcggtgcaa gccctccctg   17760
ctcccgggtg cggggtaggg ggcagaggca caaacagcaa gcacagcccg ggctgctggg   17820
ctgcagtgag gccctgcccc caaacccact ggctttccga agggcaatgc tctgggcttc   17880
cgtgccatgg agcccacagc cttgccagga aggcaccctc tgcagagatc gttttggaag   17940
tgtctgcctc agcaagcagg tggaggggaa tagagtgtta gcaaggcaag acaggcaaga   18000
ctcgggtgat ggcagcaagg atatggggga ggcagagcgg ccaacaggga cctaggatga   18060
atcccaggtt tgggtgggag atgtggattt tccatcaaac cctcccgggc tgggaagaa    18120 tctgtcttga tccccatttt gcagaggagg gaacgggatc tctgagaggt tgcctgccgt   18180
gtctggttct acctcaaatg gcagcgtgca ctgcagaaaa agtccggtg caggccagca    18240 gaacaccaga gttacggcat gcccttccct tagaaggtcc cagaatttcc tcagccctca   18300 cttteccaca caagcttcta aattggggcc ctcgggact catcccttcc tagacttcta    18360
tccgccaccc cccaccccct ggtccccccc cagacacaca ccaaggactt ctgaaatgct   18420
gagtacatac agtggtttcc tcccttctgt ccaaatgtgg ttgccatcag cgtgatcaac   18480
gagagccaaa gggggacaaa gatcgggatg caggagaagg cgttgtggcc atccagtttg   18540
tgaaccagca gaatctaaag aaaagagacat agtcccggtt gatgccagca ccgaaaatgg   18600
gcagaggcgg aagccagact tcattaggca gttcctcccc accaccccac cccgcgtga    18660 gctcccacaa gagggaacat cagcaccgcc agaaaaaggc aggaaaccac ctatccctgg   18720
```

```
ggaaagctcg aaatgagctt ttatgtccct cttcagagct cggcaatagc ctatccactt    18780
gaaaagttcc cagtgccagc agttttatgg caaactcctc cgggtgtttg ttctaaggag    18840
tcaacagctc ccattctaga attctccacg tgactccaat acacaaatct gacatcccac    18900
tctgctttcc ccagagtgga aactggagcc atacagaggc accatggcta aaaaggtgca    18960
ctcttctccc tgccagcccc acgtgctgcc cccaagagaa aggaaggatg ctctcctttc    19020
accgaagctc cctctcggag atggctgtgt tctctcccct ctcctggagt gggctcactg    19080
tgagctcgag ggacagaggc tgcctttcta ggggtgcaga atcctgtcag gggaagcgca    19140
agcttcaggg gctgaagagg cttcccgtgg aacgcttacc tcaaatgtaa aaggggcac    19200 gacgatggtc atccagctca gggccatggt tatgtgtgtc ctgcgctgtc cgcaatcaca    19260
tccatagagc gcaagaacaa gacggaccac acaatgtagt agaggaccac caggcacaga    19320
aaggacatga gaatccacag cgggacacac acaacctggg ggtgggtgag agaacagcaa    19380
gagaagtctc tttagagctt ccaacctggc ctctgatgga aggcatcttt agcaccttgc    19440
tgtgtctgtc cagttaaggc ggtccttcct gtgagccgaa taaggaccgt tccatctccc    19500
aggactgctg ggagcatcgc tcaggacaga aaaggtatgg tatgttcact atggggcctg    19560
ctgccaccag gggacacaca cgctcagtga gtcatcagtc cctcttcctt tgggtgacag    19620
acagccctgc acctggctcc gcagcctcta ctcttccaga ggcccactct cccacactct    19680
ctcaggctcc tctaggttct gctgccatca cagcttcccg ggaaatggga cacaactgtc    19740
accctgtgca cacacacaag atctcacccc aacagactct cttcacaggc aacattccca    19800
caacctgctg ggggtacttt ggcaacacaa atgggaatgg gctccccaga aagtctggct    19860
gcctgggctc ctaaggatcc ctaacctcac ccctaccaag ttagtgaact ggcgggttg    19920 atgctggata caggttgatg ctggatacgt agcgctgccg ggtcgtgacc cctaaggaat    19980
tatccaaact cttgttttta gatgctttat tatatcaaac tctcctttaa acaagtggcc    20040
catctgctgg gatttggaag cctgtaatac tgaaattttc atcataatgg aaattttaaa    20100
aacagaattt gacccacctg tttttaaaac actttcatta cttaacaaga ggtctaatct    20160
tgggcaagtc ttgaaatttc tctggcctta gtttcccatg tgttaaatga aacttgaagc    20220
agttggtctc ttatagtctc ctgactctaa cattctaaga attatatttg tacaataact    20280
caaaaatcac ataatttaat ttaccatatg gactccaaaa tatattttct cattaggcta    20340
aacttgatct gcattttctg gatgtgtcca tattcttgga ctacactaaa acatgatacc    20400
aatgcttcct ctcaccataa accctcactt cgctttctac atttaagaat tttatagctg    20460
gaagagtcct taacagaaaa taccatctaa taattacccc tcaaaatcga aaagtcctta   20520
tctgttctta tgctagttat aagaatgagg cagcatttca cataatggtt ataaacactg    20580
ccacaagaag attcatgatg tgttgtttat ctgtagctct catcatactc tgtcatataa    20640
ctatagcatt aagattttaa tgttctatat attcttctaa gacagtgttt accagagtaa    20700
ggcacaaaag atccactggt ttgcaagaaa gattagaact tttaaatttt ttacctcacc    20760
ttgtttaatc tatattttg tatgtatttt gtaacatata tattattatt accataaatc    20820
atatataatt taaatgcat atattagggg taaatgctca ggaaactttt tataaattgg    20880
gcatgcaaat acaagtttga agactcactg ttctaggtat taaaagtaaa gttataacca    20940
agtaaagctt ccacctttc atgtctcaaa gcagtttatt gttggaggta agatctctta    21000
gaagcctaaa caggtccaag tacagaatga agtaaggcta gcccataact tgtggcaagc    21060
aattcatact atttctctca tgctgagctc tcctcagtga agcagctact atagacaact    21120
```

```
gcagcctatt ggtagcctat tttacaggca ggaaaaaaat tactttttat tcaaagtgga   21180
actcaggaca tggggagaaa atgaatacaa aaaatagggt caatccaaag gcacacagca   21240
aatgagtaac acagttatgt ttttttccca tttgtatgag gtcccagtaa attctaagta   21300
aactgcaaat ttaataatac actaaaaaag ccatgcaatt gttcaaatga atcccagcat   21360
ggtacaagga gtacagacac tagagtctaa aaaacaaaag aatgccatta ttgagttttt   21420
gaattatatc aagtagttac atctctactt aataaatgag aaaaacgagg ataagaggcc   21480
atttgataaa atgaaaatag ccaagaagtg gtattagaga cttgaataca ggtattcggg   21540
tccaaagttc atctgctcaa atactaactg gggaaaagag ggaaaaatat ttatatacat   21600
atatatctgc acacaaaaat accccaaaa gacaaaatga ggccaggcag ggtggctcac   21660
acccgtaatc ccggtacttt gggaggctga ggcaggtgga tacctgagat caggagttgg   21720
agatcagcct ggtcaacatg gtgaaaccct gtctctacta aagataaaaa aattagccag   21780
gcatggtggc gtgcgcctgt aatcccagct acttgggagt ctgaggcagg agaatcactt   21840
gaactgggaa gggaggttg cagtgagcca agatcgtact actgcactcc agcctgggca   21900
gcagagtgag actccatcac aaaaataaat aaataaataa aatacaatga aacagaaagt   21960
tcaaataatc ccataatctt accaccaaga aataactttc actcgttata cttattgatt   22020
tttccataat aaatgtactt tactgtgact atcatgaaaa gaaagttatt ttagaaacag   22080
agaactgttt cagatcaaat ctatgtagta gaacagagcc attaggtggg aaagacgaga   22140
tcaaactaaa tctcagaagg cctaaaaggc taggtccatt ccagcactaa aaactgacca   22200
gacaagtaat ggcttcaaca gcttctaaat atggacaaag catgctgaaa gggaaggaca   22260
ggtctaacag tggtatatga aatgaacagg aggggcaaag ctcatttctc ctctgaagtt   22320
ttccaaagat gctgaggagg acattagttt gacatgaccc tgatatggga caagataatt   22380
tcacagaagt tttacatgtt aaagttttct tatagatact cattcaagta agcaatgaac   22440
actaaaatct aaagaaagaa aagagcttta gagtcaggtc tgtattcaaa ttcaagctct   22500
accacttact ggttctgtga ctttgggcaa gtcttttaac cttattaagt cttaatttcc   22560
tgatttgtaa aatggggata tcgtctccct cacaggattg ttgtgaaact tttatgagat   22620
taatgccttt atatttggca tagtgtaagt aaacaataac tggcagcttc aaaaaaaaaa   22680
agcagtagca ttccatcatt tattattggt tactctcaaa aagttttca atgtactaga   22740 agataaaatat tcaaataccct taatatctcc attattttca ggtaaacagc atgctcctga   22800
acaaccaatg ggtcaacaaa taattaaaa gggaaatcta aaaacatctt gatattaaac   22860
tacatggaag cacaatatac caaaaccaat ggttcacact aggagaattt taaggtacaa   22920
gaaaactctt tgagatttct taaaataata gtatgtctga atttattgag tgatttacca   22980
gaaactgttg taagagctct acttgcatta tagcacttaa tcctcttaac tctatggctg   23040
ctattatcaa cctcacccta atcacatatg ggacacagag aggttaagta acttgcccaa   23100
ggtcagagtt aggaagtact aagccatgct ttgaatcagt tgtcaggctc cggaactcac   23160
actttcagcc actacataat actgctttgc tatcttttag gaaactatgt gagtctacct   23220
cacatagact cacataggtt tgttttttt tttttttaa aggctatctt ttcccccatc    23280
aatgtttttt gaaggatccc aaattagagt cccacagagg cagacagcag tacttgacaa   23340
tatggacatt taaggttaat gttggattct actgtctttt tactacatga cctagggaac   23400
gataattaac ctagactgct tccaagggtt aaataaccca tttagttata ctatgtaaat   23460
tatctcttag tgattgattg aaagcacact gttactaatt gactcggtat gaagtgcttt   23520
```

```
tttttcttcc ctttcaagat acatacctttt ccagttaaag ttgagagatc atctccacca    23580
attactttta tgtccctgt tgactggtca ttctagttaa aaaaaaaaaa aactatatat      23640
atatatatct acacacacat atgtatatgt atatccttat gtacacacac aaacttcaaa     23700
ttaaatgaga actagaagat ttgagaagtt agctagctaa tatccatagc attatgatat     23760
tctaaatgat atgaattata agaattaggt ttcctgaaat gaatgactag aaaactttca     23820
agtagagatt agtaaaaatt aaaagtcct aatcggccat tactgatttg atgtttttaa     23880
gagtcctaaa aaatgggtta catccatttt taagtgggta gtattataac agccacccat     23940
cttcaatcac agtgatttct gaattgtgag ggaagttatt agcatgacag gtgtctggtt    24000
ctggccctgt acgattccca tgagtcaagc aaattgtaag ggctggtcta tatcacaccc    24060
aaccccaagg atatgtccct caaaagtcta gcccaggccc cgtcatcttc agcatcatct    24120
gggaaaccag gtctgattag tagtccttta aggaatacct cttaggctcc cattttactg    24180
ctatcacaga atccaataaa accttacag gagattcaat gggaaatgct caacacccac    24240
tgtagttggt ggtgacaatg accataattt ggctgtgctg gattcaggac agaaaatttg    24300
ggtgaaagag caggtgaaca aaagagcttc gacttgccct agcagagagc aagccatacc    24360
ataccacaaa gccacagcaa ttacaacggt gcagtaccag cacagtaaat gaacaaagta    24420
gagcccagaa acagacccag aactatatga ggatttagta tacaataaag atggtatttc    24480
gagtcagtag ggaaaagatg aattattcaa taaatgatgt ttggccaact agtaacccat    24540
ttgggaaaaa ataaaagtat ggtccctacc tcacagcata cacaaaaata aattccagac    24600
ggattaaaat ctaaatgtaa aaaataaagc cataagtgga ctggaagaaa atagagaatt    24660
ttttttaaca tccgtagaaa gggtaaaaac ccaggcatga catgaaccaa aactgaagag    24720
gttctgtaac aaataccccc ttttatatat tgggctccaa caataagaac ccataggaaa    24780
atggagaatg aacacaaata gacaatttat agaagagaag gttataaggt gtaaaattat    24840
atctatctga gaaacaaaca ctaaaacaat gtgattctac tgttctccca cccatactgg    24900
caaaacttaa gcctgataat atgctgaggg gaaataagca ctcttgttgg tgagagtatt    24960
aattggcata gcttcttttg aaaatgacat agcaataccct gttaaaattg caaacatgca    25020
tgtcacttaa tccagtaatc ccacttctgg gaatcaatgc tacaaaaaca ctgacaagta    25080
tacaaagata cattcaagag tgttcactgg gccgggtgcg gtggcttcat gcctgtaatc    25140
ccagggaggc agaggcaaga cgatcgcttg accccaggag ttcaaggcca gcccgagaaa    25200
cacagcaaga ccctgtctct cttttttta tttaaaaaat aaatgttcac tgtatcagtt    25260
gttcacaaaa acaaaccaac atgtccatta acagggaacc atttaaatta atcaagttca    25320
tctacacaat gtaataccat gcaactatta aaaagcacct gataatccaa agcacactga    25380
gacagaataa tgctattaaa aacaccaagt agtggaacac tgtgttgcct atgacaccat    25440
ttttattcaa catttaaaca aatttgtaac agcaattaca tgagtagtga caatggcgtt    25500
tatgagactt ttcacttta tgtgcttcta tttttgttat gcttctatat atacatccat    25560
ttattatgga gtgttacttt caaaaatcac aaatgggcca gtattatttg gtgttgcaag    25620
gtgagcatat gacttctgat atcaacctt gcatattact tctcaattta gggaaattac    25680
agacatccct tattctaact aacttaaaac ccagcatttc aaacatacag aattgatggg    25740
gaaaaaaaag aaagaagaaa gaaagaaaag gcaacaagct tcagatgaca gtgactcaca    25800
tcaaattatt tataaaatct gttaaatagt gccatcttct ggagatacct ggtattacag    25860
tccaactcca gttgatgtct ttacagagac aagaggaata aaggaaaaaa tattcaagaa    25920
```

```
ctgaaaagta tggagtcatg gaaaaattgc tgtgatccaa aggctacggt gataggacaa    25980
gaaacaagag aactccaagc agtaagacac tgctgttcta ttagcatcca aacctccata    26040
ctcctgtttg ccccaaggct tttttaaaaa atagagacag gatctcacta ttttgctcag    26100
gctggtcttg aactcctgga ctcaagctat cctcctgcct cggcctccta aagtgccgag    26160
attacaggct tgagtcacca tacctggcta tttattttt cttaactctc ttgcctggcc    26220
tatagccacc atggaagcta ataaagaata ttaatttaag agtaatggta tagttcacta    26280
cattggaata caggtataag tgcctacatt gtacatgaat ggcatacatg gatcaattac    26340
cccacctggg tggccaaagg aactgcgcga acctccctcc ttggctgtct ggaacaagct    26400
tcccactaga tcccttact gagtgcctcc ctcatcttta attatggtta agtctaggat    26460
aacaggactg gcaaaggtga ggggaaagct tcctccagag ttgctctacc ctctcctcta    26520
ccgtcctatc tcctcactcc tctcagccaa ggagtccaat ctgtcctgaa ctcagagcgt    26580
cactgtcaac tacataaaat tgccagagaa gctctttggg actacaaaca catcccttta    26640
atgtctttat ttctattttg tctacctctt cagtctaggt gaaaaatag gaaggataat    26700 agggaagaac tttgttatg cctacttatc cgccccttagg aattttgaaa acctctaggt    26760
agcaataaga actgcagcat ggtatagaaa agaggagga aagctgtata gaatgcata    26820 ataaatgggg aggaaagaa ctgcttggaa caaacaggga ggttgaacta aaggagaga    26880 aagcagagag gctaatcaac aaggctgggt tcccaagagg gcatgatgag actattacta    26940
aggtaggaat tactaagggc tccatgtccc cttagtggct tagtactatg tagcttgctt    27000
tctgcagtga acttcagacc cttcttttag gatcctagaa tggactttt ttttttatcg    27060 gaaaacagtc attctctcaa cattcaagca ggccccaagt ctaccacact caatcacatt    27120
ttctcttcat atcataatct ctcaaccatt ctctgtcctt ttaactgttt ttctataccc    27180
tgatcaaatg ccaacaaaag tgagaatgtt agaatcatgt attttagag gtagactgta    27240 tctcagataa aaaaaaggg cagatattcc attttccaaa atatgtatgc agaaaaaata    27300
agtatgaaag gacatatgct caggtaacaa gttaatttgt ttacttgtat tttatgaatt    27360
ccctaaaacc tacgtcaccc gccccgttcc cacgccccgc gccacgtcac aaactccacc    27420
ccctcattat catattggct tcaatccaaa ataaggtata ttattgatga tgttaattaa    27480
catgcatgga tccatatgcg gtgtgaaata ccgcacagat gcgtaaggag aaaataccgc    27540
atcaggcgct cttccgcttc ctcgctcact gactcgctgc gctcggtcgt tcggctgcgg    27600
cgagcggtat cagctcactc aaaggcggta atacggttat ccacagaatc aggggataac    27660
gcaggaaaga acatgtgagc aaaaggccag caaaaggcca ggaaccgtaa aaaggccgcg    27720
ttgctggcgt ttttccatag gctccgcccc cctgacgagc atcacaaaaa tcgacgctca    27780
agtcagaggt ggcgaaaccc gacaggacta taaagatacc aggcgtttcc ccctggaagc    27840
tccctcgtgc gctctcctgt tccgaccctg ccgcttaccg gatacctgtc cgcctttctc    27900
ccttcgggaa gcgtggcgct ttctcatagc tcacgctgta ggtatctcag ttcggtgtag    27960
gtcgttcgct ccaagctggg ctgtgtgcac gaaccccccg ttcagcccga ccgctgcgcc    28020
ttatccggta actatcgtct tgagtccaac ccggtaagac acgacttatc gccactggca    28080
gcagccactg gtaacaggat tagcagagcg aggtatgtag cggtgctac agagttcttg    28140 aagtggtggc ctaactacgg ctacactaga aggacagtat ttggtatctg cgctctgctg    28200
aagccagtta ccttcggaaa aagagttggt agctcttgat ccgcaaaca aaccaccgct    28260 ggtagcggtg gtttttttgt ttgcaagcag cagattacgc gcagaaaaaa aggatctcaa    28320
```

```
gaagatcctt tgatcttttc tacggggtct gacgctcagt ggaacgaaaa ctcacgttaa  28380
gggattttgg tcatgagatt atcaaaaagg atcttcacct agatcctttt aaattaaaaa  28440
tgaagtttta aatcaatcta agtatatat gagtaaactt ggtctgacag ttaccaatgc  28500
ttaatcagtg aggcacctat ctcagcgatc tgtctatttc gttcatccat agttgcctga  28560
ctccccgtcg tgtagataac tacgatacgg agggcttac catctggccc cagtgctgca  28620
atgataccgc gagacccacg ctcaccggct ccagatttat cagcaataaa ccagccagcc  28680
ggaagggccg agcgcagaag tggtcctgca actttatccg cctccatcca gtctattaat  28740
tgttgccggg aagctagagt aagtagttcg ccagttaata gtttgcgcaa cgttgttgcc  28800
attgctgcag ccatgagatt atcaaaaagg atcttcacct agatcctttt cacgtagaaa  28860
gccagtccgc agaaacggtg ctgaccccgg atgaatgtca gctactgggc tatctggaca  28920
agggaaaacg caagcgcaaa gagaaagcag gtagcttgca gtgggcttac atggcgatag  28980
ctagactggg cggttttatg gacagcaagc gaaccggaat tgccagctgg ggcgccctct  29040
ggtaaggttg ggaagccctg caaagtaaac tggatggctt tcttgccgcc aaggatctga  29100
tggcgcagga tcaagctc tgatcaagag acaggatgag gatcgtttcg catgattgaa  29160
caagatggat tgcacgcagg ttctccggcc gcttgggtgg agaggctatt cggctatgac  29220
tgggcacaac agacaatcgg ctgctctgat gccgccgtgt tccggctgtc agcgcagggg  29280
cgcccggttc tttttgtcaa gaccgacctg tccggtgccc tgaatgaact gcaagacgag  29340
gcagcgcggc tatcgtggct ggccacgacg ggcgttcctt gcgcagctgt gctcgacgtt  29400
gtcactgaag cgggaaggga ctggctgcta ttgggcgaag tgccggggca ggatctcctg  29460
tcatctcacc ttgctcctgc cgagaaagta tccatcatgg ctgatgcaat gcggcggctg  29520
catacgcttg atccggctac ctgcccattc gaccaccaag cgaaacatcg catcgagcga  29580
gcacgtactc ggatggaagc cggtcttgtc gatcaggatg atctggacga agagcatcag  29640
gggctcgcgc cagccgaact gttcgccagg ctcaaggcga gcatgcccga cggcgaggat  29700
ctcgtcgtga cccatggcga tgcctgcttg ccgaatatca tggtggaaaa tggccgcttt  29760
tctggattca tcgactgtgg ccggctgggt gtggcggacc gctatcagga catagcgttg  29820
gctacccgtg atattgctga agagcttggc ggcgaatggg ctgaccgctt cctcgtgctt  29880
tacggtatcg ccgctcccga ttcgcagcgc atcgccttct atcgccttct tgacgagttc  29940
ttctgaattt tgttaaaatt tttgttaaat cagctcattt tttaaccaat aggccgaaat  30000
cggcaaaatc ccttataaat caaaagaata gaccgagata gggttgagtg ttgttccagt  30060
ttggaacaag agtccactat taagaacgt ggactccaac gtcaaagggc gaaaaaccgt  30120
ctatcagggc gatggcccac tacgtgaacc atcaccctaa tcaagttttt tggggtcgag  30180
gtgccgtaaa gcactaaatc ggaacccta agggagcccc cgatttagag cttgacgggg  30240
aaagccggcg aacgtggcga gaaggaagg gaagaaagcg aaaggagcgg gcgctagggc  30300
gctggcaagt gtagcggtca cgctgcgcgt aaccaccaca cccgccgcgc ttaatgcgcc  30360
gctacagggc gcgtccattc gccattcagg atcgaattaa ttcttaatta acatcatcaa  30420
taatatacct tattttggat tgaagccaat atgataatga gggggtggag tttgtgacgt  30480
ggcgcggggc gtgggaacgg ggcgggtgac gtagtagtgt ggcggaagtg tgatgttgca  30540
agtgtggcgg aacacatgta agcgacggat gtggcaaaag tgacgttttt ggtgtgcgcc  30600
ggtgtacaca ggaagtgaca atttcgcgc ggttttaggc ggatgttgta gtaaatttgg  30660
gcgtaaccga gtaagatttg gccattttcg cgggaaaact gaataagagg aagtgaaatc  30720
```

-continued tgaataattt tgtgttactc atagcgcgta atactg                30756

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Synthetic
      Foward PCR primer (containing a Fse I restriction site)

<400> SEQUENCE: 17
tatttattgg ccggccgcgt taagatacat tgatgag                37

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic
      Reverse PCR primer (containing a Sbf I restriction site)

<400> SEQUENCE: 18
tatttattcc tgcaggtcgt aggtcaaggt agtaga                 36

<210> SEQ ID NO 19
<211> LENGTH: 1224
<212> TYPE: DNA
<213> ORGANISM: Rattus norvegicus

<400> SEQUENCE: 19
atgcctcaca gtcaaatatc tcctgcagaa ggctctagaa ggatccttga agaataccac      60
atagatgaag atgtgggctt tgctctacca catccactgg aggagctgcc tgatacgtac     120
agaccttgga tccttgtggc tagaaatctg cctaagctga ttgagaatgg aagctccga      180 gaagaagtcg agaagctgcc cacactgcgc accgaagaac tgaggggaca caggttacag     240
cgcctggcac atttggccct ggggtacatc accatggcgt atgtgtggaa ccgaggggat     300
gatgatattc gaaaggtgct gccccgcaat cttgccgttc cctactgcga gctctcggag     360
aagctggggc tgcctcccat tctgtcttac gcagactgcg tcctggcaaa ctggaagaaa     420
aaggacccca atgggcccat gacatacgag aacatggaca ttctgttctc gtttcctggt     480
ggggactgcg ataaaggctt cttcctggtc tctctaatgg tggaaatcgc agcttctcct     540
gcaatcaaag caattcctac tgtatccagt gcagtagagc atcaagaccc gaaagcactg     600
gagaaggcac tgtgtagtat agctgccagt ctggagaaag ccaaggaaat ttttaagagg     660
atgcgtgact tcgtggatcc agacaccttt ttccacgttc ttcgcatata tttgtctggt     720
tggaagggca accctaagct gccggagggt ctgctgtacg agggcgtctg ggacacccc      780 aaaaaatttt caggggggcag tgcaggccag agcagcatct ttcagagtct tgatgtcctt     840
ctgggaataa agcatgacgt tggtgaagga tctgctgcag aattcctcca ggaaatgaga     900
gagtacatgc ctccagccca ccggaacttc ctctcctcct tagagtcagc tcccccagtc     960
cgtgagtttg tcattttaag acgcaatgaa gacttgaagg aggcttataa tgagtgtgtg    1020
aatggcctgg tctccctcag aatgttccac ctctcgatag tagatactta cattgtgaag    1080
ccttcgaagc agaagcccat gggtggccac aagtcagaag agccctcaaa cacgaaaaac    1140
agagggactg ggggtactga cgtcatgaat ttcctgagga gtgtgaaaga tacaaccaag    1200
aaagcccttc tgagttggcc ttag                                           1224

```
<210> SEQ ID NO 20
<211> LENGTH: 1212
<212> TYPE: DNA
<213> ORGANISM: Homo sapiens

<400> SEQUENCE: 20
atggcacacg ctatggaaaa ctcctggaca atcagtaaag agtaccatat tgatgaagaa        60
gtgggctttg ctctgccaaa tccacaggaa aatctacctg atttttataa tgactggatg       120
ttcattgcta aacatctgcc tgatctcata gagtctggcc agcttcgaga aagagttgag       180
aagttaaaca tgctcagcat tgatcatctc acagaccaca agtcacagcg ccttgcacgt       240
ctagttctgg gatgcatcac catggcatat gtgtgggca aaggtcatgg agatgtccgt       300
aaggtcttgc caagaaatat tgctgttcct tactgccaac tctccaagaa actggaactg       360
cctcctattt tggtttatgc agactgtgtc ttggcaaact ggaagaaaaa ggatcctaat       420
aagcccctga cttatgagaa catggacgtt ttgttctcat tcgtgatgg agactgcagt       480 aaaggattct tcctggtctc tctattggtg gaaatagca ctgcttctgc aatcaaagta       540
attcctactg tattcaaggc aatgcaaatg caagaacggg acactttgct aaaggcgctg       600
ttggaaatag cttcttgctt ggagaaagcc cttcaagtgt tcaccaaat ccacgatcat        660 gtgaacccaa agcatttt cagtgttctt cgcatatatt tgtctggctg aaaggcaac         720 ccccagctat cagacggtct ggtgtatgaa gggttctggg aagacccaaa ggagtttgca       780
gggggcagtg caggccaaag cagcgtcttt cagtgctttg acgtcctgct gggcatccag       840
cagactgctg tggaggaca tgctgctcag ttcctccagg acatgaagaag atatatgcca       900 ccagctcaca ggaacttcct gtgctcatta gagtcaaatc cctcagtccg tgagtttgtc       960
ctttcaaaag gtgatgctgg cctgcgggaa gcttatgacg cctgtgtgaa agctctggtc      1020
tccctgagga gctaccatct gcaaatcgtg actaagtaca tcctgattcc tgcaagccag      1080
cagccaaagg agaataagac ctctgaagac ccttcaaaac tggaagccaa aggaactgga      1140
ggcactgatt taatgaattt cctgaagact gtaagaagta caactgagaa atccctttg      1200 aaggaaggtt aa                                                         1212

<210> SEQ ID NO 21
<211> LENGTH: 2440
<212> TYPE: DNA
<213> ORGANISM: Artificial Sequence
<220> FEATURE:
<223> OTHER INFORMATION: Description of Artificial Sequence: Rat IDO
      expression cassette
<220> FEATURE:
<221> NAME/KEY: misc_feature
<222> LOCATION: (1)..(2440)
<223> OTHER INFORMATION: n= a, c, g, t, unknown or other

<400> SEQUENCE: 21
tatttattcc tgcaggtcgt aggtcaaggt agtagagttt gcgggcagga cggggcgacc        60
atcaatgctg gagcccatca cattctgacg caccccggcc catggggca tgcgcgttgt        120 caaatatgag ctcacaatgc ttccatcaaa cgagttggtg ctcatggcgg cggcggctgc       180
tgcaaaacag atacaaaact acataagacc cccaccttat atattctttc ccacccttan       240
nntaatagta atcaattacg gggtcattag ttcatagccc atatatggag ttccgcgttg       300
gtaaatggcc cgcctggctg accgcccaac gacccccgcc cattgacgtc aataatgacg       360
tatgttccca tagtaacgcc aatagggact ttccattgac gtcaatgggt ggagtattta       420
cggtaaactg cccacttggc agtacatcaa gtgtatcata tgccaagtac gccccctatt       480
```

```
gacgtcaatg acggtaaatg gcccgcctgg cattatgccc agtacatgac cttatgggac    540
tttcctactt ggcagtacat ctacgtatta gtcatcgcta ttaccatggt gatgcggttt    600
tggcagtaca tcaatgggcg tggatagcgg tttgactcac ggggatttcc aagtctccac    660
cccattgacg tcaatgggag tttgttttgg caccaaaatc aacgggactt tccaaaatgt    720
cgtaacaact ccgccccatt gacgcaaatg ggcggtaggc gtgtacggtg ggaggtctat    780
ataagcagag ctggtttagt gaaccgtcag atccgctaga gatctggtac cgtcgacgcg    840
gccgcgggaa ttcgattatg cctcacagtc aaatatctcc tgcagaaggc tctagaagga    900
tccttgaaga ataccacata gatgaagatg tgggctttgc tctaccacat ccactggagg    960
agctgcctga tacgtacaga ccttggatcc ttgtggctag aaatctgcct aagctgattg   1020
agaatgggaa gctccgagaa gaagtcgaga agctgcccac actgcgcacc gaagaactga   1080
ggggacacag gttacagcgc ctggcacatt tggccctggg gtacatcacc atggcgtatg   1140
tgtggaaccg aggggatgat gatattcgaa aggtgctgcc ccgcaatctt gccgttccct   1200
actgcgagct ctcggagaag ctggggctgc ctcccattct gtcttacgca gactgcgtcc   1260
tggcaaactg gaagaaaaag daccccaatg ggcccatgac atacgagaac atggacattc   1320
tgttctcgtt tcctggtggg gactgcgata aaggcttctt cctggtctct ctaatggtgg   1380
aaatcgcagc ttctcctgca atcaaagcaa ttcctactgt atccagtgca gtagagcatc   1440
aagacccgaa agcactggag aaggcactgt gtagtatagc tgccagtctg gagaaagcca   1500
aggaaatttt taagaggatg cgtgacttcg tggatccaga cccttttttc cacgttcttc   1560
gcatatattt gtctggttgg aagggcaacc ctaagctgcc ggagggtctg ctgtacgagg   1620
gcgtctggga caccccaaa aaattttcag ggggcagtgc aggccagagc agcatctttc   1680
agagtcttga tgtccttctg ggaataaagc atgacgttgg tgaaggatct gctgcagaat   1740
tcctccagga aatgagagag tacatgcctc agcccaccg gaacttcctc tcctccttag   1800
agtcagctcc cccagtccgt gagtttgtca ttttaagacg caatgaagac ttgaaggagg   1860
cttataatga gtgtgtgaat ggcctggtct ccctcagaat gttccaccct cgatagtag    1920 atacttacat tgtgaagcct tcgaagcaga agcccatggg tggccacaag tcagaagagc   1980
cctcaaacac ggaaaacaga gggactgggg gtactgacgt catgaatttc ctgaggagtg   2040
tgaaagatac aaccaagaaa gcccttctga gttggcctta gaatcactag ataagatatc   2100
cgatcnntgg agttcgtgac cgccgccggg atcactctcg gcatggacga gctgtacaag   2160
tccggactca gatccaccgg atctagntaa ctgatcataa tcagccatac cacatttgta   2220
gaggttttac ttgctttaaa aaacctccca cacctccccc tgaacctgaa acataaaatg   2280
aatgcaattg ttgttgttaa cttgtttatt gcagcttata atggttacaa ataaagcaat   2340
agcatcacaa atttcacaaa taaagcattt ttttcactgc attctagttg tggtttgtcc   2400
aaactcatca atgtatctta acgcggccgg ccaataaata                         2440
```

<210> SEQ ID NO 22
<211> LENGTH: 2387
<212> TYPE: DNA
<213> ORGANISM: Artificial Sequence
<220> FEATURE:
<223> OTHER INFORMATION: Description of Artificial Sequence: Human IDO
      expression cassette
<220> FEATURE:
<221> NAME/KEY: misc_feature
<222> LOCATION: (1)..(2387)
<223> OTHER INFORMATION: n= a, c, g, t, unknown or other

<400> SEQUENCE: 22

```
tatttattcc tgcaggtcgt aggtcaaggt agtagagttt gcgggcagga cggggcgacc    60
atcaatgctg gagcccatca cattctgacg caccccggcc catggggca tgcgcgttgt   120
caaatatgag ctcacaatgc ttccatcaaa cgagttggtg ctcatggcgg cggcggctgc   180
tgcaaaacag atacaaaact acataagacc cccaccttat atattctttc ccacccttan   240
nntaatagta atcaattacg gggtcattag ttcatagccc atatatggag ttccgcgtta   300
cataacttac ggtaaatggc ccgcctggct gaccgcccaa cgaccccgc ccattgacgt    360
caataatgac gtatgttccc atagtaacgc caatagggac tttccattga cgtcaatggg   420
tggagtattt acggtaaact gcccacttgg cagtacatca agtgtatcat atgccaagta   480
cgcccctat tgacgtcaat gacggtaaat ggcccgcctg gcattatgcc cagtacatga    540
ccttatggga ctttcctact tggcagtaca tctacgtatt agtcatcgct attaccatgg   600
tgatgcggtt ttggcagtac atcaatgggc gtggatagcg gtttgactca cggggatttc   660
caagtctcca ccccattgac gtcaatggga gtttgttttg gcaccaaaat caacgggact   720
ttccaaaatg tcgtaacaac tccgccccat tgacgcaaat gggcggtagg cgtgtacggt   780
gggaggtcta tataagcaga ctggtttag tgaaccgtca gatccgctag agatctccag    840
aggagcagac tacaagaatg gcacacgcta tggaaaactc ctggacaatc agtaaagagt   900
accatattga tgaagaagtg ggctttgctc tgccaaatcc acaggaaaat ctacctgatt   960
tttataatga ctggatgttc attgctaaac atctgcctga tctcatagag tctggccagc  1020
ttcgagaaag agttgagaag ttaaacatgc tcagcattga tcatctcaca gaccacaagt  1080
cacagcgcct tgcacgtcta gttctgggat gcatcaccat ggcatatgtg tggggcaaag  1140
gtcatggaga tgtccgtaag gtcttgccaa gaaatattgc tgttccttac tgccaactct  1200
ccaagaaact ggaactgcct cctatttggg tttatgcaga ctgtgtcttg gcaaactgga  1260
agaaaaggga tcctaataag ccctgactt atgagaacat ggacgttttg ttctcatttc   1320
gtgatggaga ctgcagtaaa ggattcttcc tggtctctct attggtggaa atagcagctg  1380
cttctgcaat caaagtaatt cctactgtat tcaaggcaat gcaaatgcaa gaacgggaca  1440
ctttgctaaa ggcgctgttg gaaatagctt cttgcttgga gaaagccctt caagtgtttc  1500
accaaatcca cgatcatgtg aacccaaaag cattttttcag tgttcttcgc atatatttgt  1560
ctggctggaa aggcaacccc cagctatcag acggtctggt gtatgaaggg ttctgggaag  1620
acccaaagga gtttgcaggg ggcagtgcag gccaaagcag cgtctttcag tgctttgacg  1680
tcctgctggg catccagcag actgctggtg gaggacatgc tgctcagttc ctccaggaca  1740
tgagaagata tatgccacca gctcacagga acttcctgtg ctcattagag tcaaatccct  1800
cagtccgtga gtttgtcctt tcaaaaggtg atgctggcct gcgggaagct tatgacgcct  1860
gtgtgaaagc tctggtctcc ctgaggagct accatctgca aatcgtgact aagtacatcc  1920
tgattcctgc aagccagcag ccaaaggaga ataagacctc tgaagaccct tcaaaactgg  1980
aagccaaagg aactggaggc actgattaa tgaatttcct gaagactgta agaagtacaa   2040
ctgagaaatc ccttttgaag gaaggttaat gtaacccaac aagagcactc gagcctaagc  2100
ttctagataa gatatccgat ccaccggatc tagataactg atcataatca gccataccac  2160
atttgtagag gttttacttg cttaaaaaaa cctcccacac ctccccctga acctgaaaca  2220
taaaatgaat gcaattgttg ttgttaacttt gtttattgca gcttataatg gttacaaata  2280
aagcaatagc atcacaaatt tcacaaataa agcattttt tcactgcatt ctagttgtgg   2340
tttgtccaaa ctcatcaatg tatcttaacg cggccggcca ataaata                2387
```

<210> SEQ ID NO 23
<211> LENGTH: 30756
<212> TYPE: DNA
<213> ORGANISM: Artificial Sequence
<220> FEATURE:
<223> OTHER INFORMATION: Description of Artificial Sequence: Synthetic gutless backbone
<220> FEATURE:
<221> NAME/KEY: misc_feature
<222> LOCATION: (1)..(30756)
<223> OTHER INFORMATION: n=a, c, g, t, unknown or other

<400> SEQUENCE: 23

```
gtacggaagc ccggaaggag gggcaggggg cggtggctca ggtttctccg ggcggcggcg      60
gcggcggcgg cggcgacggc gacggcgacg gcagcgggga cggcagcagt agcgggagca     120
gcagcgtgga cgcggctggc gctggcgcca tgaacccgct gtaaggcgca ggctgtgcag     180
cacggggtgc gggggaggag gaggaggacg ccgcggtgaa gttctccgcc atgaacctga     240
ggggcctctt ccaggacttc aacccgaggt gaggcggcgt cgttggcgcc cccgggagtc     300
cgcgctgcgg gctcgggcgc gggctggtgt tcggctccgg ggaggcacgg cgggcgagat     360
gctgcagccc gaggacccgg gcgcctgccc gagcctccct gcgggtgcaa gcggtcccca     420
ggcaaaacag tcggcctcgg cgcccgcccg cttcctcctc ccgtgcccgg tgctttcagc     480
ccctgcccgg ccacggccgg aagggcccgg ccgcgagccc cgtcctgccc aagggaacc     540
ccattctttt ctgcttgctg tccctcattg gtgtcccaac ttcttcgtct cggttccatc     600
ctcttctgcg ccgctgcggg ccctccattc tccgcgtcag ggccgtctca ctcgacccaa     660
cacccctacc cccacccag ctgtttcctc cagttcctcg cagtccttgg ggttttcctt     720
gggtttatgc ccatccctct cttgtttgct tctttgttga acggataccT gaaacactgt     780
tgaatccttg gagtcagtgt cggggtatgg caataccttta tataatgcat ttctgggtga     840
gcctgatcat tttccatact cattttctca tcagtcttca ctacaagttt atttgcagga     900
agtagatatt gctgtccttc ttttccagat ggggaacacc cagtggacag tgtggagaaa     960
acactggcta agcactcaag cgcctgtcct tgcacttgcc cgactgtttt gtaactgttc    1020
tttaccccag gctgtgagct ccctgaagct gagaccatct cctgctcatc tcagtgtccc    1080
cagcgcctcc cacccaccgt atctggcaca tagtaggcac atataaaatg tttgtggaac    1140
taaactgagc ccaaagactt ggattggaga cgaggccata tgtaactggg tgattctctg    1200
cccttctttg gccttctgt aaaatgagga gttggcctaa ctgatctctt aaatgcacta    1260
ctctccgaaa ggagtatccg tttcccttat ttgccagttg ggaagacgtg ctcagtaaat    1320
atttgtgtgc tgtaacctat gttaggtgct ttagatgctg gcggtctcag catggggtga    1380
agaagggctt gtacacttaa gatgccttac agtactgtgc agtgctgtac tgcggggcc    1440
aactctgggg acctatgcct tggctgcttg ttgaggatga aaggaagttt taggggagta    1500
tttgtatgtt gagggtgcag tctccctagg gatggtgaca ttttaacttg tgagtcattg    1560
tgactttgta tgtgcccta ttccactttg agttcatgtt ctggttagga gtgccagtgt    1620
ctctaacacg gtgcagacat tatcattgtt ggcttcgaag gcatagagga ggtaacagaa    1680
ctaactgcag tcccttcctc tgctgcatca gggggttaag attggtctgc agggtagtag    1740
ggttggtgct gtggctggac aagccctgta tgtcttctat ttggagatgg tgataagaaa    1800
gttaagtaaa aactgaattg ttttgtgccc ttgggcaact cacttatcta ttgttttatc    1860
tgtagaatga gtataatctc tcagtggggt agggaggcca attaaggatt gattacaaag    1920
```

```
tgccttacaa atagaaagct acagtgactt gtttgcaagg tgacagagaa ttcagaagcc    1980
tcaagaaact gccttaagtg atcaaacagg ctaacggagt tgccaaagca aaatagtgct    2040
gcactgatac tacctttaac cgttttttcc tttagccctt ttccccccaa aaaaattagt    2100
atatgaaatt acagtgaaat acctggtatc taagcagatt tatagtaatt ctcaacatat    2160
tcatcaatct cttaattcta cctgcattaa aatgtatttc tacctgaaaa gtttaaaggt    2220
cttttatact gtgccatttt cctgattcat tgttgccaga ggtagtgagt tccttaattt    2280
tacagatatt tcaagaggac attggccagg tattattggt aaatcagatt tgttttttta    2340
gctggtagtg tttcacctct cctgagcact cctagttttt gacagtgtgc tttagtctcc    2400
ttccatgctg aggaaggcct tctctatagg agaaagaaaa ctgaggggtg tacacaggaa    2460
gttaccttat gctggggact caaaccttga tgctactgct ttgctccctg cctctatttt    2520
tgaaccaatt caacatctcc ctcctacccc aggaccttgt cacacactgt tctctttacc    2580
aggaatgttt ccctctcttt tcctctcctc cagacctagt gaactcctat ttatcctcac    2640
ttggcacttg ctaagggaag cattcctgac ttccctgacc agatttactg ctccctgttt    2700
ctacagttcc tgtagtattt actactcctc catcatagtg catatttgta cccttgtgtc    2760
tgtctggatg cttatttgat taatacctgc ctcccccact aaactttaag ctccatgggg    2820
tcaaggccgt gactgtgtca gtatcgtagc ctgcatactt ggaatagtac ctggctcaat    2880
aaatatttgt ggagtaaata actgaataac tctccagagc ctataagata aatctagagc    2940
tgctgctttc aatcactgct ttcctggtgg tctgtggcct ggttctcttt cttctcacac    3000
tcttcccacc ttcagagtgc agccattgct ttggagagat gggagagaac atggcactaa    3060
ggcagaatat ggctatattt actttgaaga gcatgtcttt gtcatagaaa tagtcactgt    3120
catggtttgg tgggtcccaa ggcatgggtc atggctccag atccccttc cagccttttg    3180 gatcttggta agtctgaacc cactgctgcg ttggcaaggc tctggaaact atagtgacag    3240
agaatgattc acaagtgtca acactcagat gtacagggct gccagctgac ccactctacc    3300
tatttccatc tggcactgaa ctggttgatc atgaacttct tttcataatt gcttttttagt    3360 tatgcaggtt aagacatgcc gaaacagatg taccggaccc acaaacaagt ccttccttga    3420
atgcctgagg cttcctaaca gtgaaagagc cctgttctta gagtaggcaa actgattctg    3480
aggcattgta ggtggtaggg atctggtagt aggtagcatt aggtgggctc ccggcactca    3540
ccatggagcc ttgaaatttt ctgctacttt gggggagttg ctggttcaga gaaggcccct    3600
ccaccctggt agccatgtgg cactggaagg ctgtgaaaac tctgctgggc cttcttagtc    3660
atctgttgtg agctcctgat gggagtgtgg tgtatccctc aggtgtgcta gactggaaca    3720
aaggctgaga agtgttgctc tgggggttcc aacttgtggg catggggtac tgatgagatc    3780
agtagtgttt ggagacttct gtatgctcca tcttcagaag acattctgga gtccatataa    3840
gttatcttgt ctcttgtttg aagcaggaaa aaggaatgcg attgctggta atatagttca    3900
ctaaagtcag ctacctggcc tctaacagtt atttgcaaag tatattataa cattgattcc    3960
tcaaacatct agattcctat ctcgtgccaa gtgatgtact aggtgctcta agtacaaaaa    4020
taaaggaata tagtcctcct ctcaatgcgt aagcctagtg gaagaagcag aaatgaaagg    4080
gaaataagaa ttcaatagag tatgaggcat tacagtgaaa gaaaccaaat gtcttagaag    4140
tacaaatggc agagctacta attctgtctc gagcaggcag ggaagagtct atagtggaaa    4200 tgactttga gctagatttt gaattgagct agtcttttga gccagacttt tgagctagaa    4260
ttgtagggtt gtcatcagac cagagagtag gaagggtacc ttgtgaggaa gagagagaga    4320
```

```
gatcagattg ttactgtgtc tatgtagaaa aggaagacat aagaaactcc attttgatct   4380
gtactaagaa aaattgtttc tgctttgaga tgctgttaac ctgtaacttt agtcccaacc   4440
ctgtgctcac agaaacctgt gctgtaatga atcaaggttt aatggattta gggctgtgca   4500
ggatgtacct tgttaacaat atgtttgcag gcagtatgct tggtaaaagt catcgccatt   4560
ctccattctc gattaaccag ggacacagtg cactgcggaa ggccgcaggg acatctgccc   4620
aagaaagcct gggtattgtc caaggtttcc ccccactgag acagcctgag atatggcctt   4680
gtgggaaagg aaagacctta ccaccccca gcccgacacc cgtaaagtgt ctgtgctgag   4740
gaggagtagt gaaagagcgg ggcctctttg cagttgagat aagaggaagg cttctgtctc   4800
ctgctcatcc ctgggaatgg aatgtctctg tgtaaagctg accattccca ttcgttctat   4860
tctgagatag gagaaaacca ccctgtggct ggaggcgaag tatgctggca gcaatactgc   4920
tctgttactc tttgctacac tgagttgttt gggtaaagag aaacataaat ctagcctgcg   4980
tgcacatcca ggcacagtac cttccttga acttattcat gatacagatt cctttgctca   5040
cgtttccctg ctgaccttct ccccacctgt tgccctgcta cactcccctc gctaagatag   5100 taaaataat gatcagtaaa tactgaggta actcagaggc tagcgctggt gcgggtcctc   5160
cgtatgctga gtgccggtcc cctgggccca ctgttctttc tctatacttt gtttctgtgt   5220
cttatttctt ttctcagtct cgtcccacct gacgagaaat acccacaggt gtggaggggc   5280
tggccccttt cagtatctca gaagggacaa agtacacaaa ggcatgggt catgatagtg   5340 cctggtatgt tcaggtagtg aagaggtcca tgtggtatga gcactgcaga tgatatgtgt   5400
cgtatgaatt aaaaatacat agttactgca aatagttttt acaggttatt gttttttaaga   5460 aagcagtatc taatgcacga gtgtactgtc agtactgtca atgaactact taccactcaa   5520
gtgactgctt acgcgtcgaa tcactagtga attcgcggcc gcctcgagtc tagaactagt   5580
ggatccccca acgggccct ctagacgcgt tgacattgat tattgactag ttattaatag   5640
taatcaatta cggggtcatt agttcatagc ccatgatatc atatggagtt ccgcgttaca   5700
taacttacgg taaatggccc gcctggctga ccgcccaacg accccgccc attgacgtca   5760 ataatgacgt atgttcccat agtaacgcca atagggactt tccattgacg tcaatgggtg   5820
gagtatttac ggtaaactgc ccacttggca gtacatcaag tgtatcatat gccaagtacg   5880 ccccctatt gacgtcaatg acggtaaatg gcccgcctgg cattatgccc agtncatgac   5940
cttatgggac tttcctactt ggcagacatc tacgtattag tcatcgctat taccatggtg   6000
atgcggtttt ggcagtacat caatgggcgt ggatagcggt ttgactcacg ggatttttcc   6060
aagtctccac cccattgacg tcaatgggag tttgttttgg caccaaaatc aacgggactt   6120
tccaaaatgt cgtaacaact ccgccccatt gacgcaaatg ggcggtaggc gtgtacggtg   6180
ggaggtctat ataagcagag ctctctggct aactagagaa ccctgctta ctggcttatc   6240 gagatatctg cagaattcat ctgtcgactc ctaccgcag cgcgcagcgg caagaagtgt   6300
ctgggctggg acggacagga gaggctgtcg ccatcggcgt cctgtgcccc tctgctccgg   6360
cacggccctg tcgcagtgcc cgcgcttttcc ccggcgcctg cacgcggcgc gcctgggtaa   6420
catgcttggg gtcctggtcc ttggcgcgct ggccctggcc ggcctggggt tccccgcacc   6480
cgcagagccg cagccgggtg gcagccagtg cgtcagcac gactgcttcg cgctctaccc   6540
gggccccgcg accttcctca atgccagtca gatctgcgac ggactgcggg gccacctaat   6600
gacagtgcgc tcctcggtgg ctgccgatgt catttccttg ctactgaacg gcgacggcgg   6660
cgttggccgc cggcgcctct ggatcggcct gcagctgcca cccggctgcg gcgacccaa   6720
```

```
gcgcctcggg ccccctgcgcg gcttccagtg ggttacggga gacaacaaca ccagctatag   6780
caggtgggca cggctcgacc tcaatggggc tccctctgc ggcccgttgt gcgtcgctgt   6840
ctccgctgct gaggccactg tgcccagcga ccgatctgg gaggagcagc agtgcgaagt   6900
gaaggccgat ggcttcctct gcgagttcca cttcccagcc acctgcaggc cactggctgt   6960
ggagcccggc gccgcggctg ccgccgtctc gatcacctac ggcaccccgt tcgcggcccg   7020
cggagcggac ttccaggcgc tgccggtggg cagctccgcc gcggtggctc ccctcggctt   7080
acagctaatg tgcaccgcgc cgcccggagc ggtccagggg cactgggcca gggaggcgcc   7140
gggcgcttgg gactgcagcg tggagaacgg cggctgcgag cacgcgtgca atgcgatccc   7200
tggggctccc cgctgccagt gcccagccgg cgccgccctg caggcagacg ggcgctcctg   7260
caccgcatcc gcgacgcagt cctgcaacga cctctgcgag cacttctgcg ttcccaaccc   7320
cgaccagccg ggctcctact cgtgcatgtg cgagaccggc taccggctgg cggccgacca   7380
acaccggtgc gaggacgtgg atgactgcat actggagccc agtccgtgtc cgcagcgctg   7440
tgtcaacaca cagggtggct tcgagtgcca ctgctaccct aactacgacc tggtggacgg   7500
cgagtgtgtg gagcccgtgg acccgtgctt cagagccaac tgcgagtacc agtgccagcc   7560
cctgaaccaa actagctacc tctgcgtctg cgccgagggc ttcgcgccca ttccccacga   7620
gccgcacagg tgccagatgt tttgcaacca gactgcctgt ccagccgact gcgaccccaa   7680
cacccaggct agctgtgagt gccctgaagg ctacatcctg gacgacggtt tcatctgcac   7740
ggacatcgac gagtgcgaaa acggcggctt ctgctccggg gtgtgccaca acctccccgg   7800
taccttcgag tgcatctgcg ggcccgactc ggcccttgcc cgccacattg gcaccgactg   7860
tgactccggc aaggtggacg gtggcgacag cggctctggc gagcccccgc ccagcccgac   7920
gcccggctcc accttgactc ctccggccgt ggggctcgtg cattcgggct tgctcatagg   7980
catctccatc gcgagcctgt gcctggtggt ggcgcttttg gcgctcctct gccacctgcg   8040
caagaagcag ggcgccgcca gggccaagat ggagtacaag tgcgcggccc cttccaagga   8100
ggtagtgctg cagcacgtgc ggaccgagcg gacgccgcag agactctgag cggcctccgt   8160
ccaggagcct ggctccgtcc aggagcctgt gcctcctcac cccagctttt gctaccaaag   8220
caccttagct ggcattacag ctggagaaga ccctcccccgc acccccaag ctgttttctt   8280 ctattccatg gctaactggc gagggggtga ttagagggag gagaatgagc ctcggcctct   8340
tccgtgacgt cactggacca ctgggcaatg atggcaattt tgtaacgaag acacagactg   8400
cgatttgtcc caggtcctca ctaccggcg caggagggtg agcgttattg gtcggcagcc   8460
ttctgggcag accttgacct cgtgggctag ggatgactaa atatttatt tttttaagt   8520 atttaggttt ttgtttgttt cctttgttct tacctgtatg tctccagtat ccactttgca   8580
cagctctccg gtctctctct ctctacaaac tcccacttgt catgtgacag gtaaactatc   8640
ttggtgaatt ttttttcct agccctctca catttatgaa gcaagcccca cttattcccc   8700
attcttccta gttttctcct cccaggaact gggccaactc acctgagtca ccctacctgt   8760
gcctgaccct acttctttg ctcttagctg tctgctcaga cagaacccct acatgaaaca   8820
gaaacaaaaa cactaaaaat aaaaatggcc atttgctttt tcaccagatt tgctaattta   8880
tcctgaaatt tcagattccc agagcaaaat aattttaaac aaaggttgag atgtaaaagg   8940
tattaaattg atgttgctgg actgtcatag aaattacacc caaagaggta tttatcttta   9000
cttttaaaca gtgagcctga attttgttgc tgttttgatt tgtactgaaa atggtaatt   9060 gttgctaatc ttcttatgca atttccttt ttgttattat tacttatttt tgacagtgtt   9120
```

```
gaaaatgttc agaaggttgc tctagattga gagaagagac aaacacctcc caggagacag    9180
ttcaagaaag cttcaaactg catgattcat gccaattagc aattgactgt cactgttcct    9240
tgtcactggt agaccaaaat aaaaccagct ctactggtct tgtggaattg ggagcttggg    9300
aatggatcct ggaggatgcc caattagggc ctagccttaa tcaggtcctc agagaatttc    9360
taccatttca gagaggcctt ttggaatgtg gcccctgaac aagaattgga agctgccctg    9420
cccatgggag ctggttagaa atgcagaatc ctaggctcca ccccatccag ttcatgagaa    9480
tctatattta acaagatctg caggggggtgt gtctgctcag taatttgagg acaaccattc    9540
cagactgctt ccaattttct ggaatacatg aaatatagat cagttataag tagcaggcca    9600
agtcaggccc ttatttcaa gaaactgagg aattttcttt gtgtagcttt gctctttggt    9660
agaaaaggct aggtacacag ctctagacac tgccacacag ggtctgcaag gtctttggtt    9720
cagctaagct aggaatgaaa tcctgcttca gtgtatggaa ataaatgtat catagaaatg    9780
taacttttgt aagacaaagg ttttcctctt ctattttgta aactcaaaat atttgtacat    9840
agttatttat ttattggaga taatctagaa cacaggcaaa atccttgctt atgacatcac    9900
ttgtacaaaa taaacaaata acaatgtgaa aaaaaaaaa aaaaaaaaa aaaaaaaaa        9960 aaaaaaagg tagcagtcga cagatgaatt ccaccacact ggactagtgg atccgagctc    10020
ggtaccaagc ttaagtttgg gctgcaggaa ttctgatggc tctcaaaatt cctgcctcct    10080
ttagggataa aagactttaa gacttttta caaaaagaa aagaaaaaa aaaattcctg        10140 cctcctggtg tacacacaca gaagggttcc ctcccctga atgtgaccag gatctgtgaa    10200
aataacggga tagccgctcc tgtgattagg ttatgtggta gactagagca agattctcct    10260
gctggttttg aagaagtcag ctgccatgtt gtgagactgt catgggctag ggcatgagcc    10320
tttaaatatc tgggagcaac ccctggccag cagccagtga gaaaacgggc cctcagtcct    10380
acaatcacaa ggaactaaat tctgccaaca acctgaagga actttgaaga ggatcatgag    10440
tcccttgatt cagcttgatg agcccctgag cagaggatac agctaacttg tactagggaa    10500
gtataaaaaa catgcatggg aatgatatat atcaacttta aggataattg tcatacttct    10560
gggaatgaag ggaaagaaat ggggctttag ttgtattatg atctttaatt tctcaaaaaa    10620
aataagatca gaagcaaata tggcaaaatg ttaatacttt tgtgggtacg taggtattca    10680
gcataccctt ttttctgagt tcaaaatatt ttataattaa aatgaaatgc aggccaggca    10740
cagtggctca tgcctataat accagcactt tgcgaggccg aggtgggagg atggcttgag    10800
gccagaccag cctggccaac atggcaaaac cccatctcta cttaaaaaaa aaaaaactat    10860
atatatatat atgtgtgtgt gtgtgtatat atatatatgt atatatattt atatatgtgt    10920
gtatatatat atatgtatat atatttatat atgtgtgtgt atatatatat atacacacac    10980
acacatatat acatacatac atacacacac acacacacac aattagccag gcatggtggc    11040
gcacacctgt agtcccagct acttgggagg ctgagacatg agaattgctt gaacctggga    11100
ggcagagtag ttagtgagct gagatcatac cactgcactc cagcctggtg acagagtgag    11160
actctgtctt aaaaaaaata aaattaaaa ttaaatgcaa aaggtccaag tgaattgaag    11220
aggaaagggg tatcaaggaa ggttttgtgg aggtgacgtt tgagctgggt cttaaatgac    11280
ttaaacatgg gataagaagg gagggaataa ggacatttca ggtacgagaa ataaggagca    11340
aacagtggaa acaacctaac gtctgtcaac cagtgaatgg ataacaaaaa tgtaattcag    11400
atggtatcca acttacgatg gttcaacatg agatttttct gactttagga tagatttatc    11460
aaagtagtaa atccatttc aacttatgat attttcaact tcagatgggt ttatcaggac    11520
```

```
acagttgagg aacacctgtc tatccataca atttggcaat aaaaaggaaa tgagtgcaga    11580
tatactccac aacatgaatg aaccttgaaa acattaagtg agagaagcca gatacaaaag    11640
gccacatatt gtatgattct atttatacaa aatgtccaga ataggcaaat cttatagaca    11700
gcaagtaggt agatgatcag tttgctaggt gctgggggaa gggaaatgg  ggagtgatgg    11760 ctaaggggat tgggtttctt tgtggggcaa tgaaaatgtt ttaaaattga gcgtgataat    11820
gattgcacaa tgctgcatat atatataatc tatagattat atatatataa agagaggctg    11880
ttagacagtg ataagtgata tatatatata tatacataga gagagagaga gagagagaga    11940
gaggctgtta gtgataagtg atcaggaaaa taaaagtatt gaggaggaat acgaagttga    12000
cggtgtgaaa acatgagatt ttatatagga tggccaggga aggccttaat gagaaagtga    12060
cttatgagta aaaacaaggg atcctaaacc ttagcatgca tcagaatcac tcggaaactt    12120
gttaaagcat agcttgctgg gcctcatcac agatattttg attcggtagg ttcttgtctg    12180 atattaaatac ttttggtcta gggaaccaca ttttgagaac cactgagcta aaggaagtaa    12240
aggtttccct tagtttacta gctggtaaca ctggcccagg aggcctttct ggaaaaggtc    12300
ccagtcccca aaggaagctg gggactcgcg ttcacatcgt caaggtttac caagttgtgg    12360
cgggcctttc cgtcttggaa aaagcctcaa aatggcagat taggtgtcc  atggccggcg    12420 gaaagggtct ttgaagttgc agaccaggag ggaagaagat tctgggcctc ccccatgcag    12480
tgtcagctgg caacagaatg caccccggct gggttggagg ccctgggtac tggctcttcc    12540
acaccagggg cccacctacc aagggcagca ggagcatctg cacctcctgc gccaggcgcc    12600
cttcagtgct tccacttgag cacctctcca gacaccagct agggtgacag tggtacaaat    12660
accagactcc cctggcctgc tcacctcaca gggtaatgtg ctgtggagtc aggggggacac   12720 agcaaccacc agatgacatg gctggccccg gggaggacga cacgcagata cggctacttg    12780
gcacctgtga tattttacac actcgagagg ggcccgcacc atcctcagcc ctctccccac    12840
attcactctt agttcatgtc acctccaccc agaggggac  acaggccac  agcgatggcc    12900 ccacaccctg cctgaggtcg cccacttccc aggaggcagt cctgggactt ccacccgacc    12960
aggccccaga gcccaccgac ttaacccctc cagaggcttg tcgttcatta ccttattcaa    13020
gatggagacc agccttttg cggagaaaat gcgggtgaag gtcctgaaag tgcattgacg     13080
ccgttttcgg aagccataca agtttagctg gcggaagaag ctctttatcg aagttgtggc    13140
aaacactttg tgtgcgacgt ccccttttgag aatctccttt tcaaagagtt tttgattgat   13200
cactctacaa gccccactgt catcccacca gatggacgaa aactggttgc tgctgaccag    13260
tctccacagt ttctgtggaa aggggaggga gaggagatta tcttctccct ggggcgggac    13320
gtcaccgtca gggtgcggcc ttctgaacga agcttcctcg gccagaggtt ggaaagcgat    13380
ttcttctgtc agcagcctca agttagggct cccagtggac cccgggtcgt cccaggcagg    13440
ggaaggatct gctgggtgaa ggtaggtctc tgactgcaac tggggaggga aaggcacccct   13500 ttccaagcca tgatcctgtc ctctcgaatt tctttcttca cagcgagcca tactcaatga    13560
tcgcttgtcc tccatctggc aaacttgcta gtgcagtgtg ccagcagca  cccccttggca   13620 gtcatgtaac cagccccatg acatcataaa ggggctctga ctgccggggg gtggcatctc    13680
cacccccagc aagttgtgta ataaagggcc aaggcagaca agtagctgcc catctgcatg    13740
tgcacattct ggtcctcaca gtcatttcaa tgggaaagat gacactagtg cacaagagtg    13800
ccgaggggcc ctgccacacc gtagatgcag acctggagcg gtccccttgt cctagagctc    13860
ctgagccagg cacaactaca gcaaagccct ggctcaggaa ggtcagagct caccgtctga    13920
```

```
gtcatgggcc cacagacccc agcacatgac tgacactcgg aagcacagaa caaagggtag    13980
gacggtgccc atgggtcagg ctgtagccac gccaccctt ccaccctgtc ctagccagag    14040
gcagcaatgt gctccataca gatcctccta acacacccac actgtcggtc cccagcacgc    14100
agatgcccga cagccccta ggcaaatggc ttagctgact gccccaccac acgccgtcgc    14160
catgcagtcc agtggggagt cggaggcagc ctccttcctg cctctcctcg gcctgcacgt    14220
gtccccccac caggcagaga cccttctaca ccccgggtgt ctgcggtcac atcgcggtgg    14280
ggcatgcagc tgttggcctt cgagcatgtt ttgttttcct tggccagtgt ctccagagaa    14340
acgcacgtgg gtttgtgtcc agcggtccat ctctgcaaca gttgttcctt gggattgga    14400 tgctaggagg tcacgggaga ggtgtccatc caaagcagtg tctgtgtcac acactgtccc    14460
cacacacagg gccacctctg cacagactcc cccgactcga ttctgggcac agagctcagt    14520
gaccttccag agactgccac gaaccggtga tgcctccacg cttgagacat cctgaccgca    14580
gggcccaagg cgcactggct cagggggtga cagtgagggg tctgcaaaca gactgctgat    14640
gctcaacccg gccgctgccg agctgtgtga cttgggcacg tcacttaacc tctctcggcc    14700
tctgtctcct cccggggata agagtagtag cacctgcttc ccggggctgt gaggatccag    14760
tgggacgtat aggaactagc gaggcaccgg cagttgggtc agagctactg ttgtcacttc    14820
acaaggcatt ttcttcaaca gcaagtcgga aatctcatga gcctaaggca gaatccacct    14880
gtggcctctg gttacaaccc acaggactga aaatccttcc agccacagca actggtgaat    14940
ttcctggtca attgccacaa gtcatgagct gaacccccact tgagtttcag ttcaggcaga    15000
actctagaga cgactagggc aagctagaca gcgactgcag agccttttgt tgcagcgtga    15060
gcagtcctca gctgttgaca tcactgggga gcaaacgagg accaggagcg gtgaaaggac    15120
agtgtctgct gcagattgtc gtagcaccca aggaacactc cagaaagcct cctaagcagt    15180
aacaagtgtg gcaaggtgta gcccagccaa cagtggcatc tgcgaggcgt ccctccttc    15240 ctcccactac cccgtatacc ctgggacctg tgcactgaag gactcattct aaaggctgtg    15300
cccctgcagc cgccagcctc actcactggc tgcctgtgcc agctagagat ttctttcctc    15360
tgaggctggc tgagaggacc actccagttt cctggcccat ccagcaaaga agatacacat    15420
catgcacgtg taaatgagg aaccggttta ttgaacagct taaggagagc aaaaatagtg    15480
gctttagcta cattttttac acactgagca ggaaagtcta aaccatcccg ttcccctgta    15540
ccccaaagag aacagggctt gctggaggcc agtgccaagg gcggagtcgt gctcgcagca    15600
gacttgaatt aaccccatgt aggccggcga gcagttgccc gcgtgaaaac accaccctct    15660
tctcctggct gagaagatca aagctctttt tttacccttct tttcagcaaa ggacctattt    15720
gttttcaggc aggaggatgt taaacttgca gcctctgaca cacggtggaa cctgcagtgc    15780
ttggagaaac ggcacgcaca cgtgaaaaca tcatgcctac tccaaagcct tcttgttgct    15840
ggcaggaggg aagcttgaga ctttcccacg catagtcgtg accgcgtgg ccgtttctgc    15900 tctcagcaac attctctagt gttccggctt caagcagcgc ttgtcaggtt tgaagctagc    15960
cactattctg agaacgtcag aaaagcatgg accatctctt gcttggtgtt gccgttgtgg    16020
cagtagcagc tactacgtac ctgcacgagt tccagggcag aagtggcaat gtcccatgaa    16080
ggcgtggcac cccacggggg ggggggggga gtgtgccacg ggcgtccact tctgcagcag    16140
aaggcatgtg cctacagcac aagcttgtaa aaaaatactt gaacagaata tgctgtacag    16200
aactaggggt taacaccgca tatgaagatg ctaaaacatt tgtataaata ctctgtatac    16260
aagcatggag tcactcccgt agaaagggct catccgtgag gctatgaaaa actgctgtca    16320
```

```
gcatgcccaa agagaaacta cttccacagt aggaacagaa aaaaggactg tgctgtgtct   16380
aaacacgtgg tgcatcagag acatagttac agttcctact gactgcccca gccacgacct   16440
gggagtgctg aggacctggg agtgctcagc gagctgcagg aggtcagccc tgtggagaaa   16500
tacatttcta aacaatactt ttgattggga tttcagcacc gtatagacag atgttccttc   16560
tgggggcctg gcaagcagcc atctcccagt gggtctgacg gggaagaggg gtacctggag   16620
cccctcccag acagacggta atcccacccc tgttctcaca ctcttcctgg catccgcatc   16680
tgctggcaca caccccgtc acctgccact tccgcgtccc gtcgtggtga gtggctgata    16740
ggcgctggat gcaaacaagg catgagatgg acgtacctgg agacccagct ccagtactgg   16800
ttctggtctg cggggtgaac gaggggggcag aggaaggcgg agagagtgcg tcccagtcca  16860
cttaagctct gtccccggaa gtggcatcta atctggcatt tcgatattta atttgggagg   16920
tgggagcaca tacttcccag ggctctgggt aatgaccacc ctggccttct ttcgaaacat   16980
gggtgcgatt ttaggggggct ccggaactgg ggtctcttcg gtttcttcat tatcttcgtg  17040
atggagatca taggaaatgt ttccatattc tcgtagaaat gggaagattt caagcagaaa   17100
ctgacagaaa tctttgcgga taccaaacca ccctgaaaaa taagaatttt ttatttcaca   17160
cacgaggctc aactgaccttt cctgttaact ttctttccgt aacaagaagt ttcactccta  17220
caatgtcata acatacttta tccagactcc tgagtcacaa agcctgaaca gggcttgagt   17280
acccaaaatg gggaagaagt gcaaatgcta gctctgtggt gcttggagtg gggttcccgg   17340
accggcaggg acagcgtcca cggggcctag ttagggatgc cattctcggg ccccagccca   17400
gacctccaga aactgagtcg ggctagggtg ggctccagcg gtccccttttt cctggccctt  17460 ttgggattct gctggatgcc caaatttgag aactactgct ccagtgagtc tcaaaatatc   17520
tgtggtgcgc agactacggt gtcttccgct aatcttctcc agccaggata aactcatgga   17580
tgacagtgcc acccaagaac aagatttctg tcaccctctg gaatccgtga gggcggtagt   17640
catgcacggg ttggccagga gggggcctga actcatggag ccaccttaaa gccactttcc   17700
cagtcccact actcctctct gtaggctact ggagtgtcag ctcggtgcaa gccctccctg   17760
ctcccgggtg cggggtaggg ggcagaggca caaacagcaa gcacagcccg ggctgctggg   17820
ctgcagtgag gccctgcccc caaacccact ggctttccga agggcaatgc tctgggcttc   17880
cgtgccatgg agcccacagc cttgccagga aggcaccctc tgcagagatc gtttttggaag 17940 tgtctgcctc agcaagcagg tggaggggaa tagagtgtta gcaaggcaag acaggcaaga   18000
ctcgggtgat ggcagcaagg atatggggga ggcagagcgg ccaacaggga cctaggatga   18060
atcccaggtt tgggtgggag atgtggattt tccatcaaac cctcccgggc ctgggaagaa   18120
tctgtcttga tccccatttt gcagaggagg gaacgggatc tctgagaggt tgcctgccgt   18180
gtctggttct acctcaaatg gcagcgtgca ctgcgagaaa agtcccggtg caggccagca   18240
gaacaccaga gttacggcat gcccttccct tagaaggtcc cagaatttcc tcagccctca   18300
ctttcccaca caagcttcta aattggggcc ctcggggact catcccttcc tagacttcta   18360
tccgccaccc cccacccccct ggtccccccc cagacacaca ccaaggactt ctgaaatgct  18420
gagtacatac agtggtttcc tcccttctgt ccaaatgtgg ttgccatcag cgtgatcaac   18480
gagagccaaa gggggacaaa gatcgggatg caggagaagg cgttgtggcc atccagtttg   18540
tgaaccagca gaatctaaag aaagagacat agtcccggtt gatgccagca ccgaaaatgg   18600
gcagaggcgg aagccagact tcattaggca gttcctcccc accaccccac cccgcgtga    18660 gctcccacaa gagggaacat cagcaccgcc agaaaaaggc aggaaaccac ctatccctgg   18720
```

```
ggaaagctcg aaatgagctt ttatgtccct cttcagagct cggcaatagc ctatccactt    18780
gaaaagttcc cagtgccagc agttttatgg caaactcctc cgggtgtttg ttctaaggag    18840
tcaacagctc ccattctaga attctccacg tgactccaat acacaaatct gacatcccac    18900
tctgctttcc ccagagtgga aactggagcc atacagaggc accatggcta aaaaggtgca    18960
ctcttctccc tgccagcccc acgtgctgcc cccaagagaa aggaaggatg ctctcctttc    19020
accgaagctc cctctcggag atggctgtgt tctctcccct ctcctggagt gggctcactg    19080
tgagctcgag ggacagaggc tgcctttcta ggggtgcaga atcctgtcag gggaagcgca    19140
agcttcaggg gctgaagagg cttcccgtgg aacgcttacc tcaaatgtaa aaggggcac    19200
gacgatggtc atccagctca gggccatggt tatgtgtgtc ctgcgctgtc cgcaatcaca    19260
tccatagagc gcaagaacaa gacggaccac acaatgtagt agaggaccac caggcacaga    19320
aaggacatga gaatccacag cgggacacac acaacctggg ggtgggtgag agaacagcaa    19380
gagaagtctc tttagagctt ccaacctggc ctctgatgga aggcatcttt agcaccttgc    19440
tgtgtctgtc cagttaaggc ggtccttcct gtgagccgaa taaggaccgt tccatctccc    19500
aggactgctg ggagcatcgc tcaggacaga aaaggtatgg tatgttcact atggggcctg    19560
ctgccaccag gggacacaca cgctcagtga gtcatcagtc cctcttcctt tgggtgacag    19620
acagccctgc acctggctcc gcagcctcta ctcttccaga ggcccactct cccacactct    19680
ctcaggctcc tctaggttct gctgccatca cagcttcccg ggaaatggga cacaactgtc    19740
accctgtgca cacacacaag atctcacccc aacagactct cttcacaggc aacattccca    19800
caacctgctg ggggtacttt ggcaacacaa atgggaatgg gctccccaga aagtctggct    19860
gcctgggctc ctaaggatcc ctaacctcac ccctaccaag ttagtgaact tggcgggttg    19920
atgctggata caggttgatg ctggatacgt agcgctgccg ggtcgtgacc cctaaggaat    19980
tatccaaact cttgttttta gatgctttat tatatcaaac tctcctttaa acaagtggcc    20040
catctgctgg gatttggaag cctgtaatac tgaaattttc atcataatgg aaattttaaa    20100
aacagaattt gacccacctg tttttaaaac actttcatta cttaacaaga ggtctaatct    20160
tgggcaagtc ttgaaatttc tctggcctta gtttcccatg tgttaaatga aacttgaagc    20220
agttggtctc ttatagtctc ctgactctaa cattctaaga attatatttg tacaataact    20280
caaaaatcac ataatttaat ttaccatatg gactccaaaa tatattttct cattaggcta    20340
aacttgatct gcattttctg gatgtgtcca tattcttgga ctacactaaa acatgatacc    20400
aatgcttcct ctcaccataa accctcactt cgctttctac atttaagaat tttatagctg    20460
gaagagtcct taacagaaaa taccatctaa taattacccc tcaaaatcga gaaagtccta    20520
tctgttctta tgctagttat aagaatgagg cagcatttca cataatggtt ataaacactg    20580
ccacaagaag attcatgatg tgttgtttat ctgtagctct catcatactc tgtcatataa    20640
ctatagcatt aagattttaa tgttctatat attcttctaa gacagtgttt accagagtaa    20700
ggcacaaaag atccactggt ttgcaagaaa gattagaact tttaaatttt ttacctcacc    20760
ttgtttaatc tatatttttg tatgtatttt gtaacatata tattattatt accataaatc    20820
atatataatt taaaatgcat atattagggg taaatgctca ggaaactttt tataaattgg    20880
gcatgcaaat acaagtttga agactcactg ttctaggtat taaaagtaaa gttataacca    20940
agtaaagctt ccacctttc atgtctcaaa gcagtttatt gttggaggta agatctctta    21000
gaagcctaaa caggtccaag tacagaatga agtaaggcta gcccataact tgtggcaagc    21060
aattcatact atttctctca tgctgagctc tcctcagtga agcagctact atagacaact    21120
```

```
gcagcctatt ggtagcctat tttacaggca ggaaaaaaat tactttttat tcaaagtgga    21180
actcaggaca tggggagaaa atgaatacaa aaaatagggt caatccaaag gcacacagca    21240
aatgagtaac acagttatgt tttttttccca tttgtatgag gtcccagtaa attctaagta   21300
aactgcaaat ttaataatac actaaaaaag ccatgcaatt gttcaaatga atcccagcat    21360
ggtacaagga gtacagacac tagagtctaa aaaacaaaag aatgccatta ttgagttttt    21420
gaattatatc aagtagttac atctctactt aataaatgag aaaacgagg ataagaggcc     21480 atttgataaa atgaaaatag ccaagaagtg gtattagaga cttgaataca ggtattcggg    21540
tccaaagttc atctgctcaa atactaactg ggaaaagag ggaaaaatat ttatatacat     21600
atatatctgc acacaaaaat accccccaaaa gacaaaatga ggccaggcag ggtggctcac   21660
acccgtaatc ccggtacttt gggaggctga ggcaggtgga tacctgagat caggagttgg    21720
agatcagcct ggtcaacatg gtgaaaccct gtctctacta aagataaaaa aattagccag    21780
gcatggtggc gtgcgcctgt aatcccagct acttgggagt ctgaggcagg agaatcactt    21840
gaactgggaa ggggaggttg cagtgagcca agatcgtact actgcactcc agcctgggca    21900
gcagagtgag actccatcac aaaaataaat aaataaataa aatacaatga aacagaaagt    21960
tcaaataatc ccataatctt accaccaaga aataactttc actcgttata cttattgatt    22020
tttccataat aaatgtactt tactgtgact atcatgaaaa gaaagttatt ttagaaacag    22080
agaactgttt cagatcaaat ctatgtagta gaacagagcc attaggtggg aaagacgaga    22140
tcaaactaaa tctcagaagg cctaaaaggc taggtccatt ccagcactaa aaactgacca    22200
gacaagtaat ggcttcaaca gcttctaaat atggacaaag catgctgaaa gggaaggaca    22260
ggtctaacag tggtatatga aatgaacagg aggggcaaag ctcatttctc ctctgaagtt    22320
ttccaaagat gctgaggagg acattagttt gacatgaccc tgatatggga caagataatt    22380
tcacagaagt tttacatgtt aaagttttct tatagatact cattcaagta agcaatgaac    22440
actaaaatct aaagaaagaa aagagcttta gagtcaggtc tgtattcaaa ttcaagctct    22500
accacttact ggttctgtga ctttgggcaa gtcttttaac cttattaagt cttaatttcc    22560
tgatttgtaa aatggggata tcgtctccct cacaggattg ttgtgaaact tttatgagat    22620
taatgccttt atatttggca tagtgtaagt aaacaataac tggcagcttc aaaaaaaaaa    22680
agcagtagca ttccatcatt tattattggt tactctcaaa aagttttttca atgtactaga   22740 agataaatat tcaaatacct taatatctcc attattttca ggtaaacagc atgctcctga    22800
acaaccaatg ggtcaacaaa taattaaaa gggaaatcta aaaacatctt gatattaaac     22860
tacatggaag cacaatatac caaaaccaat ggttcacact aggagaattt taaggtacaa    22920
gaaaactctt tgagatttct taaaataata gtatgtctga atttattgag tgatttacca    22980
gaaactgttg taagagctct acttgcatta tagcacttaa tcctcttaac tctatggctg    23040
ctattatcaa cctcacccta atcacatatg ggacacagag aggttaagta acttgcccaa    23100
ggtcagagtt aggaagtact aagccatgct ttgaatcagt tgtcaggctc cggaactcac    23160
actttcagcc actacataat actgctttgc tatcttttag gaaactatgt gagtctacct    23220
cacatagact cacataggtt tgtttttttt ttttttttaa aggctatctt ttccccccatc    23280 aatgttttt gaaggatccc aaattagagt cccacagagg cagacagcag tacttgcaaa    23340
tatggacatt taaggttaat gttggattct actgtctttt tactacatga cctagggaac    23400
gataattaac ctagactgct tccaagggtt aaataaccca tttagttata ctatgtaaat    23460
tatctcttag tgattgattg aaagcacact gttactaatt gactcggtat gaagtgcttt    23520
```

```
tttttcttcc ctttcaagat acatacctttt ccagttaaag ttgagagatc atctccacca   23580
attactttta tgtcccctgt tgactggtca ttctagttaa aaaaaaaaaa aactatatat   23640
atatatatct acacacacat atgtatatgt atatccttat gtacacacac aaacttcaaa   23700
ttaaatgaga actagaagat ttgagaagtt agctagctaa tatccatagc attatgatat   23760
tctaaatgat atgaattata agaattaggt ttcctgaaat gaatgactag aaaactttca   23820
agtagagatt agtaaaaatt aaaaagtcct aatcggccat tactgatttg atgttttttaa  23880
gagtcctaaa aaatgggtta catccatttt taagtgggta gtattataac agccacccat   23940
cttcaatcac agtgatttct gaattgtgag ggaagttatt agcatgacag gtgtctggtt   24000
ctggccctgt acgattccca tgagtcaagc aaattgtaag ggctggtcta tatcacaccc   24060
aaccccaagg atatgtccct caaaagtcta gcccaggccc cgtcatcttc agcatcatct   24120
gggaaaccag gtctgattag tagtccttta aggaatacct cttaggctcc cattttactg   24180
ctatcacaga atccaataaa acccttacag gagattcaat gggaaatgct caacacccac   24240
tgtagttggt ggtgacaatg accataattt ggctgtgctg gattcaggac agaaaatttg   24300
ggtgaaagag caggtgaaca aaagagcttc gacttgccct agcagagagc aagccatacc   24360
ataccacaaa gccacagcaa ttacaacggt gcagtaccag cacagtaaat gaacaaagta   24420
gagcccagaa acagacccag aactatatga ggatttagta tacaataaag atggtatttc   24480
gagtcagtag ggaaaagatg aattattcaa taaatgatgt ttggccaact agtaacccat   24540
ttgggaaaaa ataaaagtat ggtccctacc tcacagcata cacaaaaata aattccagac   24600
ggattaaaat ctaaatgtaa aaaataaagc cataagtgga ctggaagaaa atagagaatt   24660
tttttaaca tccgtagaaa gggtaaaaac ccaggcatga catgaaccaa aactgaagag   24720
gttctgtaac aaataccccc ttttatatat tgggctccaa caataagaac ccataggaaa   24780
atggagaatg aacacaaata gacaatttat agaagagaag gttataaggt gtaaaattat   24840
atctatctga gaaacaaaca ctaaaacaat gtgattctac tgttctccca cccatactgg   24900
caaaacttaa gcctgataat atgctgaggg gaaataagca ctcttgttgg tgagagtatt   24960
aattggcata gcttcttttg aaaatgacat agcaatacct gttaaaattg caaacatgca   25020
tgtcacttaa tccagtaatc ccacttctgg gaatcaatgc tacaaaaaca ctgacaagta   25080
tacaaagata cattcaagag tgttcactgg gccgggtgcg gtggcttcat gcctgtaatc   25140
ccagggaggc agaggcaaga cgatcgcttg accccaggag ttcaaggcca gcccgagaaa   25200
cacagcaaga ccctgtctct cttttttta tttaaaaaat aaatgttcac tgtatcagtt   25260
gttcacaaaa acaaaccaac atgtccatta acagggaacc atttaaatta atcaagttca   25320
tctacacaat gtaataccat gcaactatta aaaagcacct gataatccaa agcacactga   25380
gacagaataa tgctattaaa aacaccaagt agtggaacac tgtgttgcct atgacaccat   25440
ttttattcaa catttaaaca aatttgtaac agcaattaca tgagtagtga caatggcgtt   25500
tatgagactt ttcactttta tgtgcttcta tttttgttat gcttctatat atacatccat   25560
ttattatgga gtgttacttt caaaaatcac aaatgggcca gtattatttg gtgttgcaag   25620
gtgagcatat gacttctgat atcaaccttt gcatattact tctcaattta gggaaattac   25680
agacatccct tattctaact aacttaaaac ccagcatttc aaacatacag aattgatggg   25740
gaaaaaaaag aaagaagaaa gaaagaaaag gcaacaagct tcagatgaca gtgactcaca   25800
tcaaattatt tataaaatct gttaaatagt gccatcttct ggagatacct ggtattacag   25860
tccaactcca gttgatgtct ttacagagac aagaggaata aaggaaaaaa tattcaagaa   25920
```

```
ctgaaaagta tggagtcatg gaaaaattgc tgtgatccaa aggctacggt gataggacaa    25980
gaaacaagag aactccaagc agtaagacac tgctgttcta ttagcatcca aacctccata    26040
ctcctgtttg ccccaaggct tttttaaaaa atagagacag gatctcacta ttttgctcag    26100
gctggtcttg aactcctgga ctcaagctat cctcctgcct cggcctccta aagtgccgag    26160
attacaggct tgagtcacca tacctggcta tttatttttt cttaactctc ttgcctggcc    26220
tatagccacc atggaagcta ataaagaata ttaatttaag agtaatggta tagttcacta    26280
cattggaata caggtataag tgcctacatt gtacatgaat ggcatacatg gatcaattac    26340
cccacctggg tggccaaagg aactgcgcga acctccctcc ttggctgtct ggaacaagct    26400
tcccactaga tccctttact gagtgcctcc ctcatcttta attatggtta agtctaggat    26460
aacaggactg caaaggtga ggggaaagct tcctccagag ttgctctacc ctctcctcta    26520
ccgtcctatc tcctcactcc tctcagccaa ggagtccaat ctgtcctgaa ctcagagcgt    26580
cactgtcaac tacataaaat tgccagaaga gctctttggg actacaaaca cataccctta    26640
atgtctttat ttctatttg tctacctctt cagtctaggt gaaaaatag gaaggataat    26700 agggaagaac tttgtttatg cctacttatc cgccccctagg aattttgaaa acctctaggt    26760
agcaataaga actgcagcat ggtatagaaa aagaggagga aagctgtata gaaatgcata    26820
ataaatgggc aggaaaagaa ctgcttggaa caaacaggga ggttgaacta taggagaga    26880 aagcagagag gctaatcaac aaggctgggt tcccaagagg gcatgatgag actattacta    26940
aggtaggaat tactaagggc tccatgtccc cttagtggct tagtactatg tagcttgctt    27000
tctgcagtga acttcagacc cttcttttag gatcctagaa tggactttt ttttttatcg    27060 gaaaacagtc attctctcaa cattcaagca ggccccaagt ctaccacact caatcacatt    27120
ttctcttcat atcataatct ctcaaccatt ctctgtcctt ttaactgttt ttctataccc    27180
tgatcaaatg ccaacaaaag tgagaatgtt agaatcatgt atttttagag gtagactgta    27240
tctcagataa aaaaaaggg cagatattcc attttccaaa atatgtatgc agaaaaaata    27300
agtatgaaag gacatatgct caggtaacaa gttaatttgt ttacttgtat tttatgaatt    27360
ccctaaaacc tacgtcaccc gccccgttcc cacgccccgc gccacgtcac aaactccacc    27420
ccctcattat catattggct tcaatccaaa ataaggtata ttattgatga tgttaattaa    27480
catgcatgga tccatatgcg gtgtgaaata ccgcacagat gcgtaaggag aaaataccgc    27540
atcaggcgct cttccgcttc ctcgctcact gactcgctgc gctcggtcgt tcggctgcgg    27600
cgagcggtat cagctcactc aaaggcggta atacggttat ccacagaatc agggGataac    27660
gcaggaaaga acatgtgagc aaaaggccag caaaaggcca ggaaccgtaa aaaggccgcg    27720
ttgctggcgt ttttccatag gctccgcccc cctgacgagc atcacaaaaa tcgacgctca    27780
agtcagaggt ggcgaaaccc gacaggacta taaagatacc aggcgtttcc ccctggaagc    27840
tccctcgtgc gctctcctgt tccgaccctg ccgcttaccg gatacctgtc cgcctttctc    27900
ccttcgggaa gcgtggcgct ttctcatagc tcacgctgta ggtatctcag ttcggtgtag    27960
gtcgttcgct ccaagctggg ctgtgtgcac gaaccccccg ttcagcccga ccgctgcgcc    28020
ttatccggta actatcgtct tgagtccaac ccggtaagac acgacttatc gccactggca    28080
gcagccactg gtaacaggat tagcagagcg aggtatgtag gcggtgctac agagttcttg    28140
aagtggtggc ctaactacgg ctacactaga aggacagtat ttggtatctg cgctctgctg    28200
aagccagtta ccttcggaaa aagagttggt agctcttgat ccggcaaaca aaccaccgct    28260
ggtagcggtg gttttttgt ttgcaagcag cagattacgc gcagaaaaaa aggatctcaa    28320
```

```
gaagatccttt tgatcttttc tacggggtct gacgctcagt ggaacgaaaa ctcacgttaa    28380
gggattttgg tcatgagatt atcaaaaagg atcttcacct agatccttt aaattaaaaa      28440 tgaagtttta aatcaatcta agtatatat gagtaaactt ggtctgacag ttaccaatgc      28500
ttaatcagtg aggcacctat ctcagcgatc tgtctatttc gttcatccat agttgcctga    28560
ctccccgtcg tgtagataac tacgatacgg gagggcttac catctggccc cagtgctgca    28620
atgataccgc gagacccacg ctcaccggct ccagatttat cagcaataaa ccagccagcc    28680
ggaagggccg agcgcagaag tggtcctgca actttatccg cctccatcca gtctattaat    28740
tgttgccggg aagctagagt aagtagttcg ccagttaata gtttgcgcaa cgttgttgcc    28800
attgctgcag ccatgagatt atcaaaaagg atcttcacct agatccttt cacgtagaaa     28860 gccagtccgc agaaacggtg ctgacccccgg atgaatgtca gctactgggc tatctggaca   28920
agggaaaacg caagcgcaaa gagaaagcag gtagcttgca gtgggcttac atggcgatag    28980
ctagactggg cggttttatg gacagcaagc gaaccggaat tgccagctgg ggcgccctct    29040
ggtaaggttg ggaagccctg caaagtaaac tggatggctt tcttgccgcc aaggatctga    29100
tggcgcaggg gatcaagctc tgatcaagag acaggatgag gatcgtttcg catgattgaa    29160
caagatggat tgcacgcagg ttctccggcc gcttgggtgg agaggctatt cggctatgac    29220
tgggcacaac agacaatcgg ctgctctgat gccgccgtgt tccggctgtc agcgcagggg    29280
cgcccggttc ttttttgtcaa gaccgacctg tccggtgccc tgaatgaact gcaagacgag    29340
gcagcgcggc tatcgtggct ggccacgacg ggcgttcctt gcgcagctgt gctcgacgtt    29400
gtcactgaag cgggaaggga ctggctgcta ttgggcgaag tgccggggca ggatctcctg    29460
tcatctcacc ttgctcctgc cgagaaagta tccatcatgg ctgatgcaat gcggcggctg    29520
catacgcttg atccggctac ctgcccattc gaccaccaag cgaaacatcg catcgagcga    29580
gcacgtactc ggatggaagc cggtcttgtc gatcaggatg atctggacga agagcatcag    29640
gggctcgcgc cagccgaact gttcgccagg ctcaaggcga gcatgcccga cggcgaggat    29700
ctcgtcgtga cccatggcga tgcctgcttg ccgaatatca tggtggaaaa tggccgcttt    29760
tctggattca tcgactgtgg ccggctgggt gtggcggacc gctatcagga catagcgttg    29820
gctacccgtg atattgctga agagcttggc ggcgaatggg ctgaccgctt cctcgtgctt    29880
tacggtatcg ccgctcccga ttcgcagcgc atcgccttct atcgccttct tgacgagttc    29940
ttctgaattt tgttaaaatt tttgttaaat cagctcattt tttaaccaat aggccgaaat    30000
cggcaaaatc ccttataaat caaaagaata gaccgagata gggttgagtg ttgttccagt    30060
ttggaacaag agtccactat taaagaacgt ggactccaac gtcaaagggc gaaaaaccgt    30120
ctatcagggc gatggcccac tacgtgaacc atcaccctaa tcaagttttt tggggtcgag    30180
gtgccgtaaa gcactaaatc ggaaccctaa agggagcccc cgatttagag cttgacgggg    30240
aaagccggcg aacgtggcga gaaggaagg gaagaaagcg aaaggagcgg cgctagggc    30300 gctggcaagt gtagcggtca cgctgcgcgt aaccaccaca cccgccgcgc ttaatgcgcc    30360
gctacagggc gcgtccattc gccattcagg atcgaattaa ttcttaatta acatcatcaa    30420
taatatacct tattttggat tgaagccaat atgataatga ggggtggag tttgtgacgt     30480 ggcgcggggc gtgggaacgg ggcgggtgac gtagtagtgt ggcggaagtg tgatgttgca    30540
agtgtggcgg aacacatgta agcgacggat gtggcaaaag tgacgttttt ggtgtgcgcc    30600
ggtgtacaca ggaagtgaca attttcgcgc ggttttaggc ggatgttgta gtaaatttgg    30660
gcgtaaccga gtaagatttg gccattttcg cgggaaaact gaataagagg aagtgaaatc    30720
```

-continued tgaataattt tgtgttactc atagcgcgta atactg    30756

<210> SEQ ID NO 24
<211> LENGTH: 32392
<212> TYPE: DNA
<213> ORGANISM: Artificial Sequence
<220> FEATURE:
<223> OTHER INFORMATION: Description of Artificial Sequence: Synthetic
      PrIDO-final
<220> FEATURE:
<221> NAME/KEY: misc_feature
<222> LOCATION: (1)..(32392)
<223> OTHER INFORMATION: n= a, c, g, t , unknown or other

<400> SEQUENCE: 24

```
gtacggaagc ccggaaggag gggcaggggg cggtggctca ggtttctccg ggcggcggcg    60
gcggcggcgg cggcgacggc gacggcgacg gcagcgggga cggcagcagt agcgggagca   120
gcagcgtgga cgcggctggc gctggcgcca tgaacccgct gtaaggcgca ggctgtgcag   180
cacggggtgc gggggaggag gaggaggacg ccgcggtgaa gttctccgcc atgaacctga   240
ggggcctctt ccaggacttc aacccgaggt gaggcggcgt cgttggcgcc cccgggagtc   300
cgcgctgcgg gctcgggcgc gggctggtgt tcggctccgg ggaggcacgg cgggcgagat   360
gctgcagccc gaggacccgg gcgcctgccc gagcctccct gcgggtgcaa gcggtcccca   420
ggcaaaacag tcggcctcgg cgcccgcccg cttcctcctc ccgtgccegg tgctttcagc   480
ccctgcccgg ccacggccgg aagggcccgg ccgcgagccc cgtcctgccc caagggaacc   540
ccattctttt ctgcttgctg tccctcattg gtgtcccaac ttcttcgtct cggttccatc   600
ctcttctgcg ccgctgcggg ccctccattc tccgcgtcag ggccgtctca ctcgacccaa   660
cacccctacc cccaccccag ctgtttcctc cagttcctcg cagtccttgg ggttttcctt   720
gggtttatgc ccatccctct cttgtttgct tctttgttga acggatacct gaaacactgt   780
tgaatccttg gagtcagtgt cggggtatgg caatacctta tataatgcat ttctgggtga   840
gcctgatcat tttccatact cattttctca tcagtcttca ctacaagttt atttgcagga   900
agtagatatt gctgtccttc ttttccagat ggggaacacc cagtggacag tgtggagaaa   960
acactggcta agcactcaag cgcctgtcct tgcacttgcc cgactgtttt gtaactgttc  1020
tttaccccag gctgtgagct ccctgaagct gagaccatct cctgctcatc tcagtgtccc  1080
cagcgcctcc cacccaccgt atctggcaca tagtaggcac atataaaatg tttgtggaac  1140
taaactgagc ccaaagactt ggattggaga cgaggccata tgtaactggg tgattctctg  1200
cccttctttg gcccttctgt aaaatgagga gttggcctaa ctgatctctt aaatgcacta  1260
ctctccgaaa ggagtatccg tttcccttat ttgccagttg ggaagacgtg ctcagtaaat  1320
atttgtgtgc tgtaacctat gttaggtgct ttagatgctg gcggtctcag catggggtga  1380
agaagggctt gtacacttaa gatgccttac agtactgtgc agtgctgtac tgcggggggcc  1440
aactctgggg acctatgcct tggctgcttg ttgaggatga aggaagttt agggggagta  1500
tttgtatgtt gagggtgcag tctccctagg gatggtgaca ttttaacttg tgagtcattg  1560
tgactttgta tgtgccctta ttccactttg agttcatgtt ctggttagga gtgccagtgt  1620
ctctaacacg gtgcagacat tatcattgtt ggcttcgaag gcatagagga ggtaacagaa  1680
ctaactgcag tcccttcctc tgctgcatca ggggttaag attggtctgc agggtagtag  1740
ggttggtgct gtggctggac aagccctgta tgtcttctat ttggagatgg tgataagaaa  1800
gttaagtaaa aactgaattg ttttgtgccc ttgggcaact cacttatcta ttgttttatc  1860
tgtagaatga gtataatctc tcagtggggt agggaggcca attaaggatt gattacaaag  1920
```

```
tgccttacaa atagaaagct acagtgactt gtttgcaagg tgacagagaa ttcagaagcc    1980
tcaagaaact gccttaagtg atcaaacagg ctaacggagt tgccaaagca aaatagtgct    2040
gcactgatac tacctttaac cgttttttcc tttagcccct tccccccaa aaaaattagt     2100 atatgaaatt acagtgaaat acctggtatc taagcagatt tatagtaatt ctcaacatat    2160
tcatcaatct cttaattcta cctgcattaa aatgtatttc tacctgaaaa gtttaaaggt    2220
cttttatact gtgccatttt cctgattcat tgttgccaga ggtagtgagt tccttaattt    2280
tacagatatt tcaagaggac attggccagg tattattggt aaatcagatt tgttttttta    2340
gctggtagtg tttcacctct cctgagcact cctagttttt gacagtgtgc tttagtctcc    2400
ttccatgctg aggaaggcct tctctatagg agaaagaaaa ctgaggggtg tacacaggaa    2460
gttaccttat gctggggact caaaccttga tgctactgct ttgctccctg cctctatttt    2520
tgaaccaatt caacatctcc ctcctacccc aggaccttgt cacacactgt tctctttacc    2580
aggaatgttt ccctctcttt tcctctcctc cagacctagt gaactcctat ttatcctcac    2640
ttggcacttg ctaagggaag cattcctgac ttccctgacc agatttactg ctccctgttt    2700
ctacagttcc tgtagtattt actactcctc catcatagtg catatttgta cccttgtgtc    2760
tgtctggatg cttatttgat taatacctgc ctcccccact aaactttaag ctccatgggg    2820
tcaaggccgt gactgtgtca gtatcgtagc ctgcatactt ggaatagtac ctggctcaat    2880
aaatatttgt ggagtaaata actgaataac tctccagagc ctataagata aatctagagc    2940
tgctgctttc aatcactgct ttcctggtgg tctgtggcct ggttctcttt cttctcacac    3000
tcttcccacc ttcagagtgc agccattgct ttggagagat gggagagaac atggcactaa    3060
ggcagaatat ggctatattt actttgaaga gcatgtcttt gtcatagaaa tagtcactgt    3120
catggtttgg tgggtcccaa ggcatgggtc atggctccag atcccctttc cagccttttg    3180
gatcttggta agtctgaacc cactgctgcg ttggcaaggc tctggaaact atagtgacag    3240
agaatgattc acaagtgtca cactcagat gtacagggct gccagctgac ccactctacc    3300
tatttccatc tggcactgaa ctggttgatc atgaacttct tttcataatt gcttttagt    3360 tatgcaggtt aagacatgcc gaaacagatg taccggaccc acaaacaagt ccttccttga    3420
atgcctgagg cttcctaaca gtgaaagagc cctgttctta gagtaggcaa actgattctg    3480
aggcattgta ggtggtaggg atctggtagt aggtagcatt aggtgggctc ccggcactca    3540
ccatggagcc ttgaaatttt ctgctacttt gggggagttg ctggttcaga aaggcccctt    3600
ccaccctggt agccatgtgg cactggaagg ctgtgaaaac tctgctgggc cttcttagtc    3660
atctgttgtg agctcctgat gggagtgtgg tgtatccctc aggtgtgcta gactggaaca    3720
aaggctgaga agtgttgctc tgggggttcc aacttgtggg catggggtac tgatgagatc    3780
agtagtgttt ggagacttct gtatgctcca tcttcagaag acattctgga gtccatataa    3840
gttatcttgt ctcttgtttg aagcaggaaa aaggaatgcg attgctggta atatagttca    3900
ctaaagtcag ctacctggcc tctaacagtt atttgcaaag tatattataa cattgattcc    3960
tcaaacatct agattcctat ctcgtgccaa gtgatgtact aggtgctcta agtacaaaaa    4020 taaggaata tagtcctcct ctcaatgcgt aagcctagtg gaagaagcag aaatgaaagg    4080
gaaataagaa ttcaatagag tatgaggcat tacagtgaaa gaaaccaaat gtcttagaag    4140
tacaaatggc agagctacta attctgtctc gagcaggcag ggaagagtct atagtggaaa    4200 tgactttga gctagatttt gaattgagct agtcttttga gccagacttt tgagctagaa    4260
ttgtagggtt gtcatcagac cagagagtag gaagggtacc ttgtgaggaa gagagagaga    4320
```

```
gatcagattg ttactgtgtc tatgtagaaa aggaagacat aagaaactcc attttgatct    4380
gtactaagaa aaattgtttc tgctttgaga tgctgttaac ctgtaacttt agtcccaacc    4440
ctgtgctcac agaaacctgt gctgtaatga atcaaggttt aatggattta gggctgtgca    4500
ggatgtacct tgttaacaat atgtttgcag gcagtatgct tggtaaaagt catcgccatt    4560
ctccattctc gattaaccag ggacacagtg cactgcggaa ggccgcaggg acatctgccc    4620
aagaaagcct gggtattgtc caaggtttcc ccccactgag acagcctgag atatggcctt    4680
gtgggaaagg aaagacctta ccacccccca gcccgacacc cgtaaagtgt ctgtgctgag    4740
gaggagtagt gaaagagcgg ggcctctttg cagttgagat aagaggaagg cttctgtctc    4800
ctgctcatcc ctgggaatgg aatgtctctg tgtaaagctg accattccca ttcgttctat    4860
tctgagatag gagaaaacca ccctgtggct ggaggcgaag tatgctggca gcaatactgc    4920
tctgttactc tttgctacac tgagttgttt gggtaaagag aaacataaat ctagcctgcg    4980
tgcacatcca ggcacagtac cttccttga acttattcat gatacagatt cctttgctca     5040
cgtttccctg ctgaccttct ccccacctgt tgccctgcta cactcccctc gctaagatag    5100
taaaaataat gatcagtaaa tactgaggta actcagaggc tagcgctggt gcgggtcctc    5160
cgtatgctga gtgccggtcc cctgggccca ctgttctttc tctatacttt gtttctgtgt    5220
cttatttctt ttctcagtct cgtcccacct gacgagaaat acccacaggt gtggaggggc    5280
tggccccttt cagtatctca gaagggacaa agtacacaaa ggcatggggt catgatagtg    5340
cctggtatgt tcaggtagtg aagaggtcca tgtggtatga gcactgcaga tgatatgtgt    5400
cgtatgaatt aaaaatacat agttactgca aatagttttt acaggttatt gttttttaaga   5460 aagcagtatc taatgcacga gtgtactgtc agtactgtca atgaactact taccactcaa    5520
gtgactgctt acgcgtcgaa tcactagtga attcgcggcc gcctcgagtc tagaactagt    5580
ggatccccca acgggccct ctagacgcgt tgacattgat tattgactag ttattaatag     5640
taatcaatta cggggtcatt agttcatagc ccatgatatc atatggagtt ccgcgttaca    5700
taacttacgg taaatggccc gcctggctga ccgcccaacg accccgccc attgacgtca      5760 ataatgacgt atgttcccat agtaacgcca atagggactt ccattgacg tcaatgggtg      5820 gagtatttac ggtaaactgc ccacttggca gtacatcaag tgtatcatat gccaagtacg    5880 ccccctatt gacgtcaatg acggtaaatg gcccgcctgg cattatgccc agtncatgac      5940
cttatgggac tttcctactt ggcagacatc tacgtattag tcatcgctat taccatggtg    6000
atgcggtttt ggcagtacat caatgggcgt ggatagcggt ttgactcacg ggatttttcc    6060
aagtctccac cccattgacg tcaatgggag tttgttttgg caccaaaatc aacgggactt    6120
tccaaaatgt cgtaacaact ccgccccatt gacgcaaatg ggcggtaggc gtgtacggtg    6180
ggaggtctat ataagcagag ctctctggct aactagagaa cccctgctta ctggcttatc    6240
gagatatctg cagaattcat ctgtcgactg ctaccggcag cgcgcagcgg caagaagtgt    6300
ctgggctggg acggacagga gaggctgtcg ccatcggcgt cctgtgcccc tctgctccgg    6360 cacgccctg tcgcagtgcc cgcgcttttcc ccggcgcctg cacgcggcgc gcctgggtaa    6420
catgcttggg gtcctggtcc ttggcgcgct ggcctggcc ggccgcgtta agatacattg      6480
atgagtttgg acaaaccaca actagaatgc agtgaaaaaa atgctttatt tgtgaaattt    6540
gtgatgctat tgctttattt gtaaccatta taagctgcaa taaacaagtt aacaacaaca    6600
attgcattca ttttatgttt caggttcagg gggaggtgtg ggaggttttt taaagcaagt    6660
aaaacctcta caaatgtggt atggctgatt atgatcagtt anctagatcc ggtggatctg    6720
```

```
agtccggact tgtacagctc gtccatgccg agagtgatcc cggcggcggt cacgaactcc  6780
anngatcgga tatcttatct agtgattcta aggccaactc agaagggctt tcttggttgt  6840
atctttcaca ctcctcagga aattcatgac gtcagtaccc ccagtccctc tgttttccgt  6900
gtttgagggc tcttctgact tgtggccacc catgggcttc tgcttcgaag gcttcacaat  6960
gtaagtatct actatcgaga ggtggaacat tctgagggag accaggccat tcacacactc  7020
attataagcc tccttcaagt cttcattgcg tcttaaaatg acaaactcac ggactggggg  7080
agctgactct aaggaggaga ggaagttccg gtgggctgga ggcatgtact ctctcatttc  7140
ctggaggaat tctgcagcag atccttcacc aacgtcatgc tttattccca gaaggacatc  7200
aagactctga agatgctgc tctggcctgc actgccccct gaaaatttt tgggggtgtc  7260
ccagacgccc tcgtacagca gaccctccgg cagcttaggg ttgcccttcc aaccagacaa  7320
atatatgcga agaacgtgga aaaggtgtc tggatccacg aagtcacgca tcctcttaaa  7380
aatttccttg gctttctcca gactggcagc tatactacac agtgccttct ccagtgcttt  7440
cgggtcttga tgctctactg cactggatac agtaggaatt gctttgattg caggagaagc  7500
tgcgatttcc accattagag agaccaggaa gaagcccttta tcgcagtccc caccaggaaa  7560
cgagaacaga atgtccatgt tctcgtatgt catgggccca ttggggtcct ttttcttcca  7620
gtttgccagg acgcagtctg cgtaagacag aatgggaggc agcccagct tctccgagag  7680
ctcgcagtag ggaacggcaa gattgcgggg cagcaccttt cgaatatcat catcccctcg  7740
gttccacaca tacgccatgg tgatgtaccc cagggccaaa tgtgccaggc gctgtaacct  7800
gtgtcccctc agttcttcgg tgcgcagtgt gggcagcttc tcgacttctt ctcggagctt  7860
cccattctca atcagcttag gcagatttct agccacaagg atccaaggtc tgtacgtatc  7920
aggcagctcc tccagtggat gtggtagagc aaagcccaca tcttcatcta tgtggtattc  7980
ttcaaggatc cttctagagc cttctgcagg agatatttga ctgtgaggca taatcgaatt  8040
cccgcggccg cgtcgacggt accagatctc tagcggatct gacggttcac taaaccagct  8100
ctgcttatat agacctccca ccgtacacgc ctaccgccca tttgcgtcaa tggggcggag  8160
ttgttacgac attttggaaa gtcccgttga ttttggtgcc aaaacaaact cccattgacg  8220
tcaatgggt ggagacttgg aaatcccgt gagtcaaacc gctatccacg cccattgatg  8280
tactgccaaa accgcatcac catggtaata gcgatgacta atacgtagat gtactgccaa  8340
gtaggaaagt cccataaggt catgtactgg gcataatgcc aggcgggcca tttaccgtca  8400
ttgacgtcaa tagggggcgt acttggcata tgatacactt gatgtactgc caagtgggca  8460
gtttaccgta aatactccac ccattgacgt caatggaaag tcccattggc gttactatg  8520
ggaacatacg tcattattga cgtcaatggg cggggtcgt tgggcggtca gccaggcggg  8580
ccatttacca acgcggaact ccatatatgg gctatgaact aatgacccg taattgatta  8640
ctattannnt aagggtggga agaatatat aaggtggggg tcttatgtag ttttgtatct  8700
gttttgcagc agccgccgcc gccatgagca ccaactcgtt tgatggaagc attgtgagct  8760
catatttgac aacgcgcatg ccccatgggc cggggtgcg tcagaatgtg atgggctcca  8820
gcattgatgg tcgccccgtc ctgcccgcaa actctactac cttgacctac gacctgcagg  8880
cagacgggcg ctcctgcacc gcatccgcga cgcagtcctg caacgacctc tgcgagcact  8940
tctgcgttcc caaccccgac cagccgggct cctactcgtg catgtgcgag accggctacc  9000
ggctggcggc cgaccaacac cggtgcgagg acgtggatga ctgcatactg agcccagtc  9060
cgtgtccgca gcgctgtgtc aacacacagg gtggcttcga gtgccactgc taccctaact  9120
```

```
acgacctggt ggacggcgag tgtgtggagc ccgtggaccc gtgcttcaga gccaactgcg   9180
agtaccagtg ccagcccctg aaccaaacta gctacctctg cgtctgcgcc gagggcttcg   9240
cgcccattcc ccacgagccg cacaggtgcc agatgttttg caaccagact gcctgtccag   9300
ccgactgcga ccccaacacc caggctagct gtgagtgccc tgaaggctac atcctggacg   9360
acggtttcat ctgcacggac atcgacgagt gcgaaaacgg cggcttctgc tccggggtgt   9420
gccacaacct ccccggtacc ttcgagtgca tctgcgggcc cgactcggcc cttgcccgcc   9480
acattggcac cgactgtgac tccggcaagg tggacggtgg cgacagcggc tctggcgagc   9540
ccccgcccag cccgacgccc ggctccacct tgactcctcc ggccgtgggg ctcgtgcatt   9600
cgggcttgct cataggcatc tccatcgcga gcctgtgcct ggtggtggcg cttttggcgc   9660
tcctctgcca cctgcgcaag aagcagggcg ccgccagggc caagatggag tacaagtgcg   9720
cggccccttc caaggaggta gtgctgcagc acgtgcggac cgagcggacg ccgcagagac   9780
tctgagcggc ctccgtccag gagcctggct ccgtccagga gcctgtgcct cctcacccccc   9840 agctttgcta ccaaagcacc ttagctggca ttacagctgg agaagaccct ccccgcaccc   9900
cccaagctgt tttcttctat tccatggcta actggcgagg gggtgattag agggaggaga   9960
atgagcctcg gcctcttccg tgacgtcact ggaccactgg gcaatgatgg caattttgta  10020
acgaagacac agactgcgat ttgtcccagg tcctcactac cgggcgcagg agggtgagcg  10080
ttattggtcg gcagccttct gggcagacct tgacctcgtg ggctagggat gactaaaata  10140 tttattttt ttaagtattt aggttttgt ttgtttcctt tgttcttacc tgtatgtctc  10200
cagtatccac tttgcacagc tctccggtct ctctctctct acaaactccc acttgtcatg  10260
tgacaggtaa actatcttgg tgaattttt tttcctagcc ctctcacatt tatgaagcaa  10320
gccccactta ttccccattc ttcctagttt tctcctccca ggaactgggc caactcacct  10380
gagtcaccct acctgtgcct gaccctactt cttttgctct tagctgtctg ctcagacaga  10440
acccctacat gaaacagaaa caaaaacact aaaaataaaa atggccattt gcttttcac  10500 cagatttgct aatttatcct gaaatttcag attcccagag caaaataatt ttaaacaaag  10560
gttgagatgt aaaaggtatt aaattgatgt tgctggactg tcatagaaat tacacccaaa  10620
gaggtattta tctttacttt taaacagtga gcctgaattt tgttgctgtt ttgatttgta  10680
ctgaaaaatg gtaattgttg ctaatcttct tatgcaattt ccttttttgt tattattact  10740
tatttttgac agtgttgaaa atgttcagaa ggttgctcta gattgagaga agagacaaac  10800
acctcccagg agacagttca agaaagcttc aaactgcatg attcatgcca attagcaatt  10860
gactgtcact gttccttgtc actggtagac caaaataaaa ccagctctac tggtcttgtg  10920
gaattgggag cttgggaatg gatcctggag gatgcccaat tagggcctag ccttaatcag  10980
gtcctcagag aatttctacc atttcagaga ggccttttgg aatgtggccc ctgaacaaga  11040
attggaagct gccctgccca tgggagctgg ttagaaatgc agaatcctag gctccacccc  11100
atccagttca tgagaatcta tatttaacaa gatctgcagg gggtgtgtct gctcagtaat  11160
ttgaggacaa ccattccaga ctgcttccaa ttttctggaa tacatgaaat atagatcagt  11220
tataagtagc aggccaagtc aggcccctat tttcaagaaa ctgaggaatt ttctttgtgt  11280
agctttgctc tttggtagaa aaggctaggt acacagctct agacactgcc acacagggtc  11340
tgcaaggtct ttggttcagc taagctagga atgaaatcct gcttcagtgt atggaaataa  11400
atgtatcata gaaatgtaac ttttgtaaga caaaggtttt cctcttctat tttgtaaact  11460
caaaatattt gtacatagtt atttattttat tggagataat ctagaacaca ggcaaaatcc  11520
```

```
ttgcttatga catcacttgt acaaaataaa caaataacaa tgtgaaaaaa aaaaaaaaaa    11580
aaaaaaaaaa aaaaaaaaaa aaaaggtagc agtcgacaga tgaattccac cacactggac    11640
tagtggatcc gagctcggta ccaagcttaa gtttgggctg caggaattct gatggctctc    11700
aaaattcctg cctcctttag ggataaaaga ctttaagact ttttaacaaa aagaaaaag     11760
aaaaaaaaaa ttcctgcctc ctggtgtaca cacacagaag ggttccctcc ccttgaatgt    11820
gaccaggatc tgtgaaaata acgggatagc cgctcctgtg attaggttat gtggtagact    11880
agagcaagat tctcctgctg gttttgaaga agtcagctgc catgttgtga gactgtcatg    11940
ggctagggca tgagccttta aatatctggg agcaacccct ggccagcagc cagtgagaaa    12000
acgggccctc agtcctacaa tcacaaggaa ctaaattctg ccaacaacct gaaggaactt    12060
tgaagaggat catgagtccc ttgattcagc ttgatgagcc cctgagcaga ggatacagct    12120
aacttgtact agggaagtat aaaaaacatg catgggaatg atatatatca acttttaagga   12180
taattgtcat acttctggga atgaagggaa agaaatgggg ctttagttgt attatgatct    12240
ttaatttctc aaaaaaaata agatcagaag caaatatggc aaaatgttaa tacttttgtg    12300
ggtacgtagg tattcagcat acccttttt ctgagttcaa aatattttat aattaaaatg     12360
aaatgcaggc caggcacagt ggctcatgcc tataatacca gcactttgcg aggccgaggt    12420
gggaggatgg cttgaggcca gaccagcctg gccaacatgg caaaacccca tctctactta    12480
aaaaaaaaaa aactatatat atatatatgt gtgtgtgtgt gtatatatat atatgtatat    12540
atatttatat atgtgtgtat atatatatat gtatatatat ttatatatgt gtgtgtatat    12600
atatatatac acacacacac atatatacat acatacatac acacacacac acacacaatt    12660
agccaggcat ggtggcgcac acctgtagtc ccagctactt gggaggctga acatgagaa     12720
ttgcttgaac ctgggaggca gagtagttag tgagctgaga tcataccact gcactccagc    12780
ctggtgacag agtgagactc tgtcttaaaa aaaataaaaa ttaaaattaa atgcaaaagg    12840
tccaagtgaa ttgaagagga aaggggtatc aaggaaggtt ttgtggaggt gacgtttgag    12900
ctgggtctta aatgacttaa acatgggata agaagggagg gaataaggac atttcaggta    12960
cgagaaataa ggagcaaaca gtggaaacaa cctaacgtct gtcaaccagt gaatggataa    13020
caaaaatgta attcagatgg tatccaactt acgatggttc aacatgagat ttttctgact    13080
ttaggataga tttatcaaag tagtaaatcc attttcaact tatgatattt tcaacttcag    13140
atgggtttat caggacacag ttgaggaaca cctgtctatc catacaattt ggcaataaaa    13200
aggaaatgag tgcagatata ctccacaaca tgaatgaacc ttgaaaacat taagtgagag    13260
aagccagata caaaaggcca catattgtat gattctattt atacaaaatg tccagaatag    13320
gcaaatctta tagacagcaa gtaggtagat gatcagtttg ctaggtgctg ggggaagggg    13380
aaatggggag tgatggctaa ggggattggg tttctttgtg gggcaatgaa aatgttttaa    13440
aattgagcgt gataatgatt gcacaatgct gcatatatat ataatctata gattatatat    13500
atataaagag aggctgttag acagtgataa gtgatatata tatatatata catagagaga    13560
gagagagaga gagagagagg ctgttagtga taagtgatca ggaaaataaa agtattgagg    13620
aggaatacga agttgacggt gtgaaaacat gagattttat ataggatggc cagggaaggc    13680
cttaatgaga aagtgactta tgagtaaaaa caagggatcc taaaccttag catgcatcag    13740
aatcactcgg aaacttgtta aagcatagct tgctgggcct catcacagat attttgattc    13800
ggtaggttct tgtctgatat taatacttt ggtctaggga accacatttt gagaaccact     13860
gagctaaagg aagtaaaggt ttcccttagt ttactagctg gtaacactgg cccaggaggc    13920
```

```
ctttctggaa aaggtcccag tccccaaagg aagctgggga ctcgcgttca catcgtcaag   13980
gtttaccaag ttgtggcggg cctttccgtc ttggaaaaag cctcaaaatg gcagattagg   14040
gtgtccatgg ccggcggaaa gggtctttga agttgcagac caggaggaa gaagattctg   14100
ggcctccccc atgcagtgtc agctggcaac agaatgcacc ccggctgggt tggaggccct   14160
gggtactggc tcttccacac cagggccca cctaccaagg gcagcaggag catctgcacc   14220
tcctgcgcca ggcgcccttc agtgcttcca cttgagcacc tctccagaca ccagctaggg   14280
tgacagtggt acaaatacca gactcccctg gcctgctcac ctcacagggt aatgtgctgt   14340
ggagtcaggg ggacacagca accaccagat gacatggctg gccccgggga ggacgacacg   14400
cagatacggc tacttggcac ctgtgatatt ttacacactc gagaggggcc cgcaccatcc   14460
tcagccctct ccccacattc actcttagtt catgtcacct ccaccagag ggggacacag   14520
gcccacagcg atggcccac accctgcctg aggtcgccca cttcccagga ggcagtcctg   14580
ggacttccac ccgaccaggc cccagagccc accgacttaa cccctccaga ggcttgtcgt   14640
tcattacctt attcaagatg gagaccagcc ttttgcgga gaaatgcgg gtgaaggtcc   14700
tgaaagtgca ttgacgccgt tttcggaagc catacaagtt tagctggcgg aagaagctct   14760
ttatcgaagt tgtggcaaac actttgtgtg cgacgtccct tttgagaatc tccttttcaa   14820
agagttttg attgatcact ctacaagccc cactgtcatc ccaccagatg gacgaaaact   14880
ggttgctgct gaccagtctc cacagtttct gtggaaaggg gagggagagg agattatctt   14940
ctccctgggg cgggacgtca ccgtcagggt gcggccttct gaacgaagct tcctcggcca   15000
gaggttggaa agcgatttct tctgtcagca gcctcaagtt agggctccca gtggaccccg   15060
ggtcgtccca ggcaggggaa ggatctgctg ggtgaaggta ggtctctgac tgcaactggg   15120
gagggaaagg cacccttttcc aagccatgat cctgtcctct cgaatttctt tcttcacagc   15180
gagccatact caatgatcgc ttgtcctcca tctggcaaac ttgctagtgc agtgtggcca   15240
gcagcacccc ttggcagtca tgtaaccagc cccatgacat cataaagggg ctctgactgc   15300
cggggggtgg catctccacc cccagcaagt tgtgtaataa agggccaagg cagacaagta   15360
gctgcccatc tgcatgtgca cattctggtc ctcacagtca tttcaatggg aaagatgaca   15420
ctagtgcaca agagtgccga ggggccctgc cacaccgtag atgcagacct ggagcggtcc   15480
ccttgtccta gagctcctga gccaggcaca actacagcaa agccctggct caggaaggtc   15540
agagctcacc gtctgagtca tgggcccaca gaccccagca catgactgac actcggaagc   15600
acagaacaaa gggtaggacg gtgcccatgg gtcaggctgt agccacgcca ccctttccac   15660
cctgtcctag ccagaggcag caatgtgctc catacagatc ctcctaacac acccacactg   15720
tcggtcccca gcacgcagat gcccgacagc cccttaggca aatggcttag ctgactgccc   15780
caccacacgc cgtcgccatg cagtccagtg gggagtcgga ggcagcctcc ttcctgcctc   15840
tcctcggcct gcacgtgtcc ccccaccagg cagagaccct tctacacccc gggtgtctgc   15900
ggtcacatcg cggtgggca tgcagctgtt ggccttcgag catgttttgt tttccttggc   15960
cagtgtctcc agagaaacgc acgtgggttt gtgtccagcg gtccatctct gcaacagttg   16020
ttcctttggg attggatgct aggaggtcac gggagaggtg tccatccaaa gcagtgtctg   16080
tgtcacacac tgtccccaca cacagggcca cctctgcaca gactccccg actcgattct   16140
gggcacagag ctcagtgacc ttccagagac tgccacgaac cggtgatgcc tccacgcttg   16200
agacatcctg accgcagggc ccaaggcgca ctggctcagg gggtgacagt gaggggtctg   16260
caaacagact gctgatgctc aacccggccg ctgccgagct gtgtgacttg ggcacgtcac   16320
```

```
ttaacctctc tcggcctctg tctcctcccg gggataagag tagtagcacc tgcttcccgg   16380
ggctgtgagg atccagtggg acgtatagga actagcgagg caccggcagt tgggtcagag   16440
ctactgttgt cacttcacaa ggcattttct tcaacagcaa gtcggaaatc tcatgagcct   16500
aaggcagaat ccacctgtgg cctctggtta caacccacag gactgaaaat ccttccagcc   16560
acagcaactg gtgaatttcc tggtcaattg ccacaagtca tgagctgaac cccacttgag   16620
tttcagttca ggcagaactc tagagacgac tagggcaagc tagacagcga ctgcagagcc   16680
ttttgttgca gcgtgagcag tcctcagctg ttgacatcac tggggagcaa acgaggacca   16740
ggagcggtga aaggacagtg tctgctgcag attgtcgtag cacccaagga acactccaga   16800
aagcctccta agcagtaaca agtgtggcaa ggtgtagccc agccaacagt ggcatctgcg   16860
aggcgtcccc tccttcctcc cactaccccg tatacctgg gacctgtgca ctgaaggact   16920
cattctaaag gctgtgcccc tgcagccgcc agcctcactc actggctgcc tgtgccagct   16980
agagatttct ttcctctgag gctggctgag gaccactc cagtttcctg gcccatccag    17040
caaagaagat acacatcatg cacgtgtaaa atgaggaacc ggtttattga acagcttaag   17100
gagagcaaaa atagtggctt tagctacatt ttttacacac tgagcaggaa agtctaaacc   17160
atcccgttcc cctgtacccc aaagagaaca gggcttgctg gaggccagtg ccaagggcgg   17220
agtcgtgctc gcagcagact tgaattaacc ccatgtaggc cggcgagcag ttgcccgcgt   17280
gaaaacacca ccctcttctc ctggctgaga agatcaaagc tcttttttta ccctcttttc   17340
agcaaaggac ctatttgttt tcaggcagga ggatgttaaa cttgcagcct ctgacacacg   17400
gtggaacctg cagtgcttgg agaaacggca cgcacacgtg aaaacatcat gcctactcca   17460
aagccttctt gttgctggca ggagggaagc ttgagacttt cccacgcata gtcgtgaccc   17520
gcgtggccgt ttctgctctc agcaacattc tctagtgttc cggcttcaag cagcgcttgt   17580
caggtttgaa gctagccact attctgagaa cgtcagaaaa gcatggacca tctcttgctt   17640
ggtgttgccg ttgtggcagt agcagctact acgtacctgc acgagttcca gggcagaagt   17700
ggcaatgtcc catgaaggcg tggcacccca cggggggggg ggggagtgt gccacgggcg    17760 tccacttctg cagcagaagg catgtgccta cagcacaagc ttgtaaaaaa atacttgaac   17820
agaatatgct gtacagaact aggggttaac accgcatatg aagatgctaa acatttgta    17880 taaatactct gtatacaagc atggagtcac tcccgtagaa agggctcatc cgtgaggcta   17940
tgaaaaactg ctgtcagcat gcccaaagag aaactactc cacagtagga acagaaaaaa    18000
ggactgtgct gtgtctaaac acgtggtgca tcagagacat agttacagtt cctactgact   18060
gccccagcca cgacctggga gtgctgagga cctgggagtg ctcagcgagc tgcaggaggt   18120
cagccctgtg gagaaataca tttctaaaca atactttga ttgggatttc agcaccgtat    18180
agacagatgt tccttctggg ggcctggcaa gcagccatct cccagtgggt ctgacgggga   18240
agaggggtac ctggagcccc tcccagacag acggtaatcc caccctgtt ctcacactct    18300 tcctggcatc cgcatctgct ggcacacacc cccgtcacct gccacttccg cgtcccgtcg   18360
tggtgagtgg ctgataggcg ctggatgcaa acaaggcatg agatgacgt acctggagac    18420 ccagctccag tactggttct ggtctgcggg gtgaacgagg gggcagagga aggcggagag   18480
agtgcgtccc agtccactta agctctgtcc ccggaagtgg catctaatct ggcatttcga   18540
tatttaattt gggaggtggg agcacatact tcccagggct ctgggtaatg accaccctgg   18600
ccttctttcg aaacatgggt gcgattttag ggggctccgg aactgggtc tcttcggttt    18660 cttcattatc ttcgtgatgg agatcatagg aaatgtttcc atattctcgt agaaatggga   18720
```

```
agatttcaag cagaaactga cagaaatctt tgcggatacc aaaccaccct gaaaaataag  18780 aatttttat ttcacacacg aggctcaact gaccttcctg ttaactttct ttccgtaaca   18840
agaagtttca ctcctacaat gtcataacat actttatcca gactcctgag tcacaaagcc  18900
tgaacagggc ttgagtaccc aaaatgggga agaagtgcaa atgctagctc tgtggtgctt  18960
ggagtggggt tcccggaccg gcagggacag cgtccacggg gcctagttag ggatgccatt  19020
ctcgggcccc agcccagacc tccagaaact gagtcgggct agggtgggct ccagcggtcc  19080 cctttcctg gccctttgg gattctgctg gatgcccaaa tttgagaact actgctccag    19140
tgagtctcaa aatatctgtg gtgcgcagac tacggtgtct tccgctaatc ttctccagcc  19200
aggataaact catggatgac agtgccaccc aagaacaaga tttctgtcac cctctggaat  19260
ccgtgagggc ggtagtcatg cacgggttgg ccaggagggg gcctgaactc atggagccac  19320
cttaaagcca ctttcccagt cccactactc ctctctgtag gctactggag tgtcagctcg  19380
gtgcaagccc tccctgctcc cgggtgcggg tagggggca gaggcacaaa cagcaagcac    19440
agcccgggct gctgggctgc agtgaggccc tgcccccaaa cccactggct ttccgaaggg  19500
caatgctctg gcttccgtg ccatggagcc cacagccttg ccaggaaggc accctctgca    19560
gagatcgttt tggaagtgtc tgcctcagca agcaggtgga ggggaataga gtgttagcaa  19620
ggcaagacag gcaagactcg ggtgatggca gcaaggatat gggggaggca gagcggccaa  19680
cagggaccta ggatgaatcc caggtttggg tgggagatgt ggattttcca tcaaaccctc  19740
ccgggcctgg gaagaatctg tcttgatccc cattttgcag aggagggaac gggatctctg  19800
agaggttgcc tgccgtgtct ggttctacct caaatggcag cgtgcactgc gagaaaagtc  19860
ccggtgcagg ccagcagaac accagagtta cggcatgccc ttcccttaga aggtcccaga  19920
atttcctcag ccctcacttt cccacacaag cttctaaatt ggggccctcg gggactcatc  19980
ccttcctaga cttctatccg ccaccccca cccctggtc ccccccaga cacacaccaa      20040 ggacttctga aatgctgagt acatacagtg gtttcctccc ttctgtccaa atgtggttgc  20100
catcagcgtg atcaacgaga gccaaagggg gacaaagatc gggatgcagg agaaggcgtt  20160
gtggccatcc agtttgtgaa ccagcagaat ctaaagaaag agacatagtc ccggttgatg  20220
ccagcaccga aaatgggcag aggcggaagc cagacttcat taggcagttc ctccccacca  20280
ccccaccccc gcgtgagctc ccacaagagg gaacatcagc accgccagaa aaaggcagga  20340
aaccacctat ccctggggaa agctcgaaat gagcttttat gtccctcttc agagctcggc  20400
aatagcctat ccacttgaaa agttcccagt gccagcagtt ttatggcaaa ctcctccggg  20460
tgtttgttct aaggagtcaa cagctcccat tctagaattc tccacgtgac tccaatacac  20520
aaatctgaca tcccactctg ctttccccag agtggaaact ggagccatac agaggcacca  20580
tggctaaaaa ggtgcactct ctccctgcc agccccacgt gctgccccca agagaaagga   20640
aggatgctct cctttcaccg aagctccctc tcggagatgg ctgtgttctc tccctctcc   20700 tggagtgggc tcactgtgag ctcgaggac agaggctgcc tttctagggg tgcagaatcc   20760
tgtcagggga agcgcaagct tcaggggctg aagaggcttc ccgtggaacg cttacctcaa  20820
atgtaagaag gggcacgacg atggtcatcc agctcagggc catggttatg tgtgtcctgc  20880
gctgtccgca atcacatcca tagagcgcaa gaacaagacg gaccacacaa tgtagtagag  20940
gaccaccagg cacagaaagg acatgagaat ccacagcggg acacacacaa cctgggggtg  21000
ggtgagagaa cagcaagaga agtctctta gagcttccaa cctggcctct gatgaaaggc    21060
atctttagca ccttgctgtg tctgtccagt taaggcggtc cttcctgtga gccgaataag  21120
```

```
gaccgttcca tctcccagga ctgctgggag catcgctcag gacagaaaag gtatggtatg   21180
ttcactatgg ggcctgctgc caccagggga cacacacgct cagtgagtca tcagtccctc   21240
ttcctttggg tgacagacag ccctgcacct ggctccgcag cctctactct tccagaggcc   21300
cactctccca cactctctca ggctcctcta ggttctgctg ccatcacagc ttcccgggaa   21360
atgggacaca actgtcaccc tgtgcacaca cacaagatct caccccaaca gactctcttc   21420
acaggcaaca ttcccacaac ctgctggggg tactttggca acacaaatgg gaatgggctc   21480
cccagaaagt ctggctgcct gggctcctaa ggatccctaa cctcacccct accaagttag   21540
tgaacttggc gggttgatgc tggatacagg ttgatgctgg atacgtagcg ctgccgggtc   21600
gtgaccccta aggaattatc caaactcttg tttttagatg ctttattata tcaaactctc   21660
ctttaaacaa gtggcccatc tgctgggatt tggaagcctg taatactgaa attttcatca   21720
taatggaaat tttaaaaaca gaatttgacc cacctgtttt taaaacactt tcattactta   21780
acaagaggtc taatcttggg caagtcttga aatttctctg gccttagttt cccatgtgtt   21840
aaatgaaact tgaagcagtt ggtctcttat agtctcctga ctctaacatt ctaagaatta   21900
tatttgtaca ataactcaaa aatcacataa tttaatttac catatggact ccaaaatata   21960
ttttctcatt aggctaaact tgatctgcat tttctggatg tgtccatatt cttggactac   22020
actaaaacat gataccaatg cttcctctca ccataaaccc tcacttcgct ttctacattt   22080
aagaattta tagctggaag agtccttaac agaaaatacc atctaataat taccccctcaa   22140
aatcgagaaa gtcctatctg ttcttatgct agttataaga atgaggcagc atttcacata   22200
atggttataa acactgccac aagaagattc atgatgtgtt gtttatctgt agctctcatc   22260
atactctgtc atataactat agcattaaga ttttaatgtt ctatatattc ttctaagaca   22320
gtgtttacca gagtaaggca caaaagatcc actggtttgc aagaaagatt agaaccttta   22380
aatttttac ctcaccttgt ttaatctata ttttgtatg tattttgtaa catatatatt   22440
attattacca taaatcatat ataatttaaa atgcatatat taggggtaaa tgctcaggaa   22500
acttttata aattgggcat gcaaatacaa gtttgaagac tcactgttct aggtattaaa   22560
agtaaagtta taaccaagta aagcttccac cttttcatgt ctcaaagcag tttattgttg   22620
gaggtaagat ctcttagaag cctaaacagg tccaagtaca gaatgaagta aggctagccc   22680
ataacttgtg gcaagcaatt catactattt ctctcatgct gagctctcct cagtgaagca   22740
gctactatag acaactgcag cctattggta gcctattta caggcaggaa aaaaattact   22800
ttttattcaa agtggaactc aggacatggg gagaaaatga atacaaaaaa tagggtcaat   22860
ccaaaggcac acagcaaatg agtaacacag ttatgtttt tccccatttg tatgaggtcc   22920
cagtaaattc taagtaaact gcaaatttaa taatacacta aaaaagccat gcaattgttc   22980
aaatgaatcc cagcatggta caaggagtac agacactaga gtctaaaaaa caaagaatg   23040
ccattattga gttttttgaat tatatcaagt agttacatct ctacttaata aatgagaaaa   23100
acgaggataa gaggccattt gataaaatga aaatagccaa gaagtggtat tagagacttg   23160
aatacaggta ttcgggtcca aagttcatct gctcaaatac taactgggga aaagagggaa   23220
aaatatttat atacatatat atctgcacac aaaaatacccc caaaagaca aaatgaggcc   23280
aggcagggtg gctcacaccc gtaatcccgg tactttggga ggctgaggca ggtggatacc   23340
tgagatcagg agttggagat cagcctggtc aacatggtga aaccctgtct ctactaaaga   23400
taaaaaaatt agccaggcat ggtggcgtgc gcctgtaatc ccagctactt gggagtctga   23460
ggcaggagaa tcacttgaac tgggaagggg aggttgcagt gagccaagat cgtactactg   23520
```

```
cactccagcc tgggcagcag agtgagactc catcacaaaa ataaataaat aaataaaata   23580
caatgaaaca gaaagttcaa ataatcccat aatcttacca ccaagaaata actttcactc   23640
gttatactta ttgattttc cataataaat gtactttact gtgactatca tgaaaagaaa    23700
gttattttag aaacagagaa ctgtttcaga tcaaatctat gtagtagaac agagccatta   23760
ggtgggaaag acgagatcaa actaaatctc agaaggccta aaaggctagg tccattccag   23820
cactaaaaac tgaccagaca agtaatggct tcaacagctt ctaaatatgg acaaagcatg   23880
ctgaaaggga aggacaggtc taacagtggt atatgaaatg aacaggaggg gcaaagctca   23940
tttctcctct gaagttttcc aaagatgctg aggaggacat tagtttgaca tgaccctgat   24000
atgggacaag ataatttcac agaagtttta catgttaaag ttttcttata gatactcatt   24060
caagtaagca atgaacacta aaatctaaag aaagaaaaga gctttagagt caggtctgta   24120
ttcaaattca agctctacca cttactggtt ctgtgacttt gggcaagtct tttaacctta   24180
ttaagtctta atttcctgat ttgtaaaatg gggatatcgt ctccctcaca ggattgttgt   24240 gaaacttta tgagattaat gcctttatat ttggcatagt gtaagtaaac aataactggc    24300
agcttcaaaa aaaaaagca gtagcattcc atcatttatt attggttact ctcaaaaagt    24360
ttttcaatgt actagaagat aaatattcaa ataccttaat atctccatta ttttcaggta   24420
aacagcatgc tcctgaacaa ccaatgggtc aacaaataaa ttaaaaggga aatctaaaaa   24480
catcttgata ttaaactaca tggaagcaca atataccaaa accaatggtt cacactagga   24540
gaattttaag gtacaagaaa actctttgag atttcttaaa ataatagtat gtctgaattt   24600
attgagtgat ttaccagaaa ctgttgtaag agctctactt gcattatagc acttaatcct   24660
cttaactcta tggctgctat tatcaacctc accctaatca catatgggac acagagaggt   24720
taagtaactt gcccaaggtc agagttagga agtactaagc catgctttga atcagttgtc   24780
aggctccgga actcacactt tcagccacta cataatactg ctttgctatc ttttaggaaa   24840
ctatgtgagt ctacctcaca tagactcaca taggtttgtt tttttttttt ttttaaggc   24900 tatcttttcc cccatcaatg tttttgaag atcccaaat tagagtccca cagaggcaga    24960
cagcagtact tgacaatatg gacatttaag gttaatgttg gattctactg tcttttact   25020 acatgaccta gggaacgata attaacctag actgcttcca agggttaaat aacccattta   25080
gttatactat gtaaattatc tcttagtgat tgattgaaag cacactgtta ctaattgact   25140
cggtatgaag tgcttttttt tcttcccttt caagatacat accttccag ttaaagttga    25200 gagatcatct ccaccaatta cttttatgtc ccctgttgac tggtcattct agttaaaaaa   25260
aaaaaaaact atatatatat atatctacac acacatatgt atatgtatat ccttatgtac   25320
acacacaaac ttcaaattaa atgagaacta gaagatttga gaagttagct agctaatatc   25380
catagcatta tgatattcta aatgatatga attataagaa ttaggtttcc tgaaatgaat   25440
gactagaaaa ctttcaagta gagattagta aaaattaaaa agtcctaatc ggccattact   25500
gatttgatgt ttttaagagt cctaaaaaat gggttacatc cattttaag tgggtagtat    25560 tataacagcc acccatcttc aatcacagtg atttctgaat tgtgagggaa gttattagca   25620
tgacaggtgt ctggttctgg ccctgtacga ttcccatgag tcaagcaaat tgtaagggct   25680
ggtctatatc acacccaacc ccaaggatat gtccctcaaa agtctagccc aggcccgtc    25740 atcttcagca tcatctggga aaccaggtct gattagtagt cctttaagga atacctctta   25800
ggctcccatt ttactgctat cacagaatcc aataaaccc ttacaggaga ttcaatggga    25860
aatgctcaac acccactgta gttggtggtg acaatgacca taatttggct gtgctggatt   25920
```

```
caggacagaa aatttgggtg aaagagcagg tgaacaaaag agcttcgact tgccctagca   25980
gagagcaagc cataccatac cacaaagcca cagcaattac aacggtgcag taccagcaca   26040
gtaaatgaac aaagtagagc ccagaaacag acccagaact atatgaggat ttagtataca   26100
ataaagatgg tatttcgagt cagtagggaa aagatgaatt attcaataaa tgatgtttgg   26160
ccaactagta acccatttgg gaaaaaataa agtatggtc cctacctcac agcatacaca   26220
aaaataaatt ccagacggat taaaatctaa atgtaaaaaa taaagccata agtggactgg   26280
aagaaaatag agaattttt ttaacatccg tagaaagggt aaaaacccag gcatgacatg    26340
aaccaaaact gaagaggttc tgtaacaaat acccccttt atatattggg ctccaacaat    26400
aagaacccat aggaaaatgg agaatgaaca caaatagaca atttatagaa gagaaggtta   26460
taaggtgtaa aattatatct atctgagaaa caaacactaa aacaatgtga ttctactgtt   26520
ctcccaccca tactggcaaa acttaagcct gataatatgc tgaggggaaa taagcactct   26580
tgttggtgag agtattaatt ggcatagctt cttttgaaaa tgacatagca atacctgtta   26640
aaattgcaaa catgcatgtc acttaatcca gtaatcccac ttctgggaat caatgctaca   26700
aaaacactga caagtataca aagatacatt caagagtgtt cactgggccg ggtgcggtgg   26760
cttcatgcct gtaatcccag ggaggcagag gcaagacgat cgcttgaccc caggagttca   26820
aggccagccc gagaaacaca gcaagaccct gtctctcttt tttttattta aaaaataaat   26880
gttcactgta tcagttgttc acaaaaacaa accaacatgt ccattaacag ggaaccattt   26940
aaattaatca agttcatcta cacaatgtaa taccatgcaa ctattaaaaa gcacctgata   27000
atccaaagca cactgagaca gaataatgct attaaaaaca ccaagtagtg gaacactgtg   27060
ttgcctatga caccatttt attcaacatt taaacaaatt tgtaacagca attacatgag    27120
tagtgacaat ggcgtttatg agactttca cttttatgtg cttctatttt tgttatgctt    27180
ctatatatac atccatttat tatggagtgt tactttcaaa aatcacaaat gggccagtat   27240
tatttggtgt tgcaaggtga gcatatgact tctgatatca acctttgcat attacttctc   27300
aatttaggga aattacagac atcccttatt ctaactaact taaaacccag catttcaaac   27360
atacagaatt gatggggaaa aaaaagaaag aagaaagaaa gaaaaggcaa caagcttcag   27420
atgacagtga ctcacatcaa attatttata aaatctgtta aatagtgcca tcttctggag   27480 ataccctggta ttacagtcca actccagttg atgtctttac agagacaaga ggaataaagg   27540
aaaaaatatt caagaactga aaagtatgga gtcatggaaa aattgctgtg atccaaaggc   27600
tacggtgata ggacaagaaa caagagaact ccaagcagta agacactgct gttctattag   27660
catccaaacc tccatactcc tgtttgcccc aaggctttt taaaaatag agacaggatc     27720 tcactatttt gctcaggctg gtcttgaact cctggactca agctatcctc ctgcctcggc   27780
ctcctaaagt gccgagatta caggcttgag tcaccatacc tggctattta ttttttctta   27840
actctcttgc ctggcctata gccaccatgg aagctaataa agaatattaa tttaagagta   27900
atggtatagt tcactacatt ggaatacagg tataagtgcc tacattgtac atgaatggca   27960
tacatggatc aattaccca cctgggtggc caaaggaact gcgcgaacct ccctccttgg    28020
ctgtctggaa caagcttccc actagatccc tttactgagt gcctccctca tctttaatta   28080
tggttaagtc taggataaca ggactggcaa aggtgagggg aaagcttcct ccagagttgc   28140
tctaccctct cctctaccgt cctatctcct cactcctctc agccaaggag tccaatctgt   28200
cctgaactca gagcgtcact gtcaactaca taaaattgcc agagaagctc tttgggacta   28260
caaacacata cccttaatgt ctttatttct attttgtcta cctcttcagt ctaggtgaaa   28320
```

```
aaataggaag gataataggg aagaactttg tttatgccta cttatccgcc cctaggaatt   28380
ttgaaaacct ctaggtagca ataagaactg cagcatggta tagaaaaaga ggaggaaagc   28440
tgtatagaaa tgcataataa atgggcagga aaagaactgc ttggaacaaa cagggaggtt   28500
gaactataag gagagaaagc agagaggcta atcaacaagg ctgggttccc aagagggcat   28560
gatgagacta ttactaaggt aggaattact aagggctcca tgtcccctta gtggcttagt   28620
actatgtagc ttgctttctg cagtgaactt cagacccttc ttttaggatc ctagaatgga   28680 ctttttttt ttatcggaaa acagtcattc tctcaacatt caagcaggcc ccaagtctac   28740
cacactcaat cacattttct cttcatatca taatctctca accattctct gtccttttaa   28800
ctgtttttct ataccctgat caaatgccaa caaaagtgag aatgttagaa tcatgtattt   28860
ttagaggtag actgtatctc agataaaaaa aaagggcaga tattccattt tccaaaatat   28920
gtatgcagaa aaaataagta tgaaggaca tatgctcagg taacaagtta atttgtttac   28980
ttgtatttta tgaattccct aaaacctacg tcacccgccc cgttcccacg ccccgcgcca   29040
cgtcacaaac tccaccccct cattatcata ttggcttcaa tccaaaataa ggtatattat   29100
tgatgatgtt aattaacatg catggatcca tatgcggtgt gaaataccgc acagatgcgt   29160
aaggagaaaa taccgcatca ggcgctcttc cgcttcctcg ctcactgact cgctgcgctc   29220
ggtcgttcgg ctgcggcgag cggtatcagc tcactcaaag gcggtaatac ggttatccac   29280
agaatcaggg gataacgcag gaaagaacat gtgagcaaaa ggccagcaaa aggccaggaa   29340
ccgtaaaaag gccgcgttgc tggcgttttt ccataggctc cgcccccctg acgagcatca   29400 caaaatcga cgctcaagtc agaggtggcg aaacccgaca ggactataaa gataccaggc   29460
gtttccccct ggaagctccc tcgtgcgctc tcctgttccg accctgccgc ttaccggata   29520
cctgtccgcc tttctccctt cgggaagcgt ggcgctttct catagctcac gctgtaggta   29580
tctcagttcg gtgtaggtcg ttcgctccaa gctgggctgt gtgcacgaac ccccgttca    29640 gcccgaccgc tgcgccttat ccggtaacta tcgtcttgag tccaacccgg taagacacga   29700
cttatcgcca ctggcagcag ccactggtaa caggattagc agagcgaggt atgtaggcgg   29760
tgctacagag ttcttgaagt ggtggcctaa ctacggctac actagaagga cagtatttgg   29820
tatctgcgct ctgctgaagc cagttacctt cggaaaaaga gttggtagct cttgatccgg   29880
caaacaaacc accgctggta gcggtggttt ttttgtttgc aagcagcaga ttacgcgcag   29940
aaaaaaagga tctcaagaag atcctttgat cttttctacg gggtctgacg ctcagtggaa   30000
cgaaaactca cgttaaggga ttttggtcat gagattatca aaaaggatct tcacctagat   30060
ccttttaaat taaaaatgaa gttttaaatc aatctaaagt atatatgagt aaacttggtc   30120
tgacagttac caatgcttaa tcagtgaggc acctatctca gcgatctgtc tatttcgttc   30180
atccatagtt gcctgactcc ccgtcgtgta gataactacg atacgggagg gcttaccatc   30240
tggccccagt gctgcaatga taccgcgaga cccacgctca ccggctccag atttatcagc   30300
aataaaccag ccagccggaa gggccgagcg cagaagtggt cctgcaactt tatccgcctc   30360
catccagtct attaattgtt gccgggaagc tagagtaagt agttcgccag ttaatagttt   30420
gcgcaacgtt gttgccattg ctgcagccat gagattatca aaaaggatct tcacctagat   30480
ccttttcacg tagaaagcca gtccgcagaa acggtgctga ccccgatga atgtcagcta   30540 ctgggctatc tggacaaggg aaaacgcaag cgcaaagaga agcaggtag cttgcagtgg   30600 gcttacatgg cgatagctag actgggcggt tttatggaca gcaagcgaac cggaattgcc   30660
agctggggcg ccctctggta aggttgggaa gccctgcaaa gtaaactgga tggctttctt   30720
```

```
gccgccaagg atctgatggc gcaggggatc aagctctgat caagagacag gatgaggatc    30780
gtttcgcatg attgaacaag atggattgca cgcaggttct ccggccgctt gggtggagag    30840
gctattcggc tatgactggg cacaacagac aatcggctgc tctgatgccg ccgtgttccg    30900
gctgtcagcg caggggcgcc cggttctttt tgtcaagacc gacctgtccg gtgccctgaa    30960
tgaactgcaa gacgaggcag cgcggctatc gtggctggcc acgacgggcg ttccttgcgc    31020
agctgtgctc gacgttgtca ctgaagcggg aagggactgg ctgctattgg gcgaagtgcc    31080
ggggcaggat ctcctgtcat ctcaccttgc tcctgccgag aaagtatcca tcatggctga    31140
tgcaatgcgg cggctgcata cgcttgatcc ggctacctgc ccattcgacc accaagcgaa    31200
acatcgcatc gagcgagcac gtactcggat ggaagccggt cttgtcgatc aggatgatct    31260
ggacgaagag catcaggggc tcgcgccagc cgaactgttc gccaggctca aggcgagcat    31320
gcccgacggc gaggatctcg tcgtgaccca tggcgatgcc tgcttgccga atatcatggt    31380
ggaaaatggc cgcttttctg gattcatcga ctgtggccgg ctgggtgtgg cggaccgcta    31440
tcaggacata gcgttggcta cccgtgatat tgctgaagag cttggcggcg aatgggctga    31500
ccgcttcctc gtgctttacg gtatcgccgc tcccgattcg cagcgcatcg ccttctatcg    31560
ccttcttgac gagttcttct gaattttgtt aaaattttg ttaaatcagc tcattttta    31620 accataggc cgaaatcggc aaaatcccctt ataaatcaaa gaatagacc gagataggt    31680 tgagtgttgt tccagtttgg aacaagagtc cactattaaa gaacgtggac tccaacgtca    31740
aagggcgaaa aaccgtctat cagggcgatg gcccactacg tgaaccatca ccctaatcaa    31800
gttttttggg gtcgaggtgc cgtaaagcac taaatcggaa ccctaaaggg agcccccgat    31860
ttagagcttg acggggaaag ccggcgaacg tggcgagaaa ggaagggaag aaagcgaaag    31920
gagcgggcgc tagggcgctg gcaagtgtag cggtcacgct gcgcgtaacc accacacccg    31980
ccgcgcttaa tgcgccgcta cagggcgcgt ccattcgcca ttcaggatcg aattaattct    32040
taattaacat catcaataat ataccttatt ttggattgaa gccaatatga aatgagggg    32100 gtggagtttg tgacgtggcg cggggcgtgg aacggggcg ggtgacgtag tagtgtggcg    32160
gaagtgtgat gttgcaagtg tggcggaaca catgtaagcg acggatgtgg caaaagtgac    32220 gttttttggtg tgcgccggtg tacacaggaa gtgacaattt tcgcgcggtt ttaggcggat    32280
gttgtagtaa atttgggcgt aaccgagtaa gatttggcca ttttcgcggg aaaactgaat    32340
aagaggaagt gaaatctgaa taattttgtg ttactcatag cgcgtaatac tg            32392
```

<210> SEQ ID NO 25
<211> LENGTH: 32339
<212> TYPE: DNA
<213> ORGANISM: Artificial Sequence
<220> FEATURE:
<223> OTHER INFORMATION: Description of Artificial Sequence: Synthetic
      PhIDO-final
<220> FEATURE:
<221> NAME/KEY: misc_feature
<222> LOCATION: (1)..(32339)
<223> OTHER INFORMATION: n= a, c, g, t, unknown or other

<400> SEQUENCE: 25

```
gtacggaagc ccggaaggag gggcaggggg cggtggctca ggtttctccg ggcggcggcg       60
gcggcggcgg cggcgacggc gacggcgacg gcagcgggga cggcagcagt agcgggagca      120
gcagcgtgga cgcggctggc gctggcgcca tgaacccgct gtaaggcgca ggctgtgcag      180
cacggggtgc gggggaggag gaggaggacg ccgcggtgaa gttctccgcc atgaacctga      240
```

```
ggggcctctt ccaggacttc aacccgaggt gaggcggcgt cgttggcgcc cccgggagtc    300
cgcgctgcgg gctcgggcgc gggctggtgt tcggctccgg ggaggcacgg cgggcgagat    360
gctgcagccc gaggacccgg gcgcctgccc gagcctccct gcgggtgcaa gcggtcccca    420
ggcaaaacag tcggcctcgg cgcccgcccg cttcctcctc ccgtgcccgg tgctttcagc    480
ccctgcccgg ccacggccgg aagggcccgg ccgcgagccc cgtcctgccc caagggaacc    540
ccattctttt ctgcttgctg tccctcattg gtgtcccaac ttcttcgtct cggttccatc    600
ctcttctgcg ccgctgcggg ccctccattc tccgcgtcag ggccgtctca ctcgacccaa    660
caccccctacc cccaccccag ctgtttcctc cagttcctcg cagtccttgg ggttttcctt    720
gggtttatgc ccatccctct cttgtttgct tctttgttga acggatacct gaaacactgt    780
tgaatccttg gagtcagtgt cggggtatgg caataccta  tataatgcat ttctgggtga    840
gcctgatcat tttccatact cattttctca tcagtcttca ctacaagttt atttgcagga    900
agtagatatt gctgtccttc ttttccagat ggggaacacc cagtggacag tgtggagaaa    960
acactggcta agcactcaag cgcctgtcct tgcacttgcc cgactgtttt gtaactgttc   1020
tttaccccag gctgtgagct ccctgaagct gagaccatct cctgctcatc tcagtgtccc   1080
cagcgcctcc cacccaccgt atctggcaca tagtaggcac atataaaatg tttgtggaac   1140
taaactgagc ccaaagactt ggattggaga cgaggccata tgtaactggg tgattctctg   1200
cccttctttg gcccttctgt aaaatgagga gttggcctaa ctgatctctt aaatgcacta   1260
ctctccgaaa ggagtatccg tttcccttat ttgccagttg ggaagacgtg ctcagtaaat   1320
atttgtgtgc tgtaacctat gttaggtgct ttagatgctg gcggtctcag catggggtga   1380
agaagggctt gtacacttaa gatgcctac  agtactgtgc agtgctgtac tgcggggggcc   1440
aactctgggg acctatgcct tggctgcttg ttgaggatga aaggaagttt taggggagta   1500
tttgtatgtt gagggtgcag tctccctagg gatggtgaca ttttaacttg tgagtcattg   1560
tgactttgta tgtgcccctta ttccactttg agttcatgtt ctggttagga gtgccagtgt   1620
ctctaacacg gtgcagacat tatcattgtt ggcttcgaag gcatagagga ggtaacagaa   1680
ctaactgcag tcccttcctc tgctgcatca gggggttaag attggtctgc agggtagtag   1740
ggttggtgct gtggctggac aagccctgta tgtcttctat ttggagatgg tgataagaaa   1800
gttaagtaaa aactgaattg ttttgtgccc ttgggcaact cacttatcta ttgttttatc   1860
tgtagaatga gtataatctc tcagtggggt agggaggcca attaaggatt gattacaaag   1920
tgccttacaa atagaaagct acagtgactt gtttgcaagg tgacagagaa ttcagaagcc   1980
tcaagaaact gccttaagtg atcaaacagg ctaacggagt tgccaaagca aaatagtgct   2040
gcactgatac tacctttaac cgttttttcc tttagcccct tccccccaa  aaaaattagt   2100
atatgaaatt acagtgaaat acctggtatc taagcagatt tatagtaatt ctcaacatat   2160
tcatcaatct cttaattcta cctgcattaa aatgtatttc tacctgaaaa gtttaaaggt   2220
cttttatact gtgccatttt cctgattcat tgttgccaga ggtagtgagt tccttaattt   2280
tacagatatt tcaagaggac attggccagg tattattggt aaatcagatt tgttttttta   2340
gctggtagtg tttcacctct cctgagcact cctagttttt gacagtgtgc tttagtctcc   2400
ttccatgctg aggaaggcct tctctatagg agaaagaaaa ctgaggggtg tacacaggaa   2460
gttaccttat gctggggact caaaccttga tgctactgct ttgctccctg cctctatttt   2520
tgaaccaatt caacatctcc ctcctacccc aggaccttgt cacacactgt tctctttacc   2580
aggaatgttt ccctctcttt tcctctcctc cagacctagt gaactcctat ttatcctcac   2640
```

```
ttggcacttg ctaagggaag cattcctgac ttccctgacc agatttactg ctccctgttt      2700
ctacagttcc tgtagtattt actactcctc catcatagtg catatttgta cccttgtgtc      2760
tgtctggatg cttatttgat taatacctgc ctcccccact aaactttaag ctccatgggg      2820
tcaaggccgt gactgtgtca gtatcgtagc ctgcatactt ggaatagtac ctggctcaat      2880
aaatatttgt ggagtaaata actgaataac tctccagagc ctataagata aatctagagc      2940
tgctgctttc aatcactgct ttcctggtgg tctgtggcct ggttctcttt cttctcacac      3000
tcttcccacc ttcagagtgc agccattgct ttggagagat gggagagaac atggcactaa      3060
ggcagaatat ggctatattt actttgaaga gcatgtcttt gtcatagaaa tagtcactgt      3120
catggtttgg tgggtcccaa ggcatgggtc atggctccag atcccctttc cagccttttg      3180
gatcttggta agtctgaacc cactgctgcg ttggcaaggc tctggaaact atagtgacag      3240
agaatgattc acaagtgtca acactcagat gtacagggct gccagctgac ccactctacc      3300
tatttccatc tggcactgaa ctggttgatc atgaacttct tttcataatt gcttttttagt      3360
tatgcaggtt aagacatgcc gaaacagatg taccggaccc acaaacaagt ccttccttga      3420
atgcctgagg cttcctaaca gtgaaagagc cctgttctta gagtaggcaa actgattctg      3480
aggcattgta ggtggtaggg atctggtagt aggtagcatt aggtgggctc ccggcactca      3540
ccatggagcc ttgaaatttt ctgctacttt ggggagttg ctggttcaga gaaggccctt      3600
ccaccctggt agccatgtgg cactggaagg ctgtgaaaac tctgctgggc cttcttagtc      3660
atctgttgtg agctcctgat gggagtgtgg tgtatccctc aggtgtgcta gactggaaca      3720
aaggctgaga agtgttgctc tgggggttcc aacttgtggg catggggtac tgatgagatc      3780
agtagtgttt ggagacttct gtatgctcca tcttcagaag acattctgga gtccatataa      3840
gttatcttgt ctcttgtttg aagcaggaaa aaggaatgcg attgctggta atatagttca      3900
ctaaagtcag ctacctggcc tctaacagtt atttgcaaag tatattataa cattgattcc      3960
tcaaacatct agattcctat ctcgtgccaa gtgatgtact aggtgctcta agtacaaaaa      4020
taaaggaata tagtcctcct ctcaatgcgt aagcctagtg aagaagcag aaatgaaagg      4080
gaaataagaa ttcaatagag tatgaggcat tacagtgaaa gaaaccaaat gtcttagaag      4140
tacaaatggc agagctacta attctgtctc gagcaggcag ggaagagtct atagtggaaa      4200
tgactttttga gctagatttt gaattgagct agtcttttga gccagacttt tgagctagaa      4260
ttgtagggtt gtcatcagac cagagagtag gaagggtacc ttgtgaggaa gagagagaga      4320
gatcagattg ttactgtgtc tatgtagaaa aggaagacat aagaaactcc attttgatct      4380
gtactaagaa aaattgtttc tgctttgaga tgctgttaac ctgtaacttt agtcccaacc      4440
ctgtgctcac agaaacctgt gctgtaatga atcaaggttt aatggattta gggctgtgca      4500
ggatgtacct tgttaacaat atgtttgcag gcagtatgct tggtaaaagt catcgccatt      4560
ctccattctc gattaaccag ggacacagtg cactgcggaa ggccgcaggg acatctgccc      4620
aagaaagcct gggtattgtc caaggtttcc ccccactgag acagcctgag atatggcctt      4680
gtgggaaagg aaagacctta ccaccccca gcccgacacc cgtaaagtgt ctgtgctgag      4740
gaggagtagt gaaagagcgg ggcctctttg cagttgagat aagaggaagg cttctgtctc      4800
ctgctcatcc ctgggaatgg aatgtctctg tgtaaagctg accattccca ttcgttctat      4860
tctgagatag gagaaaacca ccctgtggct ggaggcgaag tatgctggca gcaatactgc      4920
tctgttactc tttgctacac tgagttgttt gggtaaagag aaacataaat ctagcctgcg      4980
tgcacatcca ggcacagtac ctttccttga acttattcat gatacagatt cctttgctca      5040
```

```
cgtttccctg ctgaccttct ccccacctgt tgccctgcta cactcccctc gctaagatag    5100
taaaaataat gatcagtaaa tactgaggta actcagaggc tagcgctggt gcgggtcctc    5160
cgtatgctga gtgccggtcc cctgggccca ctgttctttc tctatacttt gtttctgtgt    5220
cttatttctt ttctcagtct cgtcccacct gacgagaaat acccacaggt gtggaggggc    5280
tggccccttt cagtatctca gaagggacaa agtacacaaa ggcatggggt catgatagtg    5340
cctggtatgt tcaggtagtg aagaggtcca tgtggtatga gcactgcaga tgatatgtgt    5400
cgtatgaatt aaaaatacat agttactgca aatagttttt acaggttatt gttttttaaga    5460 aagcagtatc taatgcacga gtgtactgtc agtactgtca atgaactact taccactcaa    5520
gtgactgctt acgcgtcgaa tcactagtga attcgcggcc gcctcgagtc tagaactagt    5580
ggatccccca acgggccct  ctagacgcgt tgacattgat tattgactag ttattaatag    5640
taatcaatta cggggtcatt agttcatagc ccatgatatc atatggagtt ccgcgttaca    5700
taacttacgg taaatggccc gcctggctga ccgcccaacg accccgccc  attgacgtca    5760 ataatgacgt atgttcccat agtaacgcca atagggactt tccattgacg tcaatgggtg    5820
gagtatttac ggtaaactgc ccacttggca gtacatcaag tgtatcatat gccaagtacg    5880 ccccccctatt gacgtcaatg acggtaaatg gcccgcctgg cattatgccc agtncatgac    5940
cttatgggac tttcctactt ggcagacatc tacgtattag tcatcgctat taccatggtg    6000
atgcggtttt ggcagtacat caatgggcgt ggatagcggt ttgactcacg ggatttttcc    6060
aagtctccac cccattgacg tcaatgggag tttgttttgg caccaaaatc aacgggactt    6120
tccaaaatgt cgtaacaact ccgccccatt gacgcaaatg ggcggtaggc gtgtacggtg    6180
ggaggtctat ataagcagag ctctctggct aactagagaa cccctgctta ctggcttatc    6240
gagatatctg cagaattcat ctgtcgactg ctaccggcag cgcgcagcgg caagaagtgt    6300
ctgggctggg acgacagga  gaggctgtcg ccatcggcgt cctgtgcccc tctgctccgg    6360
cacggccctg tcgcagtgcc cgcgcttttcc ccggcgcctg cacgcggcgc gcctgggtaa    6420
catgcttggg gtcctggtcc ttggcgcgct ggcctggcc  ggccgcgtta agatacattg    6480
atgagtttgg acaaaccaca actagaatgc agtgaaaaaa atgctttatt tgtgaaattt    6540
gtgatgctat tgctttattt gtaaccatta taagctgcaa taaacaagtt aacaacaaca    6600
attgcattca ttttatgttt caggttcagg gggaggtgtg ggaggttttt taaagcaagt    6660
aaaacctcta caaatgtggt atggctgatt atgatcagtt atctagatcc ggtggatcgg    6720
atatcttatc tagaagctta ggctcgagtg ctcttgttgg gttacattaa ccttccttca    6780
aaagggattt ctcagttgta cttcttacag tcttcaggaa attcattaaa tcagtgcctc    6840
cagttccttt ggcttccagt tttgaagggt cttcagaggt cttattctcc tttggctgct    6900
ggcttgcagg aatcaggatg tacttagtca cgatttgcag atggtagctc ctcagggaga    6960
ccagagcttt cacacaggcg tcataagctt cccgcaggcc agcatcacct tttgaaagga    7020
caaactcacg gactgaggga tttgactcta atgagcacag aagttcctg  tgagctggtg    7080 gcatatatct tctcatgtcc tggaggaact gagcagcatg tcctccacca gcagtctgct    7140
ggatgcccag caggacgtca aagcactgaa agacgctgct ttggcctgca ctgccccctg    7200
caaactcctt tgggtcttcc cagaacccctt catacaccag accgtctgat agctgggggt    7260 tgccttttcca gccagacaaa tatatgcgaa gaacactgaa aaatgctttt gggttcacat    7320
gatcgtggat ttggtgaaac acttgaaggg ctttctccaa gcaagaagct atttccaaca    7380
gcgcctttag caaagtgtcc cgttcttgca tttgcattgc cttgaataca gtaggaatta    7440
```

```
ctttgattgc agaagcagct gctatttcca ccaatagaga gaccaggaag aatcctttac    7500
tgcagtctcc atcacgaaat gagaacaaaa cgtccatgtt ctcataagtc aggggcttat    7560
taggatcctt tttcttccag tttgccaaga cacagtctgc ataaaccaaa ataggaggca    7620
gttccagttt cttggagagt tggcagtaag gaacagcaat atttcttggc aagaccttac    7680
ggacatctcc atgacctttg ccccacacat atgccatggt gatgcatccc agaactagac    7740
gtgcaaggcg ctgtgacttg tggtctgtga gatgatcaat gctgagcatg tttaacttct    7800
caactctttc tcgaagctgg ccagactcta tgagatcagg cagatgttta gcaatgaaca    7860
tccagtcatt ataaaaatca ggtagatttt cctgtggatt tggcagagca aagcccactt    7920
cttcatcaat atggtactct ttactgattg tccaggagtt ttccatagcg tgtgccattc    7980
ttgtagtctg ctcctctgga gatctctagc ggatctgacg gttcactaaa ccagctctgc    8040
ttatatagac ctcccaccgt acacgcctac cgcccatttg cgtcaatggg cggagttgt     8100 tacgacattt tggaaagtcc cgttgatttt ggtgccaaaa caaactccca ttgacgtcaa    8160
tggggtggag acttggaaat ccccgtgagt caaaccgcta ccacgccca ttgatgtact     8220 gccaaaaccg catcaccatg gtaatagcga tgactaatac gtagatgtac tgccaagtag    8280
gaaagtccca taaggtcatg tactgggcat aatgccaggc gggccattta ccgtcattga    8340
cgtcaatagg gggcgtactt ggcatatgat cacttgatg tactgccaag tgggcagttt     8400
accgtaaata ctccacccat tgacgtcaat ggaaagtccc tattggcgtt actatgggaa    8460
catacgtcat tattgacgtc aatgggcggg ggtcgttggg cggtcagcca ggcgggccat    8520
ttaccgtaag ttatgtaacg cggaactcca tatatgggct atgaactaat gaccccgtaa    8580
ttgattacta ttannntaag ggtgggaaag aatatataag gtgggggtct tatgtagttt    8640
tgtatctgtt ttgcagcagc cgccgccgcc atgagcacca actcgtttga tggaagcatt    8700
gtgagctcat atttgacaac gcgcatgccc ccatgggccg gggtgcgtca gaatgtgatg    8760
ggctccagca ttgatggtcg ccccgtcctg cccgcaaact ctactacctt gacctacgac    8820
ctgcaggcag acgggcgctc ctgcaccgca tccgcgacgc agtcctgcaa cgacctctgc    8880
gagcacttct gcgttcccaa ccccgaccag ccgggctcct actcgtgcat gtgcgagacc    8940
ggctaccggc tggcggccga ccaacaccgg tgcgaggacg tggatgactg catactggag    9000
cccagtccgt gtccgcagcg ctgtgtcaac acacagggtg gcttcgagtg ccactgctac    9060
cctaactacg acctggtgga cggcgagtgt gtggagcccg tggacccgtg cttcagagcc    9120
aactgcgagt accagtgcca gcccctgaac caaactagct acctctgcgt ctgcgccgag    9180
ggcttcgcgc ccattcccca cgagccgcac aggtgccaga tgttttgcaa ccagactgcc    9240
tgtccagccg actgcgaccc caacacccag gctagctgtg agtgccctga aggctacatc    9300
ctggacgacg gtttcatctg cacggacatc gacgagtgcg aaaacggcgg cttctgctcc    9360
ggggtgtgcc acaacctccc cggtaccttc gagtgcatct gcgggccga ctcggccctt     9420 gcccgccaca ttggcaccga ctgtgactcc ggcaaggtgg acggtggcga cagcggctct    9480
ggcgagcccc cgcccagccc gacgcccggc tccaccttga ctcctccggc cgtgggctc     9540 gtgcattcgg gcttgctcat aggcatctcc atcgcgagcc tgtgcctggt ggtggcgctt    9600
ttggcgctcc tctgccacct gcgcaagaag caggcgccg ccaggccaa gatgagtac      9660 aagtgcgcgg ccccttccaa ggaggtagtg ctgcagcacg tgcggaccga gcggacgccg    9720
cagagactct gagcggcctc cgtccaggag cctggctccg tccaggagcc tgtgcctcct    9780
cacccccagc tttgctacca aagcacctta gctggcatta cagctggaga agaccctccc    9840
```

```
cgcacccccc aagctgtttt cttctattcc atggctaact ggcgaggggg tgattagagg    9900
gaggagaatg agcctcggcc tcttccgtga cgtcactgga ccactgggca atgatggcaa    9960
ttttgtaacg aagacacaga ctgcgatttg tcccaggtcc tcactaccgg gcgcaggagg   10020
gtgagcgtta ttggtcggca gccttctggg cagaccttga cctcgtgggc tagggatgac   10080
taaaatattt atttttttta agtatttagg ttttttgtttg tttcctttgt tcttacctgt   10140
atgtctccag tatccacttt gcacagctct ccggtctctc tctctctaca aactcccact   10200
tgtcatgtga caggtaaact atcttggtga atttttttt cctagccctc tcacatttat   10260
gaagcaagcc ccacttattc cccattcttc ctagttttct cctcccagga actgggccaa   10320
ctcacctgag tcaccctacc tgtgcctgac cctacttctt ttgctcttag ctgtctgctc   10380
agacagaacc cctacatgaa acagaaacaa aaacactaaa aataaaaatg gccatttgct   10440
ttttcaccag atttgctaat ttatcctgaa atttcagatt cccagagcaa ataaattta   10500
aacaaaggtt gagatgtaaa aggtattaaa ttgatgttgc tggactgtca tagaaattac   10560
acccaaagag gtatttatct ttacttttaa acagtgagcc tgaattttgt tgctgttttg   10620
atttgtactg aaaaatggta attgttgcta atcttcttat gcaatttcct ttttgttat   10680
tattacttat ttttgacagt gttgaaaatg ttcagaaggt tgctctagat tgagagaaga   10740
gacaaacacc tcccaggaga cagttcaaga aagcttcaaa ctgcatgatt catgccaatt   10800
agcaattgac tgtcactgtt ccttgtcact ggtagaccaa aataaaacca gctctactgg   10860
tcttgtggaa ttgggagctt gggaatggat cctggaggat gcccaattag ggcctagcct   10920
taatcaggtc ctcagagaat ttctaccatt tcagagaggc cttttggaat gtggcccctg   10980
aacaagaatt ggaagctgcc ctgcccatgg gagctggtta gaaatgcaga atcctaggct   11040
ccaccccatc cagttcatga gaatctatat ttaacaagat ctgcaggggg tgtgtctgct   11100
cagtaatttg aggacaacca ttccagactg cttccaattt tctggaatac atgaaatata   11160
gatcagttat aagtagcagg ccaagtcagg cccttatttt caagaaactg aggaattttc   11220
tttgtgtagc tttgctcttt ggtagaaaag gctaggtaca cagctctaga cactgccaca   11280
cagggtctgc aaggtctttg gttcagctaa gctaggaatg aaatcctgct tcagtgtatg   11340
gaaataaatg tatcatagaa atgtaacttt tgtaagacaa aggttttcct cttctatttt   11400
gtaaactcaa aatatttgta catagttatt tatttattgg agataatcta gaacacaggc   11460
aaaatccttg cttatgacat cacttgtaca aaataaacaa ataacaatgt gaaaaaaaa   11520
aaaaaaaaaa aaaaaaaaa aaaaaaaaaa aggtagcagt cgacagatga attccaccac   11580
actggactag tggatccgag ctcggtacca agcttaagtt tgggctgcag gaattctgat   11640
ggctctcaaa attcctgcct cctttaggga taaaagactt taagactttt taacaaaaaa   11700
gaaaagaaa aaaaaaattc ctgcctcctg gtgtacacac acagaagggt tccctcccct   11760
tgaatgtgac caggatctgt gaaaataacg ggatagccgc tcctgtgatt aggttatgtg   11820
gtagactaga gcaagattct cctgctggtt ttgaagaagt cagctgccat gttgtgagac   11880
tgtcatgggc tagggcatga gccttttaaat atctgggagc aacccctggc cagcagccag   11940
tgagaaaacg ggccctcagt cctacaatca caaggaacta aattctgcca acaacctgaa   12000
ggaactttga agaggatcat gagtcccttg attcagcttg atgagcccct gagcaggga   12060
tacagctaac ttgtactagg gaagtataaa aaacatgcat gggaatgata tatatcaact   12120
ttaaggataa ttgtcatact tctgggaatg aagggaaaga aatgggggctt tagttgtatt   12180
atgatctttta atttctcaaa aaaaataaga tcagaagcaa atatggcaaa atgttaatac   12240
```

```
ttttgtgggt acgtaggtat tcagcatacc cttttttctg agttcaaaat attttataat    12300
taaaatgaaa tgcaggccag gcacagtggc tcatgcctat aataccagca ctttgcgagg    12360
ccgaggtggg aggatggctt gaggccagac cagcctggcc aacatggcaa aaccccatct    12420
ctacttaaaa aaaaaaaaac tatatatata tatatgtgtg tgtgtgtgta tatatatata    12480
tgtatatata tttatatatg tgtgtatata tatatatgta tatatattta tatatgtgtg    12540
tgtatatata tatatacaca cacacacata tatacataca tacatacaca cacacacaca    12600
cacaattagc caggcatggt ggcgcacacc tgtagtccca gctacttggg aggctgagac    12660
atgagaattg cttgaacctg ggaggcagag tagttagtga gctgagatca taccactgca    12720
ctccagcctg gtgacagagt gagactctgt cttaaaaaaa ataaaaatta aaattaaatg    12780
caaaaggtcc aagtgaattg aagaggaaag gggtatcaag gaaggttttg tggaggtgac    12840
gtttgagctg ggtcttaaat gacttaaaca tgggataaga agggagggaa taaggacatt    12900
tcaggtacga gaaataagga gcaaacagtg gaaacaacct aacgtctgtc aaccagtgaa    12960
tggataacaa aaatgtaatt cagatggtat ccaacttacg atggttcaac atgagatttt    13020 tctgactttta ggatagattt atcaaagtag taaatccatt ttcaacttat gatattttca    13080
acttcagatg ggtttatcag gacacagttg aggaacacct gtctatccat acaatttggc    13140
aataaaaagg aaatgagtgc agatatactc cacaacatga atgaaccttg aaaacattaa    13200
gtgagagaag ccagatacaa aaggccacat attgtatgat tctatttata caaaatgtcc    13260
agaataggca aatcttatag acagcaagta ggtagatgat cagtttgcta ggtgctgggg    13320 gaagggaaa tggggagtga tggctaaggg gattgggttt cttttgtgggg caatgaaaat    13380 gttttaaaat tgagcgtgat aatgattgca caatgctgca tatatatata atctatagat    13440
tatatatata taaagagagg ctgttagaca gtgataagtg atatatatat atatatacat    13500
agagagagag agagagagag agagaggctg ttagtgataa gtgatcagga aaataaaagt    13560
attgaggagg aatacgaagt tgacggtgtg aaaacatgag attttatata ggatggccag    13620
ggaaggcctt aatgagaaag tgacttatga gtaaaaacaa gggatcctaa accttagcat    13680
gcatcagaat cactcggaaa cttgttaaag catagcttgc tgggcctcat cacagatatt    13740
ttgattcggt aggttcttgt ctgatattaa tacttttggt ctagggaacc acattttgag    13800
aaccactgag ctaaaggaag taaaggtttc ccttagttta ctagctggta acactggccc    13860
aggaggcctt tctggaaaag gtcccagtcc ccaaaggaag ctgggggactc gcgttcacat    13920 cgtcaaggtt taccaagttg tggcgggcct ttccgtcttg gaaaaagcct caaaatggca    13980
gattagggtg tccatggccg gcggaaaggg tctttgaagt tgcagaccag gagggaagaa    14040
gattctgggc ctccccccatg cagtgtcagc tggcaacaga atgcacccccg gctgggttgg    14100 aggccctggg tactggctct tccacaccag gggcccacct accaagggca gcaggagcat    14160
ctgcacctcc tgcgccaggc gcccttcagt gcttccactt gagcacctct ccagacacca    14220
gctagggtga cagtggtaca aataccagac tcccctggcc tgctcacctc acagggtaat    14280
gtgctgtgga gtcagggggga cacagcaacc accagatgac atggctggcc ccggggagga    14340
cgacacgcag atacggctac ttggcacctg tgatatttta cacactcgag aggggcccgc    14400
accatcctca gccctctccc cacattcact cttagttcat gtcacctcca cccagagggg    14460
gacacaggcc cacagcgatg gccccacacc ctgcctgagg tcgcccactt cccaggaggc    14520
agtcctggga cttccacccg accaggcccc agagcccacc gacttaaccc ctccagaggc    14580
ttgtcgttca ttaccttatt caagatggag accagccttt ttgcggagaa aatgcgggtg    14640
```

```
aaggtcctga aagtgcattg acgccgtttt cggaagccat acaagtttag ctggcggaag    14700
aagctcttta tcgaagttgt ggcaaacact ttgtgtgcga cgtccctttt gagaatctcc    14760 tttttcaaaga gttttttgatt gatcactcta caagccccac tgtcatccca ccagatggac   14820
gaaaactggt tgctgctgac cagtctccac agtttctgtg gaaaggggag ggagaggaga    14880
ttatcttctc cctggggcgg gacgtcaccg tcagggtgcg gccttctgaa cgaagcttcc    14940
tcggccagag gttggaaagc gatttcttct gtcagcagcc tcaagttagg gctcccagtg    15000
gaccccgggt cgtcccaggc agggaagga tctgctgggt gaaggtaggt ctctgactgc    15060
aactggggag ggaaaggcac cctttccaag ccatgatcct gtcctctcga atttcttttct    15120 tcacagcgag ccatactcaa tgatcgcttg tcctccatct ggcaaacttg ctagtgcagt    15180
gtggccagca gcacccttg gcagtcatgt aaccagcccc atgacatcat aaaggggctc    15240
tgactgccgg ggggtggcat ctccacccc agcaagttgt gtaataaagg gccaaggcag    15300
acaagtagct gcccatctgc atgtgcacat tctggtcctc acagtcattt caatgggaaa    15360
gatgacacta gtgcacaaga gtgccgaggg gccctgccac accgtagatg cagacctgga    15420
gcggtcccct tgtcctagag ctcctgagcc aggcacaact acagcaaagc cctggctcag    15480
gaaggtcaga gctcaccgtc tgagtcatgg gcccacagac cccagcacat gactgacact    15540
cggaagcaca gaacaaaggg taggacggtg cccatgggtc aggctgtagc cacgccaccc    15600
tttccaccct gtcctagcca gaggcagcaa tgtgctccat acagatcctc ctaacacacc    15660
cacactgtcg gtccccagca cgcagatgcc cgacagcccc ttaggcaaat ggcttagctg    15720
actgccccac cacacgccgt cgccatgcag tccagtgggg agtcggaggc agcctccttc    15780
ctgcctctcc tcggcctgca cgtgtccccc caccaggcag agaccttct acaccccggg    15840 tgtctgcggt cacatcgcgg tggggcatgc agctgttggc cttcgagcat gttttgttt    15900 ccttggccag tgtctccaga gaaacgcacg tgggtttgtg tccagcggtc catctctgca    15960
acagttgttc ctttgggatt ggatgctagg aggtcacggg agaggtgtcc atccaaagca    16020
gtgtctgtgt cacacactgt ccccacacac agggccacct ctgcacagac tcccccgact    16080
cgattctggg cacagagctc agtgaccttc cagagactgc cacgaaccgg tgatgcctcc    16140
acgcttgaga catcctgacc gcagggccca aggcgcactg gctcagggg tgacagtgag    16200 gggtctgcaa acagactgct gatgctcaac ccggccgctg ccgagctgtg tgacttgggc    16260
acgtcactta acctctctcg gcctctgtct cctcccgggg ataagagtag tagcacctgc    16320
ttcccggggc tgtgaggatc cagtgggacg tataggaact agcgaggcac cggcagttgg    16380
gtcagagcta ctgttgtcac ttcacaaggc attttcttca acagcaagtc ggaaatctca    16440
tgagcctaag gcagaatcca cctgtggcct ctggttacaa cccacaggac tgaaaatcct    16500
tccagccaca gcaactggtg aatttcctgg tcaattgcca caagtcatga gctgaacccc    16560
acttgagttt cagttcaggc agaactctag agacgactag gcaagctag acagcgactg    16620 cagagccttt tgttgcagcg tgagcagtcc tcagctgttg acatcactgg ggagcaaacg    16680
aggaccagga gcggtgaaag gacagtgtct gctgcagatt gtcgtagcac caaggaaca    16740 ctccagaaag cctcctaagc agtaacaagt gtggcaaggt gtagcccagc caacagtggc    16800
atctgcgagg cgtcccctcc ttcctcccac taccccgtat accctgggac ctgtgcactg    16860
aaggactcat tctaaaggct gtgcccctgc agccgccagc ctcactcact ggctgcctgt    16920
gccagctaga gatttctttc ctctgaggct ggctgagagg accactccag tttcctggcc    16980
catccagcaa agaagataca catcatgcac gtgtaaaatg aggaaccggt ttattgaaca    17040
```

```
gcttaaggag agcaaaaata gtggctttag ctacattttt tacacactga gcaggaaagt   17100
ctaaaccatc ccgttcccct gtaccccaaa gagaacaggg cttgctggag gccagtgcca   17160
agggcggagt cgtgctcgca gcagacttga attaacccca tgtaggccgg cgagcagttg   17220
cccgcgtgaa acaccaccc tcttctcctg gctgagaaga tcaaagctct ttttttaccc    17280
tcttttcagc aaaggaccta tttgttttca ggcaggagga tgttaaactt gcagcctctg   17340
acacacggtg gaacctgcag tgcttggaga acggcacgc acacgtgaaa acatcatgcc    17400
tactccaaag ccttcttgtt gctggcagga gggaagcttg agactttccc acgcatagtc   17460 gtgaccgcg tggccgtttc tgctctcagc aacattctct agtgttccgg cttcaagcag    17520
cgcttgtcag gtttgaagct agccactatt ctgagaacgt cagaaaagca tggaccatct   17580
cttgcttggt gttgccgttg tggcagtagc agctactacg tacctgcacg agttccaggg   17640
cagaagtggc aatgtcccat gaaggcgtgg caccccacgg ggggggggg ggagtgtgcc    17700 acgggcgtcc acttctgcag cagaaggcat gtgcctacag cacaagcttg taaaaaata    17760 cttgaacaga atatgctgta cagaactagg ggttaacacc gcatatgaag atgctaaaac   17820
atttgtataa atactctgta tacaagcatg gagtcactcc cgtagaaagg gctcatccgt   17880
gaggctatga aaaactgctg tcagcatgcc caaagagaaa ctacttccac agtaggaaca   17940
gaaaaaggga ctgtgctgtg tctaaacacg tggtgcatca gagacatagt tacagttcct   18000
actgactgcc ccagccacga cctgggagtg ctgaggacct gggagtgctc agcgagctgc   18060
aggaggtcag ccctgtggag aaatacattt ctaaacaata cttttgattg ggatttcagc   18120
accgtataga cagatgttcc ttctgggggc ctggcaagca gccatctccc agtgggtctg   18180
acggggaaga ggggtacctg gagcccctcc cagacagacg gtaatcccac ccctgttctc   18240
acactcttcc tggcatccgc atctgctggc acacaccccc gtcacctgcc acttccgcgt   18300
cccgtcgtgg tgagtggctg ataggcgctg gatgcaaaca aggcatgaga tggacgtacc   18360
tggagaccca gctccagtac tggttctggt ctgcggggtg aacgaggggg cagaggaagg   18420
cggagagagt gcgtcccagt ccacttaagc tctgtcccg gaagtggcat ctaatctggc    18480
atttcgatat ttaatttggg aggtgggagc acatacttcc cagggctctg ggtaatgacc   18540
accctggcct tctttcgaaa catgggtgcg atttttaggg gctccggaac tgggtctct    18600 tcggtttctt cattatcttc gtgatggaga tcataggaaa tgtttccata ttctcgtaga   18660
aatgggaaga tttcaagcag aaactgacag aaatctttgc ggataccaaa ccaccctgaa   18720
aaataagaat ttttatttc acacacgagg ctcaactgac cttcctgtta actttctttc    18780
cgtaacaaga agtttcactc ctacaatgtc ataacatact ttatccagac tcctgagtca   18840
caaagcctga acagggcttg agtacccaaa atggggaaga agtgcaaatg ctagctctgt   18900
ggtgcttgga gtggggttcc cggaccggca gggacagcgt ccacggggcc tagttaggga   18960
tgccattctc gggccccagc ccagacctcc agaaactgag tcgggctagg gtgggctcca   19020
gcggtcccct tttcctggcc ctttgggat tctgctggat gcccaaattt gagaactact    19080
gctccagtga gtctcaaaat atctgtggtg cgcagactac ggtgtcttcc gctaatcttc   19140
tccagccagg ataaactcat ggatgacagt gccacccaag aacaagattt ctgtcaccct   19200
ctggaatccg tgagggcggt agtcatgcac gggttggcca ggaggggcc tgaactcatg    19260 gagccacctt aaagccactt tcccagtccc actactcctc tctgtaggct actggagtgt   19320
cagctcggtg caagccctcc ctgctcccgg gtgcggggta gggggcagag gcacaaacag   19380
caagcacagc ccgggctgct gggctgcagt gaggccctgc ccccaaaccc actggctttc   19440
```

```
cgaagggcaa tgctctgggc ttccgtgcca tggagcccac agccttgcca ggaaggcacc    19500
ctctgcagag atcgttttgg aagtgtctgc ctcagcaagc aggtggaggg gaatagagtg    19560
ttagcaaggc aagacaggca agactcgggt gatggcagca aggatatggg ggaggcagag    19620
cggccaacag ggacctagga tgaatcccag gtttgggtgg gagatgtgga ttttccatca    19680
aaccctcccg ggcctgggaa gaatctgtct tgatccccat tttgcagagg agggaacggg    19740
atctctgaga ggttgcctgc cgtgtctggt tctacctcaa atggcagcgt gcactgcgag    19800
aaaagtcccg gtgcaggcca gcagaacacc agagttacgg catgcccttc ccttagaagg    19860
tcccagaatt tcctcagccc tcactttccc acacaagctt ctaaattggg gcctcgggg    19920 actcatccct tcctagactt ctatccgcca cccccaccc cctggtcccc cccagacac    19980 acaccaagga cttctgaaat gctgagtaca tacagtggtt tcctcccttc tgtccaaatg    20040
tggttgccat cagcgtgatc aacgagagcc aaaggggac aaagatcggg atgcaggaga    20100
aggcgttgtg gccatccagt ttgtgaacca gcagaatcta agaaagaga catagtcccg    20160 gttgatgcca gcaccgaaaa tgggcagagg cggaagccag acttcattag gcagttcctc    20220
cccaccaccc caccccgcg tgagctccca caagagggaa catcagcacc gccagaaaaa    20280
ggcaggaaac cacctatccc tggggaaagc tcgaaatgag ctttttatgtc cctcttcaga    20340 gctcggcaat agcctatcca cttgaaaagt tcccagtgcc agcagtttta tggcaaactc    20400
ctccgggtgt ttgttctaag gagtcaacag ctcccattct agaattctcc acgtgactcc    20460
aatacacaaa tctgacatcc cactctgctt tccccagagt ggaaactgga gccatacaga    20520
ggcaccatgg ctaaaaaggt gcactcttct ccctgccagc cccacgtgct gcccccaaga    20580
gaaaggaagg atgctctcct ttcaccgaag ctccctctcg gagatggctg tgttctctcc    20640
cctctcctgg agtgggctca ctgtgagctc gagggacaga ggctgccttt ctaggggtgc    20700
agaatcctgt caggggaagc gcaagcttca ggggctgaag aggcttcccg tggaacgctt    20760
acctcaaatg taagaagggg cacgacgatg gtcatccagc tcagggccat ggttatgtgt    20820
gtcctgcgct gtccgcaatc acatccatag agcgcaagaa caagacggac cacacaatgt    20880
agtagaggac caccaggcac agaaaggaca tgagaatcca cagcgggaca cacacaacct    20940
gggggtgggt gagagaacag caagagaagt ctctttagag cttccaacct ggcctctgat    21000
ggaaggcatc tttagcacct tgctgtgtct gtccagttaa ggcggtcctt cctgtgagcc    21060
gaataaggac cgttccatct cccaggactg ctgggagcat cgctcaggac agaaaaggta    21120
tggtatgttc actatgggc ctgctgccac caggggacac acacgctcag tgagtcatca    21180
gtccctcttc ctttgggtga cagacagccc tgcacctggc tccgcagcct ctactcttcc    21240
agaggcccac tctcccacac tctctcaggc tcctctaggt tctgctgcca tcacagcttc    21300
ccgggaaatg ggacacaact gtcaccctgt gcacacacac aagatctcac cccaacagac    21360
tctcttcaca ggcaacattc ccacaacctg ctggggtac tttggcaaca caaatggaaa    21420
tgggctcccc agaaagtctg gctgcctggg ctcctaagga tccctaacct caccctacc    21480 aagttagtga acttggcggg ttgatgctgg atacaggttg atgctggata cgtagcgctg    21540
ccgggtcgtg accctaagg aattatccaa actcttgttt ttagatgctt tattatatca    21600
aactctcctt taaacaagtg gcccatctgc tgggatttgg aagcctgtaa tactgaaatt    21660
ttcatcataa tggaaatttt aaaaacagaa tttgacccac ctgttttaa aacactttca    21720 ttacttaaca agaggtctaa tcttgggcaa gtccttgaaat ttctctggcc ttagtttccc    21780
atgtgttaaa tgaaacttga agcagttggt ctcttatagt ctcctgactc taacattcta    21840
```

```
agaattatat ttgtacaata actcaaaaat cacataattt aatttaccat atggactcca  21900
aaatatattt tctcattagg ctaaacttga tctgcatttt ctggatgtgt ccatattctt  21960
ggactacact aaaacatgat accaatgctt cctctcacca taaaccctca cttcgctttc  22020
tacatttaag aattttatag ctggaagagt ccttaacaga aaataccatc taataattac  22080
ccctcaaaat cgagaaagtc ctatctgttc ttatgctagt tataagaatg aggcagcatt  22140
tcacataatg gttataaaca ctgccacaag aagattcatg atgtgttgtt tatctgtagc  22200
tctcatcata ctctgtcata taactatagc attaagattt taatgttcta tatattcttc  22260
taagacagtg tttaccagag taaggcacaa aagatccact ggtttgcaag aaagattaga  22320
acttttaaat tttttacctc accttgttta atctatattt ttgtatgtat tttgtaacat  22380
atatattatt attaccataa atcatatata atttaaaatg catatattag gggtaaatgc  22440
tcaggaaact ttttataaat tgggcatgca aatacaagtt tgaagactca ctgttctagg  22500
tattaaaagt aaagttataa ccaagtaaag cttccacctt ttcatgtctc aaagcagttt  22560
attgttggag gtaagatctc ttagaagcct aaacaggtcc aagtacagaa tgaagtaagg  22620
ctagcccata acttgtggca agcaattcat actatttctc tcatgctgag ctctcctcag  22680
tgaagcagct actatagaca actgcagcct attggtagcc tattttacag gcaggaaaaa  22740
aattactttt tattcaaagt ggaactcagg acatggggag aaaatgaata caaaaaatag  22800
ggtcaatcca aaggcacaca gcaaatgagt aacacagtta tgttttttc ccatttgtat  22860
gaggtcccag taaattctaa gtaaactgca aatttaataa tacactaaaa aagccatgca  22920
attgttcaaa tgaatcccag catggtacaa ggagtacaga cactagagtc taaaaaacaa  22980
aagaatgcca ttattgagtt tttgaattat atcaagtagt tacatctcta cttaataaat  23040
gagaaaaacg aggataagag gccatttgat aaaatgaaaa tagccaagaa gtggtattag  23100
agacttgaat acaggtattc gggtccaaag ttcatctgct caaatactaa ctggggaaaa  23160
gagggaaaaa tatttatata catatatatc tgcacacaaa aataccccca aaagacaaaa  23220
tgaggccagg cagggtggct cacacccgta atcccggtac tttgggaggc tgaggcaggt  23280
ggatacctga gatcaggagt tggagatcag cctggtcaac atggtgaaac cctgtctcta  23340
ctaaagataa aaaaattagc caggcatggt ggcgtgcgcc tgtaatccca gctacttggg  23400
agtctgaggc aggagaatca cttgaactgg gaagggagg ttgcagtgag ccaagatcgt  23460
actactgcac tccagcctgg gcagcagagt gagactccat cacaaaaata aataaataaa  23520
taaaatacaa tgaaacagaa agttcaaata atcccataat cttaccacca agaaataact  23580
ttcactcgtt atacttattg atttttccat aataaatgta ctttactgtg actatcatga  23640
aaagaaagtt attttagaaa cagagaactg tttcagatca aatctatgta gtagaacaga  23700
gccattaggt gggaaagacg agatcaaact aaatctcaga aggcctaaaa ggctaggtcc  23760
attccagcac taaaaactga ccagacaagt aatggcttca acagcttcta aatatggaca  23820
aagcatgctg aaagggaagg acaggtctaa cagtggtata tgaaatgaac aggaggggca  23880
aagctcatt ctcctctgaa gttttccaaa gatgctgagg aggacattag tttgacatga  23940
ccctgatatg ggacaagata atttcacaga agttttacat gttaaagttt tcttatagat  24000
actcattcaa gtaagcaatg aacactaaaa tctaaagaaa gaaagagct ttagagtcag  24060
gtctgtattc aaattcaagc tctaccactt actggttctg tgactttggg caagtctttt  24120
aaccttatta agtcttaatt tcctgatttg taaaatgggg atatcgtctc cctcacagga  24180
ttgttgtgaa acttttatga gattaatgcc tttatatttg gcatagtgta agtaaacaat  24240
```

```
aactggcagc ttcaaaaaaa aaaagcagta gcattccatc atttattatt ggttactctc    24300
aaaaagtttt tcaatgtact agaagataaa tattcaaata ccttaatatc tccattattt    24360
tcaggtaaac agcatgctcc tgaacaacca atgggtcaac aaataaatta aaagggaaat    24420
ctaaaaacat cttgatatta aactacatgg aagcacaata taccaaaacc aatggttcac    24480
actaggagaa ttttaaggta caagaaaact ctttgagatt tcttaaaata atagtatgtc    24540
tgaatttatt gagtgattta ccagaaactg ttgtaagagc tctacttgca ttatagcact    24600
taatcctctt aactctatgg ctgctattat caacctcacc ctaatcacat atgggacaca    24660
gagaggttaa gtaacttgcc caaggtcaga gttaggaagt actaagccat gctttgaatc    24720
agttgtcagg ctccggaact cacactttca gccactacat aatactgctt tgctatcttt    24780
taggaaacta tgtgagtcta cctcacatag actcacatag gtttgttttt tttttttttt    24840
taaaggctat cttttccccc atcaatgttt tttgaaggat cccaaattag agtcccacag    24900
aggcagacag cagtacttga caatatggac atttaaggtt aatgttggat tctactgtct    24960
ttttactaca tgacctaggg aacgataatt aacctagact gcttccaagg gttaaataac    25020
ccatttagtt atactatgta aattatctct tagtgattga ttgaaagcac actgttacta    25080
attgactcgg tatgaagtgc tttttttttct tccctttcaa gatacatacc tttccagtta    25140
aagttgagag atcatctcca ccaattactt ttatgtcccc tgttgactgg tcattctagt    25200
taaaaaaaaa aaaactata tatatatata tctacacaca catatgtata tgtatatcct    25260
tatgtacaca cacaaacttc aaattaaatg agaactagaa gatttgagaa gttagctagc    25320
taatatccat agcattatga tattctaaat gatatgaatt ataagaatta ggtttcctga    25380
aatgaatgac tagaaaactt tcaagtagag attagtaaaa attaaaaagt cctaatcggc    25440
cattactgat ttgatgtttt taagagtcct aaaaaatggg ttacatccat ttttaagtgg    25500
gtagtattat aacagccacc catcttcaat cacagtgatt tctgaattgt gagggaagtt    25560
attagcatga caggtgtctg gttctggccc tgtacgattc ccatgagtca agcaaattgt    25620
aagggctggt ctatatcaca cccaacccca aggatatgtc cctcaaaagt ctagcccagg    25680
ccccgtcatc ttcagcatca tctgggaaac caggtctgat tagtagtcct ttaaggaata    25740
cctcttaggc tcccatttta ctgctatcac agaatccaat aaaacccttta caggagattc    25800 aatgggaaat gctcaacacc cactgtagtt ggtggtgaca atgaccataa tttggctgtg    25860
ctggattcag gacagaaaat ttgggtgaaa gagcaggtga acaaagagc ttcgacttgc    25920 cctagcagag agcaagccat accataccac aaagccacag caattacaac ggtgcagtac    25980
cagcacagta aatgaacaaa gtagagccca gaaacagacc cagaactata tgaggattta    26040
gtatacaata aagatggtat ttcgagtcag tagggaaaag atgaattatt caataaatga    26100
tgtttggcca actagtaacc catttgggaa aaaataaaag tatggtccct acctcacagc    26160
atacacaaaa ataaattcca gacgattaa aatctaaatg taaaaaataa agccataagt    26220
ggactggaag aaaatagaga attttttta acatccgtag aaagggtaaa aacccaggca    26280
tgacatgaac caaaactgaa gaggttctgt aacaaatacc ccctttata tattgggctc    26340 caacaataag aacccatagg aaaatggaga atgaacacaa atagacaatt tatagaagag    26400
aaggttataa ggtgtaaaat tatatctatc tgagaaacaa acactaaaac aatgtgattc    26460
tactgttctc ccacccatac tggcaaaact taagcctgat aatatgctga ggggaaataa    26520
gcactcttgt tggtgagagt attaattggc atagcttctt ttgaaaatga catagcaata    26580
cctgttaaaa ttgcaaacat gcatgtcact taatccagta atcccacttc tgggaatcaa    26640
```

```
tgctacaaaa acactgacaa gtatacaaag atacattcaa gagtgttcac tgggccgggt    26700
gcggtggctt catgcctgta atcccaggga ggcagaggca agacgatcgc ttgacccccag   26760 gagttcaagg ccagcccgag aaacacagca agaccctgtc tctcttttttt ttatttaaaa    26820 aataaatgtt cactgtatca gttgttcaca aaaacaaacc aacatgtcca ttaacaggga    26880
accatttaaa ttaatcaagt tcatctacac aatgtaatac catgcaacta ttaaaaagca    26940
cctgataatc caaagcacac tgagacagaa taatgctatt aaaaacacca agtagtggaa    27000
cactgtgttg cctatgacac cattttttatt caacatttaa acaaatttgt aacagcaatt    27060
acatgagtag tgacaatggc gtttatgaga cttttcactt ttatgtgctt ctattttttgt    27120 tatgcttcta tatatacatc catttattat ggagtgttac tttcaaaaat cacaaatggg    27180
ccagtattat ttggtgttgc aaggtgagca tatgacttct gatatcaacc tttgcatatt    27240
acttctcaat ttagggaaat tacagacatc ccttattcta actaacttaa aacccagcat    27300
ttcaaacata cagaattgat ggggaaaaaa aagaaagaag aaagaaagaa aaggcaacaa    27360
gcttcagatg acagtgactc acatcaaatt atttataaaa tctgttaaat agtgccatct    27420
tctggagata cctggtatta cagtccaact ccagttgatg tctttacaga gacaagagga    27480
ataaaggaaa aaatattcaa gaactgaaaa gtatggagtc atggaaaaat tgctgtgatc    27540
caaaggctac ggtgatagga caagaaacaa gagaactcca agcagtaaga cactgctgtt    27600
ctattagcat ccaaacctcc atactcctgt ttgccccaag gcttttttaa aaaatagaga    27660
caggatctca ctattttgct caggctggtc ttgaactcct ggactcaagc tatcctcctg    27720
cctcggcctc ctaaagtgcc gagattacag gcttgagtca ccatacctgg ctattttattt   27780 tttcttaact ctcttgcctg gcctatagcc accatggaag ctaataaaga atattaatttt   27840 aagagtaatg gtatagttca ctacattgga atacaggtat aagtgcctac attgtacatg    27900
aatggcatac atggatcaat tacccccacct gggtggccaa aggaactgcg cgaacctccc    27960
tccttggctg tctggaacaa gcttcccact agatcccttt actgagtgcc tccctcatct    28020
ttaattatgg ttaagtctag gataacagga ctggcaaagg tgaggggaaa gcttcctcca    28080
gagttgctct acctctcct ctaccgtcct atctcctcac tcctctcagc caaggagtcc     28140
aatctgtcct gaactcagag cgtcactgtc aactacataa aattgccaga gaagctcttt    28200
gggactacaa acacatacccc ttaatgtctt tatttctatt ttgtctacct cttcagtcta    28260
ggtgaaaaaa taggaaggat aatagggaag aactttgttt atgcctactt atccgcccct    28320
aggaattttg aaaacctcta ggtagcaata agaactgcag catggtatag aaaaagagga    28380
ggaaagctgt atagaaatgc ataataaatg ggcaggaaaa gaactgcttg gaacaaacag    28440
ggaggttgaa ctataaggag agaaagcaga gaggctaatc aacaaggctg ggttcccaag    28500
agggcatgat gagactatta ctaaggtagg aattactaag ggctccatgt ccccttagtg    28560
gcttagtact atgtagcttg ctttctgcag tgaacttcag accccttcttt taggatccta    28620 gaatggactt ttttttttta tcggaaaaca gtcattctct caacattcaa gcaggcccca    28680
agtctaccac actcaatcac attttctctt catatcataa tctctcaacc attctctgtc    28740
cttttaactg tttttctata ccctgatcaa atgccaacaa aagtgagaat gttagaatca    28800
tgtattttta gaggtagact gtatctcaga taaaaaaaaa gggcagatat tccattttcc    28860
aaaatatgta tgcagaaaaa ataagtatga aaggacatat gctcaggtaa caagttaatt    28920
tgtttacttg tattttatga attccctaaa acctacgtca cccgcccgt tcccacgccc     28980 cgcgccacgt cacaaactcc accccctcat tatcatattg gcttcaatcc aaaataaggt    29040
```

```
atattattga tgatgttaat taacatgcat ggatccatat gcggtgtgaa ataccgcaca   29100
gatgcgtaag gagaaaatac cgcatcaggc gctcttccgc ttcctcgctc actgactcgc   29160
tgcgctcggt cgttcggctg cggcgagcgg tatcagctca ctcaaaggcg gtaatacggt   29220
tatccacaga atcaggggat aacgcaggaa agaacatgtg agcaaaaggc cagcaaaagg   29280
ccaggaaccg taaaaaggcc gcgttgctgg cgttttccca taggctccgc cccctgacg   29340 agcatcacaa aaatcgacgc tcaagtcaga ggtggcgaaa cccgacagga ctataaagat   29400
accaggcgtt ccccctgga agctccctcg tgcgctctcc tgttccgacc ctgccgctta   29460
ccggatacct gtccgccttt ctcccttcgg aagcgtggc gctttctcat agctcacgct   29520
gtaggtatct cagttcggtg taggtcgttc gctccaagct gggctgtgtg cacgaacccc   29580
ccgttcagcc cgaccgctgc gccttatccg gtaactatcg tcttgagtcc aacccggtaa   29640
gacacgactt atcgccactg gcagcagcca ctggtaacag gattagcaga gcgaggtatg   29700
taggcggtgc tacagagttc ttgaagtggt ggcctaacta cggctacact agaaggacag   29760
tatttggtat ctgcgctctg ctgaagccag ttaccttcgg aaaaagagtt ggtagctctt   29820
gatccggcaa acaaaccacc gctggtagcg gtggtttttt tgtttgcaag cagcagatta   29880
cgcgcagaaa aaaggatct caagaagatc ctttgatctt ttctacgggg tctgacgctc   29940
agtggaacga aaactcacgt taagggattt tggtcatgag attatcaaaa aggatcttca   30000
cctagatcct tttaaattaa aaatgaagtt ttaaatcaat ctaaagtata tatgagtaaa   30060
cttggtctga cagttaccaa tgcttaatca gtgaggcacc tatctcagcg atctgtctat   30120
ttcgttcatc catagttgcc tgactccccg tcgtgtagat aactacgata cgggagggct   30180
taccatctgg ccccagtgct gcaatgatac cgcgagaccc acgctcaccg gctccagatt   30240
tatcagcaat aaaccagcca gccggaaggg ccgagcgcag aagtggtcct gcaactttat   30300
ccgcctccat ccagtctatt aattgttgcc gggaagctag agtaagtagt tcgccagtta   30360
atagtttgcg caacgttgtt gccattgctg cagccatgag attatcaaaa aggatcttca   30420
cctagatcct tttcacgtag aaagccagtc cgcagaaacg gtgctgaccc cggatgaatg   30480
tcagctactg ggctatctgg acaagggaaa acgcaagcgc aaagagaaag caggtagctt   30540
gcagtgggct tacatggcga tagctagact gggcggtttt atggacagca agcgaaccgg   30600
aattgccagc tggggcgccc tctggtaagg ttggaagcc ctgcaaagta aactggatgg   30660
ctttcttgcc gccaaggatc tgatggcgca ggggatcaag ctctgatcaa gagacaggat   30720
gaggatcgtt tcgcatgatt gaacaagatg gattgcacgc aggttctccg gccgcttggg   30780
tggagaggct attcggctat gactgggcac aacagacaat cggctgctct gatgccgccg   30840
tgttccggct gtcagcgcag gggcgcccgg ttctttttgt caagaccgac ctgtccggtg   30900
ccctgaatga actgcaagac gaggcagcgc ggctatcgtg gctggccacg acgggcgttc   30960
cttgcgcagc tgtgctcgac gttgtcactg aagcgggaag ggactggctg ctattgggcg   31020
aagtgccggg gcaggatctc ctgtcatctc accttgctcc tgccgagaaa gtatccatca   31080
tggctgatgc aatgcggcgg ctgcatacgc ttgatccggc tacctgccca ttcgaccacc   31140
aagcgaaaca tcgcatcgag cgagcacgta ctcggatgga agccggtctt gtcgatcagg   31200
atgatctgga cgaagagcat caggggctcg cgccagccga actgttcgcc aggctcaagg   31260
cgagcatgcc cgacggcgag gatctcgtcg tgacccatgg cgatgcctgc ttgccgaata   31320
tcatggtgga aaatggccgc ttttctggat tcatcgactg tggccggctg ggtgtggcgg   31380
accgctatca ggacatagcg ttggctaccc gtgatattgc tgaagagctt ggcggcgaat   31440
```

```
gggctgaccg cttcctcgtg ctttacggta tcgccgctcc cgattcgcag cgcatcgcct    31500
tctatcgcct tcttgacgag ttcttctgaa ttttgttaaa atttttgtta aatcagctca    31560 tttttttaacc aataggccga aatcggcaaa atcccttata aatcaaaaga atagaccgag   31620 ataggggttga gtgttgttcc agtttggaac aagagtccac tattaaagaa cgtggactcc   31680
aacgtcaaag ggcgaaaaac cgtctatcag ggcgatggcc cactacgtga accatcaccc    31740
taatcaagtt ttttgggggtc gaggtgccgt aaagcactaa atcggaaccc taaagggagc   31800
ccccgattta gagcttgacg gggaaagccg gcgaacgtgg cgagaaagga agggaagaaa    31860
gcgaaaggag cgggcgctag ggcgctggca agtgtagcgg tcacgctgcg cgtaaccacc    31920
acacccgccg cgcttaatgc gccgctacag ggcgcgtcca ttcgccattc aggatcgaat    31980
taattcttaa ttaacatcat caataatata ccttattttg gattgaagcc aatatgataa    32040
tgagggggtg gagtttgtga cgtggcgcgg ggcgtgggaa cggggcgggt gacgtagtag    32100
tgtggcggaa gtgtgatgtt gcaagtgtgg cggaacacat gtaagcgacg gatgtggcaa    32160
aagtgacgtt tttggtgtgc gccggtgtac acaggaagtg acaattttcg cgcggtttta    32220
ggcggatgtt gtagtaaatt tgggcgtaac cgagtaagat ttggccatttt tcgcgggaaa   32280 actgaataag aggaagtgaa atctgaataa ttttgtgtta ctcatagcgc gtaatactg     32339
```